United States Patent
Natoli et al.

(10) Patent No.: US 9,961,156 B2
(45) Date of Patent: May 1, 2018

(54) HEALTHCARE SEMANTIC INTEROPERABILITY PLATFORM

(71) Applicant: Intel Corporation, Santa Clara, CA (US)

(72) Inventors: Joseph D. Natoli, Phoenix, AZ (US); Kristina M. Kermanshahche, Lake Oswego, OR (US); Joshua Painter, Dublin (IE); Alan Boucher, Kennebunkport, ME (US)

(73) Assignee: Intel Corporation, Santa Clara, CA (US)

( * ) Notice: Subject to any disclaimer, the term of this patent is extended or adjusted under 35 U.S.C. 154(b) by 71 days.

(21) Appl. No.: 14/304,529

(22) Filed: Jun. 13, 2014

(65) Prior Publication Data

US 2015/0006612 A1 Jan. 1, 2015

Related U.S. Application Data

(63) Continuation of application No. 11/858,842, filed on Sep. 20, 2007, now Pat. No. 8,850,057.

(51) Int. Cl.
*G06F 15/16* (2006.01)
*H04L 29/08* (2006.01)
(Continued)

(52) U.S. Cl.
CPC .... *H04L 67/2823* (2013.01); *G06F 17/30569* (2013.01); *G06F 19/322* (2013.01);
(Continued)

(58) Field of Classification Search
CPC .... H04L 67/12; H04L 67/2814; H04L 67/327
See application file for complete search history.

(56) References Cited

U.S. PATENT DOCUMENTS 6,272,468 B1   8/2001   Melrose
6,941,557 B1 *   9/2005   Jakobson ............ G06F 9/542
                                                                    709/223

(Continued)

FOREIGN PATENT DOCUMENTS

CN     1487414     4/2004
JP     2001142956     5/2001

(Continued)

OTHER PUBLICATIONS

State Intellectual Property Office (SIPO) of the People's Republic of China, Chinese Patent Application No. 200880107453.7, dated Apr. 11, 2014.

(Continued)

*Primary Examiner* — Philip Chea
*Assistant Examiner* — Mohammed Ahmed
(74) *Attorney, Agent, or Firm* — Schwegman Lundberg & Woessner, P.A.

(57) ABSTRACT

A system and method for efficiently linking local databases having different data formats or standards into a network, wherein a content based router is provided between each of the databases and a network "party line" bus and translates data from the respective database into a common canonical form or format so that all information within the network between the content based routers complies with the common canonical form and are validated according to single standard or mechanism, for example when information first enters the network. Also provided is a tracking or audit mechanism whereby each item of information provided with a unique network identifier when it first enters the network, and is also provided with or associated with a local identifier from each local database that originates or accesses the information item and router identifiers of the content based routers corresponding to those local databases.

11 Claims, 31 Drawing Sheets

(51) Int. Cl.
    *G06F 19/00*     (2018.01)
    *H04L 12/701*     (2013.01)
    *G06F 17/30*     (2006.01)
    *H04L 12/931*     (2013.01)

(52) U.S. Cl.
    CPC .............. *H04L 45/00* (2013.01); *H04L 49/35* (2013.01); *H04L 67/12* (2013.01); *H04L 67/28* (2013.01); *H04L 67/2814* (2013.01); *H04L 67/327* (2013.01)

(56) References Cited

U.S. PATENT DOCUMENTS

| | | | |
|---|---|---|---|
| 7,167,924 B1 | 1/2007 | Symonds et al. | |
| 7,577,904 B1* | 8/2009 | Obilisetty | G06Q 10/10 715/234 |
| 2002/0038381 A1* | 3/2002 | Gendron et al. | 709/238 |
| 2002/0158765 A1* | 10/2002 | Pape | A01K 11/008 340/573.3 |
| 2004/0065402 A1 | 4/2004 | Knoerzer et al. | |
| 2004/0101186 A1* | 5/2004 | Tong et al. | 382/132 |
| 2004/0139095 A1* | 7/2004 | Trastour | H04L 69/24 |
| 2004/0225508 A1 | 11/2004 | Urali | |
| 2005/0137998 A1 | 6/2005 | Betts et al. | |
| 2005/0246629 A1* | 11/2005 | Hu | G06F 17/2247 715/237 |
| 2006/0155862 A1 | 7/2006 | Kathi et al. | |
| 2006/0222003 A1 | 10/2006 | Majumdar | |
| 2007/0050427 A1* | 3/2007 | Atkin | G06F 17/2247 |
| 2008/0069082 A1 | 3/2008 | Patrick | |
| 2008/0069124 A1 | 3/2008 | Patrick | |
| 2008/0270438 A1* | 10/2008 | Aronson et al. | 707/101 |
| 2008/0301286 A1 | 12/2008 | Little | |
| 2008/0316914 A1* | 12/2008 | Vercellone | H04L 12/2697 370/216 |
| 2009/0160658 A1 | 6/2009 | Armstrong et al. | |

FOREIGN PATENT DOCUMENTS

| | | |
|---|---|---|
| JP | 2007140831 | 6/2007 |
| JP | 2008527519 | 7/2008 |
| WO | 0231738 | 4/2002 |
| WO | 2006072609 | 7/2006 |

OTHER PUBLICATIONS

European Search Report issued in corresponding European Patent Application No. 08832059. dated: Oct. 30, 2014.
First Office Action issued in corresponding European Patent Application No. 08832059. dated: Nov. 13, 2014.
Fifth Office Action in corresponding Chinese Patent Application No. 200880107453.7. dated: Sep. 29, 2014.
Sixth Office Action in corresponding Chinese Patent Application No. 200880107453.7. dated: Feb. 3, 2015.
Japanese Office Action, Japanese Application No. JP2010525115, dated Oct. 18, 2011.
State Intellectual Property Office , People's Republic of China, Chinese Office Action, Chinese Application No. 200880107453.7, dated Oct. 29, 2012.
International Search Report and Written Opinion, dated Mar. 30, 2009, PCT International Application No. PCT/US2008/076766.
International Preliminary Report on Patentability, dated Mar. 24, 2010, PCT International Application No. PCT/US2008/076766.
International Preliminary Report on Patentability, dated Apr. 1, 2010, PCT International Application No. PCT/US2008/076766.
Pallos, Michael S., "Service-Oriented Architecture: A Primer," EAI Journal, Dec. 2001, pp. 32-35.
Bass, Christy et al., "Building a Business Case for EAI," EAI Journal, Jan. 2002, pp. 18-20.
Intel Corporation, "Service-Oriented Architecture Transforms Intel's eCommerce," IT@Intel Brief, Nov. 2005, 2 pages.
Intel Corporation, "Service-Oriented Architecture Simplifies Access to Employee Data," IT@Intel Brief, Nov. 2005, 2 pages.
Microsoft Corporation, "Service-oriented architecture: Effective care in a new healthcare economy," Apr. 17, 2006, http://www.microsoft.com/industry/healthcare/healthplans/solutions/soa.mspx?pf=true (accessed Dec. 5, 2007, 3 pages.
Wikipedia, "HL7," archived on Sep. 13, 2006, http://web.archive.org/web/20060913000000/http://en.wikipedia.org/wiki/Health_Level_7, 5 pages.
Canada Health Infoway Inc., "An overview of the Electronic Health Record Privacy and Security Conceptual Architecture," Mar. 2006, pp. i-ii, 1-23.
Intel Corporation, "Converging Technologies in Healthcare IT," IT@Intel Brief, May 2007, 4 pages.
"Bobsguide: Fidelity National Information Services," Nov. 11, 2006, http://web.archive.org/web/20061111235523/http://www.bobsguide.com/guide/prod/5-2138.html, 1 page.

* cited by examiner

Figure 7: Headwater as a Healthcare Service Network

HEALTHCARE SEMANTIC INTEROPERABILITY PLATFORM

CROSS-REFERENCE TO RELATED APPLICATIONS

This application is related to and claims the benefit under 35 U.S.C. 120 of U.S. application Ser. No. 11/858,842, filed on Sep. 20, 2007, the entire contents of which is incorporated herein by reference.

FIELD OF ART

Exemplary embodiments of the invention described herein encompass content-based routing in a distributed information network, and in particular contemplate a multi-party information network such as a Healthcare Information Network (HIN).

BACKGROUND

In many healthcare information systems today, semantically normalized & aggregated clinical data are not available and/or are not standardized sufficiently to enable cross-platform or cross-network sharing. This can result in medical errors, diagnoses and treatments based on incomplete knowledge of patient histories or vital data, harmful drug interactions, redundant testing, and other unnecessary admissions. Providing the patients electronic health record (EHR) at the point of care—the right data, to the right clinical personnel, at the right time—increases both the quality and efficiency of care. Today this is only rarely achieved when individual providers invest in very complex systems integration projects and even then, the patient record is still largely incomplete. Instead, clinical decision-making largely relies on labor-intensive and error-prone searches through available hardcopy, data repositories and "silos" of disaggregated information, to build a patchwork view of patient health.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description of the Preferred Embodiment, which is to be read in association with the accompanying drawings, wherein.

DETAILED DESCRIPTION

Figure 1:
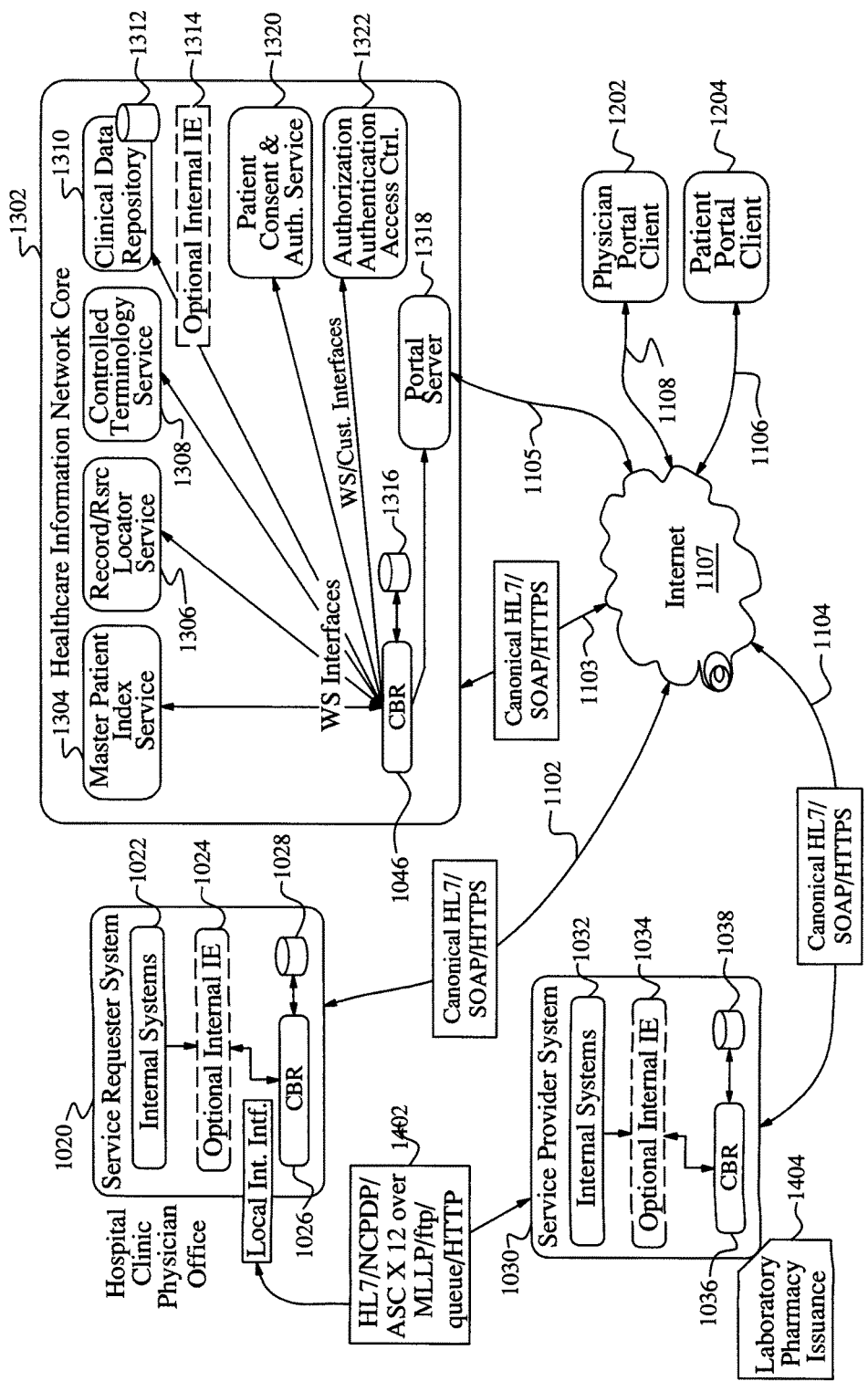
FIG. 1 illustrates an overall structure of an exemplary embodiment of the invention.

In an exemplary embodiment of the invention, a Healthcare Information Network (HIN) is formed by linking separate databases belonging to different entities (e.g. different hospitals, different health insurers, clinics, state or federal agencies and so forth) via content-based routers, e.g "Headwater" routers. The Headwater routers can function as SOA (Software Oriented Architecture) appliances that translate communications from the different (external) entities into a common or standard format or canonical, and transmit and track the communications between the Headwater routers and through the Headwater routers, between the different entities. The Headwater appliances can act as gatekeepers to the network, by filtering or validating all communications that enter or exit the network through them, thus helping ensure integrity of data within the network, and providing a degree of authentication or trust for entities that receive data from the network. In a similar fashion the Headwater appliances can provide security for the network by restricting access of external entities to the network. In exemplary embodiments, the Headwater appliances also keep track of communications that flow through them into and out of the network, thus providing traceability for transactions involving specific data, such as patient records or information.

Given "N" different standards or data formats used by different databases participating in the HIN, translating into an intermediate, common format or standard for use within the network reduces a number of necessary translation capabilities from N*(N−1) in a case where each format is translated directly into each other format, to N+1 translations thus providing greater efficiency and simplifying scalability.

Each Headwater router is assigned to one of the (external) entities or databases, and functions as that entity's link or liason to the HIN. The Headwater routers communicate between themselves using an open bus that can function as a "party line", where all of the Headwater routers can listen to communications on the bus, and can broadcast or send messages on the bus. This open bus can be a virtual bus or "party line" that routes communications between Headwater routers, through the Internet. Communications on the bus can include appropriate information such as header information so that other Headwater routers can discern where communications on the bus are intended to go, and whether the communications are of interest to the particular Headwater router listening in (for example if a particular Headwater has been assigned or has taken on a duty to archive all communications relating to a particular subject, patient, geographic region, to look out for information of particular interest to the hospital or agency to which it is assigned, and so forth). In addition, direct routing mechanisms can also be provided within the network, so that a Headwater appliance can send a communication directly to another entity on the network, such as another Headwater appliance. As those skilled in the art will appreciate, existing direct routing mechanisms can be used or adapted to facilitate this capability, and there can indexes or repositories within the network akin for example to one or more "telephone directories" that a Headwater appliance can consult to obtain, update, verify or cross-check the direct routing address or status of another entity (or of the Headwater appliance corresponding to that other entity) in the network. In-network directories can also indicate services and/or information available from or through participating Headwater appliances in the network. Thus, one or more central directories can be provided in the network to contain information about participants in the network such as Headwater appliances and also about the external entities those appliances represent, and the information can include network identifications for the participants, records regarding validation requests received from them, validation results, copies of cached transaction trace information gathered by the Headwater appliances, canonicals supported, and so forth.

The Headwater routers link disparate databases by converting all data or communications from each database into a common canonical form or standard. Thus, each Headwater in essence translates communications or data from the local entity to which it is assigned, into the common standard for communication to other Headwater routers, and converts information it receives on behalf of its local entity from the common standard into the local entity's standard or format, thus acting as a translator between its local entity and the network (and thus between its local entity and other entities served by Headwater routers local to them). The translation can include not just translation or conversion of format or structure of the data, but also semantics or meaning of the data or metadata. For example, a label of a brand-name drug can be translated or expanded to a generic or technical name (e.g. from Zestril™ to lisinopril), "heart attack" can be translated to or correlated with "myocardial infarction", and so forth. Each local entity can be responsible to provide its Headwater router with a translation key or map, that maps the local entity's data description standard and practice to the common standard or canonical for information shared between Headwater routers.

When a Headwater router receives a communication from its local entity, the Headwater router translates the communication into the common standard or canonical and can then also apply a validation mechanism (or forward the translated communication to another node or station within the network such as a network core node) to validate the translated communication. In exemplary embodiments the validation is guaranteed by the network, not simply a local interpretation by a particular developer at a particular local site. This establishes a service on the network that can execute the validation at design time (map creation) and/or runtime (message exchange). This universal/network level definition and execution of the validation in accordance with exemplary embodiments of the invention provide significant advantages. Validation means that the communication is checked for syntactic, semantic and/or grammatical correctness or proper conformance with an official definition of the common standard or canonical. If the validation fails, then the Headwater router can inform its local entity that the communication failed the validation (and convey any diagnostic information provided by the validation process). A failed validation can suggest, for example, that the translation key or map contains errors or inaccuracies that the local entity needs to correct. The validation mechanism can be uniformly applied by or among all the Headwater routers in the network, so that information within the heart o the network (i.e., passed between Headwater routers) can be trusted and easily consumed, and so that entities connected to the network by a Headwater router can trust information they receive from the network through that Headwater router. At the same time, this can minimize burden on the local or external entities ("external" to the network because they only communicate with the network through their respectively assigned Headwater routers) by making each responsible only for the mapping between its particular standard and the common standard. Records of the validation process can be kept by the Headwater router or appliance that requested the validation (locally or cached to a separate or associated data store), and/or by a central entity within or connected to the network, for example an entity such as a network core node to which the Headwater router sends a communication for validation. The records can for example indicate when validation was requested, for which communication it was requested, a result of the validation, and so forth.

Security can be provided by implementing security procedures and mechanisms via the Headwater appliances, which in exemplary embodiments can act as gatekeepers. For example, security can be certificate-based, using for example PKI (Public Key Infrastructure) processes and technologies, so that each valid Headwater appliance has a certificate, and communications with other Headwater appliances within the network are tagged or otherwise verified using the respective certificates of the communicating Headwater appliances. In an exemplary embodiment, if an entity seeking to communicate directly with the network does not have a certificate, other Headwater appliances in the network won't listen to it. The external entities represented by the Headwater appliances can also have digital certificates, and particular networks or areas of the Headwater network can be sub-certificates, which in an exemplary embodiment can be used to effectively organize the Headwater network into zones according to any desired criterion, for example geographic region, type of healthcare entity represented, and so forth. In exemplary embodiments of the invention, Virtual Private Networks, known network addressing schemes, and other techniques can be employed or adapted to provide security and/or enable party-line and direct routing communications for the Headwater network. External systems that interface to the Headwater network through Headwater appliances can use keys (e.g. in accordance with PKI) to enable, control and protect access to communications between the external system and its respective Headwater appliance.

In an exemplary embodiment, each event or piece of information is provided with a unique network identification code and a local entity identification code assigned to it by the local entity that provided it in the first place. When this event or piece of information is accessed, viewed, stored and/or modified by another entity in the network, corresponding local entity codes and Headwater router identification codes can be associated with the event or added to a record of the event to provide a tracing history of the event through and within the network. New associations can for example be broadcast within the network, and/or directly routed to one or more interested entities (e.g. a central repository or cache within the Headwater network, Headwater appliances involved with the event, and so forth) so that participating nodes in the network (e.g. a network core node, a Headwater router tasked with fulfilling a related duty, and/or an interested or responsible local entity) can update their records for the event.

For example, when a Headwater router first receives information regarding a patient such as an event, treatment or other item of information from its corresponding local system, the information will include a local system identifier for the item. The Headwater router can then create a unique network identifier to label and associate with the item.

Each Headwater router or appliance can have a unique physical identifier (e.g., TCP/IP address) and/or a unique logical identifier (e.g. a unique 128 bit character code, or other code of smaller or greater size), and the network identifier the information item can include an identifier of the Headwater concatenated or otherwise combined with a count or other generated value generated by the Headwater appliance so that different Headwater appliances can independently generate unique network identifiers. In an exemplary embodiment the Headwater appliance can then create a record that travels with the information item in the network, where the record includes the local identifier, the Headwater appliance identifier, and the network identifier. The Headwater appliance can also keep a copy of this record, and can forward a copy of the record to one or more network core nodes (e.g. that each has its own Headwater appliance linking it to the network) to provide redundancy. Whenever the information item effectively touches another Headwater appliance or passes through a Headwater appliance to be used or cached by a system local to that Headwater appliance, that Headwater appliance can add its own identifier to the record and also an additional, new local identifier generated by the corresponding local system, thereby generating a "trace" in the record. Thus, the record corresponding to the information item will include not just the network identifier and the original local and Headwater identifiers, but also identifiers of other local systems and their Headwater appliances that used or accessed the information item. When a Headwater appliance associates new or additional identifiers with the network identifier of the information item, it can broadcast this within the network so that other Headwaters that touched the information item or that have been tasked with being "interested" in the information item can receive the broadcast message and update their copies of the history/trace record for the information item. A Headwater appliance can also designate specific nodes in the message it provides to the network with the updated association information (e.g. new identifiers to be associated with the network identifier for the information item), so that those nodes will receive or notice the update and respond accordingly. Additionally or alternatively, a Headwater appliance can directly route the update to one or more entities in the network that it knows are interested in the information. Thus, each transaction of the information item with a member of the network can be recorded or cached for tracing or tracking purposes. This can enable compliance with different privacy or restricted access regulations, indicate who or what is or might be interested in the information item, provide a mechanism to identify and track disease vectors, and other things. Each Headwater appliance can have its own local cache or data store for storing trace records, canonical definitions and standards, special tasks or duties and associated rules or scripts to perform, and so forth. The data store for the Headwater appliance can be local and exclusive, or can be remote, can be shared by multiple Headwater appliances or can independently service multiple Headwater appliances, and so forth. A Headwater appliance's cache or data store can thus archive traceability data and core data (e.g. communications as well as their tracing information), and can be configured to time out or periodically flush communications while retaining trace data regarding the communications. For example, after a period of time elapses following a transit of a communication via the Headwater appliance, the communication can be flushed or deleted from the appliance's cache, while traceability or tracing information regarding the communication (as well as information to identify the communication) are retained, indefinitely or until a later date. For example, Headwater appliance caches can be configured to retain tracing information longer than then corresponding communications, and can offload or upload information that will be flushed or discarded so that it can be saved or archived elsewhere, for example in another data store associated with the Headwater appliance or a central repository or regional repository within or connected to the Headwater network. Headwater appliance caches within the network can be configured differently, for example depending for example on different factors including a size of the particular cache, an amount or intensity of traffic the Headwater appliance conveys, type(s) of communications it conveys, and so forth.

Caches or data stores associated with the Headwater appliances can provide not only traceability functions or capability, but can also be employed to provide Record Locater Services. For example, exemplary embodiments of the invention support pre-built service for health care record location, or RLS (Record Locator Service). The purpose of RLS is to provide a mechanism to determine and aggregate patient data that may be stored in disparate locations within a Health Information Network (HIN), for example a network of Headwater appliances each externally linked to a health care entity such an HMO, hospital, and so forth as described elsewhere herein. More specifically, patient data can be queried to determine how often a patient has gone to one doctor, can provide a summary of patient activity over a specified date range, or can be used to pull information in aggregate form, such as a full patient or encounter history. While the RLS service can appear as a local pre-built service to a single instance of Headwater, it can rely on a "network effect" of multiple Headwater instances in the network, that effectively share resources. Further, the pre-built RLS service can be designed to be customized to fit the exact needs of the health care deployment. In particular, the local WSDL (Web Service Data Language) service interface and database schema for the RLS store can be customized for particular applications. In this form, the RLS service can be considered a "starter" service.

For RLS, we may distinguish between multiple Headwater instances or appliances/context-based routers called nodes. In the case of a Health Information Exchange (HIE) network, in an exemplary embodiment one node, called a repository node, can be the point from which the data is queried, while the other Headwater instances keep only records of patient data that they directly participated in. In a high-level example, consider three Headwater appliances or instances linked through the Headwater network: a Doctor node, Lab node, and a HIN node. Each Headwater appliance has an associated data store or cache, including for example a persistent RLS data store. In an exemplary embodiment, the RLS data store is an interface separate from the message cache for the Headwater appliance (where, for example, the message cache saves copies of all messages that traverse or are relevant to the Headwater appliance and its corresponding external health care entity, as well as saving tracing information such as local and network identifier labels). In an exemplary embodiment, the RLS data store contrasts the message cache in that it is designed to handle longer-lived data. The RLS data store can be separate from the message cache, or can be implemented together with the message cache in a data storage device, for example a partitioned device. In an exemplary embodiment, the HIN (Health Information Network) node acts as the main repository from which all RLS queries are made. The Headwater RLS service can be compatible with non-Headwater nodes although some custom development may be required depending on particular circumstances. In an exemplary embodiment, the RLS generates and associates the identifiers, and the message caches of the corresponding Headwater appliances function at least as local stores of actual messages. In exemplary embodiments, the RLS and/or the generated and associated identifiers are implemented with the message cache or local store of messages in one database in each Headwater appliance or instance.

In our example, the HIN node is the repository node and exposes an XML web services style interface for querying patient data. A query tool can be provided, for example, a tool available to a health care entity or authorized person operating the data machinery of that entity, where the health care entity is connected to the Headwater appliance of the HIN node and effectively accesses the network through the Headwater appliance. The query tool (automatically or at the behest of a human operator) can send a special XML query structure that represents a query, to the Headwater appliance. The Headwater appliance transforms this query structure into a series of relational database queries, consults its RLS data store, and returns the patient data back to the query tool.

In an exemplary embodiment, there are two aspects of the RLS service: (a) how and where patient data is stored and (b) how and where patient data is queried. These are now described in more detail.

In accordance with exemplary embodiments of the invention, CBR for Healthcare ("Headwater") can include a number of health-care specific services for handling orders, encounters, patients, documents, and other artifacts found in the healthcare domain. RLS can work by aggregating patient data as these services are executed. Due to the "network effect" of the HIN node (or repository node), local nodes (represented by Headwater appliances in the network) can mediate their communications through the repository node. When this occurs, patient data can be stored for later retrieval in a central location. To see how patient data can be aggregated for retrieval by the RLS service we will walk through an example of a doctor ordering a lab order for a patient. The use case matches the topology described above.

The use case can be described using the following steps:

1) A Doctor orders a lab test with identifier t for a patient with an identifier p, e.g. using the following functions/procedures. Order.Initialize( ) causes the Doctor node to find the network address of the HIN node. The function Order.Put( ) sends the canonical form of the lab request to the HIN node.

2) The HIN node records patient data, for example using a Local RLS store write to store the identifiers t, p, and the date in its message cache.

3) Next, the Doctor node records patient data, for example using a Local RLS store write to record the identifiers t, p, and the date in its message cache.

4) At this point, the Doctor wishes to send the lab test to the proper lab, "a", so the Doctor node uses the function Order.Put( ) to query the HIN node for the address of the proper lab, "a".

5) The HIN node records this new patient data (e.g., uses a Local RLS store write to record or store the order intended for lab "a").

6) Finally, the Lab node records patient data, for example using a Local RLS store write to tracks the receipt of the order in the local RLS store, and transform the order from the canonical form used between Headwater appliances, as appropriate, to a local for appropriate for the underlying lab system or lab system that is external to the network and connected via the Lab Headwater appliance.

At the conclusion of this health care workflow, the repository node (HIN Node) contains the full breadth of information about what happened for this specific patient while the local nodes only contain the portions of the workflow in which they directly participated.

In an exemplary embodiment, the RLS service can be queried at the repository node in the following way. With respect to patient data queries, or requests to access data regarding a patient, the RLS service can be a pre-built service for Headwater, implemented via a WSDL interface that can navigate the local RLS store at the repository node. As mentioned earlier, the RLS service can use the message cache to trace the incoming and outgoing flow of patient data to provide the means to reconstruct end-to-end message flows. The message cache of the Headwater appliance or CBR can record identifiers such as patient identifiers, doctor and lab identifiers, record identifiers, dates, as well as the IP addresses of the nodes where each transaction took place. In an exemplary embodiment, the message cache stores patient data in a relational database accessed through the use of an XML query structure. That is, the RLS service is defined by a WSDL containing service calls that take this query structure as input. Queries can be defined by manipulating the parameters of the query structure itself. Within the Headwater system, this query structure can be transformed into the proper relational database queries and then the result can be returned as XML. This makes it possible to write custom query tools based on XML requests and responses that closely match the requirements of the workflow. Exemplary Headwater systems can include a basic query tool, and can also be customized appropriately by an end-user.

Thus the Headwater routers described herein, in conjunction with a common canonical, can be used to form a healthcare-specific interoperability platform or Health Information Network that can enable accelerated adoption of healthcare information standards, reduce cost and complexity, and enable computable semantic interoperability that in turn enables sustainable business models.

Advanced healthcare usage models that can be implemented using exemplary embodiments of the present invention (e.g., medication administration, context-aware computing, clinical trials management, and clinical decision support) can rest on the fundamental issue of interoperability. Interoperability can be provided by implementing the Headwater routers and related services through the use of SOA (Service Oriented Architecture) and Web Services. Core Headwater features can include an Enterprise Service Bus (e.g., the "party line" or virtual communication bus between Headwater routers mentioned above) with reliable messaging, XML (eXtensible Markup Language) acceleration, security & routing, BPEL (Business Process Execution Language) orchestration, semantic normalization, a service container with pipeline processing of local & external services, and integrated design-time, run-time and management environments. Using this foundation, exemplary embodiments of the invention can define a set of healthcare business objects based for example on the v3 RIM (Reference Information Model) (XML Canonicals) and exposed through web services. Different deployment models (central, federated or hybrid) can be simultaneously supported, and scalable performance (edge, regional or super-peer transaction volumes) can also be provided to drive economies of scale and "future-proof" information technology investments.

Thus, exemplary embodiments of the invention using the Headwater routers, can facilitate efficient flow of patient data among different health care entities such as healthcare organizations and stakeholders enabling the creation and sharing of normalized patient data in an affordable manner. This availability of semantically normalized & aggregated clinical data will drive new efficiencies through the reduction of medical errors, drug interactions, redundant testing and unnecessary admissions. Providing the patient's electronic health record (EHR) at the point of care with the right data, to the right clinical personnel, at the right time will increase both the quality and efficiency of care, and avoid requiring individual providers to invest in very complex systems-integration projects that might still result in largely incomplete patient records. Exemplary embodiments of the present invention also free clinical decision-making from labor-intensive and error-prone searches through available hardcopy, data repositories and silos of disaggregated information that too often result merely in a patchwork view of patient health.

Passing all communications between network entities through Headwater routers ensures consistency with a common standard, because the Headwater routers translate information into and out of the common standard or canonical and validate the information. Passing all network communications through one or more Headwater routers also enables traceability. Thus in accordance with exemplary embodiments of the invention, all exchange transactions can be secure, resilient, auditable and accountable. Local or remote validated industry services, providers and capabilities can "plug-in" seamlessly as "service actuators" or functional service process models to the platform. This approach creates an exchange model where any data exchanged between two clinical parties, will have the proper provisioning & controls to support semantic validation along the transaction pipeline.

In particular, exemplary embodiments of the invention that incorporate Headwater routers or appliances address certain industry "pain points" in deploying an interoperability solution. This is done via several mechanisms, first by reducing complexity. Simplifying interoperability reduces integration costs and time-to-implementation for healthcare exchanges. Exemplary embodiments achieve this by providing a platform-based solution which creates system-level ingredients and network-level services and applications to address data translation (semantic interoperability) for all segments in the market. Comprehensive architecture, infrastructure, software and services are also provided. Exemplary embodiments enable fast and flexible connectivity and evolution of legacy platforms over time, and can handle significant portions (e.g. 70%) of the system integration plumbing, thus enabling quick creation of network participants, consumption of value-add services, and a blending of for-profit, private network services with non-profit and public network data consumers. Since all Headwater appliance/platform-level transactions can be encrypted, audited, and can use certified payload exchange models (e.g. XML canonicals), all appliance-level peers can semantically validate payload data at either (or both) ends of the transaction, using for example Certified Ecosystem peer services. Thus, trusted Interoperable Exchange Networks can be formed using Headwater routers/appliances and associated canonicals. Edge solutions are also extensible in exemplary embodiments, by extending the platform (e.g. Headwater appliances and associated canonicals) to inside the provider, payer or physician organization, thus enabling comprehensive solutions to the interoperability challenge both within and across healthcare organizations. Exemplary embodiments also enable scalability from small-to-large healthcare environments, which preserves existing investment while scaling with the growth of the organization and supporting the evolution of legacy systems over time, while simultaneously encouraging or accelerating the adoption of the latest healthcare standards. Thus exemplary Headwater routers/appliances provide SOA (Service Oriented Architecture), Web Services and XML acceleration, security and routing coupled with a high performance BPEL-style workflow, and thereby combine the manageability of a hard appliance with the flexibility and virtualization capabilities of software for an overall lower TCO (Total Cost of Ownership) as compared to a hard appliance.

Architecturally, exemplary embodiments including Headwater appliances or routers are healthcare-specific interoperability platforms designed to reduce the cost and complexity of health information exchange. They support legacy implementations at the edge, reducing the level of effort required to participate in advanced, high performance service networks. These features are enabled by incorporation of advanced SOA design principles, especially contractual separation of concerns between service provider and consumer, and virtualization of service network end-points. Exemplary embodiments expose business objects through standard web services which closely mirror the business process; address performance curve and security considerations associated with verbose XML payloads; shift a majority of development from custom one-off implementation to reusable design-time configuration; accelerate healthcare standards adoption by making them more accessible to the average developer; reduce the amount of up front work to leverage messaging and terminology standards; reduce the learning curve in making the switch from EDI (Electronic Data Interchange) to XML; capture and codify industry domain expertise on how to correctly apply terminology standards to healthcare business objects; and connect a value proposition of secondary use of data with a scalable solution that delivers semantic interoperability.

Figures 5A, 5B, 5C:
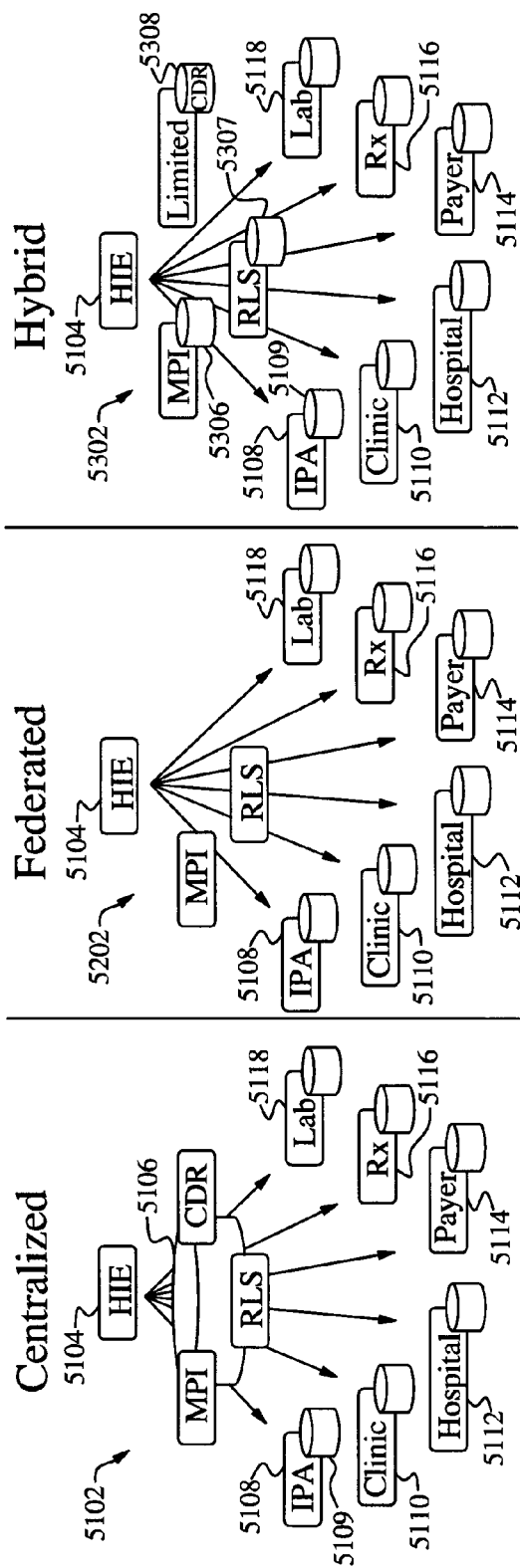
FIGS. 5A-5C illustrate deployment models supported by exemplary embodiments of the invention.

FIGS. 5A, 5B, 5C illustrate typical HIE (Healthcare Information Exchange) models, all of which can be supported individually or simultaneously by exemplary embodiments of the invention.

In particular, FIG. 5A illustrates a centralized model 5102 wherein an HIE 5104 uses a single store 5106 for patient data and offers Master Patient Index (MPI) and Record Locator Services (RLS) from this central location to other entities or nodes in the network, for example an IPA (Independent Physicians Association) 5108 with its database 5109, a clinic 5110 including a database, a hospital 5112 including a database, a healthcare payer (e.g. insurance company, government agency, etc.) 5114 with a database, a prescription or pharmaceutical provider 5116 with a database, and a lab 5118 with a database. Centralized architectures can provide an excellent model for patient consent as well as consistent security policies for patient data and the enforcement of a single standard across all participants. Furthermore, centralized models can offer secondary use of patient data, such as anonymized data analytics for business or government purposes in addition to direct clinical care.

FIG. 5B illustrates a federated model 5202, wherein the other entities or nodes (e.g. 5108, 5110, 512, 51124, 5116, 5118) and their associated local databases store the patient data and related information. Federated models provide central MPI/RLS (Master Patient Index/Record Locator Services) services for discovery of patient information, yet the clinical data remains locally stored at each source node. Federated models offer a high degree of local control, but can pose a performance burden on each end-point, since they have to be available at the time of request. Finally, there is an additional challenge to support patient consent and privacy consistently across all participating nodes.

FIG. 5C illustrates a hybrid model 5302, wherein some data is stored in central stores or databases such as 5306, 5307, 5308, but other data is stored in the local databases associated with the other entities or nodes (e.g. 5108, 5110, 512, 51124, 5116, 5118) in the network. Hybrid models store some patient information centrally and some at each node. Hybrid models offer MPI & RLS services centrally, but the actual data is split among central and local stores. The hybrid model can improve performance over a pure federated model, while keeping some data centralized, such as general patient demographics and sometimes or optionally critical care information. In the hybrid model, local nodes are queried when specific medical information is required, so all of the same availability and security considerations apply as in the federated model. Regardless of which model is chosen, the end goal is the same—managing HIE cost and complexity.

FIG. 1 illustrates an exemplary embodiment wherein a service network is created between participants in a hybrid HIE model. A first node (e.g. 1020) can request a service from another node (e.g. 1102) and their respective Headwater appliances (e.g. 1026, 1036) will provide translation and communicate through the Internet (1107), and can also seek services from, or provide information for central storage to, a network core (e.g., 1302) that also has a Headwater appliance (e.g. 1046) to provide translation, tracking and so forth.

In particular, as shown in FIG. 1 a service requester such as the node 1020 can for example be a hospital, a clinic or a physician's office. As shown in FIG. 1, the node can include internal systems 1022 (which can, for example, include database or data storage capabilities), an optional information exchange 1024, a content based router or Headwater appliance 1026 with an associated database or data storage 1028, and can also include a local internal interface to handle direct link 1402 communications with another node such as the node 1030 that uses or supports a same data format or standard, such as an HL7/NCPDP/ASC X12 over MLLP/ftp/queue/HTTP message as shown in FIG. 1 in connection with the link 1402. As shown in FIG. 1, the node 1032 can be a service provider than includes internal systems 1032 (which can, for example, include database or data storage capabilities), an optional internal information exchange 1034, a content based router or Headwater appliance 1036 connected to an associated database or data storage 1038, and which can emit a laboratory/pharmacy issuance or message 1404 directly to a compatible laboratory or pharmacy. It is possible for a node in the service network to be a service requester and/or service provider, for example a requester with respect to one event and a provider with respect to another. Also shown in FIG. 1 is a Healthcare Information Network core 1302, which can include or support: a master patient index (MPI) service 1304; a Record/Resource Locater Service 1306; a Controlled Terminology Service 1308 (e.g., to help validate data and/or correlate or interpret data terminology); a clinical data repository 1310 with an associated database or data storage 1312; an optional internal information exchange 1314; a patient consent and authorization service 1320 (e.g., to store and/or track currently effective and/or past consents or authorizations provided by, on behalf of, or relating to different patients); a portal server 1318 (e.g. to connect to the Internet and or other entities); and a content based router or Headwater appliance 1046 with an associated database or data storage 1316. The databases or storages 1028, 1038, 1316 connected to and associated with respective Headwater appliances can, for example, store mappings between a canonical for use within the network and data formats or standards used by the external entity that is connected to the network by the respective Headwater appliance, store data in association with a unique network identifier for an event or piece of information such as local identifiers for the event, and so forth. FIG. 1 also shows a physical portal client 1202 and a patient portal client 1204 that can communicate with other nodes in the network via links 1108, 1106 to the Internet 1107. Also shown in FIG. 1, the Headwater appliances 1026, 1036, 1046 communicate with each other through the Internet 1107 via links 1102, 1104, 1105 that carry communications consistent with a common canonical for use within the network, e.g. Canonical HL7/SOAP/HTTPS (which can mean, for example, a canonical that uses recognized or predetermined subsets of the standard HL7 using Simple Object Access Protocol, and XML protocol, over HyperText Transfer Protocol Secure).

Thus, in accordance with the embodiment shown in FIG. 1, a service requester such as the node 1020 can request a patient history where some of the patient information is located at the HIE network core 1302 and some at another member source node (such as a lab test from a specialty clinic stored at the service provider 1030). Within the HIE network core 1302, key infrastructure services (e.g., EIS, RLUS, CTS, CDR, PCA, AAA, etc.) can be virtualized back out to the participating nodes (e.g. 1020, 1030). In addition, the Headwater system can "plug-in" or make available additional value-added services to network participants. Examples of value-add services include: insurance eligibility, claims processing and adjudication, e-prescribing, formulary compliance, drug interaction services, and consumer services including Personal Health Records (PHRs).

As noted above, exemplary embodiments can support all three HIE deployment models (Centralized, Federated, Hybrid), and the nature or model of a specific network deployment or configuration can be dependent on the particular industry segment and workflow requirements that it serves. For example, In Ministry of Health and Government deployment models, data exchange requirements are often a subset of supported usage models, and can be largely event-driven between hierarchical super-peers across public and private networks. This deployment model can suggest a federated or hybrid model for data exchange, to maintain less information in fewer locations for shorter periods of time. Precisely because the information is always in transit, this model can require a robust network informatics exchange model with the ability to audit, validate and normalize the data "on demand" from any point in the network.

In cases where exemplary Headwater network embodiments are deployed within a local healthcare exchange, or at state, regional and privatized network levels, high volume and I/O (Input/Output) density capability can be required. These exchange models can require more variation on data and business object types, and address interactions between many disparate legacy systems across multiple industry organizations with levels of sharing agreements in place for system-to-system exchange. Such networks can require a workflow-oriented approach to how services are deployed and consumed. In this scenario participants can generally produce and consume both constructed data and data attachments, which then move between end points in the same systemic & syntactic fashion. These implementations can deploy Headwater appliances to serve as a backbone or core component in centralized or hybrid deployment models, as well as at the edge of each participant facility or node in the network in order to assemble, validate and push/pull clinical information from the core or other edge constituents.

In an exemplary embodiment, Headwater appliances are provided at the widest base of the industry triangle, in offices of individual physicians or small medical practice groups where a majority (e.g., >80%) of day-to-day healthcare transactions and interactions occur between patient and clinician. There, systemic, syntactic and semantic services, business services and clinical protocols, can be effectively applied in order to improve access, improve quality and reduce cost of delivering care.

Figure 2:
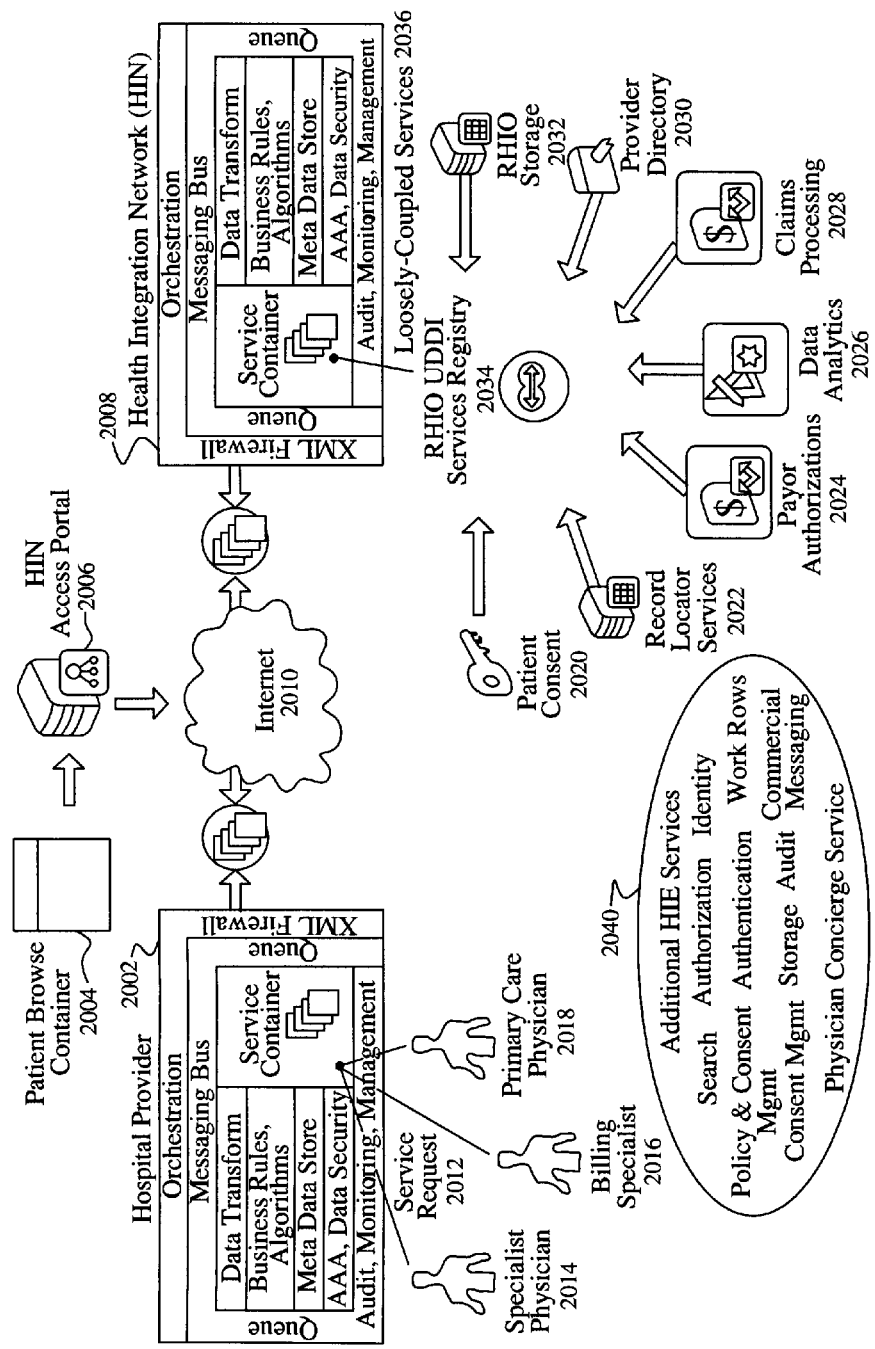
FIG. 2 illustrates a functional overview of an exemplary embodiment of the invention.

FIG. 2 illustrates capabilities and features of an exemplary embodiment. As shown in FIG. 2, a hospital provider 2002 equipped with a Headwater appliance can include a queue and a messaging bus to receive service requests (e.g. 2012) from entities such as a specialist physician 2014, a billing specialist 2016, and a primary care physician 2018 with respect to a service container that is associated with a data transform function (e.g., from an information format or standard used by the hospital provider, to a canonical for use within the network), as well as business rules, algorithms, a metadata store, data security/AAA (Authentication, Authorization, Accounting), as well as audit and monitoring or management functions. The Headwater appliance can communicate with a network node 2008 through an XML interface and the Internet 2010, where the node 2008 has a Headwater appliance providing similar capabilities. Patient information can be viewed through an access portal 2006 connected to the network through the Internet 2010, and the information can be viewed or packaged in the form of a Patient Browse Container can likewise be constrained or limited based on privileges or rights of the viewer. A Regional Health Information Organization (RHIO) Services Registry 2034 with UDDI (Universal Description, Discovery and Integration) capability can also be provided in connection with the node 2008, and can link or refer to different services such as patient consent 2020, RLS (Record Locater Services) 2022, Payer Authorizations 2024, Data Analytics 2026, Claims Processing 2028, Provider Directory 2030, and RHIO Storage 2032. Additional Healthcare Information Exchange services 2040 can also be provided, for example Search, Authorization, Identification, Policy and Consent Management, Authentication, Workflow, Storage, Audit, Commercial Messaging, Content Management, Physician Concierge Services, and so forth.

Figure 3:
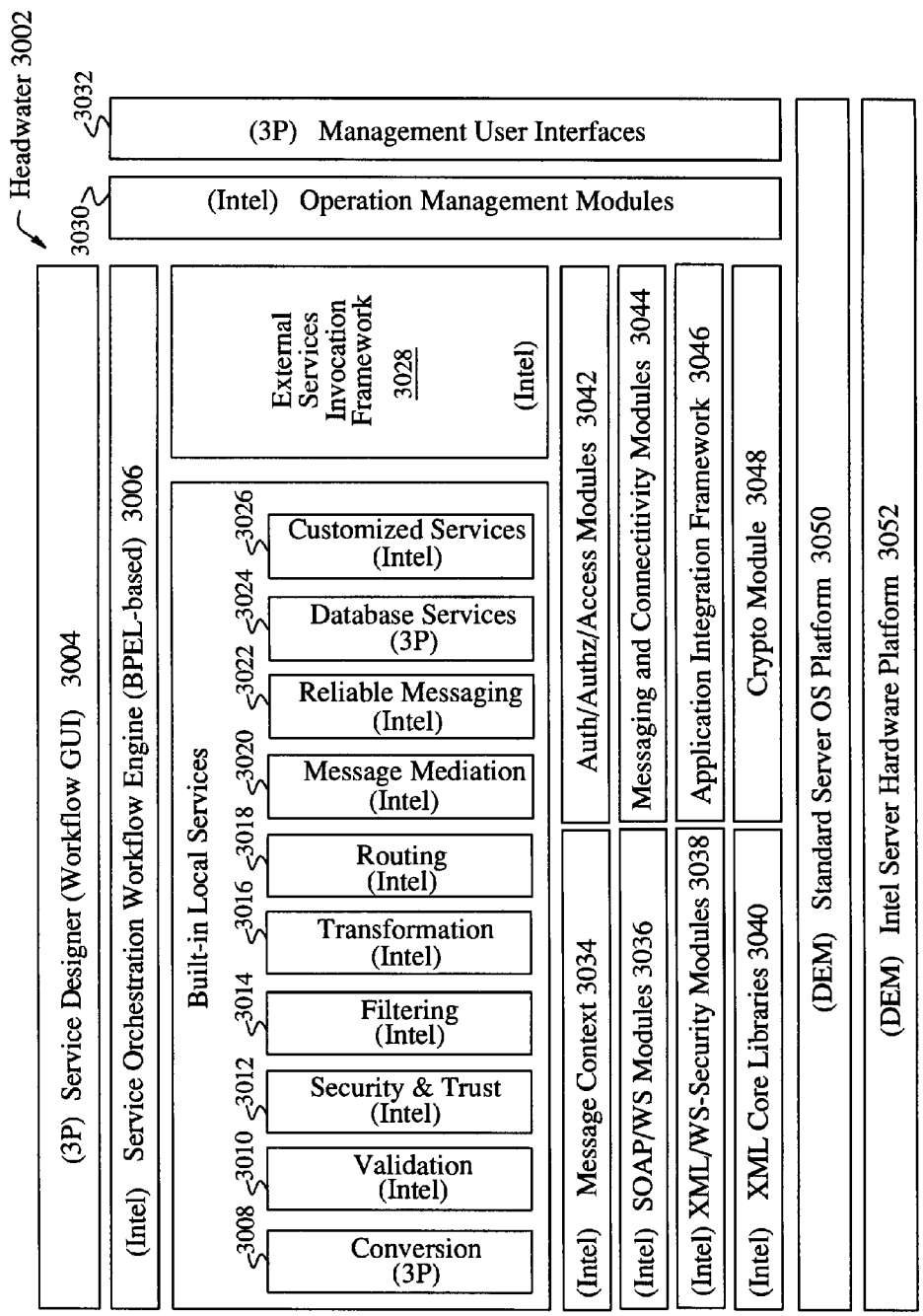
FIG. 3 illustrates software components of an exemplary content-based-router that can be used in the structure of FIG. 1.

FIG. 3 illustrates software components of an exemplary Headwater appliance 3002. As shown in FIG. 3, the appliance 3002 includes a workflow GUI (Graphical User Interface) 3004, a workflow engine 3006, management user interfaces 3032, and operation management modules 3030. Also included are a conversion module 3008 that can for example convert data into and out of canonical format or compliance, a validation module 3010 for validating data against canonical requirements or standards (including but not limited to one or more of syntax, grammar, and/or content), a security and trust module 3012 that can determine security or trust levels, a filtering module 3014, a transformation module 3016, a routing module 3018, a message mediation module 3020, a reliable messaging module 3022, a database service module 3024, and a customized services module 3026. Also included are an External Services Invocation Framework or specification 3028, and also other modules including a message context module 3034, SOAP/WS modules 3036, XML/WS Security modules 3038, XML Core Libraries module 3040, AAA modules 3042, messaging and connectivity modules 3044, application integration framework 3046, a crypto module 3048, and then a server OS (Operating System) platform 3050 and an Intel Server Hardware platform 3052. Various components of the appliance 3002 can be commercial/off-the-shelf, third-party components, and/or Intel components.

With respect to the canonical used by Headwater appliances or routers in exemplary embodiments of the invention, it can be noted that canonicals are standardized objects which can be easily modified to handle particular applications needs, at an object level. A canonical contains all information relevant to a specific business process. A canonical is structured in ways that are: independent of any application; independent (separate) from the information architecture and the technical infrastructure it is implemented upon; precise in its message definition to assure consistent implementation; visible into the data which drives business processes; variable with respect to an accommodation and unique application for a particular business need; and flexible to support ongoing changes, standards adaptations and needs.

In an exemplary embodiment of the invention, the canonical form used by the Headwater appliances represents a standardized information model, a subset of the HL7 v3 Reference Information Model (RIM), exposed as XML business objects in fine-grained and composite web services. It encompasses both syntactic transformation from the various legacy implementations of HL7, NCPDP, x12 messaging formats, as well as semantic transformation to terminology standards including SNOMED CT, LOINC, CPT, ICD9 & 10, etc. The canonical form can be represented in the HL7 Clinical Document Architecture (CDA) R2, the ASTM Critical Care Record (CCR) or the harmonized CCD. The form itself and the RIM implementations, can be constrained by: 1) applying an information modeling tool during the development and generation of the canonical; 2) its sibling schema, transforms and constraint controls on the informatics model against the standard; and 3) how legacy data mapping interfaces are applied to the overall envelope. Thus, the canonical or canonical form common to the Headwater appliances in conjunction with pre-validated BPEL orchestration can be used to implement: an entity identification service (EIS) for patient and provider identification; an RLS service for record, location and update services; a set of terminology services & semantic tooling/mapping; standard authentication and authorization mechanisms; audit, traceability, persistence and management of the canonical; and Patient Consent & Authorization (PCA) services.

Employment of a common canonical or canonical form by the Headwater appliances in a network means that every exchange of health information undergoes the same common set of interactions. This ensures data interoperability, enriches and ensures data quality, and enables a message to be fully audited qualified as it passes through the service network. Exemplary embodiments of the present invention can scale this solution by validating and constraining these interactions to a single instantiation—a repeatable set of operations in a productized form-factor—instead of costly, one-off implementations which appear to have become the status quo for healthcare worldwide.

Figure 4:
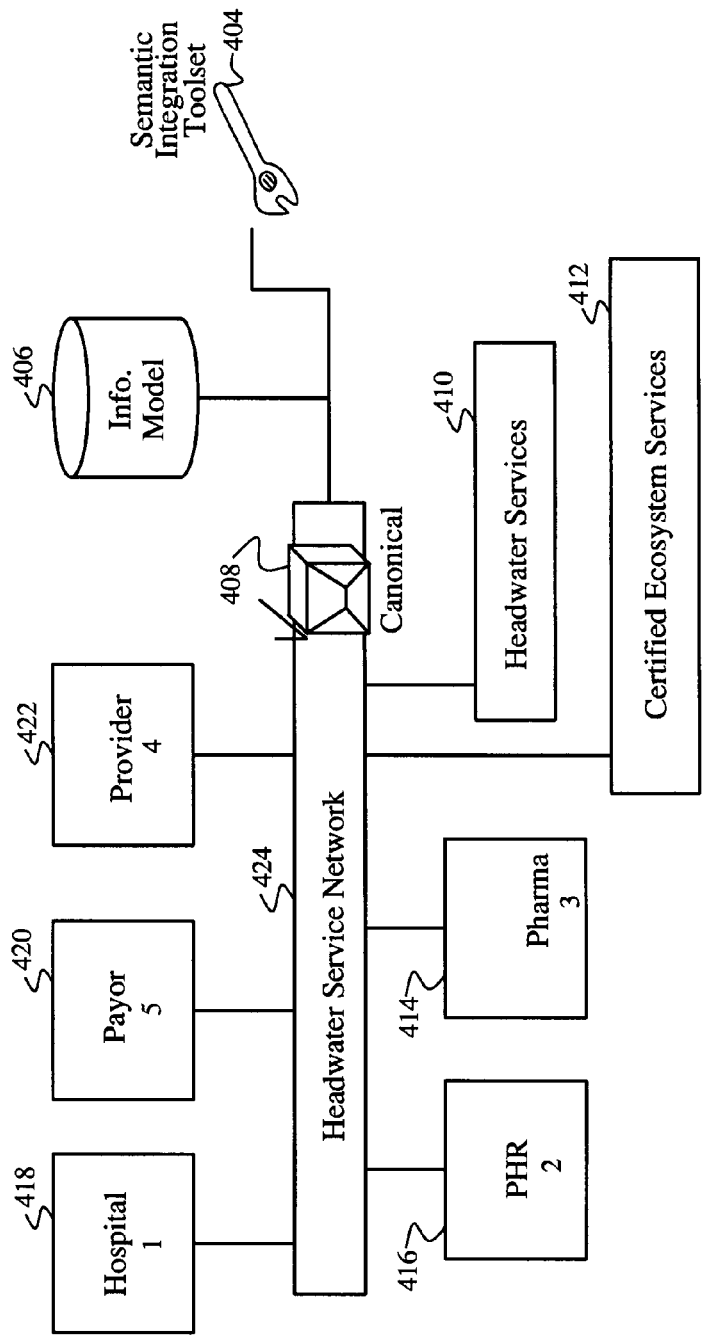
FIG. 4 illustrates a structural aspect of an exemplary embodiment of the invention.

FIG. 4 shows in simplified form, how use of the canonical benefits the network to reducing necessary translations or transformations to N+1 variations as described further above. As shown in FIG. 4, a network 402 includes a hospital 418, a payer 420, provider 422, PHR (Public Health Region) 416 and a pharmaceutical provider 414 are connected to a Headwater service network 424 and each is provided with a Headwater appliance (not shown) to translate to the common canonical and provide communication with the network, so that canonically-compliant messages (e.g., 408) can travel through the network. A semantic integration toolset 404 is also provided in connection with the network 402, as are various services 410 and certified ecosystem services 412 (which can, for example, include any services that require compliance with the canonical any additional requirements which can be stored in the information model 406 and used, for example, for validation purposes). Since a common canonical is used, each network node (4318, 420, 422, 408, 416, 414) can participate using only one connection to the network 424 through its associated Headwater appliance and one mapping from a local data format to the canonical format, instead of multiple connections and multiple maps from each local data format to each other local data format.

Figure 6:
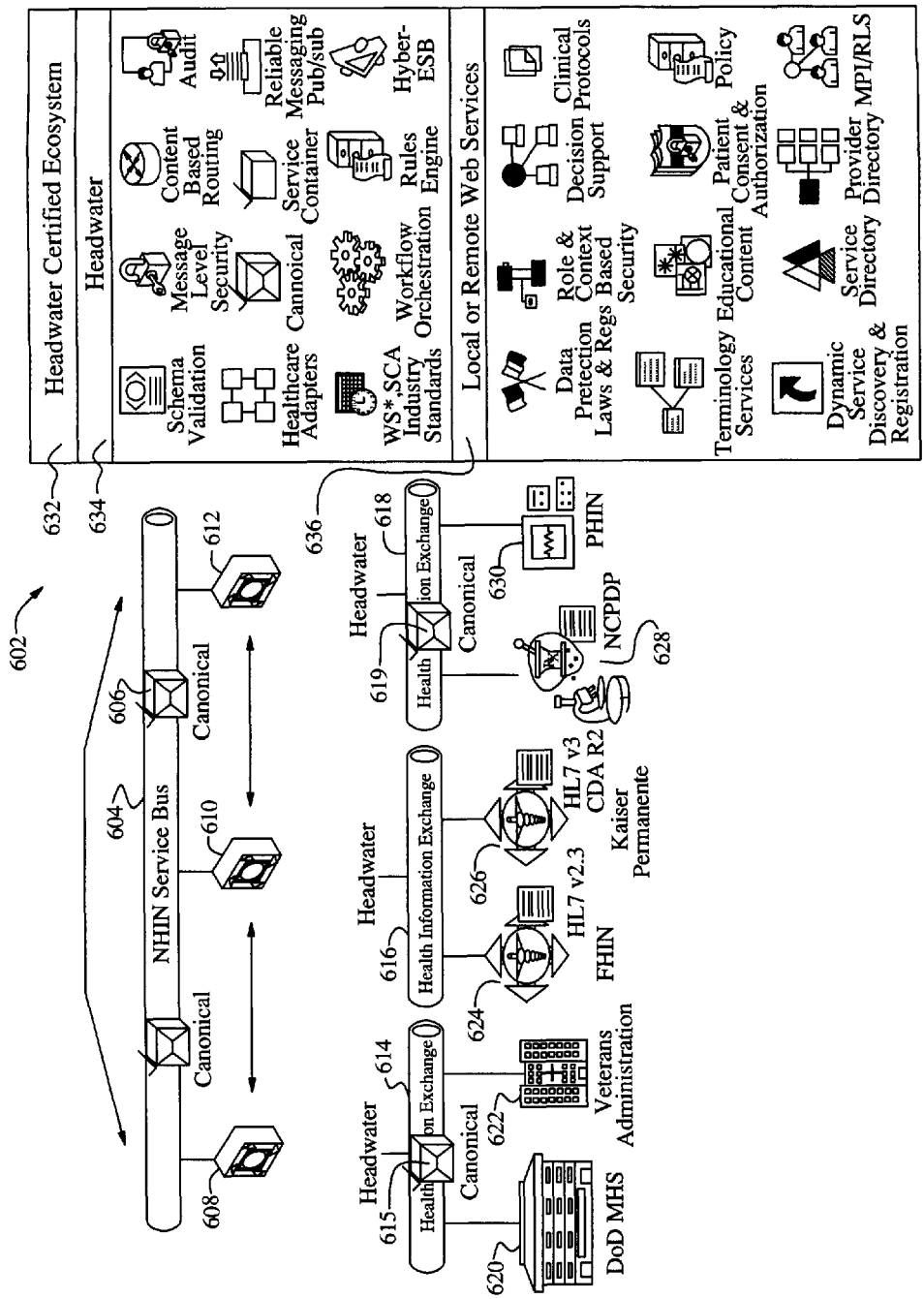
FIG. 6 illustrates a super-peer topology of an exemplary embodiment of the invention.

FIG. 6 illustrates a super-peer topology network of networks, in accordance with an exemplary embodiment. As shown in FIG. 6, separate networks 614, 616, and 618 are linked as nodes or constellations to form a larger network 602, where each of the networks 614, 616, 618 communicate with each other along a common service bus 604 via Headwater appliances 608, 610, 612. The separate networks can optionally use the common canonical within, and as shown the networks 614, 618 use the canonical (e.g., circulating canonical messages or canonically compliant messages 615, 619 within the separate networks), whereas the network 616 does not. As shown in FIG. 6, the network 614 includes a Veterans Administration hospital or entity 622 and a Department of Defense Military Health System entity 620. The network 616 includes a hospital network Kaiser Permanente 626 and a Florida Health Information Network entity 624, while the network 618 includes a medical laboratory/pharmaceutical supply 628 and a Public Health Information Network entity 630 (e.g., administered by the U.S. Center for Disease Control). The network 602 and optionally the participant networks 614, 618 can be certified ecosystems, wherein Headwater services 634 (e.g., based on Headwater appliance functionality and the corresponding canonical form or standard) are available (e.g., Service Containers, Reliable Messaging, Schema Validation, Message Level Security, Content Based Routing, Audit, WS/SCA Industry Standards compliance, workflow orchestration, Rules Engine(s), Hyper-ESB (Enterprise Service Bus), healthcare adaptors or maps (e.g. between local data formats and a common canonical), and the common canonical). Also available or recognized within the ecosystem, or within local regions of the ecosystem where the ecosystem includes the overall network as well as participating node or sub-networks (e.g., 614, 620, 622, 616, 624, 626 and so forth), are local or remote web services 636, that can for example be supplied through the Headwater appliances, such as Patient Consent and Authorization, Policy, Data Protection Laws and Regulations (and/or rules that govern information flow through the network(s) in accordance with them, for example by enforcement by the Headwater appliances on data flowing through the Headwater appliances), Role and Context-based Security (which can also be implemented by the Headwater appliances on data flowing through them), Decision Support, Clinical Protocols (library and/or rules), Dynamic Service Discovery and Registration, Service Directory, Provider Directory, MPI/RLS, Terminology Services, Educational Content, and so forth.

Figure 7:
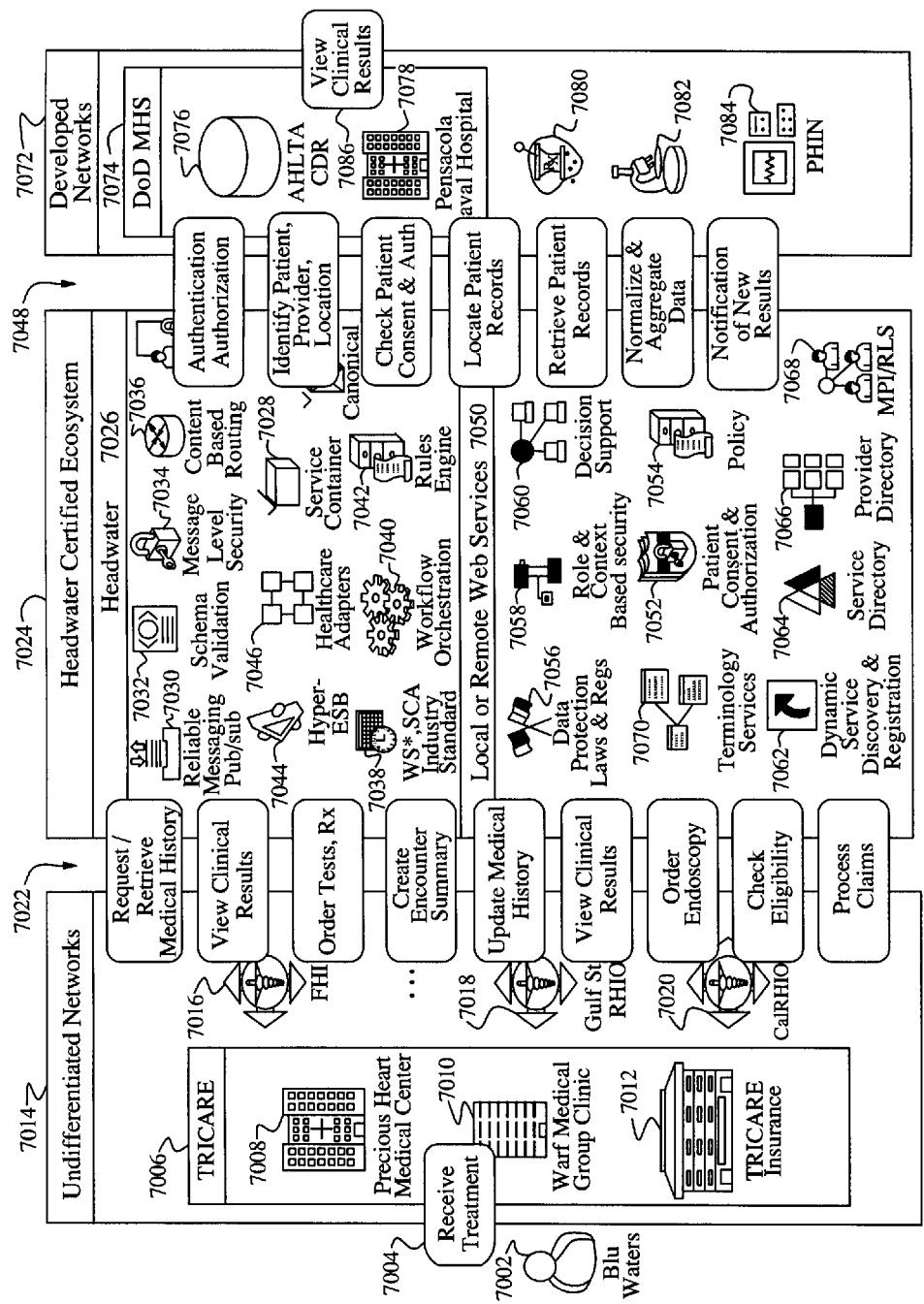
FIG. 7 illustrates a data exchange network use case in accordance with an exemplary embodiment of the invention.

FIG. 7 illustrates an exemplary data exchange network use case in accordance with an exemplary embodiment of the invention, wherein undifferentiated networks 7014 including a Tricare network 7006 that has a "Precious Heart" medical center 7008, a "Warf Medical Group" clinic 7010, and a "Tricare Insurance" provider 7012 coordinates treatment 7004 for a patient Blu Waters, 7002. The undifferentiated networks 7014 also include a Florida Health Information Network 7016, a Gulf States Regional Health Information Organization 7018, and a California Regional Health Information Organization 7020. The networks 7014 can perform various interactions 7022 with a Headwater certified ecosystem 7024, including for example requesting and receiving patient medical history information, receiving clinical/lab results, ordering tests and medications, processing claims, updating medical history records, and so forth. The ecosystem 7024 can include a Headwater appliance or appliance collection (e.g., multiple Headwater appliances grouped together to act transparently as a single entity) that provides services/capabilities including Service Containers 7028, Reliable Messaging 7030, Schema Validation 7032, Message Level Security 7034, Content Based Routing 7036, Audit, WS/SCA Industry Standards compliance 7038, workflow orchestration 7040, Rules Engine(s) 7042, Hyper-ESB (Enterprise Service Bus) 7044, and Healthcare Adapters 7046. The ecosystem 7024 can also support local or remote web services, such as Patient Consent and Authorization 7052, Policy 7054, Data Protection Laws and Regulations 7056 (and/or rules that govern information flow through the network(s) in accordance with them, for example by enforcement by the Headwater appliances on data flowing through the Headwater appliances), Role and Context-based Security 7058 (which can also be implemented by the Headwater appliances on data flowing through them), Decision Support 7060, Clinical Protocols (library and/or rules), Dynamic Service Discovery and Registration 7062, Service Directory 7064, Provider Directory 7066, MPI/RLS 7068, Terminology Services 7070, Educational Content, and so forth. The ecosystem 7024 can also perform various interactions 7048 with developed networks 7072, including for example authenticating/authorizing, locating patient records, retrieving patient records, normalizing and aggregating data, checking patient authorizations/consents, and so forth. The developed networks 7072 can include for example a Department of Defense Military Healthcare System 7074 having a database 7076 and at least one hospital 7078, and can also include pharmaceutical provider(s) 7080, one or more laboratories 7082, and a Public Health Information Network entity 7084.

Figure 8:
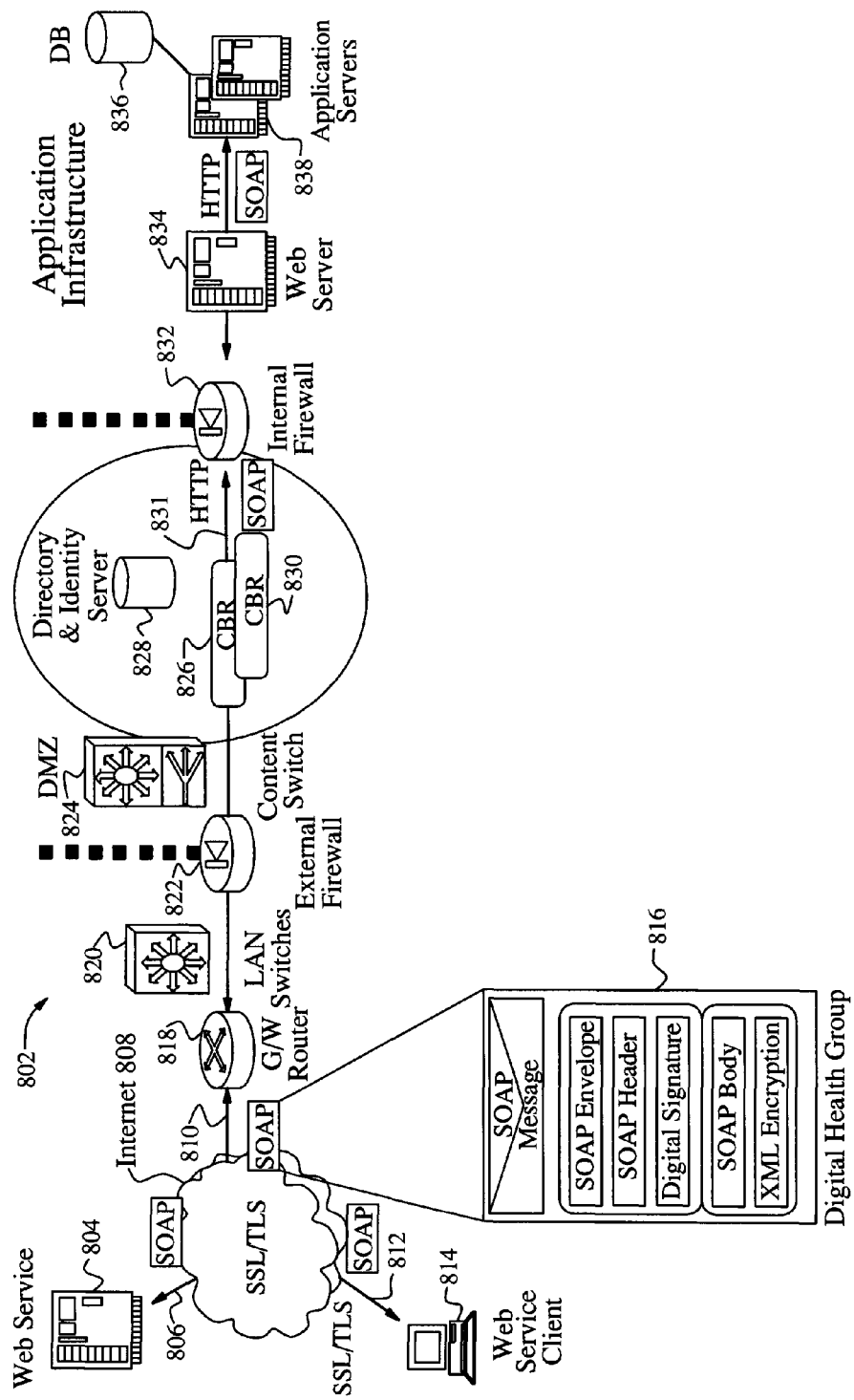
FIG. 8 illustrates XML (eXtensible Markup Language) processing capabilities of an exemplary embodiment of the invention.

FIG. 8 illustrates exemplary XML processing capabilities of an embodiment of the invention, wherein nodes including Headwater appliances exchange SOAP messages. In particular FIG. 8 shows a web service 804 and a web service client 814 that connect to the Internet 808 via links 806, 812 respectively and transmit SOAP messages (e.g., message 816) via the links. The Internet 808 conveys SOAP messages via a link 810 to a Local Area Network switch(es) 820 via a Router 818, and these messages are in turn passed through an external firewall 822 to a content switch 824 which in turn passes them to Headwater appliances 826, 830. The appliance 826 connects to a directory and identity server or data storage 828, and can transmit SOAP messages via an HTTP link 831 through an internal firewall 832 to a web server 834, which in turn conveys SOAP messages to and from application servers 838 and a database or data storage 836 via an HTTP link. This model enables Termination and Initiation; SOAP Verification; Web Services Security including Authentication/Authorization/Auditing, Signing/Verification, and Encryption/Decryption; Credential Propagation/SAML; XML Intrusion Prevention; Content based Load balancing; Protocol brokering (MQ, JMS); ebXML Security; MIME/DIME Handling; and attachment scanning.

Figure 9:
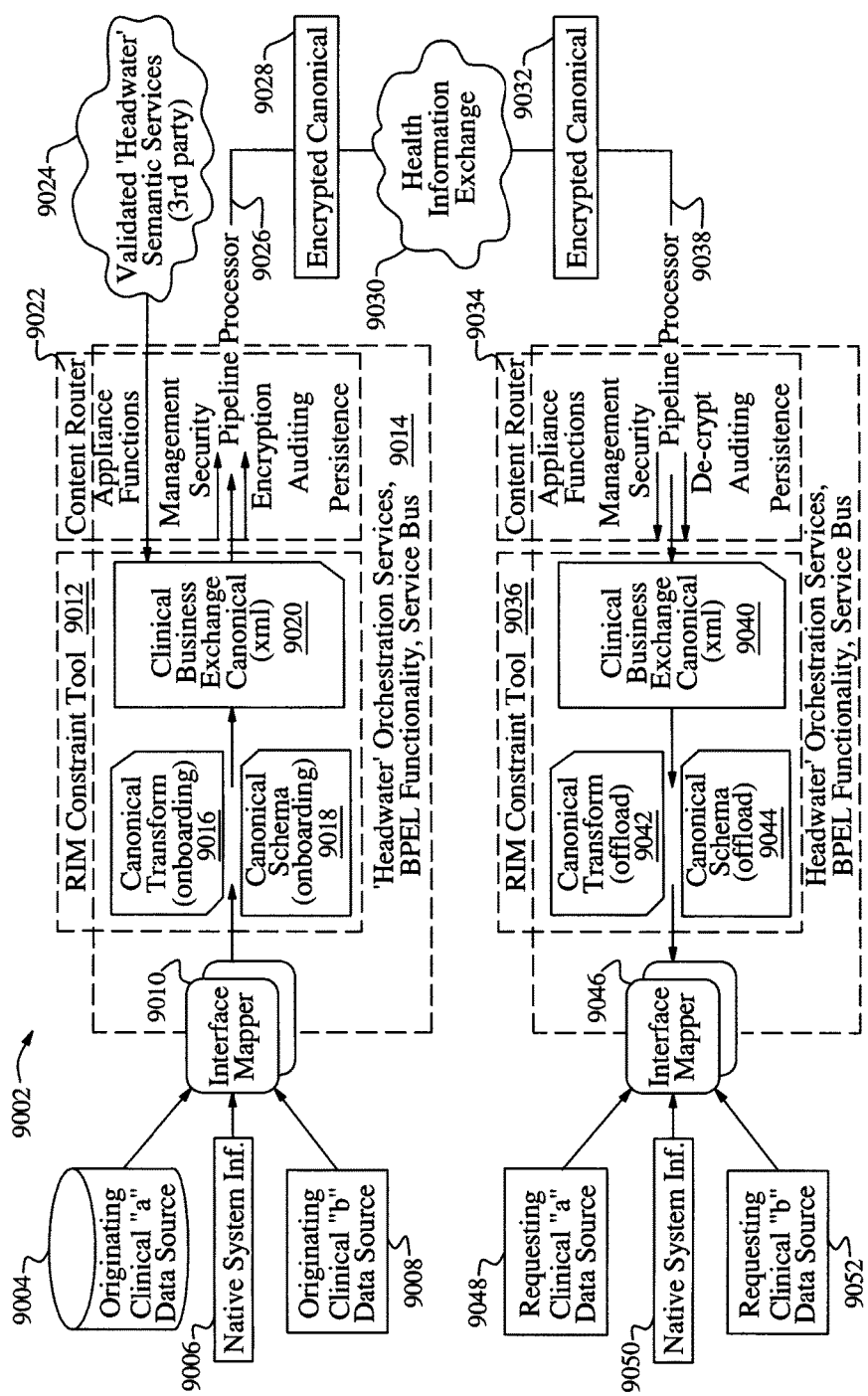
FIG. 9 illustrates a canonical process flow in accordance with an exemplary embodiment of the invention.

FIG. 9 illustrates a canonical process flow 9002 in accordance with exemplary embodiments of the invention, wherein an originating clinical data source "a" 9004 and another originating clinical data source "b" 9008 provide native system information 9006 to an interface/mapper 9010 of a service bus 9014. The mapper 9010 in turn provides the information to a canonical transform 9016 and a canonical schema 9018 of a RIM constraint tool 9012, which in turn provide output to a clinical business exchange canonical 9020 within the constraint tool 9012. The exchange canonical 9020 provides output to a pipeline processor of a content router 9022. The components 9010-9022 can all be within a Headwater appliance. The content router 9022 can send the processed data (processed by the elements 9010, 9016, 9018, 9020) to a validation service 9024 to be validated, and can send the processed data in encrypted, canonical form 9028 via a link 9026 to a health information exchange 9030. The exchange 9030 can in turn send information in encrypted, canonical form (e.g. 9032) via a link 9038 to another headwater that includes a content router 9034, exchange canonical 9040, canonical transform 9042, canonical schema 9044, and an interface/mapper 9046 that are arranged or connected in the same fashion as the elements 9010-9022. The information from the exchange 9030 passes through the elements 9034-9046 in the opposite order of the information 9006 through the elements 9010-9022 of the first Headwater appliance, and is provided as native system information 9050 to a requesting clinical "a" data source 9048 and/or a requesting clinical "b" data source 9052.

Figure 10:
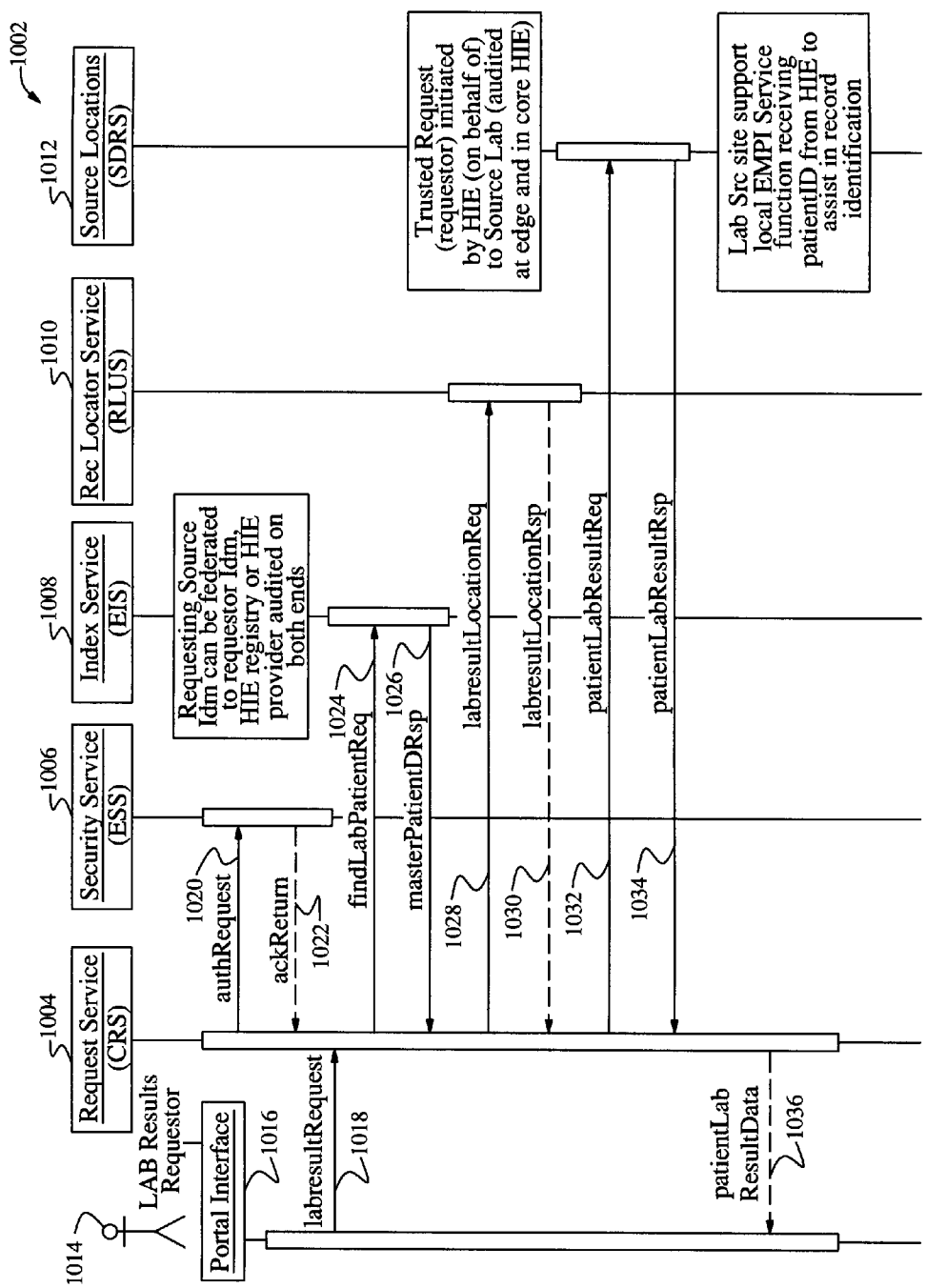
FIG. 10 illustrates a lab result process in accordance with an exemplary embodiment of the invention.

FIG. 10 illustrates flow of a lab result through a network in accordance with an embodiment of the invention. As shown in FIG. 10, a person 1014 requests laboratory test results through a portal interface 1016, which forwards a corresponding request 1018 to a request service 1004. The request service 1004 sends an authorization request 1020 to a security service 1006 and upon receiving a reply or acknowledgment 1022, sends a request 1024 to an index service 1008 to find or identify a lab that will have the desired information. The index service 1008 returns a master identifier 1026 that links the patient to the requested lab test, and the request service 1004 uses this information to send a query 1028 a locater service 1010 for a location of the lab test result. The locater service 1010 sends a reply 1030 to the request service 1004, and the request service 1004 uses information in the reply to generate and send a patient lab result request 1032 to a source location 1012 that was identified by the locater service 1010 as possessing the desired lab result information. The request 1032 can be a trusted request, for example a request initiated by (or on behalf of) a Health Information Exchange to a source laboratory, which in turn can be audited at the edge (e.g. by a Headwater appliance that connects the laboratory to the HIE network) and also a network core of the HIE. The source location 1012 can be supported by local EMPI (Enterprise Master Patient Index) service function(s), and can receive the patient's identifier from the HIE to help it identify and locate the appropriate lab test result record. The source location 1012 responds to the request by sending the lab result 1034 to the request service 1004, and the request service 1004 in turn relays the lab result information to the portal interface 1016 in a message 1036. The index service 1008 can be federated to or associated with a Health Information Exchange registry or provider, and can be audited on both ends (e.g. by entities from whom it receives requests, as well as by the HIE register or provider to whom it passes the requests).

Figure 11:
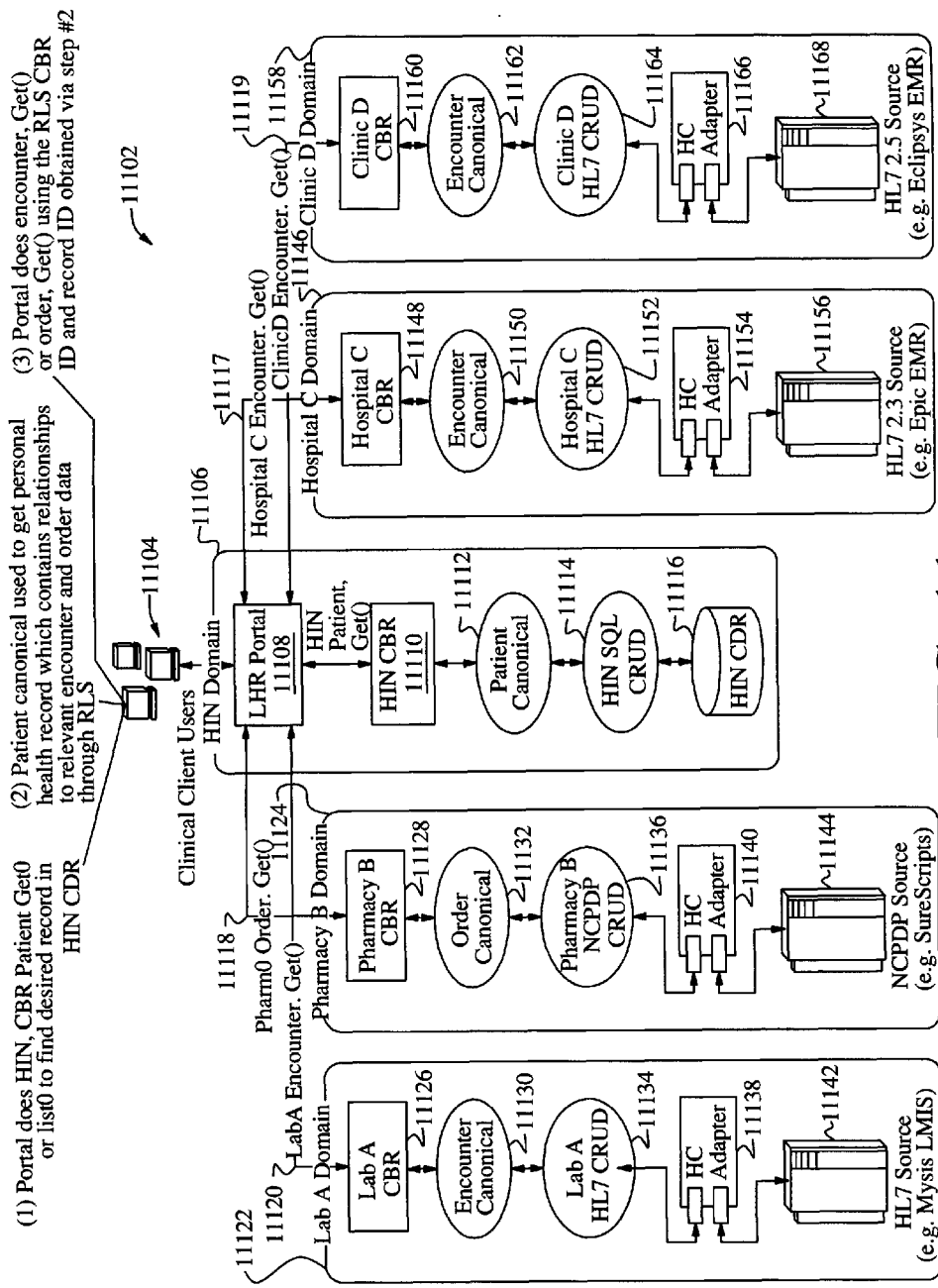
FIG. 11 illustrates a basic architecture of a Longitudinal Health Record scenario in accordance with an exemplary embodiment of the invention.

FIG. 11 illustrates a basic component architecture 11102 of a longitudinal health record (LHR) (e.g., a patient's health record that includes multiple entries over time, or time-related data). As shown in FIG. 11, clinical client users 11104 can use commands such as "get" or "list" to find desired records in a Health Information Network database or data store, and can use a patient canonical to obtain personal health records that indicate relationships or provide context for encounters (events where a patient received healthcare and/or provided health information) and orders (e.g., healthcare services or products provided to or prescribed for the patient). The clinical client users 11104 can also use returned or received Record Locater Service and record identifiers (e.g., received with the personal health records) to obtain or request details regarding encounters or orders in the patient's healthcare history. Messages from the clinical client users 11104 (which can for example include a physician at a clinic who is trying to provide medical care to a patient and desires information about the patient to help diagnose, treat, monitor, and so forth) are passed to a Heath Information Network (HIN) domain 11106, which has an LHR portal 11108 that passes requests to a Headwater appliance or router 11110 in the domain 11106, and which in turn connects to a patient canonical 112 connected to Create Read Update Delete (CRUD) mechanism 1114 connected to a data store 11116 in the domain 11106. The LHR portal 11108 of the domain 11106 also connects to a Pharmacy B domain 11124, a Lab A domain 11122, a Hospital C domain 11146, and a Clinic D domain 11158. Thus the HIN domain 11106 can forward a request 11118 for a pharmaceutical order to the Pharmacy B domain 11124, a request 11120 for a lab encounter to the Lab A domain 11122, a request 11117 for a hospital encounter to the Hospital C domain 11146, and a request 11119 for a clinic encounter to the Clinic C domain 11158. Each of the Lab A domain 11122, Pharmacy B domain 11124, Hospital C domain 11146, and Clinic D domain 11158 include respectively a Headwater appliance 11126, 11128, 11148, 11160, an encounter or order canonical 11130, 11132, 11150, 11162, a CRUD mechanism 11134, 11136, 11152, 11166, a HC (Health Care) Adapter 11138, 11140, 11154 11166, and an HL7 or NCPDP Source 11142, 11144, 11156, 11168. As used herein and shown in the Figures, HC Adaptors are elements or modules that can translate between different standards, and can for example be commercial off-the-shelf devices or mechanisms such as ItemField™ or iWay™.

FIGS. 12-16 illustrate exemplary processes for obtaining information regarding a patient's health record and specific information regarding events or other elements recorded in the patient's personal health record, in a Longitudinal Health Record scenario in accordance with an exemplary embodiment of the invention.

Figure 12:
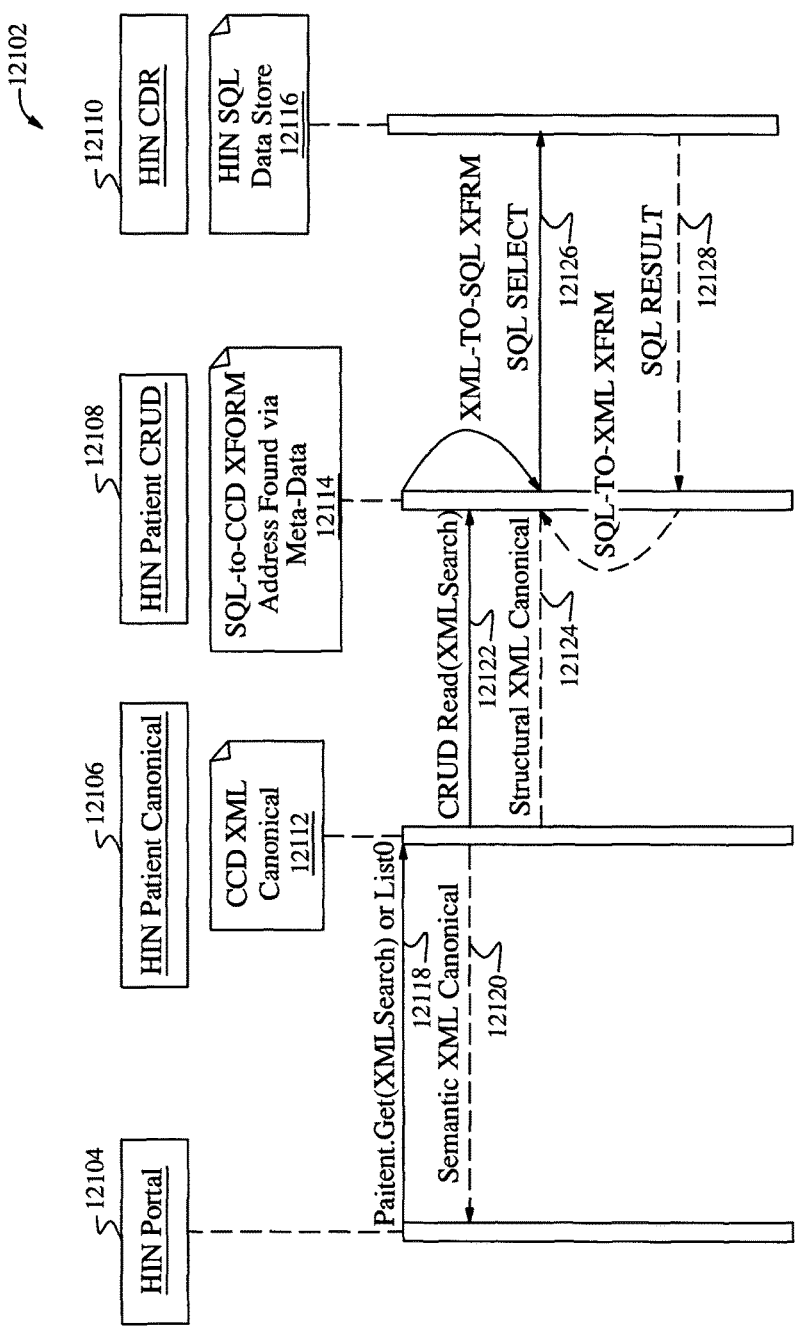
FIGS. 12-16 illustrate exemplary processes for obtaining information regarding a patient's health record and specific information regarding events or other elements recorded in the patient's personal health record, in a Longitudinal Health Record scenario in accordance with an exemplary embodiment of the invention.

As shown in FIG. 12, a doctor or nurse types in known information about the patient (such as name, sex, date of birth, address, phone number, etc.) in the Portal 12104. The portal 12104 calls the HIN CBR's Patient.Get( ) or Patient.List( ) WSDL operation to search the HIN for matching patient canonical records. The results are returned to the Portal 12104 through the patient canonical. If more than one record is returned then the Portal displays a screen giving the doctor or nurse the ability to look at relevant canonical fields to make a single record selection (such as body weight). At this point a single patient canonical record has been chosen by the doctor or nurse and the Portal can render the XML payload on the display. In particular as shown in FIG. 12, the search request 12118 proceeds from the portal 12104 to the HIN patient canonical 12106 (which contains a CCD XML canonical 12112), which in turn relays a read (XML Search) request to a HIN patient CRUD 12108 (which contains an SQL-to-CCD XFORM address 12114 that can be found via metadata). The CRUD 12108 performs an XML-SQL (Standard Query Language) transform on the request and then relays the request (now SQL compliant) to an HIN CDR data storage 12110 with an HIN SQL data store 12116, which returns an SQL result 12128 to the HIN Patient CRUD 12108. The CRUD 12108 transforms the received SQL result back into XML, and then relays the information in a structural XML canonical 12124 back to the HIN patient canonical 12106, which in turns relays the information in a semantic XML canonical 12120 to the portal 12104 thereby satisfying the original request.

Figure 13:
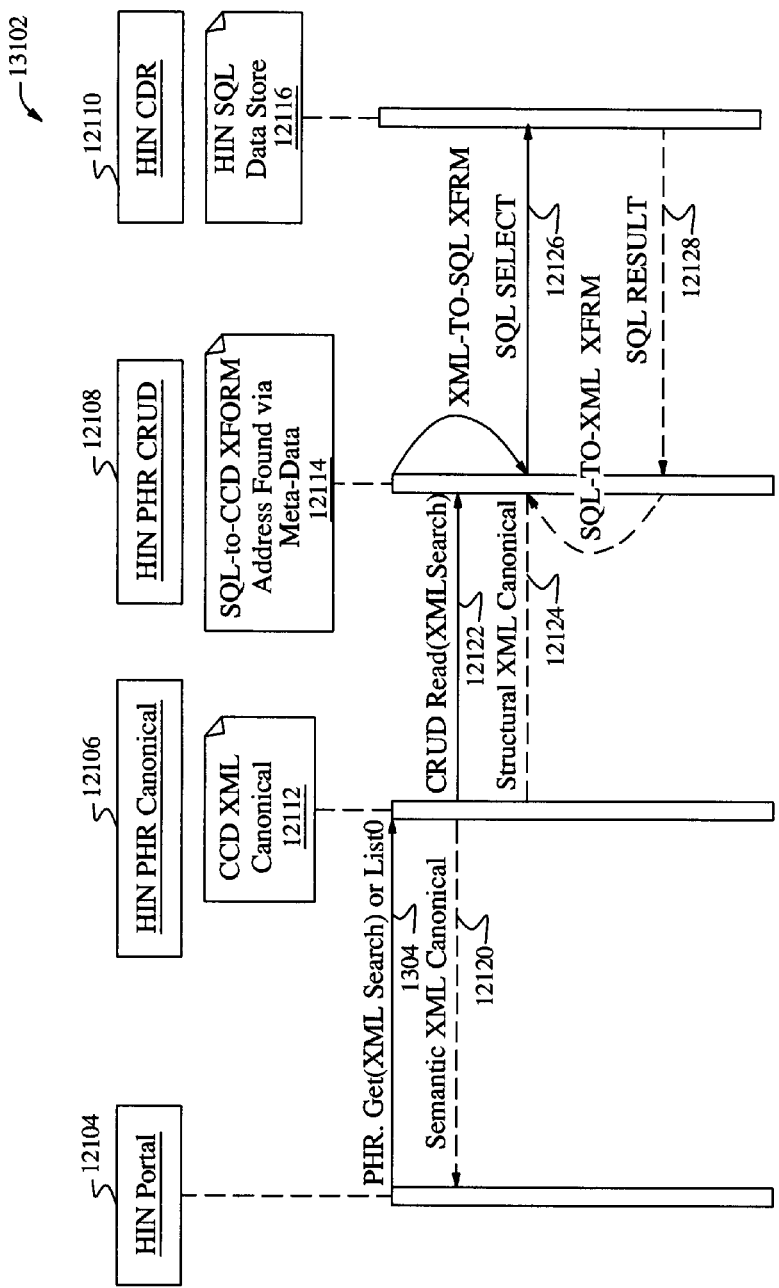

As shown in FIG. 13, the next major step is to find and display related Encounters and Orders. The patient canonical provides a key summary of patient information such as Demographics, Current Insurance, Family Doctor contacts, Chronic conditions, Allergies, Current Medications and Immunizations. Sometimes this data is sufficient to make the necessary clinical decisions, but if not then the Portal will provide a "drill down" function for the doctor or nurse to see a version of the patient's health record. To perform this "drill down" function the Portal will extract the record ID from the Patient canonical and will call the HIN CBR's PersonalHealthProfile.Get( ) WSDL operation using the patient canonical record ID and if desired a date range as the key filter criteria in the XMLSearchFilter parameter. Once the PersonalHealthRecord (PHR) canonical XML record is retrieved its XML payload can be rendered in the display. If available in the underlying HIN clinical data repository will be record ID's for related Orders, Encounters, Schedules and Documents. In particular, as shown in FIG. 13, the portal 12104 first sends an XML request 1304 for the Personal Health Record of the patient to the HIN PHR canonical 12106, which in turn passes a search request 12122 to the CRUD 12108. The CRUD 12108 transforms the request from XML into SQL and sends the transformed request 12126 to the HIN CDR 12110 with data store 12116, which replies with an SQL result 12128. The CRUD 12108 transforms the SQL result into an XML canonical 12124 and sends it to the HIN PHR canonical 12106, which sends the information in a semantic XML canonical 12120 to the portal 12104, thereby providing the patient health record per the portal request.

The Portal will then provide a hyperlink for each retrieved Order, Encounter, Schedule and Document available in the PersonalHealthRecord XML payload returned from the HIN. In a Centralized Deployment, when the hyperlink is selected (say for Encounter) then the HIN CBR Get( ) WSDL operation will be called to retrieve the Encounter (or Order or Document, etc) using the record ID obtained from the PersonalHealthRecord above.

Figure 14:
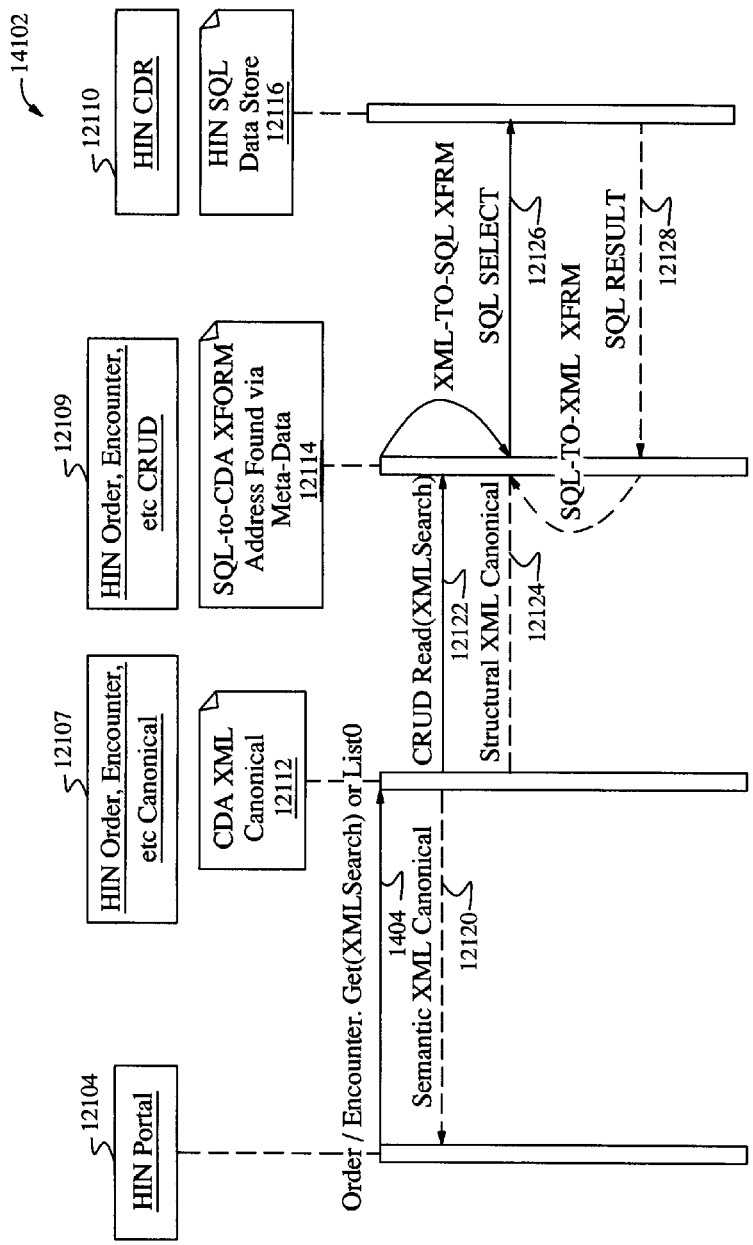

In particular as shown in FIG. 14, the portal 12104 sends a request 1404 for a particular Order or Encounter to an appropriate Encounter/Order canonical 12107, which relays a corresponding CRUD read request 12122 to a HIN Order/Encounter CRUD 12109 that in transforms the request from XML into SQL and then sends the SQL request 12126 to the HIN CDR 12110 with data store 12116. The HIN CDR 12110 replies with an SQL result 12128, which the CRUD 12109 transforms back into XML and relays as a structural XML canonical message 12124 to the canonical element 12107, which in turn relays the requested information in a semantic XML canonical 12120 to the portal 12104.

In a Federated or Hybrid Deployment, when a hyperlink is selected (say Order), the HIN CBR Locate( ) WSDL operation will be called to find the original CBR (content based router, e.g. Headwater appliance) source of the record and the associated local record ID. This RLS entry in the HIN can be established when the record was originally created in the source system and the canonical's Initialize( ) operation was executed. Once Locate( ) has been executed, the Portal will call the Get( ) operation using the network address of the CBR and the record ID returned from the Locate( ).

Figure 15:
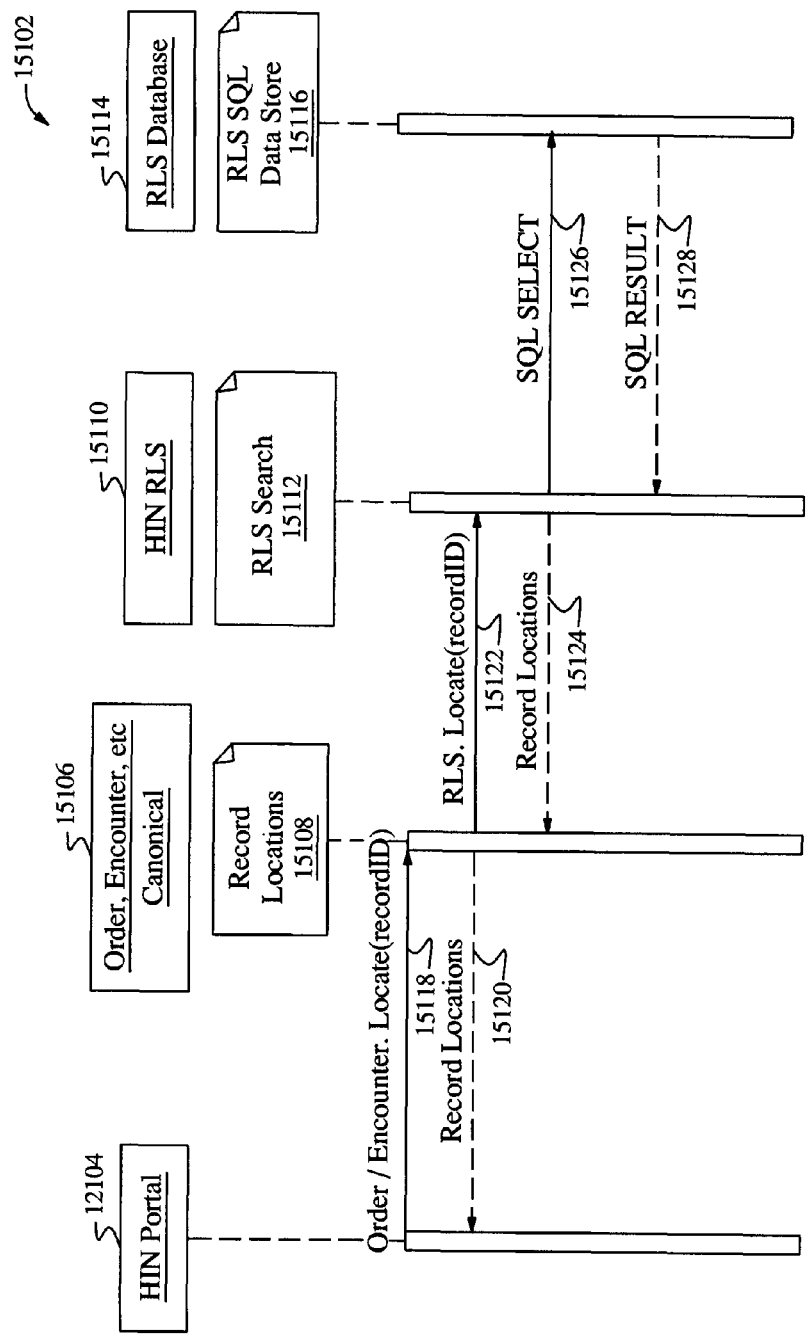

As shown in FIG. 15, the portal 12104 sends a request 15118 for a location of a particular encounter or order to the canonical 15106 having record locations 15108, which in turn sends a locate request 15122 to a HIN RLS (Record Locator Service) 15110 with an RLS Search function or database 15112. The RLS 15110 in turns sends an SQL request 15126 to an RLS database 15114 having an RLS SQL data store 15116, and the database 15114 returns an SQL result 15128 to the RLS 15110. The RLS 15110 returns the record locations detailed in the SQL result 15128 back to the canonical 15108 in a message 15124, and the canonical 15106 in turn forwards the location information to the portal 12104.

The last step is to retrieve Encounter and Order record details from the original source(s). In a Centralized Deployment when the Encounter, Order, Schedule or Document Get( ) WSDL operation is called the LHR use case has ended. In a Federated or Hybrid Deployment once the Portal calls the Encounter, Order, Schedule or Document Get( ) WSDL operation at the target CBR identified by the HIN Locate( ) the processing will get handed off to the CBR at the local site (such as the Hospital, Clinic, Lab, etc.). The local CBR at the edge of the network (say the Lab CBR) will execute the Encounter.Get( ) (or Order, Schedule, or Document) by reading the Lab CBR's instance of canonical meta-data and it will retrieve the address of a local CRUD service which handles the reading of the canonical from the Lab's information system (such as a Mysis LMIS or in the case of a Document it could be reading from X-Ray from a GE PACS).

Figure 16:
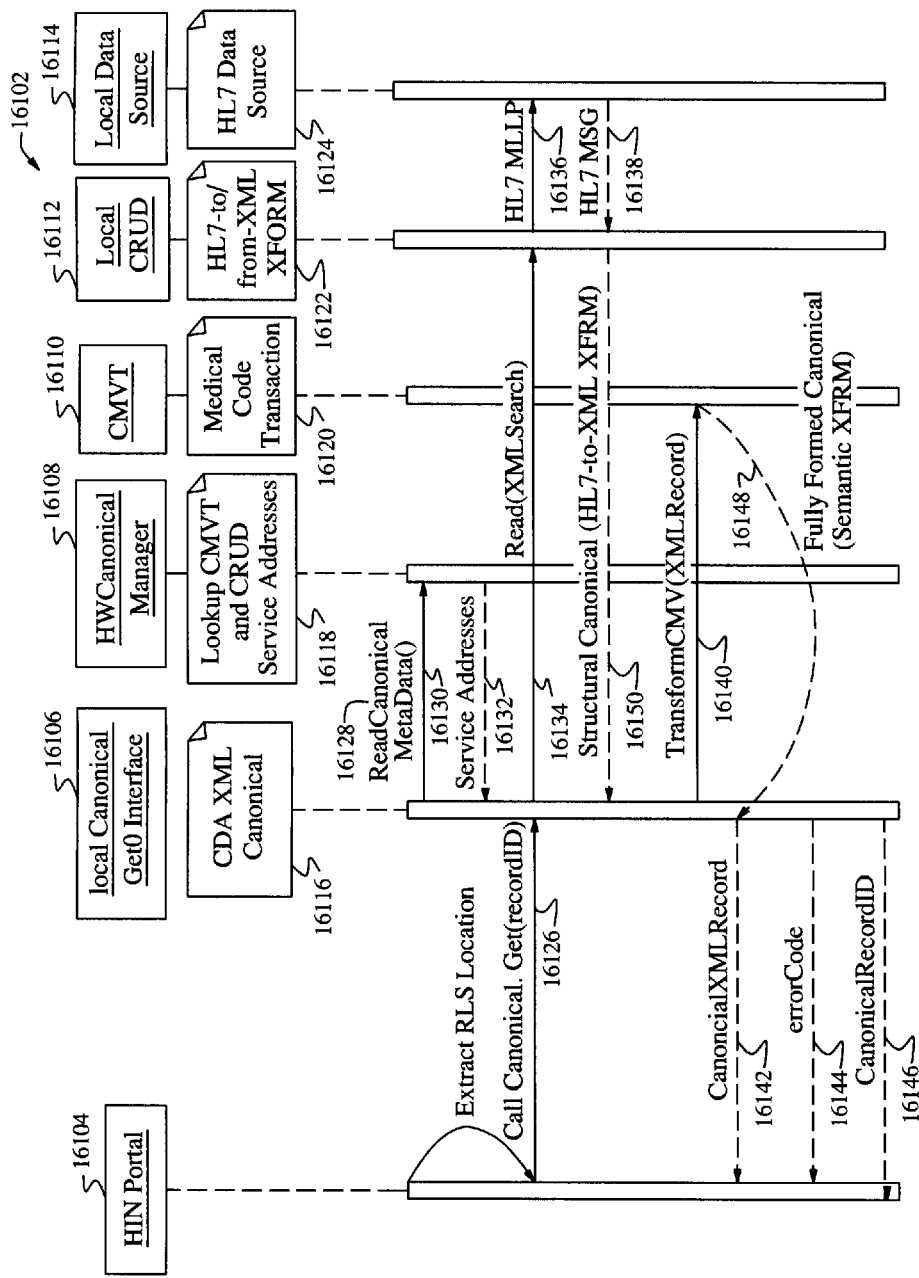

As shown in a process 16102 of FIG. 16, the portal 12104 uses the location information returned in FIG. 15 to extract an RLS location, and then requests a canonical record via message 16126, which is received by a local canonical interface 16106. The local interface 16106 sends a read request 16128 to a canonical manager 16108 having lookup CMVT (Controlled Medical Vocabulary Translation service) and CRUD service addresses 16118, and the manager 16108 replies to the interface 16106 with service addresses 16132. The interface 16106 then sends an XML read request 1634 to a local CRUD 16112, which in turn sends an HL7 MLLP message 16136 to a local data source 16114 having an HL7 data source or store 16124. The source 16114 returns an HL7 message 16138 having the requested information to the local CRUD 16112, which in turn sends the information in a structural canonical 16150 transformed from HL7 to XML to the interface 16106, which in turn relays this information 16140 to a CMVT (Controlled Medical Vocabulary Translation service) element 16110 having a medical code translation capacity or function 16120. The element 16110 fully forms the canonical via a semantic transform, and provides the fully formed canonical 16148 to the interface 16106, which in turns provides a canonical XML record 16142 to the portal 16104. The interface 16106 can also provide any error code 16144 and/or canonical record identifier 16146 to the portal 16104.

Figure 17:
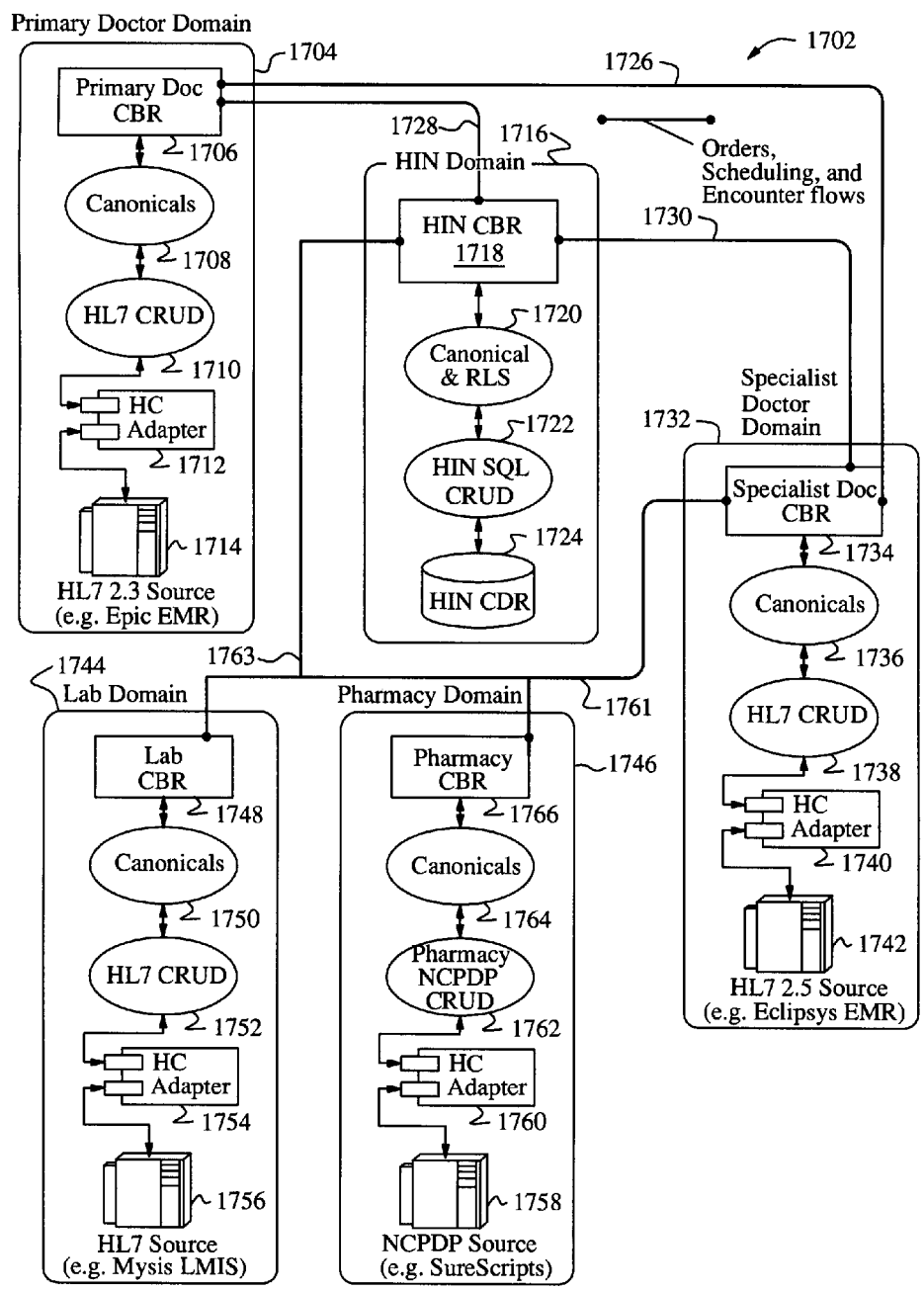
FIG. 17 illustrates a basic architecture for integrating information in a Multi-Provider Care scenario, in accordance with an exemplary embodiment of the invention.

FIG. 17 illustrates a multi-provider care (MPC) structure or model 1702 in accordance with an exemplary embodiment of the invention. In particular, FIG. 17 shows a primary doctor domain 1704, an HIN domain 1716, a specialist doctor domain 1732, a lab domain 1744, and a pharmacy domain 1746. These domains communication or share Orders/Scheduling/Encounter information or flows with each other via links. In particular, links 1726 and 1728 connect the primary doctor domain 1704 with the specialist doctor domain 1732 and the HIN domain 1716 respectively. Link 1730 connects the HIN domain 1716 with the specialist doctor domain 1732, and the links 1763 and 1761 interconnect the HIN domain 1716 and the specialist doctor domain 1732 with the lab domain 1744 and pharmacy domain 1746. Each of the domains 1704, 1716, 1732, 1744, 1746 has respectively: a CBR or Headwater appliance 1706, 1718, 1734, 1748, 1766; canonicals 1708, 1720, 1736, 1750, 1764; and HL7 or HIN SQL CRUDs 1710, 1722, 1738, 1752, 1762. The HIN domain 1716 has an HIN CDR or data store 1724, and the domains 1704, 1732, 1744, 1746 have respectively HC (Health Care) Adapters 1712, 1740, 1754, 1760 and HL7 or NCPDP sources 1714, 1742, 1756, 1758. As used herein and shown in the Figures, HC Adaptors are elements or modules that can translate between different standards, and can for example be commercial off-the-shelf devices or mechanisms such as ItemField™ or iWay™.

A basic exemplary flow for the multi-provider care scenario that is supported by the structure of FIG. 17, includes the following actions. A patient seeks primary care (usually by going to their primary or family doctor, but could be a local clinic or hospital). During the primary care visit the doctor doing the examination determines that additional testing or a specialist visit is required. The primary care doctor orders the specialist visit and the patient makes the appointment. When the patient arrives at the specialist, the patient's profile and relevant medical history is made available to the specialist's EMR through Headwater. The patient visits the specialist and the specialist determines that the patient needs lab work and a prescription. The prescription and lab test is electronically ordered through the Headwater network. The patient makes the appointment with the lab and gets the test done. The results are electronically provided to the specialist's EMR via Headwater. The specialist adds his or her notes to the visit summary and electronically returns their diagnosis, recommendations, lab results and pharmacy order back to the primary care provider.

Figure 18:
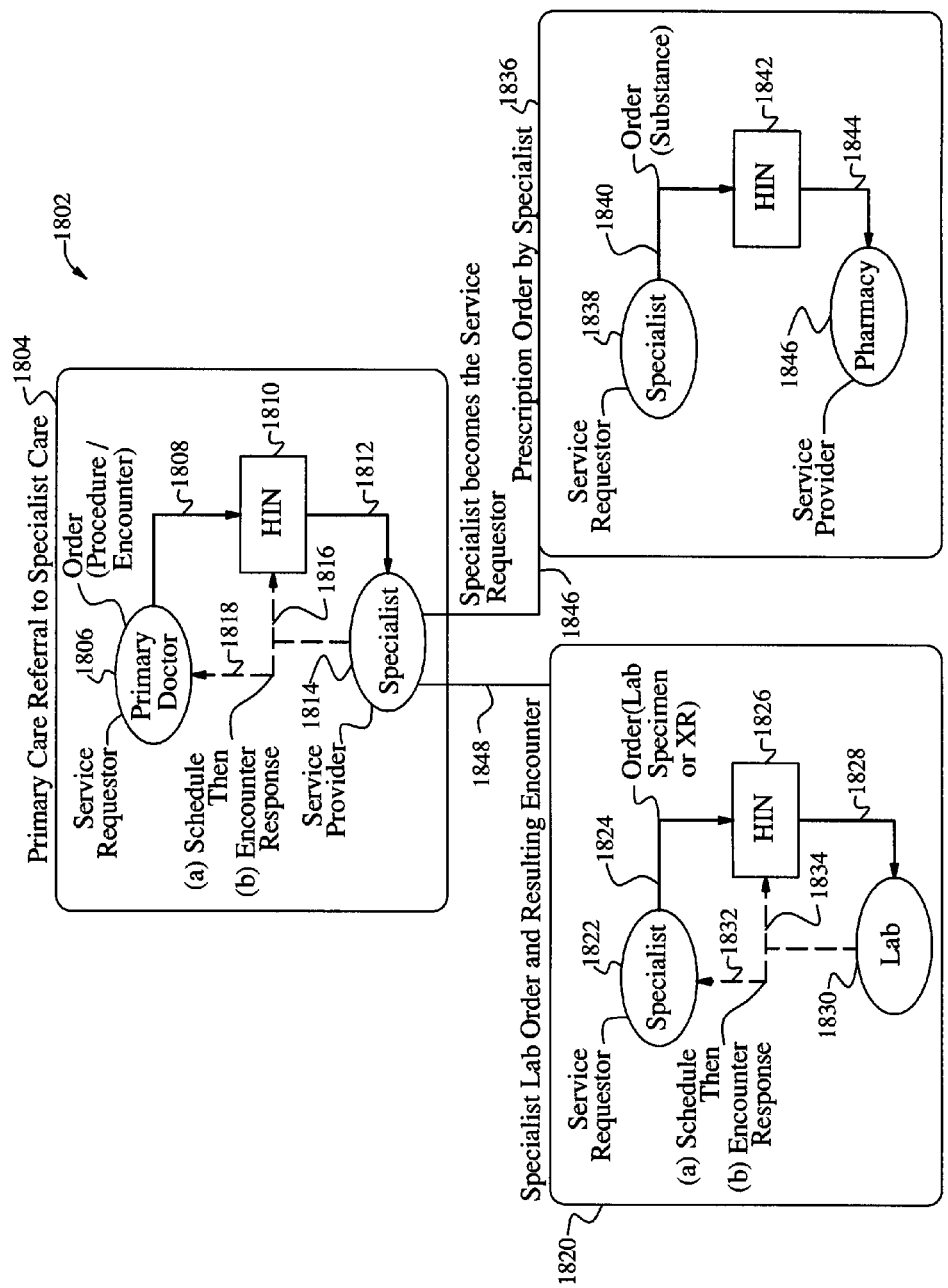
FIG. 18 illustrates an exemplary process flow for tracking information in the Multi-Provider Care scenario of FIG. 17, in accordance with an exemplary embodiment of the invention.

FIG. 18 shows flow and consequent interactions in terms of a high-level content-based-router or Headwater appliance and canonical. In particular, 1804 is a referral process from a primary care physician to a specialist, wherein the primary doctor 1806 transfers an order 1808 to a Health Information Network (HIN) 1810, which in turns sends a message 1812 to a specialist 1814 who then communicates with both the HIN 1810 via a message 1816 and the primary doctor 1806 with a message 1818 to schedule a response encounter with the patient or patient's data (e.g. lab test results, X-rays, etc.). The specialist 1814 can also become a service requester, by sending a request 1846 to engage a prescription filling process 1836. As shown in 1836, a service requester 1838 (which can be the specialist 1814, or the primary doctor 1806, or other entity) sends an order 1840 to a HIN 1842, which (approves and) relays the order to a pharmacy 1846 via a message 1844 for fulfillment. Block 1820 illustrates a process for requesting a lab test. The service requester 1822 (which can be the specialist 1814 or the primary doctor 1806, depending on circumstance) sends an order 1824 for a lab test of some kind, for example an analysis of a specimen or an X-Ray to a HIN 1826. The HIN 1826 (approves and) relays the order via a message 1828 to a lab 1830, which then communicates with the HIN via a message or link 1834 and with the service requester 1822 via a message or flow 1832 to schedule and then perform the requested action.

In sum, FIG. 18 illustrates a pattern of canonical transactions which can encompass a service requester executing a LocalCBR.Order.Initialize( ), which in turn executes HIN.Order.Put( ) to sync the HIN CDR and RLS, executing HIN. ServiceProvder.Get( ) to find the target for the order, and finally executing TargetCBR.Order.Put( ) to send the Order to the target service provider (such as specialist, lab or pharmacy). The HIN can record a copy of the Order, Schedule and Encounter in the CDR in canonical form and at least through the RLS maintaining relationships across the transactions and their association to a patient record.

The Service Provider receives the order through the CBR.Order.Put( ) operation and translates it to the local EMR/internal system via the HL7 CRUD. The Service Provider can also, for the (optional) Schedule, execute HIN.Scheduling.Put( ) to sync the HIN CDR and RLS; execute HIN.ServiceProvder.Get( ) to find the target for the order; and finally execute OrderSourceCBR.Scheduling.Put( ) to send the scheduling results back to the originating order service provider (such as primary care or specialist).

For the Encounter result, the Service Provider can: execute HIN.Encounter.Put( ) to sync the HIN CDR and RLS; execute HIN.ServiceProvder.Get( ) to find the target for the order; and finally execute OrderSourceCBR.Encounter.Put( ) to send the encounter result back to the originating order service provider (such as primary care or specialist). Note that the way the scenario is described further below asserts the use of end-point CBRs communicating point-to-point asynchronously in order to complete the full workflows. This is not the only valid deployment option, other options are possible.

Other valid deployment options include the following. First, HIN "hub-and-spoke". In this option, the source CBR or Headwater appliance accepts the Initialize( ) request, but then immediately dispatches the workflow to run in the HIN rather than in the sourceCBR. Second, Async/publish-and-subscribe. This is where the sourceCBR accepts the Initialize( ) request and puts a message into a JMS queue. Listeners on that queue then run the steps of local RLS, HIN, and targetCBR communication asyncronusly and in parallel. Results are put in a reply queue which the sourceCBR Initialize( ) function is listening for which is then used to return the outcome of the call.

Given this key repeating pattern, this use case can break down into the following seven detailed workflows or steps.

Step one, the primary clinician orders specialist care (either a procedure or encounter), and an order record is created in the primary clinician EMR. The EMR sends an event notification to the primary clincian's CBR (via JMS, MLLP, file drop, etc.), the "Inside-Out" CRUD process for the Order canonical is executed and it (1) transforms the HL7 order to CDA XML and (2) calls the Order canonical Initialize( ) operation.

The primary clinician's CBR Order.Initialize( ) workflow will: semantically normalize the XML document content using CMVT for medical vocabulary data fields and EMPI (Enterprise Master Patient Index) to add the HIN record ID for patient and service provider field references; create a HIN.ServiceProvider canonical and call its Get( ) operation to identify the CBR which represents the specialist in the order; in a centralized or hybrid deployment, call HIN.Order.Put( ) to register the order with the HIN CDR and RLS; and then call SpecialistCBR.Order.Put( ) which sends the order to the specialists EMR; then the order canonical is registered with the local CBR RLS and a placeholder relationship is establish for the specialist results and (optionally) the schedule. Finally, this step of the long-running process ends until the specialist completes the encounter in step (g) below.

Step two, (optionally) the specialist returns a schedule canonical response, and an order record has been received into the specialist EMR from step one above. That order record is put into the worklist/scheduling queue in the EMR as a result of the SpecialstCBR.Order.Put( ) operation from step one. The patient phones the specialists office and schedules an appointment. If configured, then the EMR sends an event notification of the specialists CBR that a schedule response is available. The "Inside-Out" CRUD process for the Scheduling canonical is executed and it (1) transforms the HL7 schedule to CDA XML and (2) calls the Scheduling canonical's Initialize( ) operation. As in other Initialize( ) the canonical will be semantically normalized, recorded in the HIN (for hybrid and centralized deployments), and routed to the right destination (in this case the primary care CBR). Also in this step two, the specialist will want to extract the Patient canonical and possibly the PHR canoncical from either the HIN or primary care CBR from the patient ID field in the Order (using an API sequence like LHR). This will automatically create a local patient record in the specialists EMR to be ready for the visit with the patient.

Step three, the specialist orders a prescription (substance order). This step is similar to step one above, and to step four below. An order record is created in the specialist clinician EMR. Optimally this order will maintain a reference to the primary care order ID and the specialist encounter ID. The EMR sends an event notification to the specialist clincian's CBR (via JMS, MLLP, file drop, etc.). The "Inside-Out" CRUD process for the Order canonical is executed and it (1) transforms the HL7 order to CDA XML and (2) calls the Order canonical Initialize( ) operation. The specialists clinician's CBR Order.Initialize( ) workflow will: semantically normalize the XML document content using CMVT for medical vocabulary data fields and EMPI to add the HIN record ID for patient and service provider field references; create a HIN. ServiceProvider canonical and calls its Get( ) operation to identify the CBR which represents the pharmacy in the order.

In a centralized or hybrid deployment, and call HIN.Order.Put( ) to register the order with the HIN CDR and RLS. Then, the workflow will call PharmacyCBR.Order.Put( ) which sends the order to the pharmacies order receipt system. Finally, the substance order canonical is registered with the local CBR RLS.

Step four, the specialist orders a lab (specimen or X-Ray, for example). An order record is created in the specialist clinician EMR. The EMR sends an event notification to the specialist clincian's CBR (via JMS, MLLP, file drop, etc.). The "Inside-Out" CRUD process for the Order canonical is executed and it (1) transforms the HL7 order to CDA XML and (2) calls the Order canonical Initialize( ) operation. The specialist clinician's CBR Order.Initialize( ) workflow will: Semantically normalize the XML document content using CMVT for medical vocabulary data fields and EMPI to add the HIN record ID for patient and service provider field references; create a HIN.ServiceProvider canonical; and call its Get( ) operation to identify the CBR which represents the lab in the order. In a centralized or hybrid deployment, the workflow will also call HIN.Order.Put( ) to register the order with the HIN CDR and RLS. Then, the workflow calls LabCBR.Order.Put( ) which sends the order to the labs EMR or LMIS. Then the order canonical is registered with the local CBR RLS and a placeholder relationship is established for the lab results and (optionally) the schedule. Finally, this step of the long-running process ends until the lab completes the results (encounter) in step six below.

Step five, (optionally) the lab returns a schedule canonical response. This step is similar to step two above. An order record has been received into the lab EMR from step four above. That order record is put into the worklist/scheduling queue in the EMR or LMIS as a result of the LabCBR.Order.Put( ) operation from step four. The patient phones the lab office and schedules an appointment. If configured, then the EMR sends an event notification to the labs CBR that a schedule response is available. The "Inside-Out" CRUD process for the Scheduling canonical is executed and it (1) transforms the HL7 schedule to CDA XML and (2) calls the Scheduling canonical's Initialize( ) operation.

As in other Initialize( ) the canonical will be semantically normalized, recorded in the HIN (for hybrid and centralized deployments), and routed to the right destination (in this case the specialist CBR). Also in this step five, the lab will want to extract the Patient canonical and possibly the PHR canoncical from either the HIN or specialist CBR from the patient ID field in the Order (using an API sequence like LHR). This will automatically create a local patient record in the lab EMR or LMIS to be ready for the visit with the patient.

Step six, the lab returns the encounter results back to the specialist. To complete the long running transaction between the specialist and the lab, first an encounter result record is created in the Lab EMR/LMIS. The EMR/LMIS sends an event notification to the lab's CBR (via JMS, MLLP, file drop, etc.). The "Inside-Out" CRUD process for the Encounter canonical is executed and it (1) transforms the HL7 encounter to CDA XML and (2) calls the Encounter canonical Initialize( ) operation. The lab's CBR Encounter.Initialize( ) workflow will: Semantically normalize the XML document content using CMVT for medical vocabulary data fields and EMPI to add the HIN record ID for patient and service provider field references; and create a HIN.ServiceProvider canonical and calls its Get( ) operation to identify the CBR which represents the specialist who requested the Lab encounter through the previously created order. In a centralized or hybrid deployment, the workflow also calls HIN.Encounter.Put( ) to register the encounter with the HIN CDR and RLS. Then, the workflow calls SpecialistCBR.Encounter.Put( ) which sends the encounter results for the originating order back to the specialist's EMR.

Then the encounter canonical is registered with the local CBR RLS and a resulting relationship is established for the order, encounter and (optionally) the schedule. Now the long-running transaction is complete as the order, (optional) schedule, and encounter have been recorded in the lab, HIN and specialist with all RLS entries and data relationships secured.

Step seven, the specialist finishes the encounter which includes sending the prescription and lab results back to the primary clinician. To complete the long running transaction between the primary care clinician and the specialist, first an encounter result record is created in the specialist EMR. This record should contain all references to the pharmacy order, the lab order and the correspond lab result. The EMR sends an event notification to the specialist's CBR (via JMS, MLLP, file drop, etc.). The "Inside-Out" CRUD process for the Encounter canonical is executed and it (1) transforms the HL7 encounter to CDA XML and (2) calls the Encounter canonical Initialize( ) operation. The specialists CBR Encounter.Initialize( ) workflow will: semantically normalize the XML document content using CMVT for medical vocabulary data fields and EMPI to add the HIN record ID for patient and service provider field references; and create a HIN.ServiceProvider canonical and calls its Get( ) operation to identify the CBR which represents the primary care clinician who requested the specialist encounter through the previously created order. In a centralized or hybrid deployment, the workflow also calls HIN.Encounter.Put( ) to register the encounter with the HIN CDR and RLS. The workflow then calls PrimaryCareCBR.Encounter.Put( ) which sends the encounter results for the originating order back to the primary care clinician's EMR. Then the encounter canonical is registered with the local CBR RLS and a resulting relationship is established for the order, encounter and (optionally) the schedule. Now the long-running transaction is complete as the order, (optional) schedule, and encounter have been recorded in the primary care EMR, HIN CDR and specialist EMR with all RLS entries and data relationships secured. This should include the relationship of full chain of events (specialist order, pharmacy order, lab order, lab encounter results, and specialist encounter results all related to the patient and each other).

Computable Semantic Interoperability and the Canonical Design can provide distinct benefits. In accordance with exemplary embodiments of the invention, the canonical design not only constrains the information structure and format, but also translates terminology and medications to industry standard terms <selecting amongst the right subsets of the 10-12 different, overlapping industry standards>. By achieving semantic interoperability—translating the meaning to a standard information model which can be correctly interpreted by computers and not just humans—Headwater (e.g. Headwater appliances and corresponding canonicals) supports the creation of value-add services based on top of that standardized information flow. If one discharge summary uses the term "heart attack" and another uses "myocardial infarction", that information cannot be compared without first translating it to a common set of terminologies. Similarly, a prescription filled for Lisinopril <a generic form of ACE Inhibitor (blood pressure medication)> cannot be compared with its brand name Zestril, without first translating it to a common lingua franca of prescription medications. However with such a standardized information model, advanced healthcare usage models and queries can be supported—such as a doctor who needs to quickly identify the subset of his patient population who has diabetes and have been prescribed a particular medication which was recently recalled due to safety issues.

In accordance with an exemplary embodiment, a HIPAA Audit Service is provided. U.S. laws require healthcare institutions to capture an audit trail of all access to protected healthcare information and make the audit trail available to patients on demand. Today, despite the legal requirement, no one is able to do this. Headwater is able to capture all of the information flows and create this service, by virtue of the "indexing scheme", business rules and content-based routing capabilities on the platform.

In accordance with an exemplary embodiment of the invention, a Patient Consent & Authorization (PCA) is provided. Today, patient consent for the exchange of health information is unreliably obtained and even more inconsistently applied in the industry, with each healthcare institution considering the patient's health record to be their IP as opposed to something belonging to the patient. The two primary implementation models today (all one-off and non-repeatable) are "opt-in/opt-out" whereby the patient signs over full access rights when they agree to join a particular provider network, or the PHR model—where none of the actual information sources are afforded any protection whatsoever, but only the summary access directly from the PHR browser application is "under the control and intent of the patient." Headwater could create or support a separate PCA service which gets automatically invoked for each and every service exchange—to reliably check the patient's consent policy and permit/deny/or suitably filter information to the different service requesters.

In accordance with an exemplary embodiment of the invention, a De-identification Service is provided. Many so-called "secondary uses of data" in healthcare requires the data to be first de-identified in various ways before working with the protected health information, or in other words information identifying the patient must be removed to effectively make the data anonymous to the data consumer. Clinical Trials, Population Management/Biosurveillance, Pharmacogenomics research are all examples where patient data can be extremely valuable, but must be de-identified for privacy, public policy and/or legal reasons. Headwater can readily intercept existing health information flows and create parallel route mechanisms, formatting the information separately according to the needs of the target end-point. For example, the CDC (U.S. Center for Disease Control) requires that particular lab results or "labs of interest" be automatically sent to them in de-identified format. Certain states require that lab tests cannot be transmitted without first sending it to the ordering physician, or without first re-associating the lab result with the originating encounter. Each of these requirements can be automatically met by Headwater, invoking a parallel pipeline processing mechanism and either stripping or enriching the information flow according to business rules on the platform. Typically, a de-identification service varies widely according to local, state, regional and federal laws as well as the preferred reporting format of each institution or authority.

In accordance with an exemplary embodiment of the invention, a Regulatory Compliance Service is provided. Data protection, privacy and healthcare-specific laws and regulations vary by local, state, region, and country worldwide. These laws can be codified into a rules engine and offered on a subscription basis to health information exchanges, to facilitate the correct routing, blocking, filtering and enrichment of data flows amongst the authorized participants. The example was given earlier for the CDC and biosurveillance—I have attended many healthcare conferences and learned that most institutions are not even aware of their public health legal requirements. The CDC needs to routinely update their reporting requirements as it relates to "labs of interests" and particular types of diagnoses, etc. that they need to track for public health. Similarly, the privacy and data protection laws in the EU are ever complex, with each participating country creating their own interpretation of how those laws are to be implemented including data registration and notification requirements. In the U.S., the privacy and data protection laws are less stringent but equally diverse . . . and in some cases, there are arcane laws on the books which inadvertently serve as impediments to the lawful sharing of health information exchange as part of clinical care delivery—each of these are examples of rules and policies which can be effectively applied in a consistent fashion, using a "regulatory compliance service" to ensure appropriate data handling and protection in a given region.

Additional Service Offerings that can be provided in accordance with exemplary embodiments, that are enabled by Headwater (e.g., use of the Headwater appliances and a corresponding common canonical form) include: Drug-to-Drug Interaction Check Service; Adverse Drug Event Reporting Service; Formulary, Medication Compliance Services; Clinical Trials Recruitment, Management Services; Claims Processing, Claims Adjudication Services; Chronic Disease Management Service; Clinical Decision Support Service; Pay For Performance Service; and Physician Referral, Scheduling and prescription refill Services.

Described below are exemplary requirements and associated design specifications for Headwater canonical definitions. Canonicals represent the data and rule content that configure the Content Base Router for applicable use in the Healthcare industry segment. The canonicals define WSDL (Web Services Description Language) APIs (Application Program Interfaces) for reusable services and XML payloads for standardizing healthcare data interactions which can span application and organization boundaries.

In particular, exemplary structures and behaviors of Headwater components will be described. Also described are exemplary interactions of the canonicals and other major CBR components.

Each sub-section of the canonical design contains the high-level PRD requirement name and identifier so that the reader can achieve traceability back to the original requirement. Also exemplary key text from each high-level requirement is listed and then expanded to include the additional details of the requirement and design to implement that aspect of Headwater canonicals.

Finally, not all Healthcare specific requirements listed in the Headwater and CBR PRD are met through canonical implementation (such as hard appliance requirements). Contained below are exemplary healthcare requirements which can be specifically geared to the data processing and services needed to deliver on the flow of data across healthcare applications and organizations.

In an exemplary embodiment, a Headwater canonical is a pre-configured set of content delivered with an instance of the CBR platform to support data interoperability use cases in Healthcare. More specifically, a canonical can represent a software service that handles the reading, writing and processing of healthcare data in a standard fashion.

In CBR (Content-Based Routing), a software service is represented as a WSDL API with one or many XML payloads per WSDL operation (up to one XML payload per WSDL operation parameter). The implementation of that software service can occur as an external service, Java™ local service, or as a CBR workflow. In the case of Headwater canonicals, we will most often provide the implementation as a CBR workflow with the use of external services and Java™ local services as needed to complete the workflow which represents the service's implementation.

In an exemplary embodiment, primary usage models can include a Longitudinal Health Record (LHR) model, a Multi-Provider Care (MPC) model, and an Automated Claims Processing (ACP) model.

The following discussion details an exemplary overall framework for all canonicals, including the reference object model, core use cases, and how canonical message transaction tracing/auditing can be implemented.

In an exemplary embodiment, the highest order requirements for canonicals indicate that the Headwater platform supports a pre-configured and deployment-customizable data representation which standardizes the data elements and semantics of each data element across the identified use cases in the MRD. The platform also provides support for patient demographics, medical records (including PACS), referrals, prescriptions, and claims processing. This can be broken down into the following additional detailed sub-requirements. First, the canonical data representations support clinical and administrative and/or financial transactions with a common object model. The HL7 RIM and CDA XML model can be the common data structure used throughout the canonicals, in an exemplary embodiment it is advantageously extensible to other XML representations in future revisions or site specific deployments (such as CCR or OpenEHR). Second, the canonical data representations are structurally and semantically normalized. Third, in an exemplary embodiment the canonical WSDL operation definitions and XSD schemas are explicitly typed and documented to drive proper usage. Fourth, in an exemplary embodiment the canonical data and operation representations are extensible and safely versioned. Fifth, in an exemplary embodiment the canonical data representations are able to read, written or otherwise processed regardless of the location of the source system, CBR or target system. Transaction flow spans LANs (Local Area Networks), WANs (Wide Area Networks), and the Internet as allowed by firewall security and routing rules setup by end-user organizational policies. Sixth, in an exemplary embodiment the canonical data representation are accessible by systems interfaces or application user interfaces using the same techniques. XML and WSDL can be used to deliver this function.

To support these requirements a common framework for each canonical object can be implemented.

Each canonical object can have a WSDL interface and an XML payload to describe its record structure. The XML payload which defines the structure and rules the canonical represents can be further referred to as a "canonical signifier". The canonical signifier is an XML structure which describes the XSD schema and other associated type constraints on the canonical definition (such as HL7 typeid constraints). The canonical signifier contains the canonical's XSD and more.

The general structure of exemplary WSDL and XML payloads are described below and the details of the canonical on a data type per data type basis are described further below.

In an exemplary embodiment, all canonicals can use a series of shared services and resources to support their operation. These services and resources can include, for example, a SQL store to hold the meta-data configuration of the canonical, the RLS and Audit data for logging and tracing transactions (see section 3.1.2 for the details); as well as (optionally) the mapping and config tables for the EMPI and CMVT sources. In addition, an RLS (Record Locator Service) and an Audit underlying service for logging and tracing transactions can be included. Exemplary details regarding the SQL structure for these services is described further below, as well as details for the WSDL and operations. CRUD (Create, Read, Update, Delete) utility services and their associated class factory can be included. This provides a mechanism for the canonical to be dynamically configured to map to different underlying data sources at deployment.

Regarding the canonicals, in additional to a common architectural framework, each canonical can have a common set of design and implementation characteristics, described in more detail below.

First, in an exemplary embodiment all WSDLs for all canonicals have at least the following standard operations:
  Get (input: XMLSearchStruct, output: canonicalXMLRecord, output: errorCode, output: canonicalRecordID)

"Get" is an operation for retrieving a single instance of a canonical based on parameters supplied by the "XMLSearchStruct" which uniquely identify a single record. A unique error code should be returned if zero or more than one record matches the filter criteria specified by the "XMLSearchStruct". "XMLSearchStruct" is an XML document schema for passing the canonical signifier, search and filter criteria to the canonical service. "canonicalXMLRecord" is an instance of an XML document which conforms to the schema for the specific canonical (such as for patient or order). "errorCode" is a string data type which contains the success or failure of the operation. errorCode should equal HWC_SUCCESS, HWC_NODATA, or HWC_MORETHANONE if the underlying data access technology is successful. "canonicalRecordID" is an array of HL7 IID recordID(s) which returns the semantically unique ID for the instance of the object on the Headwater network. By default this ID can be an array of one HL7 IID represented as a set of GUIDs.

Put (input: writeCommandEnum, input: putRequestSrcStruct, input: canonicalXMLRecord, output: errorCode, output: canonicalRecordID)

"Put" is an operation for writing an instance of the canonical to the Headwater platform. This includes insert and update operations. The implementation of the "Put( )" operation should automatically detect the existence of a record and do the insert or update if required. In case of an update, the canonical record ID must be supplied in the "canonicalXMLRecord" and any data supplied in the record will be updated in the storage destination that the canonical is managing. Version management is handled by identifiers in the payload and is only supported to the degree that the underlying CRUD implementation supports it. "writeCommandEnum" is an enumeration in WSDL/XML which is interpreted either as INSERT OR UPDATE. "putRequestSrcStruct" is a XML document schema which contains the canonical signifier, security, source, and network address context of the caller of the "Put( )" operation which is necessary tracing data to build the RLS and audit logs. See the appendix section for the schema definition, XML samples and other design details regarding this parameter. "canonicalXMLRecord" is the instance of an XML document which conforms to the schema for the specific canonical (such as for patient or order). "errorCode" is a string data type which contains the success or failure of the operation. errorCode should equal HWC_SUCCESS if the underlying data access technology is successful. "canonicalRecordID" is an array of HL7 IID recordID(s) which returns the semantically unique ID for the instance of the object on the Headwater network. By default this ID should be an array of one HL7 IID represented as a set of GUIDs.

Discard (input: XMLSearchStruct, input: putRequestSrcStruct, output: errorCode)

"Discard" is an operation for discarding (either physically or logically deleting records from the underlying source). A selection filter is created an all canonical records which meet that filter criteria are discarded. "putRequestSrcStruct" is a XML document schema which contains the canonical signifier, security, source, and network address context of the caller of the "Discard( )" operation which is necessary tracing data to clean the RLS and audit logs. See the appendix section for the schema definition, XML samples and other design details regarding this parameter. "errorCode" is a string data type which contains the success or failure of the operation. errorCode should equal HWC_SUCCESS if the underlying data access technology is successful.

List (input: XMLSearchStruct, input: maxResultStreams, input: previousResultID, output: canonicalXMLRecordsList, output: errorCode, output: finishedFlag, output: resultID)

"List" is an operation for returning a list of canonical instances based on the contents of the "XMLSearchStruct" in a manner consistent with "Get( )" but is capable of streaming many records from the underlying source to the calling client. "XMLSearchStruct" is an XML document schema for passing the canonical signifier, search and filter criteria to the canonical service. See the appendix section for the schema definition, XML samples and other design details regarding this parameter. "maxResultStreams" is a parameter which sets the maximum number of return calls to the List( ) method (i.e. max number of result sets). Such as if a value of 5 was set, then the underlying implementation would break the entire result set into 5 streams which could, for example, be represented on 5 web pages. "previousResultID" is a GUID (Globally Unique Identifier) id result token which describes a cookie that the underlying implementation can use to match the caller to the underlying result set. "canonicalXMLRecordsList" is multiple instances of an XML document which conforms to the schema for the specific canonical (such as a list of patients or orders). "errorCode" is a string data type which contains the success or failure of the operation. errorCode should equal HWC_SUCCESS or HWC_NODATA, if the underlying data access technology is successful. "finishedFlag" is a numeric identifier that returns 0 if all records in the underlying result set were packaged into a single return of the "canonicalXMLRecordsList" If the value is >0, then the "List( )" operation needs to be repeatedly called to extract the rest of the result set until the flag returns 0. The numeric result specifies how many results remain. "resultID" is the GUID id result token which describes a cookie the underlying implementation can use to match the caller to a following call to "List( )" if the "finishedFlag" is 0.

Locate (input: XMLSearchStruct, input: maxResultStreams, input: previousResultID, output: canonicalRecordLocationsList, output: errorCode, output: finishedFlag, output: resultID)

"Locate" is an operation for returning a list of CBR locations where the desired canonical record can be found. It is a canonical wrapper to the RLS engine. "XMLSearchStruct" is an XML document schema for passing the canonical signifier, search and filter criteria to the canonical service. "maxResultStreams" is a parameter which sets the maximum number of return calls to the List( ) method (i.e. max number of result sets). "previousResultID" is a GUID id result token which describes a cookie that the underlying implementation can use to match the caller to the underlying result set. "canonicalRecordLocationsList" is an XML document containing the list of CBR locations where instances of the desired canonical can be found. When used in combination with the "Get( )" or "List( )" method, "Locate( )" can find the targeted set of fully located record data. "errorCode" is a string data type which contains the success or failure of the operation. errorCode should equal HWC_SUCCESS or HWC_NODATA, if the underlying data access technology is successful. "finishedFlag" is a numeric identifier that returns 0 if all records in the underlying result set were packaged into a single return of the "canonicalXMLRecordsList". If the value is >0, then the "List( )" operation needs to be repeatedly called to extract the rest of the result set until the flag returns 0. The numeric result specifies how many results remain. "resultID" is the GUID id result token which describes a cookie the underlying implementation can use to match the caller to a following call to "List( )" if the "finishedFlag" is 0.

Describe (input: canonicalName, output: canonicalSignifier, output: errorCode)

"Describe( )" is an operation that is used to output the detailed schema definition of the associated canonical. See the appendix for the definition of the canonicalSignifier structure (which is a meta-container for the XML XSD schema and associated canonical conformance constraints/archtypes). "canonicalName" is a string which identifies the canonical type to describe (such as "PATIENT", "ORDER", "ENCOUNTER", etc.). In a general purpose canonical interface this will be exposed publically in the WSDL definition. However, on an explicitly type canonical definition it is an unnecessary input as the canonical will already know its type. "canonicalSignifier" is XML document which describes the schema and associated constraints for the specific canonical (such as for patient or order). "errorCode" is a string data type which contains the success or failure of the operation. errorCode should equal HWC_SUCCESS if the underlying data access technology is successful.

Initialize (input: initializeRequestSrcStruct, input: canonicalXMLRecord, output: errorCode, output canonicalRecordID)

"Initialize( )" is an operation that is used to send a record from a source system onto the Headwater network in response to record create, update or delete events. The detailed differences between Initialize( ) and Put( ) operations are described further below. "initializeRequestSrcStruct" is an XML document schema which contains the canonical signifier, security, source, and network address context of the caller of the Put( ) operation which is necessary tracing data to build the RLS and audit logs. See the appendix section for the schema definition, XML samples and other design details regarding this parameter. "canonicalXMLRecord" is the instance of an XML document which conforms to the schema for the specific canonical (such as for patient or order). "errorCode" is a string data type which contains the success or failure of the operation. errorCode should equal HWC_SUCCESS if the underlying data access technology is successful. "canonicalRecordID" is an array of HL7 IID recordID(s) which returns the semantically unique ID for the instance of the object on the Headwater network. By default this ID should be an array of one HL7 IID represented as a set of GUIDs.

Individual canonical services might have additional WSDL operations above and beyond this base set which are applicable to the specific service (as defined in Section 3.3 below), yet all canonicals will at least have these base operations to handle essential data I/O.

In exemplary embodiments of the Headwater system including for example the Headwater appliances and corresponding canonicals, valdiations and so forth, a shared standard for Headwater Canonical Data Payloads is implemented.

In exemplary embodiments, all "canonicalXML*" parameters are an XML document type based on the HL7 v 3.0 RIM. In an exemplary embodiment, the Clinical Document Architecture R2 (CDA R2) standard along with the applicable derivatives, extensions, and constraints can be used.

Figure 32:
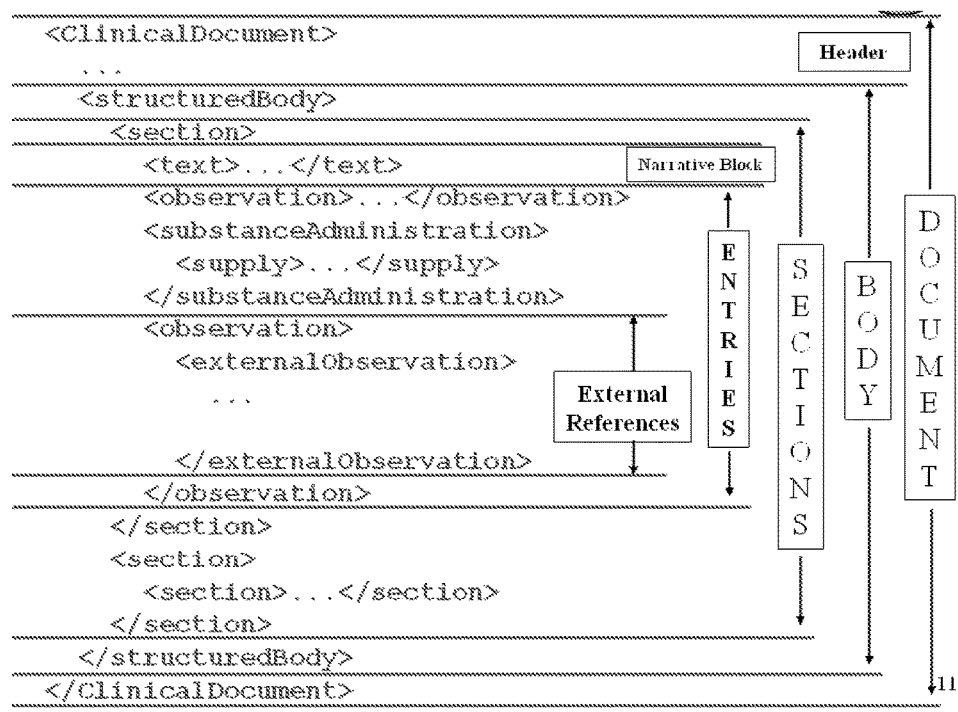
FIG. 32 illustrates an exemplary core structure of the CDA R2 document format.

The core structure of the CDA R2 document format is shown in FIG. 32.

Common mechanisms to extend, customize and constrain canonicals can also be provided, for example with respect to WSDL and XML or other, equivalent or acceptable standards.

In the case of canonical data payload, choosing CDA provides for several clean mechanisms to both constrain and customize the XML structure. These mechanisms can include the following. The CDA typeId segment can be used to associate a identifier to a XML segment. By passing the segment and the typeId which is associated to it to a schematron or a Java™ class, very specific rules can be applied to validate the XML document. This approach will be used to constrain all Headwater canonicals, and is structurally defined in the canonicalSignifier parameter for all canonical operations. See the appendix for the structure of the canonicalSignifier. Also, CDA can be extended through the use of custom namespaces on data types. For example, a specific namesspace and data type can be used to hold incremental information that is not currently supported in the CDA.XSD. This technique can be used by a PatientProfile canonical in implementing the Continuity of Care Document standard, described further below. In addition, the canonical framework can and should support an XML schema definition. Examples include the creation of a CDA-Lab.XSD (for lab results) and HeadwaterServiceProvider.XSD for the ServiceProvider canonical which implements the registry of medical professions, organizations and their relationships.

In the case of customizing the WSDL behavior, three points can be advantageously considered. First, A specific instance of a canonical (such as Order) can have their meta-data configured to point the canonical to a different CRUD, RLS, EMPI or CMVT service which can customize the outcome of a canonical operation (such as Get( ) or Put( )). For example, in one CBR configuration Orders could be addressing a CRUD service which connects to an EMR and another could be configured to communicate directly to a SQL database. The public format of the data canonical remains the same, but with meta-data configuration it can be read and written from various sources. Second, a service can have operations incrementally added to their WSDL definition (beyond the base) and workflows and/or Java™ internal services could be associated to the WSDL operation. Third, existing WSDL operations could have their workflow altered to include additional steps and/or call algorithms made available from Java™ internal services and/or external web service calls.

In exemplary embodiments, common metadata configuration can be provided for all canonicals. Finally, we need a common way to represent canonical configuration in a meta-data store. All canonicals can have a need to describe certain information which can be configured at deployment time. A primary key for most of the configuration is the CBR identifier (GUID)/name (or anything other mechanism that can uniquely identify a logical content-based router instance) and the canonical data type (such as patient or order). In an exemplary embodiment, all metadata can be related on that key. Examples include: AZHIN.stateofaz.gov, Patient; publicHW.goodhealthclinic.com, Order; publicHW.goodhealthclinic.com, Encounter; publicHW.goodhealthclinic.com, ServiceProvider. Use of the keyword "*HW_ALL*" in the key of the configuration can be used to classify a metadata attribute which represents a global setting for either all CBRs (if used in the CBR identifier) or all canonicals or both.

In an exemplary embodiment, the key information which needs to be related to the canonical includes the following. A label "CANONICAL_SIGNIFIER", which represents an expanded schema definition for the canonical data type represented either as a URL to the canonical signifier or the text containing the canonical signifier itself. A label "EMPI_ADDRESS" which represents the network address of the EMPI service that the canonical will use for semantically normalizing the record ID. The WSDL for all EMPI service instances should be the same as documented in the reference column. A label CMVT_ADDRESS, which represents the network address of the CMVT service that the canonical will use for semantically normalizing the medical vocabulary in the appropriate fields based on the canonical data type. The WSDL for all CMVT service instances can be the same as documented in the reference column. RLS_ADDRESS is a label representing the network address of the RLS service that the canonical will use for recording the network source of the data and its relationship to other transactions. The WSDL for all RLS service instances should be the same as documented in the reference column. CRUD_ADDRESS is a label representing The network address of the CRUD service that the canonical will use for structurally normalizing and de-normalizing the record data (source/destination data reads and writes). The WSDL for all CRUD service instances should be the same as documented in the reference column. AUDIT_LOG is a label representing the object identifier used to interact with the Audit Log. HIN_CBR_ADDRESS is a label representing the network address of the CBR which represents the HIN node in a centralized or hybrid CBR deployment. This parameter is NULL or empty in a fully federated deployment. INITIALIZE_WORKFLOW is a label representing the name of the CBR workflow which represents the Initialize( ) process for the canonical. GET_WORKFLOW is a label representing The name of the CBR workflow which represents the Get( ) process for the canonical. LIST_WORKFLOW is a label representing the name of the CBR workflow which represents the List( ) process for the canonical. PUT_WORKFLOW is a label representing the name of the CBR workflow which represents the Put( ) process for the canonical. LOCATE_WORKFLOW is a label representing the name of the CBR workflow which represents the Locate( ) process for the canonical. EMPI_TRAIT_XSL is a label representing an XSL (path or content) to create the EMPI traits structure from the canonical XML. EMPI_TRAIT_XSD is a label representing EMPI traits schema for the canonical.

In an exemplary embodiment, this metadata configuration can be deployable as a separate schema into either a directly attached SQL database to the CBR instance or hosted into a shared SQL data store supported by the overall site deployment.

Additionally, the HWCanonicalManager and the underlying SQL database maintain a mapping between CDA GUIDs which identify the CBR cluster instance and its network address. This should be represented as the "CBR_"+<GUID>+"_ADDRESS"=LABEL (such as "CBR_76b242b9-1246-4691-bb1d-91bb7336e76f_ADDRESS") and the network address of the CBR being represented as the meta-data value (such as "AZHIN.stateofaz.gov").

In an exemplary embodiment, a object or workflow which can be exposed a CBR local services can provide the read and write API to these meta-data parameters (the HWCanoncalManager). The HWCanoncalManager should be accessible through a WSDL interface in CBR workflows so they can be read as needed to setup and direct the behavior of the canonical operations.

In an exemplary embodiment, the signature of HWCanoncalManager WSDL APIs can be: ListCanonicals (input: cbrName, output: canonicalNames, output: errorCode). This operation returns to the caller the list of canonicals defined in the CBR instance. It should be used by the canonical management utility to describe the list of canonicals and can also be used by dynamic portal or workflows as well. "cbrName" is a string which identifies the logical name and network address of the CBR instance for which the meta data configuration should be associated. "canonicalNames" is an array of strings which identifies the canonical for which the meta-data configuration should be associated. Valid canonical name definitions will be described in section 3.3 below (such as ENCOUNTER, ORDER). "errorCode" is a string which returns HWC_SUCCESS if the underlying data access functions are successful.

WriteCanonicalDef (input: cbrName, input: canonicalName, output: errorCode) is an operation for the canonical utility and/or an automated installation program to create canonical definitions. "cbrName" is a String which identifies the logical name and network address of the CBR instance for which the meta data configuration should be associated. "canonicalName" is a string which identifies the canonical for which the meta-data configuration should be associated. Valid canonical name definitions will be described in section 3.3 below (such as ENCOUNTER, ORDER). "errorCode" is a string which returns HWC_SUCCESS if the underlying data access functions are successful.

RetireCanonicalDefinition (input: cbrName, input: canonicalName, output: errorCode is an operation that is used to logically delete or inactivate a canonical definition. "cbrName" is a string which identifies the logical name and network address of the CBR instance for which the meta data configuration should be associated. "canonicalName" is a string which identifies the canonical for which the meta-data configuration should be associated. Valid canonical name definitions will be described in section 3.3 below (such as ENCOUNTER, ORDER). "errorCode is a string which returns HWC_SUCCESS if the underlying data access functions are successful.

ListCanonicalMetaDataLabels (output: key-value-pair array<metaDataLabels, metaDataLabelDescriptions> output: errorCode) is an operation that can be used for building the configuration utilities user interface and to provide a means to support dynamic customization of the canonical meta-data parameters as needed by site deployments. "metaDataLabels" is a list of names for the meta-data parameters. The valid values are listed in the table above (such as INITIALIZE_WORKFLOW, AUDIT_LOG_CONNECT, etc.). "metaDataLabelDescriptions" is a list of associated descriptions to associated with the meta-data labels similar to the description in the table above. "errorCode" is a string which returns HWC_SUCCESS if the underlying data access functions are successful.

WriteCanonicalMetaData (input: cbrName, input: canonicalName, input: metaDataLabel, input: metaDataValue, output: errorCode) is an operation that associates a meta-data value to the targeted label by identified canonical and CBR. "cbrName" is a string which identifies the logical name and network address of the CBR instance for which the meta data configuration should be associated. "canonicalName" is a string which identifies the canonical for which the meta-data configuration should be associated. Valid canonical name definitions will be described in section 3.3 below (such as ENCOUNTER, ORDER). "metaDataLabel" is a name of the meta-data parameter. The valid values are listed in the table above (such as INITIALIZE_WORKFLOW, AUDIT_LOG_CONNECT, etc.). "metaDataValue" is a value to set the meta-data parameter to based on the description in the table above. "errorCode" is a string which returns HWC_SUCCESS if the underlying data access functions are successful.

ReadCanonicalMetaData (input: cbrName, input: canonicalName, output: metaDataLabel, output: metaDataValue, output: errorCode) is an operation that reads available meta-data configuration to drive the behavior of the canonical and/or applications and workflows. "cbrName" is a string which identifies the logical name and network address of the CBR instance for which the meta data configuration should be returned. "canonicalName" is a string which identifies the canonical for which the meta-data configuration should be returned. Valid canonical name definitions will be described in section 3.3 below (such as ENCOUNTER, ORDER). "metaDataLabel" is the name of the meta-data parameter to return. The valid values are listed in the table above (such as INITIALIZE_WORKFLOW, AUDIT_LOG_CONNECT, etc.). "metaDataValue" is the value of the returned meta-data parameter to based on the description in the table above. "errorCode" is the string which returns HWC_SUCCESS if the underlying data access functions are successful.

Lastly, in addition to the SQL schema and the API with WSDLs, the Canonical meta-data can include a UI utility to browse and edit these meta-data configuration parameters by an administrator or developer with appropriate privileges at design or deployment time. In an exemplary embodiment, the Headwater CBR management UI can include this capability. In another embodiment, a small web URL can be provided into a CBR Java™ environment to expose this. Other implementations can also be used.

In an exemplary embodiment, the Headwater platform for healthcare provides a mechanism to persistently store canonical representations of healthcare data in order to support long-running business transactions and the assembly of XML, NCPDP, ANSI X.12, and HL7 messages (or messages consistent with other standards) which require the presence, join and validation of more than one data entity (such as the patient admit HL7 process). Data persistence is supported and a user-initiated maintenance function is used to trim/delete unneeded records from the cache. This functionality can be provided, for example, from leading DBMS vendor implementations supported by the core CBR platform.

To meet this requirement the Headwater canonical architecture needs: a simple, but flexible SQL schema to store all incoming and outgoing data traffic; a WSDL interface that can provide the workflows with the means to interact with that SQL schema and associated data store; and an implementation of the WSDL interface which provides the read and write functions on the in the actual database instance.

To support the SQL data store, in an exemplary embodiment a logical ER diagram and associated DDL are provided to support the target database platforms.

In terms of the WSDL interface, this can effectively implement a Record Locator Service (RLS). Details regarding the workflows, parameters, etc of the RLS is detailed in section 3.4.3 below. The basic operations for the RLS include:

"AddRLSEntry"—Adds a entry to the RLS log for a single canonical instance. Records the date and time stamp of the creation, the record ids (local and global), the type of canonical, the canonical XML record instance, and the CBR GUID where the record came from.

"DeleteRLSEntry"—Deletes an established RLS entry.

"CreateRLSEnt Relationship"—Establishes relationships across canonical data types (such as order->schedule->result->document).

"DeleteRLSEnt Releationship"—Deletes relationships across canonical data types.

"LocateCBRSourceByFilter"—Searches the RLS record cache by canonical type attributes to find the record ID and CBR ID of records which match the search criteria.

The implementation of the WSDL operations can be implemented either as a Java™ local service or as a workflow on the CBR platform and the base line code set can be provided as a reference implementation which can be customized by site level deployments (so that more than just the basic header information in the canonical XML record could be extract to SQL and made more effectively searchable).

An advantage of this model is that all Headwater data traffic can be captured and monitored as part of the canonical operation flow. Then separate independent database processing jobs can extract, transform, and load the RLS data into data warehouse applications for analytics or other HIN functions (like auditing).

Data Sources, Transports & Transforms for Canonicals

Headwater provides a way to dynamically support many underlying source and destination data storage formats and transports. To accomplish this and to isolate the core canonical semantic transformation logic from the specific details of a source or destination format and transport, the canonical framework provides for the implementation of a component referred to as CRUD (Create, Read, Update and Delete).

The main requirements from the PRD related to CRUD include the following.

The Headwater platform for healthcare provides the means to receive, transform, route, and transmit HL7 messages and their associated data structures. This requirement can be satisfied through an ecosystem-enabling initiative with one or many healthcare ISV. Support for HL7 CDA and all HL7 versions in EDI and XML editions, including version 3.0 messages and RIM. The Headwater platform for healthcare also provides mechanism to receive, transform, route, and transmit ASTM standard Continuity of Care Record (CCR) messages and their associated data structures. This requirement can be satisfied through an ecosystem-enabling initiative with one or many healthcare ISV. The Headwater platform for healthcare also provides a mechanism to receive, transform, route, and transmit NCPDP messages and their associated data structures (electronic prescriptions). This requirement can be satisfied through an ecosystem-enabling initiative with one or many healthcare ISVs. The Headwater platform for healthcare can also provide a mechanism to receive, transform, route, and transmit HIPPA X.12, ASC X12, and ASC X12N messages and their associated data structures (for insurance transactions related to eligibility, referrals, claims and payments). This requirement can be satisfied through an ecosystem-enabling initiative with one or many healthcare ISVs. The Headwater system can also support the MLP transports required by MLP X12, NCPDP, and HL7. In an exemplary embodiment, the Headwater system also supports the file based messaging transports used in the healthcare vertical. For example, in this case, the most common protocol is FTP. These requirements can be primarily supported by the use of one or more HC (Health Care) Adapters such as ItemField™ or iWay™ (e.g. for HL7, CCR, X12 and NCPDP) to function as transform adapters and the CBR transport receive and transmit functions for receiving and sending data. Fundamentally the CRUD services can act as a WSDL "wrapper" to the configuration of these lower level transform and transport functions. The two main flows are "outside-in" (that is a client calling Get( ), Put( ) or List( )) or "inside-out" (that is a client calling Initialize( )).

In an exemplary embodiment, testable reference samples of the following CRUD services are provided. First, HL7 2.3 samples of PatientProfile, Order, Encounter, Schedule and Document. This will include HL7 files created on the file system and submitted to Initialize( ) via the inside-out technique and transforms in an HC Adaptor such as ItemField™ or iWay™ which a run through the outside-in mechanism as created by the Put( ) canonical operation. Second, a sample working connection to a HL7 EMR which has an MLLP connection to the HC Adaptor which demonstrates the "outside-in" application of Get( ) and List( ) for Patient, Order, and Encounters. Third, a working implementation of ServiceProvider with a SQL CRUD service implementation (effectively a JAXB—to/from—JDBC conversion) that supports the full flow of reading and writing the canonical for all operations in both inside-out and outside-in workflows.

The WSDL operations for the "outside-in" CRUD are fairly self-explanatory, and contain the same parameters as the core canonical operations and include for example:

Create(input: putRequestSrcStruct, input: canonicalXMLRecord, output: errorCode, output: canonicalRecordID)

Read(input: XMLSearchStruct, input: maxResultStreams, input: previousResultID, output: canonicalXMLRecordsList, output: errorCode, output: finishedFlag, output: resultID)

Update(input: putRequestSrcStruct, input: canonicalXMLRecord, output: errorCode, output: canonicalRecordID)

Delete(input: XMLSearchStruct, input: putRequestSrcStruct, output: errorCode)

Figure 19:
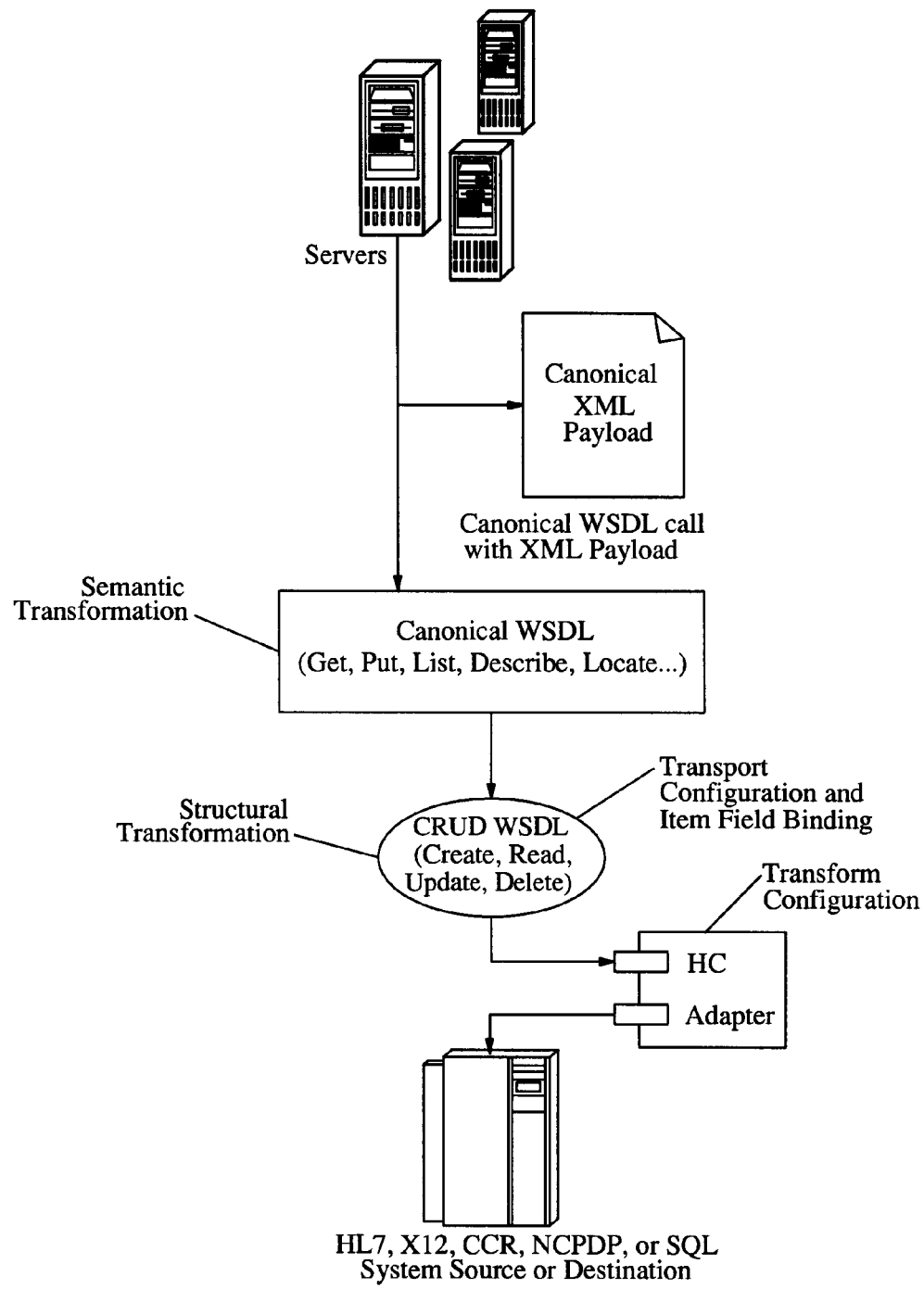
FIG. 19 illustrates exemplary CRUD (Create, Read, Update, Delete) interactions for "Outside-In".

Note that the Create( ) operation can handle inserts or "upserts" on data. Exemplary CRUD interactions for "Outside-In" are shown, for example, in FIG. 19.

Figure 20:
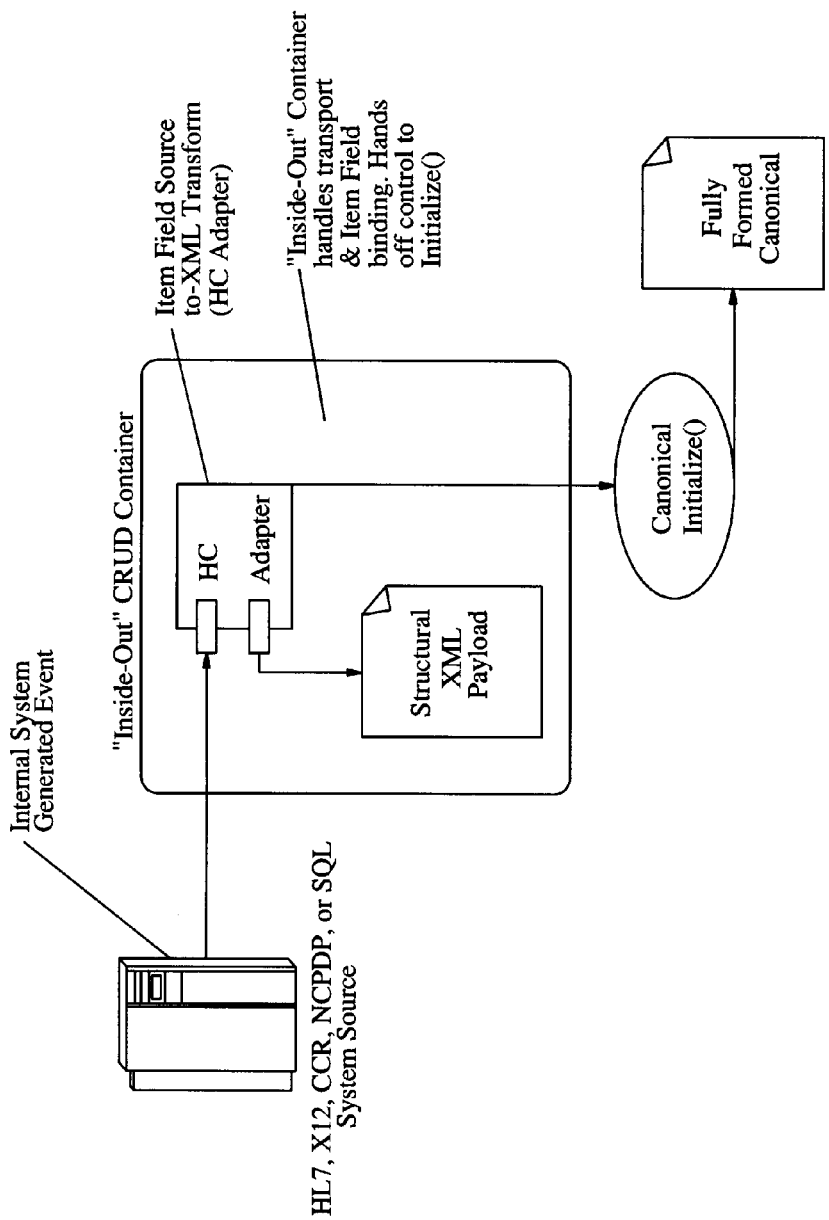
FIG. 20 illustrates exemplary CRUD interactions for "Inside-Out".
Figure 21:
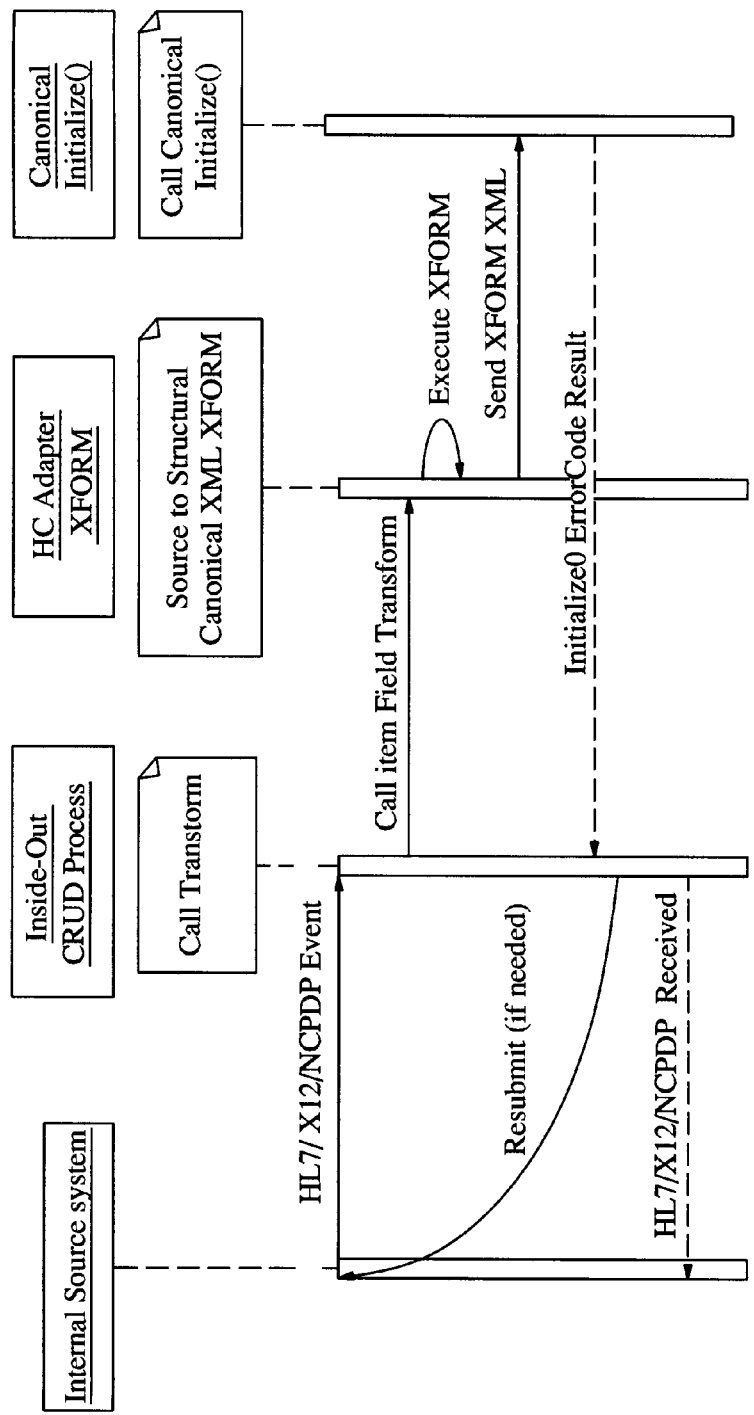
FIG. 21 illustrates an exemplary baseline sequence diagram for the architecture of FIG. 20.

Exemplary CRUD interactions for "Inside-Out" are shown, for example, in FIG. 20, where the "Inside-Out" Container handles transport and HC (Health Care) Adaptor binding, and hands off control to "Initialize( )". FIG. 21 shows an exemplary baseline sequence diagram for the architecture of FIG. 20.

Specific definitions of individual canonicals by type (such as PATIENT, ORDER, ENCOUNTER, etc) will now be discussed. For each canonical data type, a specific implementation of CDA R2 as the signifier/schema for the canonical will be discussed. A sequence diagram describing the workflow for each of the standard WSDL operations as defined above (Get( ), Put( ), List( ), Describe( ), Locate( ), and Initialize( ), etc) will also be discussed, and this will include the canonicals relationship to the RLS, EMPI, CMVT, and Audit Log services. An exemplary definition for any incremental WSDL operations will be discussed, and examples of how the canonical can apply to the main targeted use cases for Headwater will be described.

With respect to canonical schema, workflows and WSDLs, each canonical shares a common set of operations (for example, as those described further above). For most canonicals, the high-level workflow for each of these operations can be common and what will vary are the rules associated with the EMPI, CMVT, and CRUD services which are configured for a particular canonical on a specific deployed instance of CBR.

Figure 22:
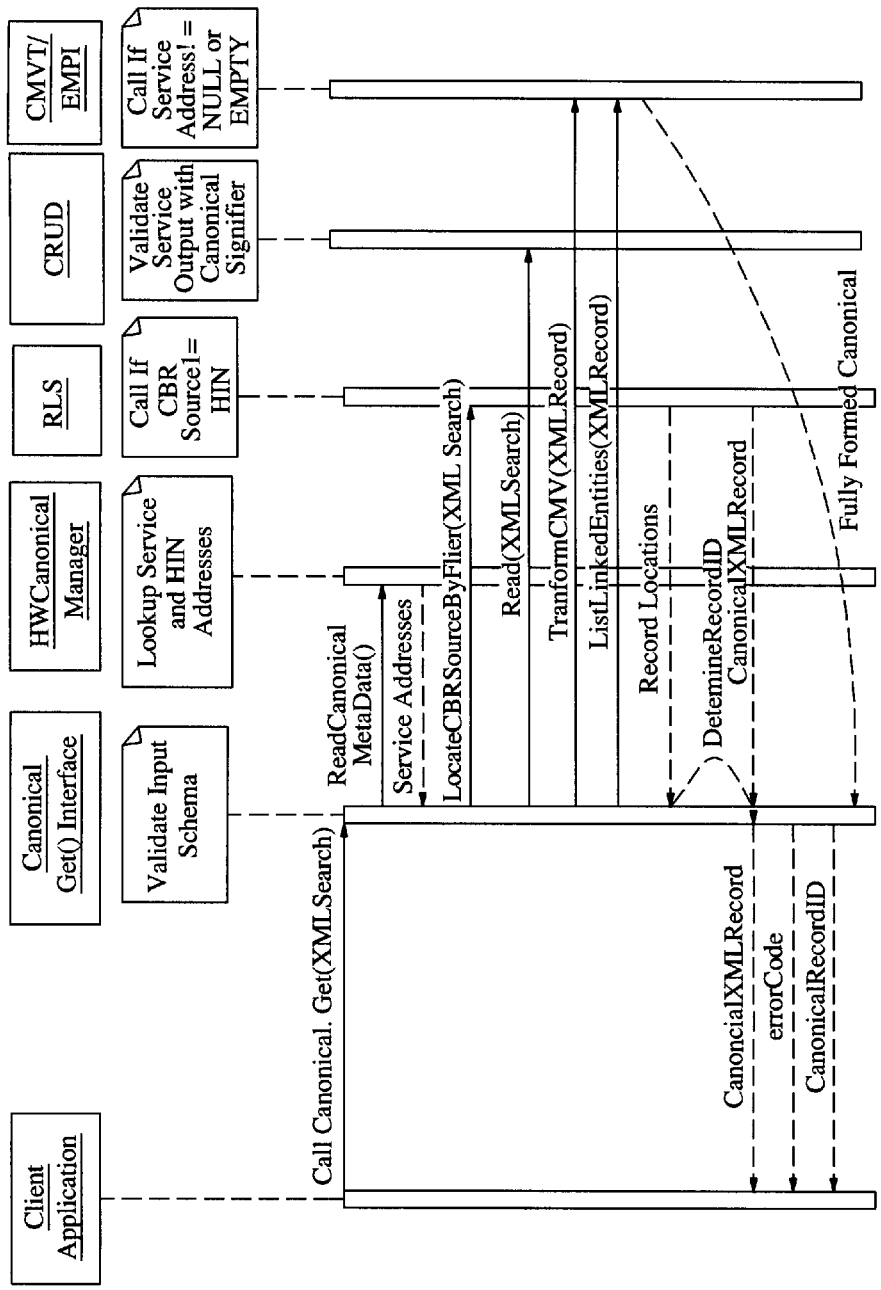
FIG. 22 illustrates an exemplary sequence diagram for Get( ).
Figure 23:
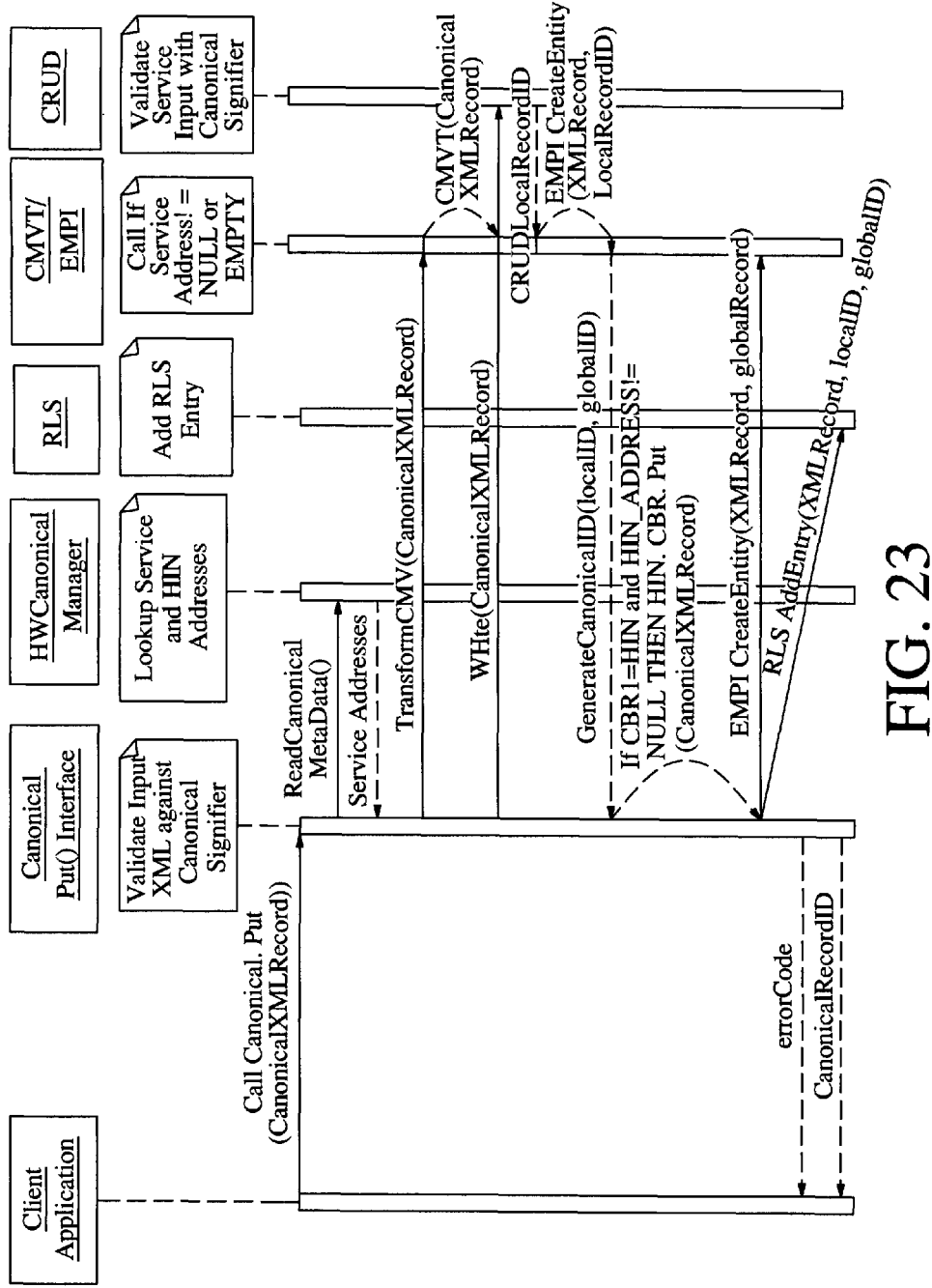
FIG. 23 illustrates an exemplary sequence diagram for Put( ).
Figure 24:
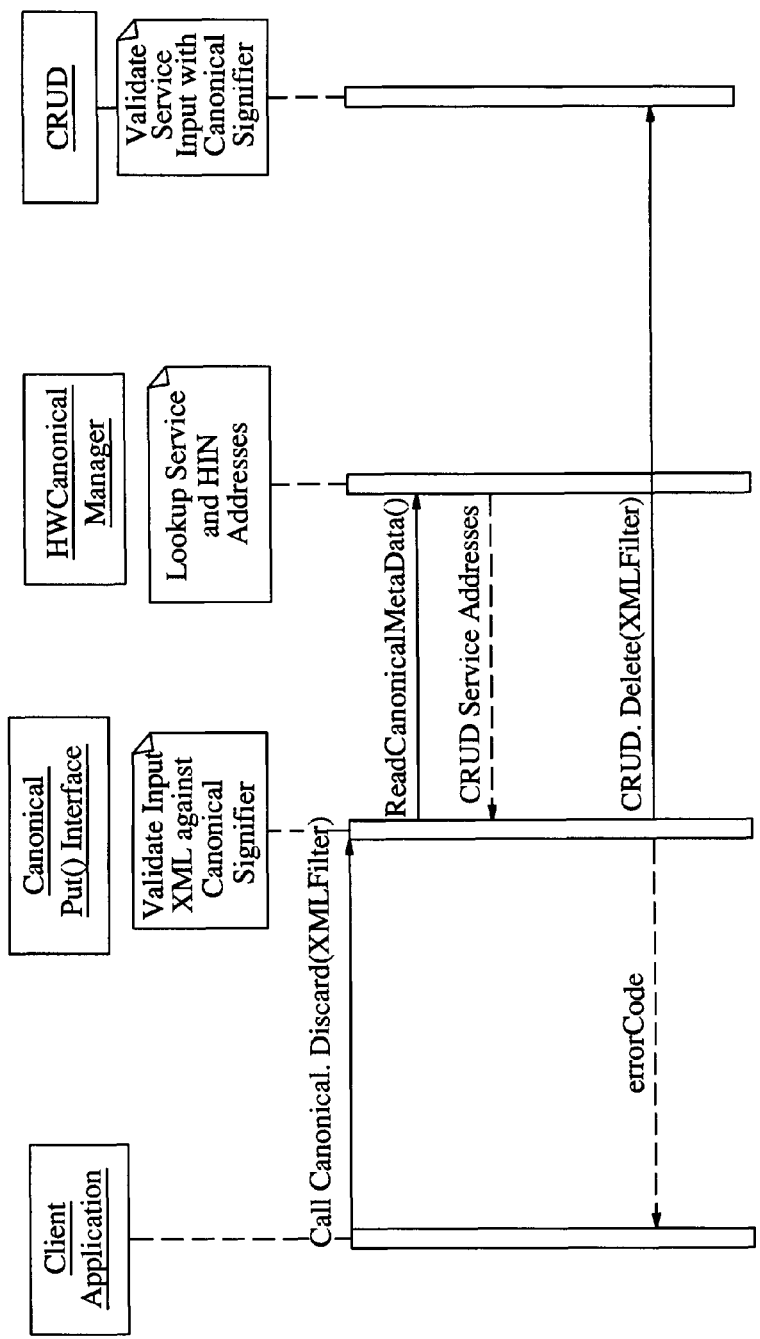
FIG. 24 illustrates an exemplary sequence diagram for Discard( ).
Figure 25:
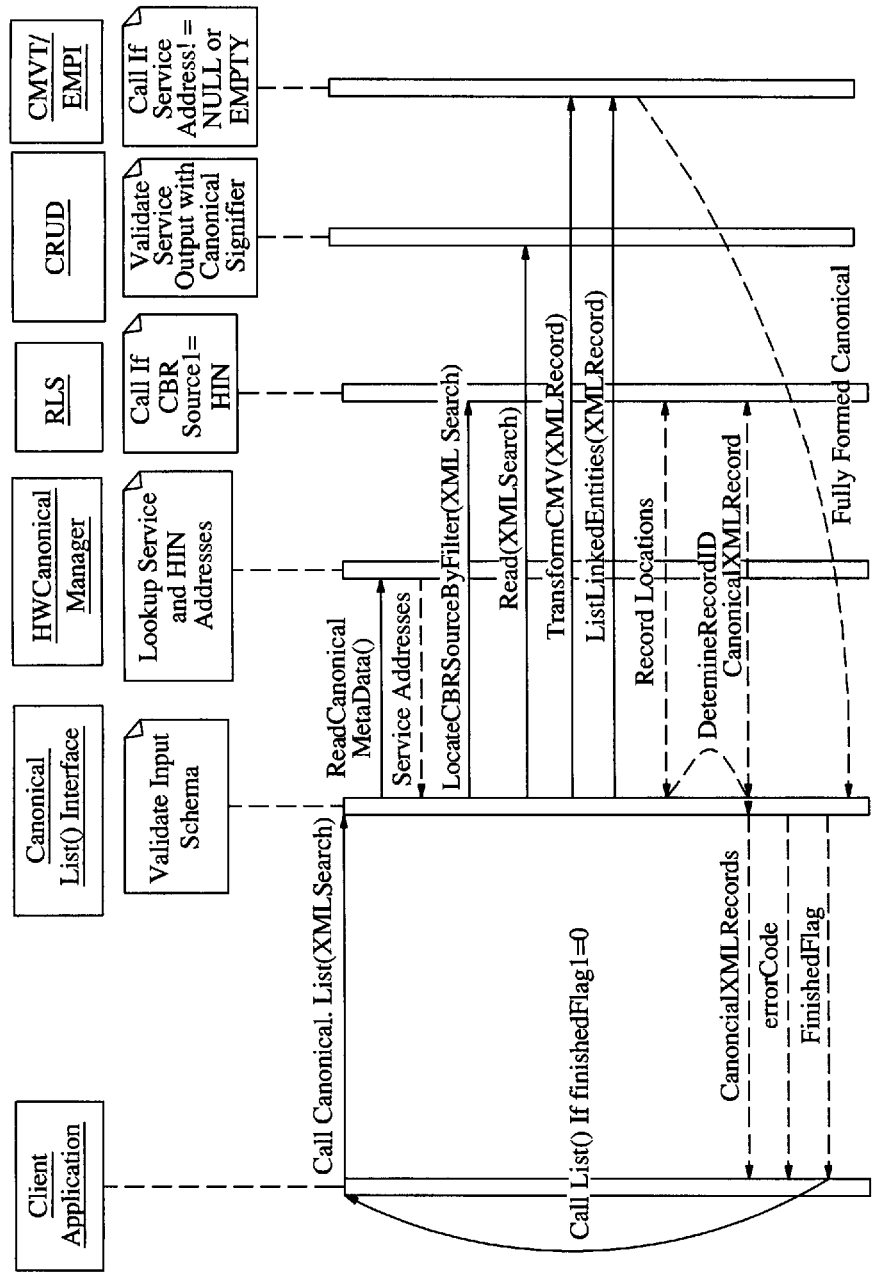
FIG. 25 illustrates an exemplary sequence diagram for List( ).
Figure 26:
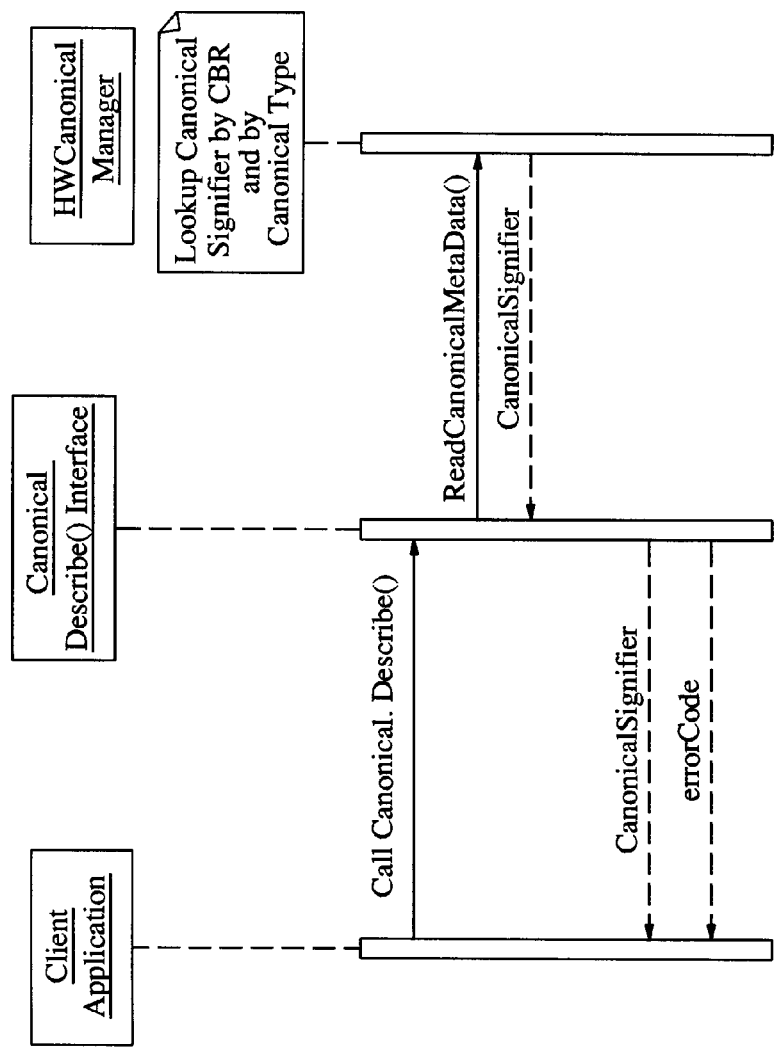
FIG. 26 illustrates an exemplary sequence diagram for Describe( ).
Figure 27:
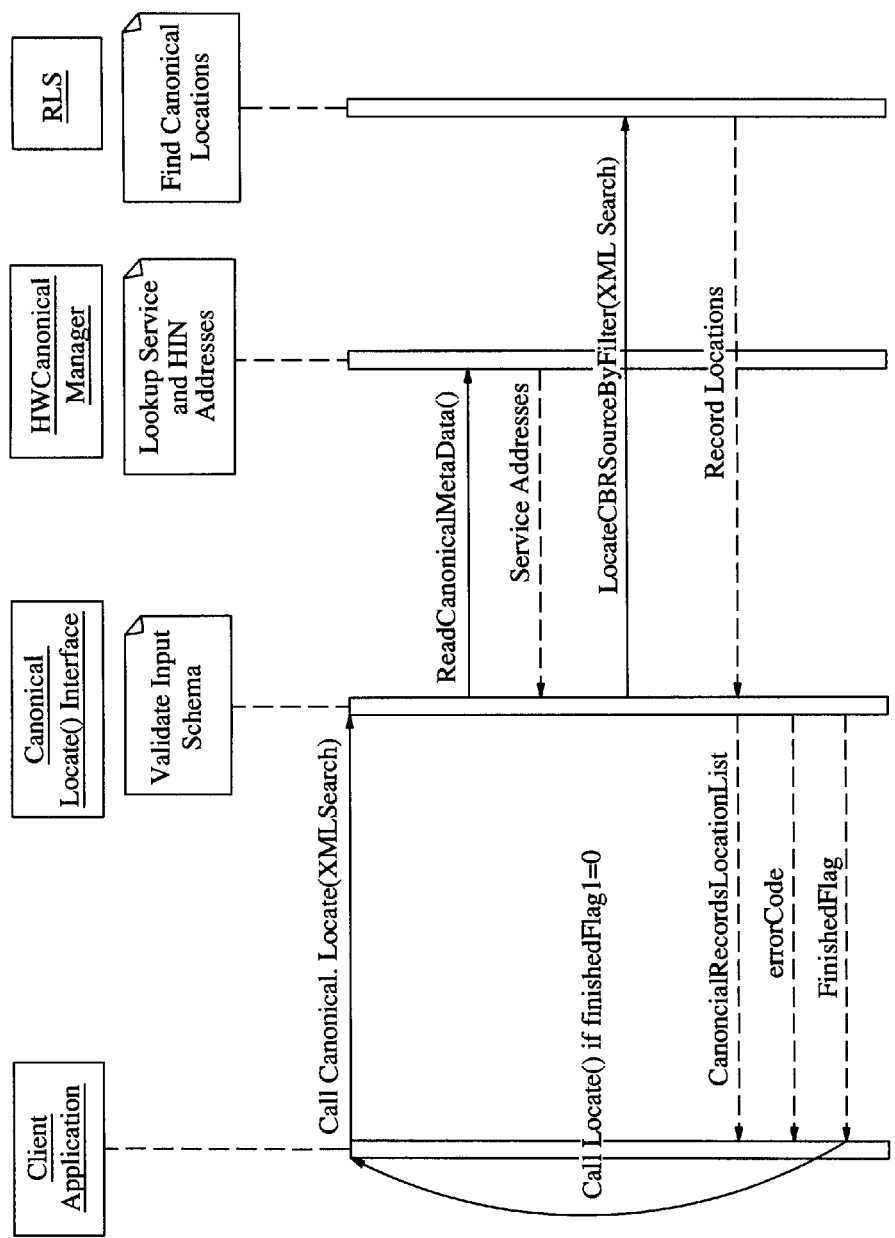
FIG. 27 illustrates an exemplary sequence diagram for Locate( ).
Figure 28:
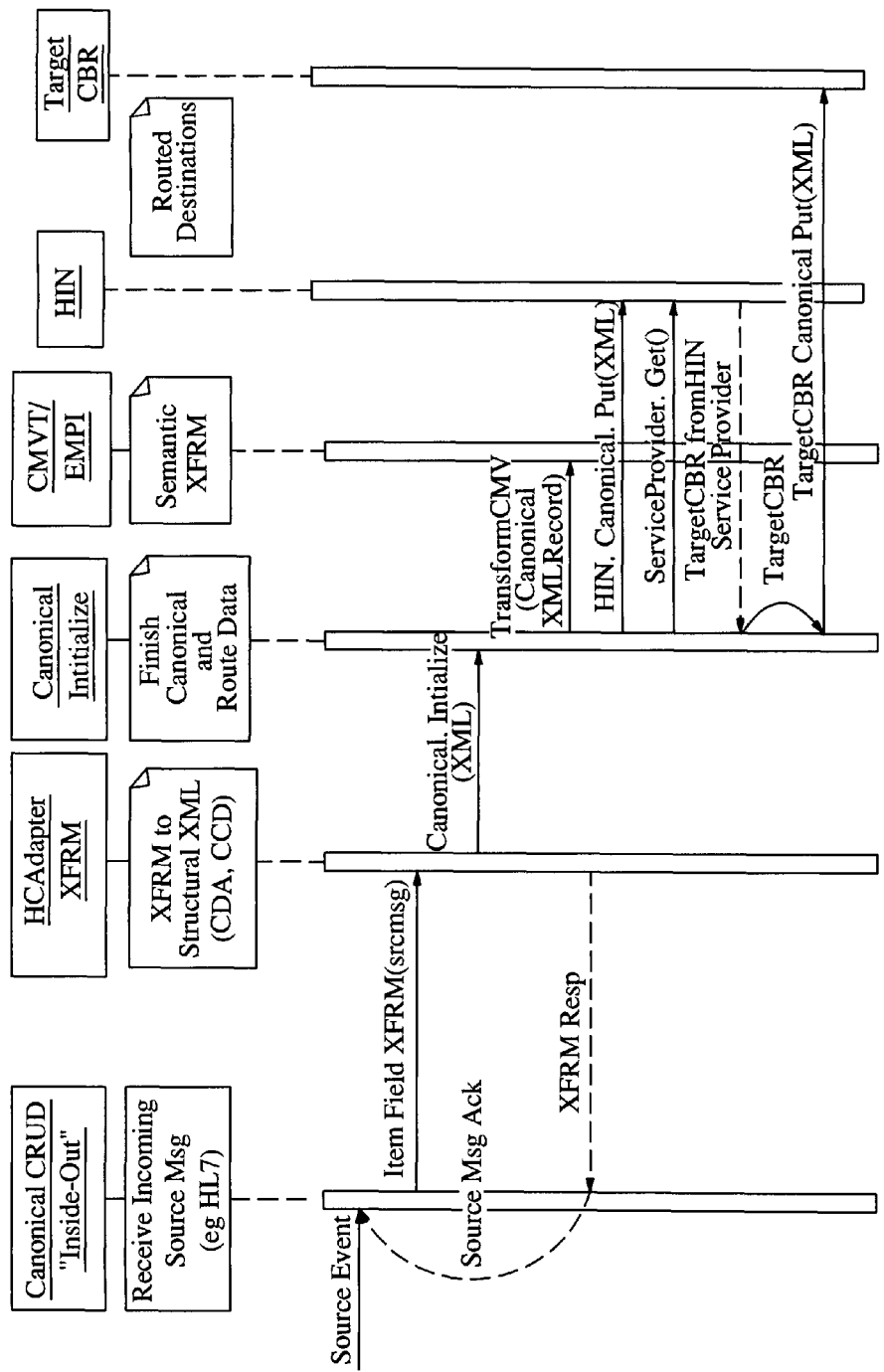
FIG. 28 illustrates an exemplary sequence diagram for Initialize( ).

The common workflows for the standard canonical WSDL operations can be represented as sequence diagrams, shown for example in FIGS. 22-28. FIG. 22 illustrates an exemplary sequence diagram for Get( ). FIG. 23 illustrates an exemplary sequence diagram for Put( ). FIG. 24 illustrates an exemplary sequence diagram for Discard( ). FIG. 25 illustrates an exemplary sequence diagram for List( ). FIG. 26 illustrates an exemplary sequence diagram for Describe( ). FIG. 27 illustrates an exemplary sequence diagram for Locate( ). FIG. 28 illustrates an exemplary sequence diagram for Initialize( ).

Next for discussion are an XSD definition, XML samples, incremental WSDL definitions and a sequence diagram which represents the additional specific WSDL operations or unique workflows for each typed canonical.

Exemplary embodiments of the Headwater platform for healthcare can provide a software service definition for Service Provider (organization, affiliation and relations, including roles and groups) including the data and common functions that deliver the service functionality. The Service definition can include an H7 version 3.0 RIM compliant data structure with the functions to create, read, update and delete the data structure the service represents. The ServiceProvider canonical can be a very important as it represents the directory of medical professionals which have access to the Headwater network, their association to participating organizations (like clinics, hospitals, etc.) and the organization's identifier CBR instance (GUID). This canonical can ensure the proper relationships across all other canonicals in the model. An implementation can be fully formed implementation from the highest level WSDL all the way through the CRUD implementation in SQL.

An exemplary schema definition of the ServiceProvider canonical is:

```xml
<?xml version="1.0"?>
<!--
HIN SysID = 76b242b9-1246-4691-bb1d-91bb7336e76f
Good Health Clinic SysID = 81821f47-8139-4766-aff0-81be0674de8f
Hospital of Health SysID = 2a4a0d0d-40f3-4bce-96ff-6939150c3973
First id extension per representedOrganization = <org CBR ID>
-->
<ServiceProviders xmlns="urn:h17-org:v3" xmlns:voc="urn:h17-org:v3/voc"
xmlns:xsi="http://www.w3.org/2001/XMLSchema-instance" xsi:schemaLocation="urn:h17-org:v3
HeadwaterServiceProviders.xsd">
<!--
Hospital of Health
-->
    <serviceProvider>
        <id nullFlavor="NI"/>
        <representedOrganization>
            <id extension="2a4a0d0d-40f3-4bce-96ff-6939150c3973" root="76b242b9-1246-4691-bb1d-91bb7336e76f"/> <!-- HIN ID -->
            <id root="2a4a0d0d-40f3-4bce-96ff-6939150c3973"/> <!-- Local ID -->
            <name>Hospital of Health</name>
        </representedOrganization>
    </serviceProvider>
<!--
Good Health Clinic
-->
    <serviceProvider>
        <id nullFlavor="NI"/>
        <representedOrganization>
            <id extension="81821f47-8139-4766-aff0-81be0674de8f" root="76b242b9-1246-4691-bb1d-91bb7336e76f"/> <!-- HIN ID -->
            <id root="81821f47-8139-4766-aff0-81be0674de8f"/> <!-- Local ID -->
            <name>Good Health Clinic</name>
        </representedOrganization>
    </serviceProvider>
<!--
Larry Laboratorian, MD (affiliated with Good Health Clinic)
-->
    <serviceProvider>
        <id extension="90886bbd-92ee-4fa9-a72f-5527804290d5" root="76b242b9-1246-4691-bb1d-91bb7336e76f"/> <!-- HIN ID -->
        <id extension="15151515" root="81821f47-8139-4766-aff0-81be0674de8f"/> <!-- Local provider ID -->
        <assignedPerson>
            <name>
                <given>Larry</given>
                <family>Laboratorian</family>
                <suffix>MD</suffix>
            </name>
        </assignedPerson>
        <representedOrganization>
            <id extension="81821f47-8139-4766-aff0-81be0674de8f" root="76b242b9-1246-4691-bb1d-91bb7336e76f"/> <!-- HIN ID -->
            <id root="81821f47-8139-4766-aff0-81be0674de8f"/> <!-- Local ID -->
            <name>Good Health Clinic</name>
        </representedOrganization>
    </serviceProvider>
<!--
Peter Pulmonologist, MD (affiliated with Good Health Clinic)
-->
    <serviceProvider>
        <id extension="124060a7-02e9-4c60-a917-4d8729fe0234" root="76b242b9-1246-4691-bb1d-91bb7336e76f"/> <!-- HIN ID -->
        <id extension="433433433" root="81821f47-8139-4766-aff0-81be0674de8f"/> <!-- Local provider ID -->
        <assignedPerson>
            <name>
                <given>Peter</given>
                <family>Pulmonologist</family>
                <suffix>MD</suffix>
            </name>
        </assignedPerson>
        <representedOrganization>
            <id extension="81821f47-8139-4766-aff0-81be0674de8f" root="76b242b9-1246-4691-bb1d-91bb7336e76f"/> <!-- HIN ID -->
            <id root="81821f47-8139-4766-aff0-81be0674de8f"/> <!-- Local ID -->
            <name>Good Health Clinic</name>
        </representedOrganization>
    </serviceProvider>
```

```
<!--
Robert Dolin, MD (affiliated with Good Health Clinic)
-->
        <serviceProvider>
                <id extension="2223222" root="76b242b9-1246-4691-bb1d-91bb7336e76f"/> <!--
HIN provider ID -->
                <id extension="34455655443" root="81821f47-8139-4766-aff0-81be0674de8f"/>
<!-- Local provider ID -->
                <assignedPerson>
                        <name>
                                <given>Robert</given>
                                <family>Doctor</family>
                                <suffix>MD</suffix>
                        </name>
                </assignedPerson>
                <representedOrganization>
                        <id extension="81821f47-8139-4766-aff0-81be0674de8f" root="76b242b9-
1246-4691-bb1d-91bb7336e76f"/> <!-- HIN ID -->
                        <id root="81821f47-8139-4766-aff0-81be0674de8f"/> <!-- Local ID -->
                        <name>Good Health Clinic</name>
                </representedOrganization>
        </serviceProvider>
```

Exemplary incremental WSDL operations for the Service Provider canonical are included below. They effectively wrap the EMPI API at the canonical call level. Their parameters will be slightly different as the record structure will be the canonical rather than the EMPI specific data structures for fields and record IDs, yet their functional purpose remains the same. Thus, WSDL operations can include: FindDuplicateDefinitions( ); LinkRecords( ); UnlinkRecords( ); MergeRecords( ); UnMergeRecords( ); InactivateRecord( ); ReactivateRecord( ).

With respect to a Patient canonical (healthcare-specific requirements/Services/Healthcare Core Enterprise Data Service/Patient), exemplary embodiments of the Headwater platform for healthcare can provide a software service definition for Patient including the data and common functions that deliver the service functionality. Service definition which includes an H7 version 3.0 RIM compliant data structure with the functions to create, read, update and delete the data structure the service represents.

An exemplary schema definition of the canonical is the continuity of care document (CCD) using limited sections (not a full patient history; for full history see health record) below. An exemplary CCD document that represents a patient profile is shown below:

```
<?xml version="1.0"?>
<?xml-stylesheet type="text/xsl" href="CCD.xsl"?>
<!-- The following sample document depicts a fictional character's health summary. Any
resemblance to a real person is coincidental. -->
<ClinicalDocument xmlns="urn:hl7-org:v3" xmlns:voc="urn:hl7-org:v3/voc"
xmlns:xsi="http://www.w3.org/2001/XMLSchema-instance" xsi:schemaLocation="urn:hl7-org:v3
CDA.xsd">
        <!--
*******************************************************
CDA Header
*******************************************************
-->
        <typeId root="2.16.840.1.113883.1.3" extension="POCD_HD000040"/>
        <templateId root="2.16.840.1.113883.10.20.1"/> <!-- CCD v1.0 Templates Root -->
        <id root="db734647-fc99-424c-a864-7e3cda82e703"/>
        <code code="34133-9" codeSystem="2.16.840.1.113883.6.1" displayName="Summarization
of episode note"/>
        <title>Good Health Clinic Continuity of Care Document</title>
        <effectiveTime value="20000407130000+0500"/>
        <confidentialityCode code="N" codeSystem="2.16.840.1.113883.5.25"/>
        <languageCode code="en-US"/>
        <recordTarget>
            <patientRole>
                <id extension="996-756-495" root="2.16.840.1.113883.19.5"/>
                <patient>
                    <name>
                        <given>Henry</given>
                        <family>Levin</family>
                        <suffix>the 7th</suffix>
                    </name>
                    <administrativeGenderCode code="M"
codeSystem="2.16.840.1.113883.5.1"/>
                    <birthTime value="19320924"/>
                </patient>
                <providerOrganization>
                    <id root="2.16.840.1.113883.19.5"/>
                    <name>Good Health Clinic</name>
                </providerOrganization>
            </patientRole>
```

```xml
</recordTarget>
<author>
        <time value="20000407130000+0500"/>
        <assignedAuthor>
                <id root="20cf14fb-b65c-4c8c-a54d-b0cca834c18c"/>
                <assignedPerson>

<name><prefix>Dr.</prefix><given>Robert</given><family>Dolin</family></name>
                </assignedPerson>
                <representedOrganization>
                        <id root="2.16.840.1.113883.19.5"/>
                        <name>Good Health Clinic</name>
                </representedOrganization>
        </assignedAuthor>
</author>
<informant>
        <assignedEntity>
                <id nullFlavor="NI"/>
                <representedOrganization>
                        <id root="2.16.840.1.113883.19.5"/>
                        <name>Good Health Clinic</name>
                </representedOrganization>
        </assignedEntity>
</informant>
<custodian>
        <assignedCustodian>
                <representedCustodianOrganization>
                        <id root="2.16.840.1.113883.19.5"/>
                        <name>Good Health Clinic</name>
                </representedCustodianOrganization>
        </assignedCustodian>
</custodian>
<legalAuthenticator>
        <time value="20000407130000+0500"/>
        <signatureCode code="S"/>
        <assignedEntity>
                <id nullFlavor="NI"/>
                <representedOrganization>
                        <id root="2.16.840.1.113883.19.5"/>
```

```xml
                <name>Good Health Clinic</name>
            </representedOrganization>
        </assignedEntity>
    </legalAuthenticator>
    <participant typeCode="IND">
        <associatedEntity classCode="GUAR">
            <id root="4ff51570-83a9-47b7-91f2-93ba30373141"/>
            <addr>
                <streetAddressLine>17 Daws Rd.</streetAddressLine>
                <city>Blue Bell</city>
                <state>MA</state>
                <postalCode>02368</postalCode>
            </addr>
            <telecom value="tel:(888)555-1212"/>
            <associatedPerson>
                <name>
                    <given>Kenneth</given>
                    <family>Ross</family>
                </name>
            </associatedPerson>
        </associatedEntity>
    </participant>
    <participant typeCode="IND">
        <associatedEntity classCode="NOK">
            <id root="4ac71514-6a10-4164-9715-f8d96af48e6d"/>
            <code code="65656005" codeSystem="2.16.840.1.113883.6.96" displayName="Biiological mother"/>
            <telecom value="tel:(999)555-1212"/>
            <associatedPerson>
                <name>
                    <given>Henrietta</given>
                    <family>Levin</family>
                </name>
            </associatedPerson>
        </associatedEntity>
    </participant>
    <documentationOf>
        <serviceEvent classCode="PCPR">
```

```xml
            <effectiveTime><low value="19320924"/><high value="20000407"/></effectiveTime>
            <performer typeCode="PRF">
                <functionCode code="PCP" codeSystem="2.16.840.1.113883.5.88"/>
                <time><low value="1990"/><high value='20000407'/></time>
                <assignedEntity>
                    <id root="20cf14fb-b65c-4c8c-a54d-b0cca834c18c"/>
                    <assignedPerson>
                        <name><prefix>Dr.</prefix><given>Robert</given><family>Dolin</family></name>
                    </assignedPerson>
                    <representedOrganization>
                        <id root="2.16.840.1.113883.19.5"/>
                        <name>Good Health Clinic</name>
                    </representedOrganization>
                </assignedEntity>
            </performer>
        </serviceEvent>
    </documentationOf>
    <!--
**********************************************************
CDA Body
**********************************************************
-->
    <component>
        <structuredBody>
            <!--
**********************************************************
Purpose section
**********************************************************
-->
<component>
<section>
    <templateId root='2.16.840.1.113883.10.20.1.13'/> <!-- Purpose section template -->
    <code code="48764-5" codeSystem="2.16.840.1.113883.6.1"/>
    <title>Summary Purpose</title>
    <text>Transfer of care</text>
    <entry typeCode="DRIV">
```

```xml
<act classCode="ACT" moodCode="EVN">
    <templateId root='2.16.840.1.113883.10.20.1.30'/> <!-- Purpose activity template -->
    <code code="23745001" codeSystem="2.16.840.1.113883.6.96" displayName="Documentation procedure"/>
    <statusCode code="completed"/>
    <entryRelationship typeCode="RSON">
        <act classCode="ACT" moodCode="EVN">
            <code code="308292007" codeSystem="2.16.840.1.113883.6.96" displayName="Transfer of care"/>
            <statusCode code="completed"/>
        </act>
    </entryRelationship>
</act>
        </entry>
</section>
</component>
        <!--
*********************************************************
Payers section
*********************************************************
-->
<component>
<section>
    <templateId root='2.16.840.1.113883.10.20.1.9'/> <!-- Payers section template -->
    <code code="48768-6" codeSystem="2.16.840.1.113883.6.1"/>
    <title>Payers</title>
    <text>
        <table border="1" width="100%">
            <thead>
            <tr><th>Payer name</th><th>Policy type / Coverage type</th><th>Covered party ID</th> <th>Authorization(s)</th></tr>
            </thead>
            <tbody>
                <tr>
                    <td>Good Health Insurance</td>
                    <td>Extended healthcare / Self</td>
                    <td>14d4a520-7aae-11db-9fe1-0800200c9a66</td>
                    <td>Colonoscopy</td>
```

```xml
            </tr>
        </tbody>
    </table>
</text>
<entry typeCode="DRIV">
    <act classCode="ACT" moodCode="DEF">
        <templateId root='2.16.840.1.113883.10.20.1.20'/> <!-- Coverage activity template -->
        <id root="1fe2cdd0-7aad-11db-9fe1-0800200c9a66"/>
        <code code="48768-6" codeSystem="2.16.840.1.113883.6.1" displayName="Payment sources"/>
        <statusCode code="completed"/>
        <entryRelationship typeCode="COMP">
            <act classCode="ACT" moodCode="EVN">
                <templateId root='2.16.840.1.113883.10.20.1.26'/> <!-- Policy activity template -->
                <id root="3e676a50-7aac-11db-9fe1-0800200c9a66"/>
                <code code="EHCPOL" codeSystem="2.16.840.1.113883.5.4" displayName="Extended healthcare"/>
                <statusCode code="completed"/>
                <performer typeCode="PRF">
                    <assignedEntity>
                        <id root="329fcdf0-7ab3-11db-9fe1-0800200c9a66"/>
                        <representedOrganization>
                            <name>Good Health Insurance</name>
                        </representedOrganization>
                    </assignedEntity>
                </performer>
                <participant typeCode="COV">
                    <participantRole>
                        <id root="14d4a520-7aae-11db-9fe1-0800200c9a66"/>
                        <code code="SELF" codeSystem="2.16.840.1.113883.5.111" displayName="Self"/>
                    </participantRole>
                </participant>
                <entryRelationship typeCode="REFR">
                    <act classCode="ACT" moodCode="EVN">
```

```
                                        <templateId
root='2.16.840.1.113883.10.20.1.19'/> <!-- Authorization activity template -->
                                        <id root="f4dce790-8328-11db-9fe1-
0800200c9a66"/>
                                        <code nullFlavor="NA"/>
                                        <entryRelationship typeCode="SUBJ">
                                            <procedure classCode="PROC"
moodCode="PRMS">
                                                <code code="73761001"
codeSystem="2.16.840.1.113883.6.96" displayName="Colonoscopy"/>
                                            </procedure>
                                        </entryRelationship>
                                    </act>
                                </entryRelationship>
                            </act>
                        </entryRelationship>
                    </act>
                </entry>
        </section>
</component>
                            <!--
*******************************************************
Advance Directives section
*******************************************************
-->
<component>
<section>
        <templateId root='2.16.840.1.113883.10.20.1.1'/> <!-- Advance directives section
template -->
        <code code="42348-3" codeSystem="2.16.840.1.113883.6.1"/>
        <title>Advance Directives</title>
        <text>
            <table border="1" width="100%">
                <thead>

<tr><th>Directive</th><th>Description</th><th>Verification</th><th>Supporting
Document(s)</th></tr>
                </thead>
                <tbody>
```

```xml
            <tr>
                <td>Resuscitation status</td>
                <td><content ID="AD1">Do not resuscitate</content></td>
                <td>Dr. Robert Dolin, Nov 07, 1999</td>
                <td><linkHtml href="AdvanceDirective.b50b7910-7ffb-4f4c-bbe4-177ed68cbbf3.pdf">Advance directive</linkHtml></td>
            </tr>
        </tbody>
    </table>
</text>
<entry typeCode="DRIV">
    <observation classCode="OBS" moodCode="EVN">
        <templateId root='2.16.840.1.113883.10.20.1.17'/> <!-- Advance directive observation template -->
        <id root="9b54c3c9-1673-49c7-aef9-b037ed72ed27"/>
        <code code="304251008" codeSystem="2.16.840.1.113883.6.96" displayName="Resuscitation"/>
        <statusCode code="completed"/>
        <value xsi:type="CD" code="304253006" codeSystem="2.16.840.1.113883.6.96" displayName="Do not resuscitate">
            <originalText><reference value="#AD1"/></originalText>
        </value>
        <participant typeCode="VRF">
            <templateId root='2.16.840.1.113883.10.20.1.58'/> <!-- Verification of an advance directive observation template -->
            <time value="19991107"/>
            <participantRole>
                <id root="20cf14fb-b65c-4c8c-a54d-b0cca834c18c"/>
            </participantRole>
        </participant>
        <entryRelationship typeCode="REFR">
            <observation classCode="OBS" moodCode="EVN">
                <templateId root='2.16.840.1.113883.10.20.1.37'/> <!-- Advance directive status observation template -->
                <code code="33999-4" codeSystem="2.16.840.1.113883.6.1" displayName="Status"/>
                <statusCode code="completed"/>
                <value xsi:type="CE" code="15240007" codeSystem="2.16.840.1.113883.6.96" displayName="Current and verified"/>
```

```
                        </observation>
                    </entryRelationship>
                    <reference typeCode="REFR">
                        <externalDocument>
                            <templateId root='2.16.840.1.113883.10.20.1.36'/> <!--
Advance directive reference template -->
                            <id root="b50b7910-7ffb-4f4c-bbe4-177ed68cbbf3"/>
                            <code code="371538006"
codeSystem="2.16.840.1.113883.6.96" displayName="Advance directive"/>
                            <text mediaType="application/pdf"><reference
value="AdvanceDirective.b50b7910-7ffb-4f4c-bbe4-177ed68cbbf3.pdf"/></text>
                        </externalDocument>
                    </reference>
                </observation>
            </entry>
</section>
</component>
                                <!--
**********************************************************
Functional Status section
**********************************************************
-->
<component>
<section>
    <templateId root='2.16.840.1.113883.10.20.1.5'/> <!-- Functional status section
template -->
    <code code="47420-5" codeSystem="2.16.840.1.113883.6.1"/>
    <title>Functional Status</title>
    <text>
        <table border="1" width="100%">
            <thead>
            <tr><th>Functional Condition</th> <th>Effective Dates</th>
<th>Condition Status</th></tr>
            </thead>
            <tbody>
            <tr><td>Dependence on cane</td><td>1998</td><td>Active</td></tr>
            <tr><td>Memory impairment</td><td>1999</td><td>Active</td></tr>
            </tbody>
        </table>
```

```xml
        </text>
        <entry typeCode="DRIV">
            <act classCode="ACT" moodCode="EVN">
                <templateId root='2.16.840.1.113883.10.20.1.27'/> <!-- Problem act template -->
                <id root="6z2fa88d-4174-4909-aece-db44b60a3abb"/>
                <code nullFlavor="NA"/>
                <entryRelationship typeCode="SUBJ">
                    <observation classCode="OBS" moodCode="EVN">
                        <templateId root='2.16.840.1.113883.10.20.1.28'/> <!-- Problem observation template -->
                        <id root="fd07111a-b15b-4dce-8518-1274d07f142a"/>
                        <code code="ASSERTION" codeSystem="2.16.840.1.113883.5.4"/>
                        <statusCode code="completed"/>
                        <effectiveTime><low value="1998"/></effectiveTime>
                        <value xsi:type="CD" code="105504002" codeSystem="2.16.840.1.113883.6.96" displayName="Dependence on cane"/>
                        <entryRelationship typeCode="REFR">
                            <observation classCode="OBS" moodCode="EVN">
                                <templateId root='2.16.840.1.113883.10.20.1.44'/> <!-- Status of functional status observation template -->
                                <code code="33999-4" codeSystem="2.16.840.1.113883.6.1" displayName="Status"/>
                                <statusCode code="completed"/>
                                <value xsi:type="CE" code="55561003" codeSystem="2.16.840.1.113883.6.96" displayName="Active"/>
                            </observation>
                        </entryRelationship>
                    </observation>
                </entryRelationship>
            </act>
        </entry>
        <entry typeCode="DRIV">
            <act classCode="ACT" moodCode="EVN">
                <templateId root='2.16.840.1.113883.10.20.1.27'/> <!-- Problem act template -->
                <id root="64606e86-c080-11db-8314-0800200c9a66"/>
```

```xml
                    <code nullFlavor="NA"/>
                    <entryRelationship typeCode="SUBJ">
                        <observation classCode="OBS" moodCode="EVN">
                            <templateId root='2.16.840.1.113883.10.20.1.28'/> <!-- Problem observation template -->
                            <id root="6be2930a-c080-11db-8314-0800200c9a66"/>
                            <code code="ASSERTION" codeSystem="2.16.840.1.113883.5.4"/>
                            <statusCode code="completed"/>
                            <effectiveTime><low value="1999"/></effectiveTime>
                            <value xsi:type="CD" code="386807006" codeSystem="2.16.840.1.113883.6.96" displayName="Memory impairment"/>
                            <entryRelationship typeCode="REFR">
                                <observation classCode="OBS" moodCode="EVN">
                                    <templateId root='2.16.840.1.113883.10.20.1.44'/> <!-- Status of functional status observation template -->
                                    <code code="33999-4" codeSystem="2.16.840.1.113883.6.1" displayName="Status"/>
                                    <statusCode code="completed"/>
                                    <value xsi:type="CE" code="55561003" codeSystem="2.16.840.1.113883.6.96" displayName="Active"/>
                                </observation>
                            </entryRelationship>
                        </observation>
                    </entryRelationship>
                </act>
        </entry>
</section>
</component>
                    <!--
********************************************************
Problems section
********************************************************
-->
<component>
<section>
        <templateId root='2.16.840.1.113883.10.20.1.11'/> <!-- Problem section template -->
```

```xml
<code code="11450-4" codeSystem="2.16.840.1.113883.6.1"/>
<title>Problems</title>
<text>
        <table border="1" width="100%">
                <thead>
                        <tr><th>Condition</th><th>Effective Dates</th><th>Condition Status</th></tr>
                </thead>
                <tbody>
                        <tr><td>Asthma</td><td>1950</td><td>Active</td></tr>
                        <tr><td>Pneumonia</td><td>Jan 1997</td><td>Resolved</td></tr>
                        <tr><td>"</td><td>Mar 1999</td><td>Resolved</td></tr>
                        <tr><td>Myocardial Infarction</td><td>Jan 1997</td><td>Resolved</td></tr>
                </tbody>
        </table>
</text>
<entry typeCode="DRIV">
        <act classCode="ACT" moodCode="EVN">
                <templateId root='2.16.840.1.113883.10.20.1.27'/> <!-- Problem act template -->
                <id root="6a2fa88d-4174-4909-aece-db44b60a3abb"/>
                <code nullFlavor="NA"/>
                <entryRelationship typeCode="SUBJ">
                        <observation classCode="OBS" moodCode="EVN">
                                <templateId root='2.16.840.1.113883.10.20.1.28'/> <!-- Problem observation template -->
                                <id root="d11275e7-67ae-11db-bd13-0800200c9a66"/>
                                <code code="ASSERTION" codeSystem="2.16.840.1.113883.5.4"/>
                                <statusCode code="completed"/>
                                <effectiveTime><low value="1950"/></effectiveTime>
                                <value xsi:type="CD" code="195967001" codeSystem="2.16.840.1.113883.6.96" displayName="Asthma"/>
                                <entryRelationship typeCode="REFR">
                                        <observation classCode="OBS" moodCode="EVN">
                                                <templateId root='2.16.840.1.113883.10.20.1.50'/> <!-- Problem status observation template -->
```

```xml
                                        <code code="33999-4"
codeSystem="2.16.840.1.113883.6.1" displayName="Status"/>
                                        <statusCode code="completed"/>
                                        <value xsi:type="CE" code="55561003"
codeSystem="2.16.840.1.113883.6.96" displayName="Active"/>
                                    </observation>
                                </entryRelationship>
                            </observation>
                        </entryRelationship>
            </act>
        </entry>
        <entry typeCode="DRIV">
            <act classCode="ACT" moodCode="EVN">
                <templateId root='2.16.840.1.113883.10.20.1.27'/> <!-- Problem act
template -->
                <id root="ec8a6ff8-ed4b-4f7e-82c3-e98e58b45de7"/>
                <code nullFlavor="NA"/>
                <entryRelationship typeCode="SUBJ">
                    <observation classCode="OBS" moodCode="EVN">
                        <templateId root='2.16.840.1.113883.10.20.1.28'/> <!--
Problem observation template -->
                        <id root="ab1791b0-5c71-11db-b0de-0800200c9a66"/>
                        <code code="ASSERTION"
codeSystem="2.16.840.1.113883.5.4"/>
                        <statusCode code="completed"/>
                        <effectiveTime><low value="199701"/></effectiveTime>
                        <value xsi:type="CD" code="233604007"
codeSystem="2.16.840.1.113883.6.96" displayName="Pneumonia"/>
                        <entryRelationship typeCode="REFR">
                            <observation classCode="OBS" moodCode="EVN">
                                <templateId
root='2.16.840.1.113883.10.20.1.50'/> <!-- Problem status observation template -->
                                <code code="33999-4"
codeSystem="2.16.840.1.113883.6.1" displayName="Status"/>
                                <statusCode code="completed"/>
                                <value xsi:type="CE" code="413322009"
codeSystem="2.16.840.1.113883.6.96" displayName="Resolved"/>
                            </observation>
                        </entryRelationship>
```

```xml
                        </observation>
                    </entryRelationship>
                </act>
            </entry>
            <entry typeCode="DRIV">
                <act classCode="ACT" moodCode="EVN">
                    <templateId root='2.16.840.1.113883.10.20.1.27'/> <!-- Problem act template -->
                    <id root="d11275e9-67ae-11db-bd13-0800200c9a66"/>
                    <code nullFlavor="NA"/>
                    <entryRelationship typeCode="SUBJ">
                        <observation classCode="OBS" moodCode="EVN">
                            <templateId root='2.16.840.1.113883.10.20.1.28'/> <!-- Problem observation template -->
                            <id root="9d3d416d-45ab-4da1-912f-4583e0632000"/>
                            <code code="ASSERTION" codeSystem="2.16.840.1.113883.5.4"/>
                            <statusCode code="completed"/>
                            <effectiveTime><low value="199903"/></effectiveTime>
                            <value xsi:type="CD" code="233604007" codeSystem="2.16.840.1.113883.6.96" displayName="Pneumonia"/>
                            <entryRelationship typeCode="REFR">
                                <observation classCode="OBS" moodCode="EVN">
                                    <templateId root='2.16.840.1.113883.10.20.1.50'/> <!-- Problem status observation template -->
                                    <code code="33999-4" codeSystem="2.16.840.1.113883.6.1" displayName="Status"/>
                                    <statusCode code="completed"/>
                                    <value xsi:type="CE" code="413322009" codeSystem="2.16.840.1.113883.6.96" displayName="Resolved"/>
                                </observation>
                            </entryRelationship>
                        </observation>
                    </entryRelationship>
                    <entryRelationship typeCode="SUBJ" inversionInd="true">
                        <observation classCode="OBS" moodCode="EVN">
                            <templateId root="2.16.840.1.113883.10.20.1.41"/> <!-- Episode observation template -->
```

```xml
                                        <code code="ASSERTION"
codeSystem="2.16.840.1.113883.5.4"/>
                                        <statusCode code="completed"/>
                                        <value xsi:type="CD" code="404684003"
codeSystem="2.16.840.1.113883.6.96" displayName="Clinical finding">
                                            <qualifier>
                                                <name code="246456000"
displayName="Episodicity"/>
                                                <value code="288527008" displayName="New
episode"/>
                                            </qualifier>
                                        </value>
                                        <entryRelationship typeCode="SAS">
                                            <act classCode="ACT" moodCode="EVN">
                                                <id root="ec8a6ff8-ed4b-4f7e-82c3-
e98e58b45de7"/>
                                                <code nullFlavor="NA"/>
                                            </act>
                                        </entryRelationship>
                                    </observation>
                                </entryRelationship>
                            </act>
                        </entry>
                        <entry typeCode="DRIV">
                            <act classCode="ACT" moodCode="EVN">
                                <templateId root='2.16.840.1.113883.10.20.1.27'/> <!-- Problem act
template -->
                                <id root="5a2c903c-bd77-4bd1-ad9d-452383fbfefa"/>
                                <code nullFlavor="NA"/>
                                <entryRelationship typeCode="SUBJ">
                                    <observation classCode="OBS" moodCode="EVN">
                                        <templateId root='2.16.840.1.113883.10.20.1.28'/> <!--
Problem observation template -->
                                        <code code="ASSERTION"
codeSystem="2.16.840.1.113883.5.4"/>
                                        <statusCode code="completed"/>
                                        <effectiveTime><low value="199701"/></effectiveTime>
                                        <value xsi:type="CD" code="22298006"
codeSystem="2.16.840.1.113883.6.96" displayName="Myocardial infarction"/>
```

```xml
<entryRelationship typeCode="REFR">
    <observation classCode="OBS" moodCode="EVN">
        <templateId root='2.16.840.1.113883.10.20.1.50'/> <!-- Problem status observation template -->
        <code code="33999-4" codeSystem="2.16.840.1.113883.6.1" displayName="Status"/>
        <statusCode code="completed"/>
        <value xsi:type="CE" code="413322009" codeSystem="2.16.840.1.113883.6.96" displayName="Resolved"/>
    </observation>
</entryRelationship>
                </observation>
            </entryRelationship>
        </act>
    </entry>
</section>
</component>
            <!--
*********************************************************
Family History section
*********************************************************
-->
<component>
<section>
    <templateId root="2.16.840.1.113883.10.20.1.4"/> <!-- Family history section template -->
    <code code="10157-6" codeSystem="2.16.840.1.113883.6.1"/>
    <title>Family history</title>
    <text>
        <paragraph>Father (deceased)</paragraph>
        <table border="1" width="100%">
            <thead>
                <tr><th>Diagnosis</th><th>Age At Onset</th></tr>
            </thead>
            <tbody>
                <tr><td>Myocardial Infarction (cause of death)</td><td>57</td></tr>
                <tr><td>Hypertension</td><td>40</td></tr>
            </tbody>
```

```
            </table>
            <paragraph>Mother (alive)</paragraph>
            <table border="1" width="100%">
                <thead>
                    <tr><th>Diagnosis</th><th>Age At Onset</th></tr>
                </thead>
                <tbody>
                    <tr><td>Asthma</td><td>30</td></tr>
                </tbody>
            </table>
    </text>
    <entry typeCode="DRIV">
        <organizer moodCode="EVN" classCode="CLUSTER">
            <templateId root="2.16.840.1.113883.10.20.1.23"/> <!-- Family history
organizer template -->
            <statusCode code="completed"/>
            <subject>
                <relatedSubject classCode="PRS">
                    <code code="9947008" codeSystem="2.16.840.1.113883.6.96"
displayName="Biological father"/>
                    <subject>
                        <administrativeGenderCode code="M"
codeSystem="2.16.840.1.113883.5.1" displayName="Male"/>
                        <birthTime value="1912"/>
                    </subject>
                </relatedSubject>
            </subject>
            <component>
                <observation classCode="OBS" moodCode="EVN">
                    <templateId root="2.16.840.1.113883.10.20.1.42"/> <!--
Family history cause of death observation template -->
                    <id root="d42ebf70-5c89-11db-b0de-0800200c9a66"/>
                    <code code="ASSERTION"
codeSystem="2.16.840.1.113883.5.4"/>
                    <statusCode code="completed"/>

<value xsi:type="CD" code="22298006"
codeSystem="2.16.840.1.113883.6.96" displayName="MI"/>
                    <entryRelationship typeCode="CAUS">
```

```xml
                                    <observation classCode="OBS" moodCode="EVN">
                                        <id root="6898fae0-5c8a-11db-b0de-0800200c9a66"/>
                                        <code code="ASSERTION" codeSystem="2.16.840.1.113883.5.4"/>
                                        <statusCode code="completed"/>
                                        <value xsi:type="CD" code="419099009" codeSystem="2.16.840.1.113883.6.96" displayName="Dead"/>
                                    </observation>
                                </entryRelationship>
                                <entryRelationship typeCode="SUBJ" inversionInd="true">
                                    <observation classCode="OBS" moodCode="EVN">
                                        <templateId root="2.16.840.1.113883.10.20.1.38"/> <!-- Age observation template -->
                                        <code code="397659008" codeSystem="2.16.840.1.113883.6.96" displayName="Age"/>
                                        <statusCode code="completed"/>
                                        <value xsi:type="INT" value="57"/>
                                    </observation>
                                </entryRelationship>
                            </observation>
                        </component>
                        <component>
                            <observation classCode="OBS" moodCode="EVN">
                                <templateId root="2.16.840.1.113883.10.20.1.22"/> <!-- Family history observation template -->
                                <id root="5bfe3ec0-5c8b-11db-b0de-0800200c9a66"/>
                                <code code="ASSERTION" codeSystem="2.16.840.1.113883.5.4"/>
                                <statusCode code="completed"/>
                                <value xsi:type="CD" code="59621000" codeSystem="2.16.840.1.113883.6.96" displayName="HTN"/>
                                <entryRelationship typeCode="SUBJ" inversionInd="true">
                                    <observation classCode="OBS" moodCode="EVN">
                                        <templateId root="2.16.840.1.113883.10.20.1.38"/> <!-- Age observation template -->
                                        <code code="397659008" codeSystem="2.16.840.1.113883.6.96" displayName="Age"/>
                                        <statusCode code="completed"/>
```

```xml
                                        <value xsi:type="INT" value="40"/>
                                    </observation>
                                </entryRelationship>
                            </observation>
                        </component>
                    </organizer>
                </entry>
                <entry typeCode="DRIV">
                    <organizer moodCode="EVN" classCode="CLUSTER">
                        <templateId root="2.16.840.1.113883.10.20.1.23"/> <!-- Family history organizer template -->
                        <statusCode code="completed"/>
                        <subject>
                            <relatedSubject classCode="PRS">
                                <code code="65656005" codeSystem="2.16.840.1.113883.6.96" displayName="Biological mother"/>
                                <subject>
                                    <administrativeGenderCode code="F" codeSystem="2.16.840.1.113883.5.1" displayName="Female"/>
                                    <birthTime value="1912"/>
                                </subject>
                            </relatedSubject>
                        </subject>
                        <component>
                            <observation classCode="OBS" moodCode="EVN">
                                <templateId root="2.16.840.1.113883.10.20.1.22"/> <!-- Family history observation template -->
                                <id root="a13c6160-5c8b-11db-b0de-0800200c9a66"/>
                                <code code="ASSERTION" codeSystem="2.16.840.1.113883.5.4"/>
                                <statusCode code="completed"/>
                                <effectiveTime>
                                    <low value="1942"/>
                                </effectiveTime>
                                <value xsi:type="CD" code="195967001" codeSystem="2.16.840.1.113883.6.96" displayName="Asthma"/>
                            </observation>
                        </component>
                    </organizer>
```

```xml
        </entry>
</section>
</component>

<!--
**********************************************************
Alerts section
**********************************************************
-->
<component>
<section>
        <templateId root="2.16.840.1.113883.10.20.1.2"/> <!-- Alerts section template -->
        <code code="48765-2" codeSystem="2.16.840.1.113883.6.1"/>
        <title>Allergies, Adverse Reactions, Alerts</title>
        <text>
                <table border="1" width="100%">
                        <thead>
                                <tr><th>Substance</th><th>Reaction</th><th>Status</th></tr>
                        </thead>
                        <tbody>
                                <tr><td>Penicillin</td><td>Hives</td><td>Active</td></tr>
                                <tr><td>Aspirin</td><td>Wheezing</td><td>Active</td></tr>
                                <tr><td>Codeine</td><td>Nausea</td><td>Active</td></tr>
                        </tbody>
                </table>
        </text>
        <entry typeCode="DRIV">
                <act classCode="ACT" moodCode="EVN">
                        <templateId root='2.16.840.1.113883.10.20.1.27'/> <!-- Problem act template -->
                        <id root="36e3e930-7b14-11db-9fe1-0800200c9a66"/>
                        <code nullFlavor="NA"/>
                        <entryRelationship typeCode="SUBJ">
                                <observation classCode="OBS" moodCode="EVN">
                                        <templateId root='2.16.840.1.113883.10.20.1.18'/> <!-- Alert observation template -->
                                        <id root="4adc1020-7b14-11db-9fe1-0800200c9a66"/>
                                        <code code="ASSERTION" codeSystem="2.16.840.1.113883.5.4"/>
```

```xml
                    <statusCode code="completed"/>
                    <value xsi:type="CD" code="282100009"
codeSystem="2.16.840.1.113883.6.96" displayName="Adverse reaction to substance"/>
                    <participant typeCode="CSM">
                        <participantRole classCode="MANU">
                            <playingEntity classCode="MMAT">
                                <code code="70618"
codeSystem="2.16.840.1.113883.6.88" displayName="Penicillin"/>
                            </playingEntity>
                        </participantRole>
                    </participant>
                    <entryRelationship typeCode="MFST" inversionInd="true">
                        <observation classCode="OBS" moodCode="EVN">
                            <templateId
root='2.16.840.1.113883.10.20.1.54'/> <!-- Reaction observation template -->
                            <code code="ASSERTION"
codeSystem="2.16.840.1.113883.5.4"/>
                            <statusCode code="completed"/>
                            <value xsi:type="CD" code="247472004"
codeSystem="2.16.840.1.113883.6.96" displayName="Hives"/>
                        </observation>
                    </entryRelationship>
                    <entryRelationship typeCode="REFR">
                        <observation classCode="OBS" moodCode="EVN">
                            <templateId
root='2.16.840.1.113883.10.20.1.39'/> <!-- Alert status observation template -->
                            <code code="33999-4"
codeSystem="2.16.840.1.113883.6.1" displayName="Status"/>
                            <statusCode code="completed"/>
                            <value xsi:type="CE" code="55561003"
codeSystem="2.16.840.1.113883.6.96" displayName="Active"/>
                        </observation>
                    </entryRelationship>
                </observation>
            </entryRelationship>
        </act>
    </entry>
    <entry typeCode="DRIV">
        <act classCode="ACT" moodCode="EVN">
```

```xml
                    <templateId root='2.16.840.1.113883.10.20.1.27'/> <!-- Problem act template -->
                    <id root="eb936010-7b17-11db-9fe1-0800200c9a66"/>
                    <code nullFlavor="NA"/>
                    <entryRelationship typeCode="SUBJ">
                        <observation classCode="OBS" moodCode="EVN">
                            <templateId root='2.16.840.1.113883.10.20.1.18'/> <!-- Alert observation template -->
                            <id root="eb936011-7b17-11db-9fe1-0800200c9a66"/>
                            <code code="ASSERTION" codeSystem="2.16.840.1.113883.5.4"/>
                            <statusCode code="completed"/>
                            <value xsi:type="CD" code="282100009" codeSystem="2.16.840.1.113883.6.96" displayName="Adverse reaction to substance"/>
                            <participant typeCode="CSM">
                                <participantRole classCode="MANU">
                                    <playingEntity classCode="MMAT">
                                        <code code="1191" codeSystem="2.16.840.1.113883.6.88" displayName="Aspirin"/>
                                    </playingEntity>
                                </participantRole>
                            </participant>
                            <entryRelationship typeCode="MFST" inversionInd="true">
                                <observation classCode="OBS" moodCode="EVN">
                                    <templateId root='2.16.840.1.113883.10.20.1.54'/> <!-- Reaction observation template -->
                                    <code code="ASSERTION" codeSystem="2.16.840.1.113883.5.4"/>
                                    <statusCode code="completed"/>
                                    <value xsi:type="CD" code="56018004" codeSystem="2.16.840.1.113883.6.96" displayName="Wheezing"/>
                                </observation>
                            </entryRelationship>
                            <entryRelationship typeCode="REFR">
                                <observation classCode="OBS" moodCode="EVN">
                                    <templateId root='2.16.840.1.113883.10.20.1.39'/> <!-- Alert status observation template -->
                                    <code code="33999-4" codeSystem="2.16.840.1.113883.6.1" displayName="Status"/>
```

```xml
                                        <statusCode code="completed"/>
                                        <value xsi:type="CE" code="55561003" codeSystem="2.16.840.1.113883.6.96" displayName="Active"/>
                                    </observation>
                                </entryRelationship>
                            </observation>
                        </entryRelationship>
                    </act>
                </entry>
                <entry typeCode="DRIV">
                    <act classCode="ACT" moodCode="EVN">
                        <templateId root='2.16.840.1.113883.10.20.1.27'/> <!-- Problem act template -->
                        <id root="c3df3b61-7b18-11db-9fe1-0800200c9a66"/>
                        <code nullFlavor="NA"/>
                        <entryRelationship typeCode="SUBJ">
                            <observation classCode="OBS" moodCode="EVN">
                                <templateId root='2.16.840.1.113883.10.20.1.18'/> <!-- Alert observation template -->
                                <id root="c3df3b60-7b18-11db-9fe1-0800200c9a66"/>
                                <code code="ASSERTION" codeSystem="2.16.840.1.113883.5.4"/>
                                <statusCode code="completed"/>
                                <value xsi:type="CD" code="282100009" codeSystem="2.16.840.1.113883.6.96" displayName="Adverse reaction to substance"/>
                                <participant typeCode="CSM">
                                    <participantRole classCode="MANU">
                                        <playingEntity classCode="MMAT">
                                            <code code="2670" codeSystem="2.16.840.1.113883.6.88" displayName="Codeine"/>
                                        </playingEntity>
                                    </participantRole>
                                </participant>
                                <entryRelationship typeCode="MFST" inversionInd="true">
                                    <observation classCode="OBS" moodCode="EVN">
                                        <templateId root='2.16.840.1.113883.10.20.1.54'/> <!-- Reaction observation template -->
                                        <code code="ASSERTION" codeSystem="2.16.840.1.113883.5.4"/>
```

```xml
                                        <statusCode code="completed"/>
                                        <value xsi:type="CD" code="73879007"
codeSystem="2.16.840.1.113883.6.96" displayName="Nausea"/>
                                    </observation>
                                </entryRelationship>
                                <entryRelationship typeCode="REFR">
                                    <observation classCode="OBS" moodCode="EVN">
                                        <templateId
root='2.16.840.1.113883.10.20.1.39'/> <!-- Alert status observation template -->
                                        <code code="33999-4"
codeSystem="2.16.840.1.113883.6.1" displayName="Status"/>
                                        <statusCode code="completed"/>
                                        <value xsi:type="CE" code="55561003"
codeSystem="2.16.840.1.113883.6.96" displayName="Active"/>
                                    </observation>
                                </entryRelationship>
                            </observation>
                        </entryRelationship>
                </act>
        </entry>
</section>
</component>
                    <!--
*********************************************************
Medications section
*********************************************************
-->
<component>
<section>
        <templateId root="2.16.840.1.113883.10.20.1.8"/> <!-- Medications section template
-->
        <code code="10160-0" codeSystem="2.16.840.1.113883.6.1"/>
        <title>Medications</title>
        <text>
                <table border="1" width="100%">
                        <thead>
                                <tr><th>Medication</th><th>Instructions</th><th>Start
Date</th><th>Status</th></tr>
                        </thead>
```

```
                    <tbody>
                            <tr><td>Albuterol inhalant</td><td>2 puffs QID PRN
wheezing</td><td> </td><td>Active</td></tr>
                            <tr><td>Clopidogrel (Plavix)</td><td>75mg PO
daily</td><td> </td><td>Active</td></tr>
                            <tr><td>Metoprolol</td><td>25mg PO
BID</td><td> </td><td>Active</td></tr>
                            <tr><td>Prednisone</td><td>20mg PO daily</td><td>Mar 28,
2000</td><td>Active</td></tr>
                            <tr><td>Cephalexin (Keflex)</td><td>500mg PO QID x 7 days (for
bronchitis)</td><td>Mar 28, 2000</td><td>No longer active</td></tr>
                    </tbody>
            </table>
    </text>
        <informant>
        <assignedEntity>
                <id extension="996-756-495" root="2.16.840.1.113883.19.5"/>
                <representedOrganization>
                        <id root="2.16.840.1.113883.19.5"/>
                        <name>Good Health Clinic</name>
                </representedOrganization>
        </assignedEntity>
    </informant>
    <entry typeCode="DRIV">
        <substanceAdministration classCode="SBADM" moodCode="EVN">
                <templateId root="2.16.840.1.113883.10.20.1.24"/> <!-- Medication
activity template -->
                <id root="cdbd33f0-6cde-11db-9fe1-0800200c9a66"/>
                <statusCode code="active"/>
                <effectiveTime xsi:type="PIVL_TS">
                        <period value="6" unit="h"/>
                </effectiveTime>
                <routeCode code="IPINHL" codeSystem="2.16.840.1.113883.5.112"
codeSystemName="RouteOfAdministration" displayName="Inhalation, oral"/>
                <doseQuantity value="2"/>
                <administrationUnitCode code="415215001"
codeSystem="2.16.840.1.113883.6.96" displayName="Puff"/>
                <consumable>
                        <manufacturedProduct>
```

```
                                <templateId root="2.16.840.1.113883.10.20.1.53"/> <!--
Product template -->
                                <manufacturedMaterial>
                                    <code code="307782"
codeSystem="2.16.840.1.113883.6.88" displayName="Albuterol 0.09 MG/ACTUAT inhalant
solution">
                                        <originalText>Albuterol
inhalant</originalText>
                                    </code>
                                </manufacturedMaterial>
                            </manufacturedProduct>
                        </consumable>
                        <precondition typeCode="PRCN">
                            <criterion>
                                <code code="ASSERTION"
codeSystem="2.16.840.1.113883.5.4"/>
                                <value xsi:type="CE" code="56018004"
codeSystem="2.16.840.1.113883.6.96" displayName="Wheezing"/>
                            </criterion>
                        </precondition>
                    </substanceAdministration>
                </entry>
                <entry typeCode="DRIV">
                    <substanceAdministration classCode="SBADM" moodCode="EVN">
                        <templateId root="2.16.840.1.113883.10.20.1.24"/> <!-- Medication
activity template -->
                        <id root="cdbd5b05-6cde-11db-9fe1-0800200c9a66"/>
                        <statusCode code="active"/>
                        <effectiveTime xsi:type="PIVL_TS">
                            <period value="24" unit="h"/>
                        </effectiveTime>
                        <routeCode code="PO" codeSystem="2.16.840.1.113883.5.112"
codeSystemName="RouteOfAdministration"/>
                        <doseQuantity value="1"/>
                        <consumable>
                            <manufacturedProduct>
                                <templateId root="2.16.840.1.113883.10.20.1.53"/> <!--
Product template -->
                                <manufacturedMaterial>
```

```xml
                                <code code="309362"
codeSystem="2.16.840.1.113883.6.88" displayName="Clopidogrel 75 MG oral tablet">
                                    <originalText>Clopidogrel</originalText>
                                </code>
                                <name>Plavix</name>
                            </manufacturedMaterial>
                        </manufacturedProduct>
                    </consumable>
                </substanceAdministration>
            </entry>
            <entry typeCode="DRIV">
                <substanceAdministration classCode="SBADM" moodCode="EVN">
                    <templateId root="2.16.840.1.113883.10.20.1.24"/> <!-- Medication activity template -->
                    <id root="cdbd5b01-6cde-11db-9fe1-0800200c9a66"/>
                    <statusCode code="active"/>
                    <effectiveTime xsi:type="PIVL_TS">
                        <period value="12" unit="h"/>
                    </effectiveTime>
                    <routeCode code="PO" codeSystem="2.16.840.1.113883.5.112"
codeSystemName="RouteOfAdministration"/>
                    <doseQuantity value="1"/>
                    <consumable>
                        <manufacturedProduct>
                            <templateId root="2.16.840.1.113883.10.20.1.53"/> <!-- Product template -->
                            <manufacturedMaterial>
                                <code code="430618"
codeSystem="2.16.840.1.113883.6.88" displayName="Metoprolol 25 MG oral tablet">
                                    <originalText>Metoprolol</originalText>
                                </code>
                            </manufacturedMaterial>
                        </manufacturedProduct>
                    </consumable>
                </substanceAdministration>
            </entry>
            <entry typeCode="DRIV">
                <substanceAdministration classCode="SBADM" moodCode="EVN">
```

```xml
                <templateId root="2.16.840.1.113883.10.20.1.24"/> <!-- Medication
activity template -->
                <id root="cdbd5b03-6cde-11db-9fe1-0800200c9a66"/>
                <statusCode code="active"/>
                <effectiveTime xsi:type="IVL_TS">
                    <low value="20000328"/>
                </effectiveTime>
                <effectiveTime xsi:type="PIVL_TS" operator="A">
                    <period value="24" unit="h"/>
                </effectiveTime>
                <routeCode code="PO" codeSystem="2.16.840.1.113883.5.112"
codeSystemName="RouteOfAdministration"/>
                <doseQuantity value="1"/>
                <consumable>
                    <manufacturedProduct>
                        <templateId root="2.16.840.1.113883.10.20.1.53"/> <!--
Product template -->
                        <manufacturedMaterial>
                            <code code="312615"
codeSystem="2.16.840.1.113883.6.88" displayName="Prednisone 20 MG oral tablet">
                                <originalText>Prednisone</originalText>
                            </code>
                        </manufacturedMaterial>
                    </manufacturedProduct>
                </consumable>
            </substanceAdministration>
        </entry>
        <entry typeCode="DRIV">
            <substanceAdministration classCode="SBADM" moodCode="EVN">
                <templateId root="2.16.840.1.113883.10.20.1.24"/> <!-- Medication
activity template -->
                <id root="cdbd5b07-6cde-11db-9fe1-0800200c9a66"/>
                <statusCode code="completed"/>
                <effectiveTime xsi:type="IVL_TS">
                    <low value="20000328"/>
                    <high value="20000404"/>
                </effectiveTime>
                <effectiveTime xsi:type="PIVL_TS" operator="A">
                    <period value="6" unit="h"/>
```

```
                </effectiveTime>
                <routeCode code="PO" codeSystem="2.16.840.1.113883.5.112"
codeSystemName="RouteOfAdministration"/>
                <doseQuantity value="1"/>
                <consumable>
                    <manufacturedProduct>
                        <templateId root="2.16.840.1.113883.10.20.1.53"/> <!--
Product template -->
                        <manufacturedMaterial>
                            <code code="197454"
codeSystem="2.16.840.1.113883.6.88" displayName="Cephalexin 500 MG oral tablet">
                                <originalText>Cephalexin</originalText>
                            </code>
                            <name>Keflex</name>
                        </manufacturedMaterial>
                    </manufacturedProduct>
                </consumable>
                <entryRelationship typeCode="RSON">
                    <observation classCode="COND" moodCode="EVN">
                        <templateId root="2.16.840.1.113883.10.20.1.28"/> <!--
Problem observation template -->
                        <id root="cdbd5b08-6cde-11db-9fe1-0800200c9a66"/>
                        <code code="ASSERTION"
codeSystem="2.16.840.1.113883.5.4"/>
                        <statusCode code="completed"/>
                        <effectiveTime xsi:type="IVL_TS">
                            <low value="20000328"/>
                        </effectiveTime>
                        <value xsi:type="CE" code="32398004"
codeSystem="2.16.840.1.113883.6.96" displayName="Bronchitis"/>
                    </observation>
                </entryRelationship>
            </substanceAdministration>
        </entry>
</section>
</component>

<!--
************************************************************
```

```
Immunizations section
********************************************************
-->
<component>
<section>
        <templateId root="2.16.840.1.113883.10.20.1.6"/> <!-- Immunizations section
template -->
        <code code="11369-6" codeSystem="2.16.840.1.113883.6.1"/>
        <title>Immunizations</title>
        <text>
                <table border="1" width="100%">
                        <thead>
                                <tr><th>Vaccine</th><th>Date</th><th>Status</th></tr>
                        </thead>
                        <tbody>
                                <tr><td>Influenza virus vaccine, IM</td><td>Nov
1999</td><td>Completed</td></tr>
                                <tr><td>Influenza virus vaccine, IM</td><td>Dec
1998</td><td>Completed</td></tr>
                                <tr><td>Pneumococcal polysaccharide vaccine, IM</td><td>Dec
1998</td><td>Completed</td></tr>
                                <tr><td>Tetanus and diphtheria toxoids,
IM</td><td>1997</td><td>Completed</td></tr>
                        </tbody>
                </table>
        </text>
        <entry typeCode="DRIV">
                <substanceAdministration classCode="SBADM" moodCode="EVN">
                        <templateId root="2.16.840.1.113883.10.20.1.24"/> <!-- Medication
activity template -->
                        <id root="e6f1ba43-c0ed-4b9b-9f12-f435d8ad8f92"/>
                        <statusCode code="completed"/>
                        <effectiveTime xsi:type="IVL_TS"><center
value="199911"/></effectiveTime>
                        <routeCode code="IM" codeSystem="2.16.840.1.113883.5.112"
codeSystemName="RouteOfAdministration" displayName="Intramuscular injection"/>
                        <consumable>
                                <manufacturedProduct>
```

```xml
                    <templateId root="2.16.840.1.113883.10.20.1.53"/> <!-- Product template -->
                    <manufacturedMaterial>
                        <code code="88" codeSystem="2.16.840.1.113883.6.59" displayName="Influenza virus vaccine">
                            <originalText>Influenza virus vaccine</originalText>
                        </code>
                    </manufacturedMaterial>
                </manufacturedProduct>
            </consumable>
        </substanceAdministration>
    </entry>
    <entry typeCode="DRIV">
        <substanceAdministration classCode="SBADM" moodCode="EVN">
            <templateId root="2.16.840.1.113883.10.20.1.24"/> <!-- Medication activity template -->
            <id root="115f0f70-1343-4938-b62f-631de9749a0a"/>
            <statusCode code="completed"/>
            <effectiveTime xsi:type="IVL_TS"><center value="199812"/></effectiveTime>
            <routeCode code="IM" codeSystem="2.16.840.1.113883.5.112" codeSystemName="RouteOfAdministration" displayName="Intramuscular injection"/>

<consumable>
                <manufacturedProduct>
                    <templateId root="2.16.840.1.113883.10.20.1.53"/> <!-- Product template -->
                    <manufacturedMaterial>
                        <code code="88" codeSystem="2.16.840.1.113883.6.59" displayName="Influenza virus vaccine">
                            <originalText>Influenza virus vaccine</originalText>
                        </code>
                    </manufacturedMaterial>
                </manufacturedProduct>
            </consumable>
        </substanceAdministration>
    </entry>
```

```xml
<entry typeCode="DRIV">
        <substanceAdministration classCode="SBADM" moodCode="EVN">
                <templateId root="2.16.840.1.113883.10.20.1.24"/> <!-- Medication activity template -->
                <id root="78598407-9f16-42d5-8ffd-09281a60fe33"/>
                <statusCode code="completed"/>
                <effectiveTime xsi:type="IVL_TS"><center value="199812"/></effectiveTime>
                <routeCode code="IM" codeSystem="2.16.840.1.113883.5.112" codeSystemName="RouteOfAdministration" displayName="Intramuscular injection"/>
                <consumable>
                        <manufacturedProduct>
                                <templateId root="2.16.840.1.113883.10.20.1.53"/> <!-- Product template -->
                                <manufacturedMaterial>
                                    <code code="33" codeSystem="2.16.840.1.113883.6.59" displayName="Pneumococcal polysaccharide vaccine">
                                                <originalText>Pneumococcal polysaccharide vaccine</originalText>
                                    </code>
                                </manufacturedMaterial>
                        </manufacturedProduct>
                </consumable>
        </substanceAdministration>
    </entry>
    <entry typeCode="DRIV">
        <substanceAdministration classCode="SBADM" moodCode="EVN">
                <templateId root="2.16.840.1.113883.10.20.1.24"/> <!-- Medication activity template -->
                <id root="261e94a0-95fb-4975-b5a5-c8e12c01c1bc"/>
                <statusCode code="completed"/>
                <effectiveTime xsi:type="IVL_TS"><center value="1997"/></effectiveTime>
                <routeCode code="IM" codeSystem="2.16.840.1.113883.5.112" codeSystemName="RouteOfAdministration" displayName="Intramuscular injection"/>
                <consumable>
                        <manufacturedProduct>
                                <templateId root="2.16.840.1.113883.10.20.1.53"/> <!-- Product template -->
```

```xml
                    <manufacturedMaterial>
                        <code code="09" codeSystem="2.16.840.1.113883.6.59" displayName="Tetanus and diphtheria toxoids">
                            <originalText>Tetanus and diphtheria toxoids</originalText>
                        </code>
                    </manufacturedMaterial>
                </manufacturedProduct>
            </consumable>
        </substanceAdministration>
    </entry>
</section>
</component>

</structuredBody>
</component>
</ClinicalDocument>
```

Exemplary incremental WSDL operations for the Patient canonical are included below. They effectively wrap the EMPI API at the canonical call level. Their parameters will be slightly different as the record structure will be the canonical rather than the EMPI specific data structures for fields and record IDs, yet their functional purpose remains the same. Exemplary incremental WSDL operations for the Patient canonical can include, for example: FindDuplicateDefinitions( ); LinkRecords( ); UnlinkRecords( ); MergeRecords( ); UnMergeRecords( ); InactivateRecord( ); and ReactivateRecord( ).

Exemplary embodiments of the Headwater platform for healthcare can provide a software service definition for a Service Provider "Order" canonical (Healthcare Specific Requirements/Services/Healthcare Core Enterprise Data Service/Order), that can for example be used with respect to labs, treatments, drugs, and so forth. An exemplary Order canonical can include the data and common functions that deliver the service functionality. The corresponding service definition can include an H7 version 3.0 RIM compliant data structure with the functions to create, read, update and delete the data structure the service represents.

In an exemplary embodiment, there are six main types of orders that can be supported to enable targeted use cases. Exemplary order types can include: Order lab imaging (like a CT scan); Order a lab specimen (like a bold test); Order a medical procedure; Order medication/drugs; Order an encounter with a doctor/specialist; and Order a durable medical good (like a wheelchair or an oxygen tank).

An exemplary schema definition of the Order canonical for its associated use cases include the following.

First, an example involving Order lab imaging (like a CT scan):

```
<?xml version="1.0"?>
<?xml-stylesheet type="text/xsl" href="CDA.xsl"?>
<!-- The following sample document depicts a fictional character's health summary. Any
resemblance to a real person is coincidental. -->
<!--
Henry Levin the 7th goes to see his primary care doctor, Dr. Doctor, complaining of
headache.
Dr. Doctor diagnoses Henry Levin the 7th as having probable migraine, but orders a CT
scan of the head to rule out a brain tumor.
Henry Levin the 7th leaves the office, and Dr. Doctor writes a visit note.
Several days later, the CT scan is performed and a report comes back to Dr. Doctor,
showing that there is no brain tumor.
HIN SysID = 76b242b9-1246-4691-bb1d-91bb7336e76f
Local SysID = 81821f47-8139-4766-aff0-81be0674de8f
-->
<ClinicalDocument xmlns="urn:hl7-org:v3" xmlns:voc="urn:hl7-org:v3/voc"
xmlns:xsi="http://www.w3.org/2001/XMLSchema-instance" xsi:schemaLocation="urn:hl7-org:v3
CDA.xsd">
        <!--
************************************************************
CDA Header
************************************************************
-->
        <typeId root="2.16.840.1.113883.1.3" extension="POCD_HD000040"/>
        <!-- typeId is required in all CDA instances, and fixed as shown here. This is how
you know the instance is a CDA R2 document. -->
        <id root="320eb621-bf5e-41d4-97b5-62c2ac359891" extension="eb7b661b-d302-4c71-
a672-d5b7b5833e3f"/>
        <!-- ClinicalDocument.id has cardinality 1..1, and carries the Local ID. -->
        <code code="119270007" codeSystem="2.16.840.1.113883.6.96" displayName="Management
procedure"/>
        <!-- This can be a fixed code, since the type of order is included below. There
may be those that are using CDA for prescriptions, in which case they may be using a
different code. -->
        <title>Good Health Clinic Order Report</title>
        <!-- This can be a fixed value, used for rendering, or could be left out. -->
        <effectiveTime value="200004071300"/>
        <!-- Required by CDA, and is the time of document creation, which isn't
necessarily the same as the time of order creation. -->
        <confidentialityCode code="N" codeSystem="2.16.840.1.113883.5.25"/>
        <recordTarget>
            <patientRole>
                <id extension="12345" root="76b242b9-1246-4691-bb1d-91bb7336e76f"/>
<!-- HIN patient ID -->
                <id extension="97531" root="81821f47-8139-4766-aff0-81be0674de8f"/>
<!-- Local patient ID -->
                <patient>
                    <name>
                        <given>Henry</given>
                        <family>Levin</family>
                        <suffix>the 7th</suffix>
                    </name>
                    <administrativeGenderCode code="M"
codeSystem="2.16.840.1.113883.5.1"/>
                    <birthTime value="19320924"/>
                </patient>
            </patientRole>
        </recordTarget>
        <author>
```

```
                <time value="200004071300"/>
                <assignedAuthor>
                        <id extension="2223222" root="76b242b9-1246-4691-bb1d-91bb7336e76f"/>
<!-- HIN provider ID -->
                        <id extension="34455655443" root="81821f47-8139-4766-aff0-
81be0674de8f"/> <!-- Local provider ID -->
                        <assignedPerson>
                                <name>
                                        <given>Robert</given>
                                        <family>Doctor</family>
                                        <suffix>MD</suffix>
                                </name>
                        </assignedPerson>
                </assignedAuthor>
        </author>
        <!-- I've made the author of the Order the author of the entire document. -->
        <custodian>
                <assignedCustodian>
                        <representedCustodianOrganization>
                                <id extension="81821f47-8139-4766-aff0-81be0674de8f"
root="76b242b9-1246-4691-bb1d-91bb7336e76f"/> <!-- HIN ID -->
                                <id root="81821f47-8139-4766-aff0-81be0674de8f"/> <!-- Local
ID -->
                                <name>Good Health Clinic</name>
                        </representedCustodianOrganization>
                </assignedCustodian>
        </custodian>
        <!-- HIN's id.extension equals Local's id.root. -->
        <legalAuthenticator>
                <time value="200004071300"/>
                <signatureCode code="S"/>
                <assignedEntity>
                        <id extension="2223222" root="76b242b9-1246-4691-bb1d-91bb7336e76f"/>
<!-- HIN provider ID -->
                        <id extension="34455655443" root="81821f47-8139-4766-aff0-
81be0674de8f"/> <!-- Local provider ID -->
                        <assignedPerson>
                                <name>
                                        <given>Robert</given>
                                        <family>Doctor</family>
                                        <suffix>MD</suffix>
                                </name>
                        </assignedPerson>
                </assignedEntity>
        </legalAuthenticator>
        <!-- Indicates that the order has been signed. -->
        <componentOf>
                <encompassingEncounter>
                        <id extension="18f649a0" root="76b242b9-1246-4691-bb1d-
91bb7336e76f"/> <!-- HIN encounter ID -->
                        <id extension="22222" root="81821f47-8139-4766-aff0-81be0674de8f"/>
<!-- Local encounter ID -->
                        <code code="AMB" codeSystem="2.16.840.1.113883.5.4"
displayName="Ambulatory"/>
                        <effectiveTime>
                                <low value="200004071300"/>
                        </effectiveTime>
                        <encounterParticipant typeCode="ATND">
                                <assignedEntity>
                                        <id extension="2223222" root="76b242b9-1246-4691-bb1d-
91bb7336e76f"/> <!-- HIN provider ID -->
                                        <id extension="34455655443" root="81821f47-8139-4766-
aff0-81be0674de8f"/> <!-- Local provider ID -->
                                        <assignedPerson>
                                                <name>
                                                        <given>Robert</given>
                                                        <family>Doctor</family>
                                                        <suffix>MD</suffix>
                                                </name>
                                        </assignedPerson>
                                </assignedEntity>
                        </encounterParticipant>
                        <location>
                                <healthCareFacility classCode="DSDLOC">
                                        <code code="GIM" codeSystem="2.16.840.1.113883.5.10588"
displayName="General internal medicine clinic"/>
                                </healthCareFacility>
                        </location>
                </encompassingEncounter>
```

```
        </componentOf>
        <!-- Different workflows may determine whether or not an order always occurs
within the context of an encounter. -->
        <!--
************************************************************
CDA Body
************************************************************
-->
        <component>
            <structuredBody>
                <!--
************************************************************
Order section
************************************************************
-->
<component>
<section>
        <code code="18776-5" codeSystem="2.16.840.1.113883.6.1"/>
        <title>Plan</title>
        <text>
                <table border="1" width="100%">
                        <thead>
                                <tr><th>Order</th><th>Indication</th></tr>
                        </thead>
                        <tbody>
                                <tr><td>CT of brain</td><td>Headache</td></tr>
                        </tbody>
                </table>
        </text>
        <entry typeCode="DRIV">
        <!-- The "DRIV" relationship can be used to indicate that the narrative block is
fully derived from the structured entries. -->
                <observation classCode="OBS" moodCode="RQO">
                        <id extension="f377aa56-145f-4d6a-95d8-69ebdc51f0b4" root="76b242b9-
1246-4691-bb1d-91bb7336e76f"/> <!-- HIN order ID -->
                        <id extension="cb9ad034-52a7-453d-8bd3-1ea0af3a542a" root="81821f47-
8139-4766-aff0-81be0674de8f"/> <!-- Local order ID -->
                        <code code="34227000" codeSystem="2.16.840.1.113883.6.96"
displayName="CT of brain"/>
                        <statusCode code="new"/>
                        <effectiveTime value="200004071300"/>
                        <entryRelationship typeCode="RSON">
                        <!-- The "RSON" relationship can be used to show the reason or
indication for the test. -->
                                <observation classCode="COND" moodCode="EVN">
                                        <code code="ASSERTION"
codeSystem="2.16.840.1.113883.5.4"/>
                                        <statusCode code="completed"/>
                                        <value xsi:type="CE" code="25064002"
codeSystem="2.16.840.1.113883.6.96" displayName="Headache"/>
                                </observation>
                        </entryRelationship>
                </observation>
        </entry>
</section>
</component>
</structuredBody>
</component>
</ClinicalDocument>
```

Another example schema definition for the Order canonical (or relevant portion thereof) relates to a lab order of a specimen (like blood):

```
<?xml version="1.0"?>
<?xml-stylesheet type="text/xsl" href="CDA.xsl"?>
<!-- The following sample document depicts a fictional character's health summary. Any
resemblance to a real person is coincidental. -->
<!--
Henry Levin the 7th goes to see his primary care doctor, Dr. Doctor, complaining of
headache.
Dr. Doctor diagnoses Henry Levin the 7th as having probable migraine, but orders a CT
scan of the head to rule out a brain tumor.
Henry Levin the 7th leaves the office, and Dr. Doctor writes a visit note.
Several days later, the CT scan is performed and a report comes back to Dr. Doctor,
showing that there is no brain tumor.
```

```
HIN SysID = 76b242b9-1246-4691-bb1d-91bb7336e76f
Local SysID = 81821f47-8139-4766-aff0-81be0674de8f
-->
<ClinicalDocument xmlns="urn:hl7-org:v3" xmlns:voc="urn:hl7-org:v3/voc"
xmlns:xsi="http://www.w3.org/2001/XMLSchema-instance" xsi:schemaLocation="urn:hl7-org:v3
CDA.xsd">
        <!--
***********************************************************
CDA Header
***********************************************************
-->
        <typeId root="2.16.840.1.113883.1.3" extension="POCD_HD000040"/>
        <!-- typeId is required in all CDA instances, and fixed as shown here. This is how
you know the instance is a CDA R2 document. -->
        <id root="320eb621-bf5e-41d4-97b5-62c2ac359891" extension="eb7b661b-d302-4c71-
a672-d5b7b5833e3f"/>
        <!-- ClinicalDocument.id has cardinality 1..1, and carries the Local ID. -->
        <code code="119270007" codeSystem="2.16.840.1.113883.6.96" displayName="Management
procedure"/>
        <!-- This can be a fixed code, since the type of order is included below. There
may be those that are using CDA for prescriptions, in which case they may be using a
different code. -->
        <title>Good Health Clinic Order Report</title>
        <!-- This can be a fixed value, used for rendering, or could be left out. -->
        <effectiveTime value="200004071300"/>
        <!-- Required by CDA, and is the time of document creation, which isn't
necessarily the same as the time of order creation. -->
        <confidentialitycode code="N" codeSystem="2.16.840.1.113883.5.25"/>
        <recordTarget>
                <patientRole>
                        <id extension="12345" root="76b242b9-1246-4691-bb1d-91bb7336e76f"/>
<!-- HIN patient ID -->
                        <id extension="97531" root="81821f47-8139-4766-aff0-81be0674de8f"/>
<!-- Local patient ID -->
                        <patient>
                                <name>
                                        <given>Henry</given>
                                        <family>Levin</family>
                                        <suffix>the 7th</suffix>
                                </name>
                                <administrativeGenderCode code="M"
codeSystem="2.16.840.1.113883.5.1"/>
                                <birthTime value="19320924"/>
                        </patient>
                </patientRole>
        </recordTarget>
        <author>
                <time value="200004071300"/>
                <assignedAuthor>
                        <id extension="2223222" root="76b242b9-1246-4691-bb1d-91bb7336e76f"/>
<!-- HIN provider ID -->
                        <id extension="34455655443" root="81821f47-8139-4766-aff0-
81be0674de8f"/> <!-- Local provider ID -->
                        <assignedPerson>
                                <name>
                                        <given>Robert</given>
                                        <family>Doctor</family>
                                        <suffix>MD</suffix>
                                </name>
                        </assignedPerson>
                </assignedAuthor>
        </author>
        <!-- I've made the author of the Order the author of the entire document. -->
        <custodian>
                <assignedCustodian>
                        <representedCustodianOrganization>
                                <id extension="81821f47-8139-4766-aff0-81be0674de8f"
root="76b242b9-1246-4691-bb1d-91bb7336e76f"/> <!-- HIN ID -->
                                <id root="81821f47-8139-4766-aff0-81be0674de8f"/> <!-- Local
ID -->
                                <name>Good Health Clinic</name>
                        </representedCustodianOrganization>
                </assignedCustodian>
        </custodian>
        <!-- HIN's id.extension equals Local's id.root. -->
        <legalAuthenticator>
                <time value="200004071300"/>
                <signatureCode code="S"/>
                <assignedEntity>
```

-continued

```
                <id extension="2223222" root="76b242b9-1246-4691-bb1d-91bb7336e76f"/>
<!-- HIN provider ID -->
                <id extension="34455655443" root="81821f47-8139-4766-aff0-81be0674de8f"/> <!-- Local provider ID -->
                <assignedPerson>
                    <name>
                        <given>Robert</given>
                        <family>Doctor</family>
                        <suffix>MD</suffix>
                    </name>
                </assignedPerson>
            </assignedEntity>
    </legalAuthenticator>
    <!-- Indicates that the order has been signed. -->
    <componentOf>
        <encompassingEncounter>
            <id extension="18f649a0" root="76b242b9-1246-4691-bb1d-91bb7336e76f"/> <!-- HIN encounter ID -->
            <id extension="22222" root="81821f47-8139-4766-aff0-81be0674de8f"/> <!-- Local encounter ID -->
            <code code="AMB" codeSystem="2.16.840.1.113883.5.4" displayName="Ambulatory"/>
            <effectiveTime>
                <low value="200004071300"/>
            </effectiveTime>
            <encounterParticipant typeCode="ATND">
                <assignedEntity>
                    <id extension="2223222" root="76b242b9-1246-4691-bb1d-91bb7336e76f"/> <!-- HIN provider ID -->
                    <id extension="34455655443" root="81821f47-8139-4766-aff0-81be0674de8f"/> <!-- Local provider ID -->
                    <assignedPerson>
                        <name>
                            <given>Robert</given>
                            <family>Doctor</family>
                            <suffix>MD</suffix>
                        </name>
                    </assignedPerson>
                </assignedEntity>
            </encounterParticipant>
            <location>
                <healthCareFacility classCode="DSDLOC">
                    <code code="GIM" codeSystem="2.16.840.1.113883.5.10588" displayName="General internal medicine clinic"/>
                </healthCareFacility>
            </location>
        </encompassingEncounter>
    </componentOf>
    <!-- Different workflows may determine whether or not an order always occurs
within the context of an encounter. -->
    <!--
**********************************************************
CDA Body
**********************************************************
-->
    <component>
        <structuredBody>
            <!--
**********************************************************
Order section
**********************************************************
-->
<component>
<section>
    <code code="18776-5" codeSystem="2.16.840.1.113883.6.1"/>
    <title>Plan</title>
    <text>Serum electrolytes</text>
    <entry>
        <observation classCode="OBS" moodCode="RQO">
            <id extension="c8e40a81-3698-4f0e-86c0-c805468a8524" root="76b242b9-1246-4691-bb1d-91bb7336e76f"/> <!-- HIN order ID -->
            <id extension="db52f2bd-5c3e-45ff-accd-6e141561a40b" root="81821f47-8139-4766-aff0-81be0674de8f"/> <!-- Local order ID -->
            <code code="20109005" codeSystem="2.16.840.1.113883.6.96" displayName="Serum electrolytes">
                <translation code="80051" codeSystem="2.16.840.1.113883.6.12" codeSystemName="CPT4"/>
            </code>
            <statusCode code="new"/>
```

```
                <effectiveTime value="200004071300"/>
            </observation>
        </entry>
    </section>
</component>
</structuredBody>
</component>
</ClinicalDocument>
```

Another example schema definition for the Order canonical (or relevant portion thereof) relates to a procedure order, for example physical therapy, and in the case below, a pulmonary study:

```
<?xml version="1.0"?>
<?xml-stylesheet type="text/xsl" href="CDA.xsl"?>
<!-- The following sample document depicts a fictional character's health summary. Any
resemblance to a real person is coincidental. -->
<!--
Henry Levin the 7th goes to see his primary care doctor, Dr. Doctor, complaining of
headache.
Dr. Doctor diagnoses Henry Levin the 7th as having probable migraine, but orders a CT
scan of the head to rule out a brain tumor.
Henry Levin the 7th leaves the office, and Dr. Doctor writes a visit note.
Several days later, the CT scan is performed and a report comes back to Dr. Doctor,
showing that there is no brain tumor.
HIN SysID = 76b242b9-1246-4691-bb1d-91bb7336e76f
Local SysID = 81821f47-8139-4766-aff0-81be0674de8f
-->
<ClinicalDocument xmlns="urn:hl7-org:v3" xmlns:voc="urn:hl7-org:v3/voc"
xmlns:xsi="http://www.w3.org/2001/XMLSchema-instance" xsi:schemaLocation="urn:hl7-org:v3
CDA.xsd">
    <!--
***********************************************************
CDA Header
***********************************************************
-->
    <typeId root="2.16.840.1.113883.1.3" extension="POCD_HD000040"/>
    <!-- typeId is required in all CDA instances, and fixed as shown here. This is how
you know the instance is a CDA R2 document. -->
    <id root="320eb621-bf5e-41d4-97b5-62c2ac359891" extension="eb7b661b-d302-4c71-a672-d5b7b5833e3f"/>
    <!-- ClinicalDocument.id has cardinality 1..1, and carries the Local ID. -->
    <code code="119270007" codeSystem="2.16.840.1.113883.6.96" displayName="Management procedure"/>
    <!-- This can be a fixed code, since the type of order is included below. There
may be those that are using CDA for prescriptions, in which case they may be using a
different code. -->
    <title>Good Health Clinic Order Report</title>
    <!-- This can be a fixed value, used for rendering, or could be left out. -->
    <effectiveTime value="200004071300"/>
    <!-- Required by CDA, and is the time of document creation, which isn't
necessarily the same as the time of order creation. -->
    <confidentialitycode code="N" codeSystem="2.16.840.1.113883.5.25"/>
    <recordTarget>
        <patientRole>
            <id extension="12345" root="76b242b9-1246-4691-bb1d-91bb7336e76f"/>
<!-- HIN patient ID -->
            <id extension="97531" root="81821f47-8139-4766-aff0-81be0674de8f"/>
<!-- Local patient ID -->
            <patient>
                <name>
                    <given>Henry</given>
                    <family>Levin</family>
                    <suffix>the 7th</suffix>
                </name>
                <administrativeGenderCode code="M"
codeSystem="2.16.840.1.113883.5.1"/>
                <birthTime value="19320924"/>
            </patient>
        </patientRole>
    </recordTarget>
    <author>
        <time value="200004071300"/>
        <assignedAuthor>
            <id extension="2223222" root="76b242b9-1246-4691-bb1d-91bb7336e76f"/>
```

```
<!-- HIN provider ID -->
                <id extension="34455655443" root="81821f47-8139-4766-aff0-
81be0674de8f"/> <!-- Local provider ID -->
                <assignedPerson>
                        <name>
                                <given>Robert</given>
                                <family>Doctor</family>
                                <suffix>MD</suffix>
                        </name>
                </assignedPerson>
        </assignedAuthor>
    </author>
    <!-- I've made the author of the Order the author of the entire document. -->
    <custodian>
        <assignedCustodian>
                <representedCustodianOrganization>
                        <id extension="81821f47-8139-4766-aff0-81be0674de8f"
root="76b242b9-1246-4691-bb1d-91bb7336e76f"/> <!-- HIN ID -->
                        <id root="81821f47-8139-4766-aff0-81be0674de8f"/> <!-- Local
ID -->
                        <name>Good Health Clinic</name>
                </representedCustodianOrganization>
        </assignedCustodian>
    </custodian>
    <!-- HIN's id.extension equals Local's id.root. -->
    <legalAuthenticator>
        <time value="200004071300"/>
        <signatureCode code="S"/>
        <assignedEntity>
                <id extension="2223222" root="76b242b9-1246-4691-bb1d-91bb7336e76f"/>
<!-- HIN provider ID -->
                <id extension="34455655443" root="81821f47-8139-4766-aff0-
81be0674de8f"/> <!-- Local provider ID -->
                <assignedPerson>
                        <name>
                                <given>Robert</given>
                                <family>Doctor</family>
                                <suffix>MD</suffix>
                        </name>
                </assignedPerson>
        </assignedEntity>
    </legalAuthenticator>
    <!-- Indicates that the order has been signed. -->
    <componentOf>
        <encompassingEncounter>
                <id extension="18f649a0" root="76b242b9-1246-4691-bb1d-
91bb7336e76f"/> <!-- HIN encounter ID -->
                <id extension="22222" root="81821f47-8139-4766-aff0-81be0674de8f"/>
<!-- Local encounter ID -->
                <code code="AMB" codeSystem="2.16.840.1.113883.5.4"
displayName="Ambulatory"/>
                <effectiveTime>
                        <low value="200004071300"/>
                </effectiveTime>
                <encounterParticipant typeCode="ATND">
                        <assignedEntity>
                                <id extension="2223222" root="76b242b9-1246-4691-bb1d-
91bb7336e76f"/> <!-- HIN provider ID -->
                                <id extension="34455655443" root="81821f47-8139-4766-
aff0-81be0674de8f"/> <!-- Local provider ID -->
                                <assignedPerson>
                                        <name>
                                                <given>Robert</given>
                                                <family>Doctor</family>
                                                <suffix>MD</suffix>
                                        </name>
                                </assignedPerson>
                        </assignedEntity>
                </encounterParticipant>
                <location>
                        <healthCareFacility classCode="DSDLOC">
                                <code code="GIM" codeSystem="2.16.840.1.113883.5.10588"
displayName="General internal medicine clinic"/>
                        </healthCareFacility>
                </location>
        </encompassingEncounter>
    </componentOf>
    <!-- Different workflows may determine whether or not an order always occurs
within the context of an encounter. -->
```

-continued

```
        <!--
***********************************************************
CDA Body
***********************************************************
-->
        <component>
            <structuredBody>
                <!--
***********************************************************
Order section
***********************************************************
-->
<component>
<section>
        <code code="18776-5" codeSystem="2.16.840.1.113883.6.1"/>
        <title>Plan</title>
        <text>Pulmonary function study</text>
        <entry>
                <observation classCode="OBS" moodCode="RQO">
                        <id extension="f5470d54-7a99-4a74-af44-a91bfc2cdb46" root="76b242b9-1246-4691-bb1d-91bb7336e76f"/> <!-- HIN order ID -->
                        <id extension="c1cb1553-55fe-452b-a31f-4394a9b25530" root="81821f47-8139-4766-aff0-81be0674de8f"/> <!-- Local order ID -->
                        <code code="23426006" codeSystem="2.16.840.1.113883.6.96" displayName="Pulmonary function study"/>
                        <statusCode code="new"/>
                        <effectiveTime value="200004071300"/>
                        <entryRelationship typeCode="RSON">
                                <observation classCode="COND" moodCode="EVN">
                                        <code code="ASSERTION" codeSystem="2.16.840.1.113883.5.4"/>
                                        <statusCode code="completed"/>
                                        <value xsi:type="CE" code="68154008" codeSystem="2.16.840.1.113883.6.96" displayName="Chronic cough"/>
                                </observation>
                        </entryRelationship>
                </observation>
        </entry>
</section>
</component>
</structuredBody>
</component>
</ClinicalDocument>
```

Another example schema definition for the Order canonical (or relevant portion thereof) relates to a medication/drug order, for example for pain killers:

```
<?xml version="1.0"?>
<?xml-stylesheet type="text/xsl" href="CDA.xsl"?>
<!-- The following sample document depicts a fictional character's health summary. Any
resemblance to a real person is coincidental. -->
<!--
Henry Levin the 7th goes to see his primary care doctor, Dr. Doctor, complaining of
headache.
Dr. Doctor diagnoses Henry Levin the 7th as having probable migraine, but orders a CT
scan of the head to rule out a brain tumor.
Henry Levin the 7th leaves the office, and Dr. Doctor writes a visit note.
Several days later, the CT scan is performed and a report comes back to Dr. Doctor,
showing that there is no brain tumor.
HIN SysID = 76b242b9-1246-4691-bb1d-91bb7336e76f
Local SysID = 81821f47-8139-4766-aff0-81be0674de8f
-->
<ClinicalDocument xmlns="urn:hl7-org:v3" xmlns:voc="urn:hl7-org:v3/voc"
xmlns:xsi="http://www.w3.org/2001/XMLSchema-instance" xsi:schemaLocation="urn:hl7-org:v3
CDA.xsd">
        <!--
***********************************************************
CDA Header
***********************************************************
-->
        <typeId root="2.16.840.1.113883.1.3" extension="POCD_HD000040"/>
        <!-- typeId is required in all CDA instances, and fixed as shown here. This is how
you know the instance is a CDA R2 document. -->
        <id root="9f1d7ce5-37c0-4da6-9364-380704a9f017" extension="eb7b661b-d302-4c71-a672-d5b7b5833e3f"/>
```

```xml
<!-- ClinicalDocument.id has cardinality 1..1, and carries the Local ID. -->
<code code="119270007" codeSystem="2.16.840.1.113883.6.96" displayName="Management procedure"/>
<!-- This can be a fixed code, since the type of order is included below. There may be those that are using CDA for prescriptions, in which case they may be using a different code. -->
<title>Good Health Clinic Order Report</title>
<!-- This can be a fixed value, used for rendering, or could be left out. -->
<effectiveTime value="200004071300"/>
<!-- Required by CDA, and is the time of document creation, which isn't necessarily the same as the time of order creation. -->
<confidentialitycode code="N" codeSystem="2.16.840.1.113883.5.25"/>
<recordTarget>
    <patientRole>
        <id extension="12345" root="76b242b9-1246-4691-bb1d-91bb7336e76f"/> <!-- HIN patient ID -->
        <id extension="97531" root="81821f47-8139-4766-aff0-81be0674de8f"/> <!-- Local patient ID -->
        <patient>
            <name>
                <given>Henry</given>
                <family>Levin</family>
                <suffix>the 7th</suffix>
            </name>
            <administrativeGenderCode code="M" codeSystem="2.16.840.1.113883.5.1"/>
            <birthTime value="19320924"/>
        </patient>
    </patientRole>
</recordTarget>
<author>
    <time value="200004071300"/>
    <assignedAuthor>
        <id extension="2223222" root="76b242b9-1246-4691-bb1d-91bb7336e76f"/> <!-- HIN provider ID -->
        <id extension="34455655443" root="81821f47-8139-4766-aff0-81be0674de8f"/> <!-- Local provider ID -->
        <assignedPerson>
            <name>
                <given>Robert</given>
                <family>Doctor</family>
                <suffix>MD</suffix>
            </name>
        </assignedPerson>
    </assignedAuthor>
</author>
<!-- I've made the author of the Order the author of the entire document. -->
<custodian>
    <assignedCustodian>
        <representedCustodianOrganization>
            <id extension="81821f47-8139-4766-aff0-81be0674de8f" root="76b242b9-1246-4691-bb1d-91bb7336e76f"/> <!-- HIN ID -->
            <id root="81821f47-8139-4766-aff0-81be0674de8f"/> <!-- Local ID -->
            <name>Good Health Clinic</name>
        </representedCustodianOrganization>
    </assignedCustodian>
</custodian>
<!-- HIN's id.extension equals Local's id.root. -->
<legalAuthenticator>
    <time value="200004071300"/>
    <signatureCode code="S"/>
    <assignedEntity>
        <id extension="2223222" root="76b242b9-1246-4691-bb1d-91bb7336e76f"/> <!-- HIN provider ID -->
        <id extension="34455655443" root="81821f47-8139-4766-aff0-81be0674de8f"/> <!-- Local provider ID -->
        <assignedPerson>
            <name>
                <given>Robert</given>
                <family>Doctor</family>
                <suffix>MD</suffix>
            </name>
        </assignedPerson>
    </assignedEntity>
</legalAuthenticator>
<!-- Indicates that the order has been signed. -->
<componentOf>
    <encompassingEncounter>
```

```
                    <id extension="18f649a0" root="76b242b9-1246-4691-bb1d-
91bb7336e76f"/> <!-- HIN encounter ID -->
                    <id extension="22222" root="81821f47-8139-4766-aff0-81be0674de8f"/>
<!-- Local encounter ID -->
                    <code code="AMB" codeSystem="2.16.840.1.113883.5.4"
displayName="Ambulatory"/>
                    <effectiveTime>
                            <low value="200004071300"/>
                    </effectiveTime>
                    <encounterParticipant typeCode="ATND">
                            <assignedEntity>
                                    <id extension="2223222" root="76b242b9-1246-4691-bb1d-
91bb7336e76f"/> <!-- HIN provider ID -->
                                    <id extension="34455655443" root="81821f47-8139-4766-
aff0-81be0674de8f"/> <!-- Local provider ID -->
                                    <assignedPerson>
                                            <name>
                                                    <given>Robert</given>
                                                    <family>Doctor</family>
                                                    <suffix>MD</suffix>
                                            </name>
                                    </assignedPerson>
                            </assignedEntity>
                    </encounterParticipant>
                    <location>
                            <healthCareFacility classCode="DSDLOC">
                                    <code code="GIM" codeSystem="2.16.840.1.113883.5.10588"
displayName="General internal medicine clinic"/>
                            </healthCareFacility>
                    </location>
            </encompassingEncounter>
    </componentOf>
    <!-- Different workflows may determine whether or not an order always occurs
within the context of an encounter. -->
    <!--
**********************************************************
CDA Body
**********************************************************
-->
    <component>
            <structuredBody>
                    <!--
**********************************************************
Order section
**********************************************************
-->
<component>
<section>
    <code code="18776-5" codeSystem="2.16.840.1.113883.6.1"/>
    <title>Plan</title>
    <text>Lisinopril (Zestril) 5mg tablet, 1 tablet a day PO; Dispense 60; 3
Refills.</text>
    <entry>
            <substanceAdministration classCode="SBADM" moodCode="RQO">
                    <id extension="4addabf3-7249-4e50-a9ae-8f40462a4117" root="76b242b9-
1246-4691-bb1d-91bb7336e76f"/> <!-- HIN order ID -->
                    <id extension="811f5ff6-33b2-4251-9646-5e6dd4a192af" root="81821f47-
8139-4766-aff0-81be0674de8f"/> <!-- Local order ID -->
                    <statusCode code="active"/>
                    <effectiveTime value="200004071300"/>
                    <effectiveTime xsi:type="PIVL_TS" operator="A">
                            <period value="24" unit="h"/>
                    </effectiveTime>
                    <routeCode code="PO" codeSystem="2.16.840.1.113883.5.112"
codeSystemName="RouteOfAdministration"/>
                    <doseQuantity value="1"/>
                    <consumable>
                            <manufacturedProduct>
                                    <manufacturedMaterial>
                                            <code code="311354"
codeSystem="2.16.840.1.113883.6.88" codeSystemName="RxNorm" displayName="Lisinopril 5 MG
oral tablet">
                                                    <originalText>Lisinopril</originalText>
                                            </code>
                                            <name>Zestril</name>
                                    </manufacturedMaterial>
                            </manufacturedProduct>
                    </consumable>
                    <entryRelationship typeCode="COMP">
```

```
                    <supply classCode="SPLY" moodCode="RQO">
                        <repeatNumber>
                            <low value="0"/>
                            <high value="4"/>
                        </repeatNumber>
                        <quantity value="60"/>
                    </supply>
                </entryRelationship>
            </substanceAdministration>
        </entry>
    </section>
</component>
</structuredBody>
</component>
</ClinicalDocument>
```

Another example schema definition for the Order canonical (or relevant portion thereof) relates to an encounter with a doctor/specialist:

```
<?xml version="1.0"?>
<?xml-stylesheet type="text/xsl" href="CDA.xsl"?>
<!-- The following sample document depicts a fictional character's health summary. Any
resemblance to a real person is coincidental. -->
<!--
Henry Levin the 7th goes to see his primary care doctor, Dr. Doctor, complaining of
headache.
Dr. Doctor diagnoses Henry Levin the 7th as having probable migraine, but orders a CT
scan of the head to rule out a brain tumor.
Henry Levin the 7th leaves the office, and Dr. Doctor writes a visit note.
Several days later, the CT scan is performed and a report comes back to Dr. Doctor,
showing that there is no brain tumor.
HIN SysID = 76b242b9-1246-4691-bb1d-91bb7336e76f
Local SysID = 81821f47-8139-4766-aff0-81be0674de8f
-->
<ClinicalDocument xmlns="urn:hl7-org:v3" xmlns:voc="urn:hl7-org:v3/voc"
xmlns:xsi="http://www.w3.org/2001/XMLSchema-instance" xsi:schemaLocation="urn:hl7-org:v3
CDA.xsd">
        <!--
*********************************************************
CDA Header
*********************************************************
-->
        <typeId root="2.16.840.1.113883.1.3" extension="POCD_HD000040"/>
        <!-- typeId is required in all CDA instances, and fixed as shown here. This is how
you know the instance is a CDA R2 document. -->
        <id root="a17d7fa9-007a-4701-8e49-d65f479657da" extension="eb7b661b-d302-4c71-
a672-d5b7b5833e3f"/>
        <!-- ClinicalDocument.id has cardinality 1..1, and carries the Local ID. -->
        <code code="119270007" codeSystem="2.16.840.1.113883.6.96" displayName="Management
procedure"/>
        <!-- This can be a fixed code, since the type of order is included below. There
may be those that are using CDA for prescriptions, in which case they may be using a
different code. -->
        <title>Good Health Clinic Order Report</title>
        <!-- This can be a fixed value, used for rendering, or could be left out. -->
        <effectiveTime value="200004071300"/>
        <!-- Required by CDA, and is the time of document creation, which isn't
necessarily the same as the time of order creation. -->
        <confidentialityCode code="N" codeSystem="2.16.840.1.113883.5.25"/>
        <recordTarget>
            <patientRole>
                <id extension="12345" root="76b242b9-1246-4691-bb1d-91bb7336e76f"/>
<!-- HIN patient ID -->
                <id extension="97531" root="81821f47-8139-4766-aff0-81be0674de8f"/>
<!-- Local patient ID -->
                <patient>
                    <name>
                        <given>Henry</given>
                        <family>Levin</family>
                        <suffix>the 7th</suffix>
                    </name>
                    <administrativeGenderCode code="M"
codeSystem="2.16.840.1.113883.5.1"/>
                    <birthTime value="19320924"/>
                </patient>
```

```
                </patientRole>
        </recordTarget>
        <author>
                <time value="200004071300"/>
                <assignedAuthor>
                        <id extension="2223222" root="76b242b9-1246-4691-bb1d-91bb7336e76f"/>
<!-- HIN provider ID -->
                        <id extension="34455655443" root="81821f47-8139-4766-aff0-
81be0674de8f"/> <!-- Local provider ID -->
                        <assignedPerson>
                                <name>
                                        <given>Robert</given>
                                        <family>Doctor</family>
                                        <suffix>MD</suffix>
                                </name>
                        </assignedPerson>
                </assignedAuthor>
        </author>
        <!-- I've made the author of the Order the author of the entire document. -->
        <custodian>
                <assignedCustodian>
                        <representedCustodianOrganization>
                                <id extension="81821f47-8139-4766-aff0-81be0674de8f"
root="76b242b9-1246-4691-bb1d-91bb7336e76f"/> <!-- HIN ID -->
                                <id root="81821f47-8139-4766-aff0-81be0674de8f"/> <!-- Local
ID -->
                                <name>Good Health Clinic</name>
                        </representedCustodianOrganization>
                </assignedCustodian>
        </custodian>
        <!-- HIN's id.extension equals Local's id.root. -->
        <legalAuthenticator>
                <time value="200004071300"/>
                <signatureCode code="S"/>
                <assignedEntity>
                        <id extension="2223222" root="76b242b9-1246-4691-bb1d-91bb7336e76f"/>
<!-- HIN provider ID -->
                        <id extension="34455655443" root="81821f47-8139-4766-aff0-
81be0674de8f"/> <!-- Local provider ID -->
                        <assignedPerson>
                                <name>
                                        <given>Robert</given>
                                        <family>Doctor</family>
                                        <suffix>MD</suffix>
                                </name>
                        </assignedPerson>
                </assignedEntity>
        </legalAuthenticator>
        <!-- Indicates that the order has been signed. -->
        <componentOf>
                <encompassingEncounter>
                        <id extension="18f649a0" root="76b242b9-1246-4691-bb1d-
91bb7336e76f"/> <!-- HIN encounter ID -->
                        <id extension="22222" root="81821f47-8139-4766-aff0-81be0674de8f"/>
<!-- Local encounter ID -->
                        <code code="AMB" codeSystem="2.16.840.1.113883.5.4"
displayName="Ambulatory"/>
                        <effectiveTime>
                                <low value="200004071300"/>
                        </effectiveTime>
                        <encounterParticipant typeCode="ATND">
                                <assignedEntity>
                                        <id extension="2223222" root="76b242b9-1246-4691-bb1d-
91bb7336e76f"/> <!-- HIN provider ID -->
                                        <id extension="34455655443" root="81821f47-8139-4766-
aff0-81be0674de8f"/> <!-- Local provider ID -->
                                        <assignedPerson>
                                                <name>
                                                        <given>Robert</given>
                                                        <family>Doctor</family>
                                                        <suffix>MD</suffix>
                                                </name>
                                        </assignedPerson>
                                </assignedEntity>
                        </encounterParticipant>
                        <location>
                                <healthCareFacility classCode="DSDLOC">
                                        <code code="GIM" codeSystem="2.16.840.1.113883.5.10588"
displayName="General internal medicine clinic"/>
```

```
                </healthCareFacility>
            </location>
        </encompassingEncounter>
    </componentOf>
    <!-- Different workflows may determine whether or not an order always occurs
within the context of an encounter. -->
        <!--
************************************************************
CDA Body
************************************************************
-->
        <component>
            <structuredBody>
                <!--
************************************************************
Order section
************************************************************
-->
<component>
<section>
        <code code="18776-5" codeSystem="2.16.840.1.113883.6.1"/>
        <title>Plan</title>
        <text>Return visit in 2 weeks</text>
        <entry>
            <encounter classCode="ENC" moodCode="RQO">
                <id extension="1b98e875-1765-4ee9-9978-a337fd0e7e89" root="76b242b9-
1246-4691-bb1d-91bb7336e76f"/> <!-- HIN order ID -->
                <id extension="90fdaa33-f769-4ad9-b380-724f53534ed1" root="81821f47-
8139-4766-aff0-81be0674de8f"/> <!-- Local order ID -->
                <code code="185389009" codeSystem="2.16.840.1.113883.6.96"
codeSystemName="SNOMED CT" displayName="Follow-up visit"/>
                <effectiveTime value="20000428"/>
            </encounter>
        </entry>
</section>
</component>
</structuredBody>
</component>
</ClinicalDocument>
```

Another example schema definition for the Order canonical (or relevant portion thereof) relates to an order a durable medical good (like a wheelchair or a oxygen tank), and can have a structure that is similar to or the same as the fundamental structure described above with respect to one or more of the Encounter, Drug/Medication Order, Procure Order, and so forth, but in an exemplary embodiment can also use the CDA supply segment as the entry instead of an observation, substance administration, or encounter.

Exemplary incremental WSDL operations for the Order canonical can include: CancelOrder (input:orderID); DetectDuplicateOrders (input: byExampleCanonical, input: dateRange, output: listOfMatchingOrderCanonicals). The DetectDuplicateOrders function can use pattern matching to identify orders for the same thing over the specified order range; such as a CT scan in the last 90 days or electrolyte panel in the last 2 years.

In an exemplary embodiment, the Headwater platform for healthcare provides a software service definition or canonical for Encounter (Healthcare Specific Requirements/Services/Healthcare Core Enterprise Data Service/Encounter), for example to handle or relate to clinical findings and recommendations. The definition can include the data and common functions that deliver the service functionality. The service definition can include an H7 version 3.0 RIM compliant data structure with the functions to create, read, update and delete the data structure the service represents.

Ecounters include visit summaries with a doctor and includes results from labs (like specimen and imaging) as well as the outcome of procedures.

An exemplary schema definition of the Encounter canonical follows.

An example schema definition for the Encounter canonical (or relevant portion thereof) relates to (e.g.,) a baseline encounter where a patient presents with a chief complaint and the doctor records a note of the visit.

```xml
<?xml version="1.0"?>
<?xml-stylesheet type="text/xsl" href="CDA.xsl"?>
<!-- The following sample document depicts a fictional character's health summary. Any
resemblance to a real person is coincidental. -->

<!--
Henry Levin the 7th goes to see his primary care doctor, Dr. Doctor, complaining of
headache.

Dr. Doctor diagnoses Henry Levin the 7th as having probable migraine, but orders a CT
scan of the head to rule out a brain tumor.

Henry Levin the 7th leaves the office, and Dr. Doctor writes a visit note.

Several days later, the CT scan is performed and a report comes back to Dr. Doctor,
showing that there is no brain tumor.

HIN SysID = 76b242b9-1246-4691-bb1d-91bb7336e76f
Local SysID = 81821f47-8139-4766-aff0-81be0674de8f
-->

<ClinicalDocument xmlns="urn:hl7-org:v3" xmlns:voc="urn:hl7-org:v3/voc"
xmlns:xsi="http://www.w3.org/2001/XMLSchema-instance" xsi:schemaLocation="urn:hl7-org:v3
CDA.xsd">
        <!--
*******************************************************
CDA Header
*******************************************************
-->
        <typeId root="2.16.840.1.113883.1.3" extension="POCD_HD000040"/>
```

```xml
        <!-- typeId is required in all CDA instances, and fixed as shown here. This is how
you know the instance is a CDA R2 document. -->

<id root="586d112f-6ab9-4686-9e16-e6f07be172bc" extension="eb7b661b-d302-4c71-a672-d5b7b5833e3f"/>
        <!-- ClinicalDocument.id has cardinality 1..1, and carries the Local ID. -->

<code code="34108-1" codeSystem="2.16.840.1.113883.6.1" codeSystemName="LOINC"
displayName="Outpatient evaluation and management">
            <translation code="ABCDEF" codeSystem="2.16.840.1.113883.6.17"
codeSystemName="myLocalCodeSystem" displayName="Outpatient visit note"/>
        </code>
        <!-- LOINC document code and it's translated code from the "myLocalCodeSystem"
code system. -->

<title>Good Health Clinic Outpatient Evaluation and Management Note</title>

<effectiveTime value="200004071300"/>
        <!-- Required by CDA, and is the time of document creation, which isn't
necessarily the same as the time of the encounter. -->

<confidentialityCode code="N" codeSystem="2.16.840.1.113883.5.25"/>

<recordTarget>
            <patientRole>
                <id extension="12345" root="76b242b9-1246-4691-bb1d-91bb7336e76f"/>
<!-- HIN patient ID -->
                <id extension="97531" root="81821f47-8139-4766-aff0-81be0674de8f"/>
<!-- Local patient ID -->
                <patient>
                    <name>
                        <given>Henry</given>
                        <family>Levin</family>
                        <suffix>the 7th</suffix>
                    </name>
                    <administrativeGenderCode code="M"
codeSystem="2.16.840.1.113883.5.1"/>
                    <birthTime value="19320924"/>
                </patient>
```

```
                </patientRole>
        </recordTarget>

<author>
                <time value="200004071300"/>
                <assignedAuthor>
                        <id extension="2223222" root="76b242b9-1246-4691-bb1d-91bb7336e76f"/>
<!-- HIN provider ID -->
                        <id extension="34455655443" root="81821f47-8139-4766-aff0-
81be0674de8f"/> <!-- Local provider ID -->
                        <assignedPerson>
                                <name>
                                        <given>Robert</given>
                                        <family>Doctor</family>
                                        <suffix>MD</suffix>
                                </name>
                        </assignedPerson>
                </assignedAuthor>
        </author>

<custodian>
                <assignedCustodian>
                        <representedCustodianOrganization>
                                <id extension="81821f47-8139-4766-aff0-81be0674de8f"
root="76b242b9-1246-4691-bb1d-91bb7336e76f"/> <!-- HIN ID -->
                                <id root="81821f47-8139-4766-aff0-81be0674de8f"/> <!-- Local
ID -->
                                <name>Good Health Clinic</name>
                        </representedCustodianOrganization>
                </assignedCustodian>
        </custodian>
        <!-- HIN's id.extension equals Local's id.root. -->

<legalAuthenticator>
                <time value="200004071300"/>
                <signatureCode code="S"/>
                <assignedEntity>
                        <id extension="2223222" root="76b242b9-1246-4691-bb1d-91bb7336e76f"/>
<!-- HIN provider ID -->
```

```xml
            <id extension="34455655443" root="81821f47-8139-4766-aff0-
81be0674de8f"/> <!-- Local provider ID -->
            <assignedPerson>
                <name>
                    <given>Robert</given>
                    <family>Doctor</family>
                    <suffix>MD</suffix>
                </name>
            </assignedPerson>
        </assignedEntity>
    </legalAuthenticator>
    <!-- Indicates that the visit note has been signed. -->

<relatedDocument typeCode="XFRM">
        <parentDocument>
            <id extension="1f7c393a-41ca-4061-9c8f-f29743f8d641" root="81821f47-
8139-4766-aff0-81be0674de8f"/> <!-- Local original document ID -->
        </parentDocument>
    </relatedDocument>
    <!-- Where the source document already exists, and is being transformed into the
required exchange format, the relatedDocument element can be used to reference the
original source document. -->

<componentOf>
        <encompassingEncounter>
            <id extension="18f649a0" root="76b242b9-1246-4691-bb1d-
91bb7336e76f"/> <!-- HIN encounter ID -->
            <id extension="22222" root="81821f47-8139-4766-aff0-81be0674de8f"/>
<!-- Local encounter ID -->
            <code code="AMB" codeSystem="2.16.840.1.113883.5.4"
displayName="Ambulatory"/>
            <effectiveTime>
                <low value="200004071300"/>
            </effectiveTime>
            <encounterParticipant typeCode="ATND">
                <assignedEntity>
                    <id extension="2223222" root="76b242b9-1246-4691-bb1d-
91bb7336e76f"/> <!-- HIN provider ID -->
```

```xml
                                <id extension="34455655443" root="81821f47-8139-4766-
aff0-81be0674de8f"/> <!-- Local provider ID -->
                                <assignedPerson>
                                        <name>
                                                <given>Robert</given>
                                                <family>Doctor</family>
                                                <suffix>MD</suffix>
                                        </name>
                                </assignedPerson>
                        </assignedEntity>
                </encounterParticipant>
                <location>
                        <healthCareFacility classCode="DSDLOC">
                                <code code="GIM" codeSystem="2.16.840.1.113883.5.10588"
displayName="General internal medicine clinic"/>
                        </healthCareFacility>
                </location>
        </encompassingEncounter>
</componentOf>
<!--
**********************************************************
CDA Body
**********************************************************
-->
        <component>
                <structuredBody>
                        <!--
**********************************************************
 Chief Complaint section
**********************************************************
-->
<component>
<section>
        <code code="10154-3" codeSystem="2.16.840.1.113883.6.1"/>
        <title>Chief Complaint</title>
        <text>Headache</text>
        <entry>
                <observation classCode="COND" moodCode="EVN">
```

```xml
            <id extension="0beec93c-2bc7-457f-98ab-e9f5d5fab4d0" root="81821f47-8139-4766-aff0-81be0674de8f"/>
            <code code="ASSERTION" codeSystem="2.16.840.1.113883.5.4"/>
            <statusCode code="completed"/>
            <value xsi:type="CD" code="25064002" codeSystem="2.16.840.1.113883.6.96" displayName="Headache"/>
        </observation>
    </entry>
</section>
</component>
            <!--
********************************************************
 History of Present Illness section
********************************************************
-->
<component>
<section>
    <code code="10164-2" codeSystem="2.16.840.1.113883.6.1"/>
    <title>History of Present Illness</title>
    <text>Complaining of a persistent sharp left frontal headache that started yesterday.</text>
    <!-- This section is often not coded (i.e. no nested observations). -->
</section>
</component>
            <!--
********************************************************
 Physical Exam section
********************************************************
-->
<component>
<section>
    <code code="11384-5" codeSystem="2.16.840.1.113883.6.1"/>
    <title>Physical Examination</title>
    <text>Normal neurological exam</text>
    <entry>
        <observation classCode="COND" moodCode="EVN">
            <code code="84728005" codeSystem="2.16.840.1.113883.6.96" displayName="Neurological exam"/>
            <statusCode code="completed"/>
```

```xml
                <value xsi:type="CD" code="17621005"
codeSystem="2.16.840.1.113883.6.96" displayName="Normal"/>
            </observation>
        </entry>
</section>
</component>
            <!--
*********************************************************
 Assessment section
*********************************************************
-->
<component>
<section>
    <code code="11496-7" codeSystem="2.16.840.1.113883.6.1"/>
    <title>Assessment</title>
    <text>Headache - presumably a migraine, but will check a CT scan to rule out a
brain tumor.</text>
    <entry>
        <observation classCode="COND" moodCode="EVN">
            <id extension="d3248e9e-a502-43ab-963c-5e0c17f6a167" root="81821f47-
8139-4766-aff0-81be0674de8f"/>
            <!-- The observation.id for headache here isn't the same as the
observation.id for headache in the Chief Complaint section. They are considered separate
objects, that can be related. -->

<code code="ASSERTION" codeSystem="2.16.840.1.113883.5.4"/>
            <statusCode code="completed"/>
            <effectiveTime><low value="20000406"/></effectiveTime>
            <value xsi:type="CD" code="25064002"
codeSystem="2.16.840.1.113883.6.96" displayName="Headache"/>
        </observation>
    </entry>
</section>
</component>
            <!--
*********************************************************
 Plan section
*********************************************************
-->
```

```xml
<component>
<section>
    <code code="18776-5" codeSystem="2.16.840.1.113883.6.1"/>
    <title>Plan</title>
    <text>
        <list>
            <item>Serum electrolytes</item>
            <item>Pulmonary function study</item>
            <item>CT of brain (indication = headache)</item>
            <item>Return visit in 2 weeks</item>
            <item>Lisinopril (Zestril) 5mg tablet, 1 tablet a day PO; Dispense 60; 3 Refills.</item>
        </list>
    </text>
<!--
Serum electrolytes
-->
    <entry>
        <observation classCode="OBS" moodCode="RQO">
            <id extension="c8e40a81-3698-4f0e-86c0-c805468a8524" root="76b242b9-1246-4691-bb1d-91bb7336e76f"/> <!-- HIN order ID -->
            <id extension="db52f2bd-5c3e-45ff-accd-6e141561a40b" root="81821f47-8139-4766-aff0-81be0674de8f"/> <!-- Local order ID -->
            <code code="20109005" codeSystem="2.16.840.1.113883.6.96" displayName="Serum electrolytes">
                <translation code="80051" codeSystem="2.16.840.1.113883.6.12" codeSystemName="CPT4"/>
            </code>
            <!-- The first code is SNOMED. The second is CPT4. -->

<statusCode code="new"/>
            <effectiveTime value="200004071300"/>
        </observation>
    </entry>
<!--
Pulmonary function study
-->
    <entry>
        <observation classCode="OBS" moodCode="RQO">
```

```xml
                <id extension="f5470d54-7a99-4a74-af44-a91bfc2cdb46" root="76b242b9-1246-4691-bb1d-91bb7336e76f"/> <!-- HIN order ID -->
                <id extension="c1cb1553-55fe-452b-a31f-4394a9b25530" root="81821f47-8139-4766-aff0-81be0674de8f"/> <!-- Local order ID -->
                <code code="23426006" codeSystem="2.16.840.1.113883.6.96" displayName="Pulmonary function study"/>
                <statusCode code="new"/>
                <effectiveTime value="200004071300"/>
                <entryRelationship typeCode="RSON">
                    <observation classCode="COND" moodCode="EVN">
                        <code code="ASSERTION" codeSystem="2.16.840.1.113883.5.4"/>
                        <statusCode code="completed"/>
                        <value xsi:type="CE" code="68154008" codeSystem="2.16.840.1.113883.6.96" displayName="Chronic cough"/>
                    </observation>
                </entryRelationship>
            </observation>
        </entry>
<!--
CT of brain (indication = headache)
-->
        <entry>
            <observation classCode="OBS" moodCode="RQO">
                <id extension="f377aa56-145f-4d6a-95d8-69ebdc51f0b4" root="76b242b9-1246-4691-bb1d-91bb7336e76f"/> <!-- HIN order ID -->
                <id extension="cb9ad034-52a7-453d-8bd3-1ea0af3a542a" root="81821f47-8139-4766-aff0-81be0674de8f"/> <!-- Local order ID -->
                <code code="34227000" codeSystem="2.16.840.1.113883.6.96" displayName="CT of brain"/>
                <statusCode code="new"/>
                <effectiveTime value="200004071300"/>
                <entryRelationship typeCode="RSON">
                <!-- The "RSON" relationship can be used to show the reason or indication for the test. -->

<observation classCode="COND" moodCode="EVN">
                        <id extension="d3248e9e-a502-43ab-963c-5e0c17f6a167" root="81821f47-8139-4766-aff0-81be0674de8f"/>
```

```
                                      <code code="ASSERTION"
codeSystem="2.16.840.1.113883.5.4"/>
                                      <statusCode code="completed"/>
                                      <value xsi:type="CE" code="25064002"
codeSystem="2.16.840.1.113883.6.96" displayName="Headache"/>
                                 </observation>
                            </entryRelationship>
                       </observation>
             </entry>
<!--
Return visit in 2 weeks
-->
             <entry>
                  <encounter classCode="ENC" moodCode="RQO">
                       <id extension="1b98e875-1765-4ee9-9978-a337fd0e7e89" root="76b242b9-
1246-4691-bb1d-91bb7336e76f"/> <!-- HIN order ID -->
                       <id extension="90fdaa33-f769-4ad9-b380-724f53534ed1" root="81821f47-
8139-4766-aff0-81be0674de8f"/> <!-- Local order ID -->
                       <code code="185389009" codeSystem="2.16.840.1.113883.6.96"
codeSystemName="SNOMED CT" displayName="Follow-up visit"/>
                       <effectiveTime value="20000428"/>
                  </encounter>
             </entry>
<!--
Lisinopril (Zestril) 5mg tablet, 1 tablet a day PO; Dispense 60; 3 Refills.
-->
             <entry>
                  <substanceAdministration classCode="SBADM" moodCode="RQO">
                       <id extension="4addabf3-7249-4e50-a9ae-8f40462a4117" root="76b242b9-
1246-4691-bb1d-91bb7336e76f"/> <!-- HIN order ID -->
                       <id extension="811f5ff6-33b2-4251-9646-5e6dd4a192af" root="81821f47-
8139-4766-aff0-81be0674de8f"/> <!-- Local order ID -->
                       <statusCode code="active"/>
                       <effectiveTime value="200004071300"/>
                       <effectiveTime xsi:type="PIVL_TS" operator="A">
                            <period value="24" unit="h"/>
                       </effectiveTime>
                       <routeCode code="PO" codeSystem="2.16.840.1.113883.5.112"
codeSystemName="RouteOfAdministration"/>
```

```
                    <doseQuantity value="1"/>
                    <consumable>
                        <manufacturedProduct>
                            <manufacturedMaterial>
                                <code code="311354" codeSystem="2.16.840.1.113883.6.88" codeSystemName="RxNorm" displayName="Lisinopril 5 MG oral tablet">
                                    <originalText>Lisinopril</originalText>
                                </code>
                                <name>Zestril</name>
                            </manufacturedMaterial>
                        </manufacturedProduct>
                    </consumable>
                    <entryRelationship typeCode="COMP">
                        <supply classCode="SPLY" moodCode="RQO">
                            <repeatNumber>
                                <low value="0"/>
                                <high value="4"/>
                            </repeatNumber>
                            <quantity value="60"/>
                        </supply>
                    </entryRelationship>
                </substanceAdministration>
            </entry>
        </section>
    </component>
</structuredBody>
</component>
</ClinicalDocument>

<?xml version="1.0"?>
<?xml-stylesheet type="text/xsl" href="CDA.xsl"?>
<!-- The following sample document depicts a fictional character's health summary. Any resemblance to a real person is coincidental. -->
```

Another example schema definition for the Encounter canonical (or relevant portion thereof) relates to a result of a lab imaging encounter (like CT scan):

```
<!--
Henry Levin the 7th goes to see his primary care doctor, Dr. Doctor, complaining of
headache.

Dr. Doctor diagnoses Henry Levin the 7th as having probable migraine, but orders a CT
scan of the head to rule out a brain tumor.

Henry Levin the 7th leaves the office, and Dr. Doctor writes a visit note.

Several days later, the CT scan is performed and a report comes back to Dr. Doctor,
showing that there is no brain tumor.

HIN SysID = 76b242b9-1246-4691-bb1d-91bb7336e76f
Local SysID = 81821f47-8139-4766-aff0-81be0674de8f
-->

<!--
There are several emerging specifications related to the use of CDA for imaging, lab,
etc. For instance:

DICOM's CDA for imaging reports: http://www.hl7.org/lib_admin/admin_detail.cfm?ID=2899
IHE's CDA for lab reports: http://www.ihe.net/Technical%5FFramework/
-->

<ClinicalDocument xmlns="urn:hl7-org:v3" xmlns:voc="urn:hl7-org:v3/voc"
xmlns:xsi="http://www.w3.org/2001/XMLSchema-instance" xsi:schemaLocation="urn:hl7-org:v3
CDA.xsd">
        <!--
********************************************************
CDA Header
********************************************************
-->
        <typeId root="2.16.840.1.113883.1.3" extension="POCD_HD000040"/>
        <!-- typeId is required in all CDA instances, and fixed as shown here. This is how
you know the instance is a CDA R2 document. -->

<id root="5cc58dd0-f4bc-44ba-9a6b-613535ebac7e" extension="eb7b661b-d302-4c71-
a672-d5b7b5833e3f"/>
        <!-- ClinicalDocument.id has cardinality 1..1, and carries the Local ID. -->
```

```xml
<code code="18748-4" codeSystem="2.16.840.1.113883.6.1" displayName="Diagnostic Imaging Report"/>
<!-- This code will vary depending on the result report type. -->

<title>Good Health Clinic Diagnostic Imaging Report</title>

<effectiveTime value="200004100800"/>
<!-- The date/time of the imaging report reflects when the radiologist dictates or creates the report, so is typically later then the date/time the CT scan was actually performed. -->

<confidentialityCode code="N" codeSystem="2.16.840.1.113883.5.25"/>

<recordTarget>
    <patientRole>
        <id extension="12345" root="76b242b9-1246-4691-bb1d-91bb7336e76f"/> <!-- HIN patient ID -->
        <id extension="97531" root="81821f47-8139-4766-aff0-81be0674de8f"/> <!-- Local patient ID -->
        <patient>
            <name>
                <given>Henry</given>
                <family>Levin</family>
                <suffix>the 7th</suffix>
            </name>
            <administrativeGenderCode code="M" codeSystem="2.16.840.1.113883.5.1"/>
            <birthTime value="19320924"/>
        </patient>
    </patientRole>
</recordTarget>

<author>
    <time value="200004071300"/>
    <assignedAuthor>
        <id extension="32121d3e-63df-48f6-929a-7919c4c2f1c1" root="76b242b9-1246-4691-bb1d-91bb7336e76f"/> <!-- HIN ID -->
```

```xml
            <id extension="344111443" root="81821f47-8139-4766-aff0-
81be0674de8f"/> <!-- Local provider ID -->
            <assignedPerson>
                <name>
                    <given>Richard</given>
                    <family>Radiologist</family>
                    <suffix>MD</suffix>
                </name>
            </assignedPerson>
        </assignedAuthor>
    </author>

<custodian>
        <assignedCustodian>
            <representedCustodianOrganization>
                <id extension="81821f47-8139-4766-aff0-81be0674de8f"
root="76b242b9-1246-4691-bb1d-91bb7336e76f"/> <!-- HIN ID -->
                <id root="81821f47-8139-4766-aff0-81be0674de8f"/> <!-- Local
ID -->
                <name>Good Health Clinic</name>
            </representedCustodianOrganization>
        </assignedCustodian>
    </custodian>
    <!-- HIN's id.extension equals Local's id.root. -->

<legalAuthenticator>
        <time value="200004071300"/>
        <signatureCode code="S"/>
        <assignedEntity>
            <id extension="32121d3e-63df-48f6-929a-7919c4c2f1c1" root="76b242b9-
1246-4691-bb1d-91bb7336e76f"/> <!-- HIN ID -->
            <id extension="344111443" root="81821f47-8139-4766-aff0-
81be0674de8f"/> <!-- Local provider ID -->
            <assignedPerson>
                <name>
                    <given>Richard</given>
                    <family>Radiologist</family>
                    <suffix>MD</suffix>
                </name>
```

```xml
                </assignedPerson>
            </assignedEntity>
    </legalAuthenticator>

<inFulfillmentOf>
            <order>
                    <id extension="f377aa56-145f-4d6a-95d8-69ebdc51f0b4" root="76b242b9-1246-4691-bb1d-91bb7336e76f"/> <!-- HIN order ID -->
                    <id extension="cb9ad034-52a7-453d-8bd3-1ea0af3a542a" root="81821f47-8139-4766-aff0-81be0674de8f"/> <!-- Local order ID -->
                    <code code="34227000" codeSystem="2.16.840.1.113883.6.96" displayName="CT of brain"/>
            </order>
    </inFulfillmentOf>
    <!-- This is a reference back to the order ID (as opposed to the order document).
-->

<documentationOf>
            <serviceEvent>
                    <id extension="ce1e732e-0d2f-481d-b883-e9daa8342305" root="81821f47-8139-4766-aff0-81be0674de8f"/> <!-- Local procedure ID -->
                    <code code="396209004" codeSystem="2.16.840.1.113883.6.96" displayName="CT of brain with and without contrast"/>
                    <effectiveTime value="200004090930"/>
            </serviceEvent>
    </documentationOf>
    <!-- This shows the procedure that was actually performed, and the date/time of
the procedure. Note that there are several identifiers for radiology procedures: Order
ID, Report ID, Study ID (or Procedure ID - used here to populate serviceEvent/code),
Series ID, Instance (or Image) ID. A Study has one to many Series, which contains one to
many Instances (or Images). DICOM servers are supposed to be able to support queries for
Study ID, Series ID, or Instance ID. -->

<!--
*********************************************************
CDA Body
*********************************************************
-->
    <component>
```

```xml
<structuredBody>
    <!--
    ********************************************************************
    Findings Section
    ********************************************************************
    -->
    <component>
    <section>
        <code code="18782-3" codeSystem="2.16.840.1.113883.6.1"/>
        <title>Radiology findings</title>
        <text>No abnormalities or mass noted</text>
        <!-- This section is often not coded (i.e. no nested observations). -->
    </section>
    </component>
    <!--
    ********************************************************************
    Assessment Section
    ********************************************************************
    -->
    <component>
    <section>
        <code code="11496-7" codeSystem="2.16.840.1.113883.6.1"/>
        <title>Assessment</title>
        <text>Normal CT of brain with and without contrast.</text>
        <entry>
            <observation classCode="COND" moodCode="EVN">
                <code code="396209004" codeSystem="2.16.840.1.113883.6.96" displayName="CT of brain with and without contrast"/>
                <statusCode code="completed"/>
                <value xsi:type="CD" code="17621005" codeSystem="2.16.840.1.113883.6.96" displayName="Normal"/>
            </observation>
        </entry>
    </section>
    </component>
</structuredBody>
</component>
</ClinicalDocument>
```

```
<?xml version="1.0"?>
<?xml-stylesheet type="text/xsl" href="CDA.xsl"?>
<!-- The following sample document depicts a fictional character's health summary. Any
resemblance to a real person is coincidental. -->

<!--
Henry Levin the 7th goes to see his primary care doctor, Dr. Doctor, complaining of
headache.

Dr. Doctor diagnoses Henry Levin the 7th as having probable migraine, but orders a CT
scan of the head to rule out a brain tumor.

Henry Levin the 7th leaves the office, and Dr. Doctor writes a visit note.

Several days later, the CT scan is performed and a report comes back to Dr. Doctor,
showing that there is no brain tumor.

HIN SysID = 76b242b9-1246-4691-bb1d-91bb7336e76f
Local SysID = 81821f47-8139-4766-aff0-81be0674de8f
-->

<!--
There are several emerging specifications related to the use of CDA for imaging, lab,
etc. For instance:

DICOM's CDA for imaging reports: http://www.hl7.org/lib_admin/admin_detail.cfm?ID=2899
IHE's CDA for lab reports: http://www.ihe.net/Technical%5FFramework/
-->

<ClinicalDocument xmlns="urn:hl7-org:v3" xmlns:voc="urn:hl7-org:v3/voc"
xmlns:xsi="http://www.w3.org/2001/XMLSchema-instance" xmlns:sdtc="urn:hl7-org:sdtc"
xsi:schemaLocation="urn:hl7-org:v3 CDALab.xsd">
        <!--
********************************************************
```

```
CDA Header
***********************************************************
-->
        <typeId root="2.16.840.1.113883.1.3" extension="POCD_HD000040"/>
        <!-- typeId is required in all CDA instances, and fixed as shown here. This is how
you know the instance is a CDA R2 document. -->

<id root="5cc58dd0-f4bc-44ba-9a6b-613535ebac7e" extension="eb7b661b-d302-4c71-
a672-d5b7b5833e3f"/>
        <!-- ClinicalDocument.id has cardinality 1..1, and carries the Local ID. -->

<code code="11502-2" codeSystem="2.16.840.1.113883.6.1" displayName="Laboratory
Report"/>
        <!-- This code may vary depending on the result report type. -->

<title>Good Health Clinic Laboratory Report</title>

<effectiveTime value="200004100800"/>
        <!-- The date/time of the lab report reflects when the report is created, which
may be later then the date/time the various lab procedures were performed. -->

<confidentialityCode code="N" codeSystem="2.16.840.1.113883.5.25"/>

<recordTarget>
                <patientRole>
                        <id extension="12345" root="76b242b9-1246-4691-bb1d-91bb7336e76f"/>
<!-- HIN patient ID -->
                        <id extension="97531" root="81821f47-8139-4766-aff0-81be0674de8f"/>
<!-- Local patient ID -->
                        <patient>
                                <name>
                                        <given>Henry</given>
                                        <family>Levin</family>
                                        <suffix>the 7th</suffix>
                                </name>
                                <administrativeGenderCode code="M"
codeSystem="2.16.840.1.113883.5.1"/>
                                <birthTime value="19320924"/>
                        </patient>
```

```
            </patientRole>
        </recordTarget>

<author>
            <time value="200004071300"/>
            <assignedAuthor>
                <id extension="e9190ebc-edb6-497e-9dcb-79a94c6dd4dd" root="76b242b9-1246-4691-bb1d-91bb7336e76f"/> <!-- HIN provider ID -->
                <id extension="789789987987" root="81821f47-8139-4766-aff0-81be0674de8f"/> <!-- Local provider ID -->
            </assignedAuthor>
        </author>
        <!-- Different workflows may ascribe authorship to a device and/or to a clinician. In this example, the author is a device, and the legalAuthenticator is the lab director. -->

<custodian>
            <assignedCustodian>
                <representedCustodianOrganization>
                    <id extension="81821f47-8139-4766-aff0-81be0674de8f" root="76b242b9-1246-4691-bb1d-91bb7336e76f"/> <!-- HIN ID -->
                    <id root="81821f47-8139-4766-aff0-81be0674de8f"/> <!-- Local ID -->
                    <name>Good Health Clinic</name>
                </representedCustodianOrganization>
            </assignedCustodian>
        </custodian>
        <!-- HIN's id.extension equals Local's id.root. -->

<legalAuthenticator>
            <time value="200004071300"/>
            <signatureCode code="S"/>
            <assignedEntity>
                <id extension="90886bbd-92ee-4fa9-a72f-5527804290d5" root="76b242b9-1246-4691-bb1d-91bb7336e76f"/> <!-- HIN ID -->
                <id extension="15151515" root="81821f47-8139-4766-aff0-81be0674de8f"/> <!-- Local provider ID -->
                <assignedPerson>
                    <name>
```

```xml
                <given>Larry</given>
                <family>Laboratorian</family>
                <suffix>MD</suffix>
            </name>
        </assignedPerson>
    </assignedEntity>
</legalAuthenticator>

<inFulfillmentOf>
    <order>
        <id extension="c8e40a81-3698-4f0e-86c0-c805468a8524" root="76b242b9-1246-4691-bb1d-91bb7336e76f"/> <!-- HIN order ID -->
        <id extension="db52f2bd-5c3e-45ff-accd-6e141561a40b" root="81821f47-8139-4766-aff0-81be0674de8f"/> <!-- Local order ID -->
        <code code="20109005" codeSystem="2.16.840.1.113883.6.96" displayName="Serum electrolytes"/>
    </order>
</inFulfillmentOf>
<!-- This is a reference back to the order ID (as opposed to the order document). -->

<!-- Note the absence of the documentationOf / serviceEvent in this example:
    <documentationOf>
        <serviceEvent>
        ...
        </serviceEvent>
    </documentationOf>
```

From the IHE profile: "This element SHALL be present when the report documents a Result Event performed by a single laboratory. In other situations (e.g. report aggregating observations from multiple laboratories) this element may not be present in the header, but carried instead in the body of the document at the entry level".

There are several identifiers (e.g. Order, Procedure, Report) for lab tests. In this case, the procedure codes (i.e. result codes) are carred in the body of the document at the entry level. -->

```
<!--
*******************************************************
```

```
CDA Body
**********************************************************
-->
        <component>
                <structuredBody>
                        <!--
************************************************************************
Results Section
************************************************************************
                -->
<component>
<section>
        <code code="30954-2" codeSystem="2.16.840.1.113883.6.1"/>
        <title>Results</title>
        <text>
                <table border="1" width="100%">
                        <thead>
                                <tr><th> </th><th>April 09, 2000</th></tr>
                        </thead>
                        <tbody>
                                <tr><td>NA (135-145meq/l)</td><td>140</td></tr>
                                <tr><td>K (3.5-5.0 meq/l)</td><td>4.0</td></tr>
                                <tr><td>CL (98-106 meq/l)</td><td>102</td></tr>
                                <tr><td>HCO3 (18-23 meq/l)</td><td>35*</td></tr>
                        </tbody>
                </table>
        </text>
        <entry typeCode="DRIV">
                <observation classCode="OBS" moodCode="EVN">
                        <id extension="dddd6c03-dabf-4178-820d-a7d101aa3603" root="81821f47-8139-4766-aff0-81be0674de8f"/> <!-- Local result ID -->
                        <code code="2951-2" codeSystem="2.16.840.1.113883.6.1" displayName="NA"/>
                        <statusCode code="completed"/>
                        <effectiveTime value="200004091300"/>
                        <value xsi:type="PQ" value="140" unit="meq/l"/>
                        <interpretationCode code="N" codeSystem="2.16.840.1.113883.5.83"/>
                        <referenceRange>
                                <observationRange>
```

```xml
                <value xsi:type="IVL_PQ">
                        <low value="135" unit="meq/l"/>
                        <high value="145" unit="meq/l"/>
                </value>
            </observationRange>
        </referenceRange>
    </observation>
</entry>
<entry>
    <observation classCode="OBS" moodCode="EVN">
        <id extension="80ae109f-a6a5-44ae-a014-2311aa6cb8dc" root="81821f47-8139-4766-aff0-81be0674de8f"/> <!-- Local result ID -->
        <code code="2823-3" codeSystem="2.16.840.1.113883.6.1" displayName="K"/>
        <statusCode code="completed"/>
        <effectiveTime value="200004091300"/>
        <value xsi:type="PQ" value="4.0" unit="meq/l"/>
        <interpretationCode code="N" codeSystem="2.16.840.1.113883.5.83"/>
        <referenceRange>
            <observationRange>
                <value xsi:type="IVL_PQ">
                        <low value="3.5" unit="meq/l"/>
                        <high value="5.0" unit="meq/l"/>
                </value>
            </observationRange>
        </referenceRange>
    </observation>
</entry>
<entry>
    <observation classCode="OBS" moodCode="EVN">
        <id extension="f116fafc-8167-47e0-9601-d5600ab7942f" root="81821f47-8139-4766-aff0-81be0674de8f"/> <!-- Local result ID -->
        <code code="2075-0" codeSystem="2.16.840.1.113883.6.1" displayName="CL"/>
        <statusCode code="completed"/>
        <effectiveTime value="200004091300"/>
        <value xsi:type="PQ" value="102" unit="meq/l"/>
        <interpretationCode code="N" codeSystem="2.16.840.1.113883.5.83"/>
        <referenceRange>
```

```xml
                    <observationRange>
                        <value xsi:type="IVL_PQ">
                            <low value="98" unit="meq/l"/>
                            <high value="106" unit="meq/l"/>
                        </value>
                    </observationRange>
                </referenceRange>
            </observation>
        </entry>
        <entry>
            <observation classCode="OBS" moodCode="EVN">
                <id extension="43ca7340-2a70-4867-b459-2ffe8cc389b6" root="81821f47-8139-4766-aff0-81be0674de8f"/> <!-- Local result ID -->
                <code code="1963-8" codeSystem="2.16.840.1.113883.6.1" displayName="HCO3"/>
                <statusCode code="completed"/>
                <effectiveTime value="200004091300"/>
                <value xsi:type="PQ" value="35" unit="meq/l"/>
                <interpretationCode code="H" codeSystem="2.16.840.1.113883.5.83"/>
                <specimen>
                    <specimenRole>
                        <sdtc:productOf>
                            <sdtc:procedure>
                                <sdtc:code/>
                                <sdtc:effectiveTime/>
                                <sdtc:targetSiteCode/>
                            </sdtc:procedure>
                        </sdtc:productOf>
                    </specimenRole>
                </specimen>
                <!-- Shows use of the CDA lab-defined extensions. -->

<referenceRange>
                    <observationRange>
                        <value xsi:type="IVL_PQ">
                            <low value="18" unit="meq/l"/>
                            <high value="23" unit="meq/l"/>
                        </value>
                    </observationRange>
```

```
                    </referenceRange>
                </observation>
            </entry>
        </section>
    </component>
</structuredBody>
</component>
</ClinicalDocument>
```

```xml
<?xml version="1.0"?>
<?xml-stylesheet type="text/xsl" href="CCD.xsl"?>
<!-- The following sample document depicts a fictional character's health summary. Any
resemblance to a real person is coincidental. -->
<ClinicalDocument xmlns="urn:hl7-org:v3" xmlns:voc="urn:hl7-org:v3/voc"
xmlns:xsi="http://www.w3.org/2001/XMLSchema-instance" xsi:schemaLocation="urn:hl7-org:v3
CDA.xsd">
        <!--
*********************************************************
CDA Header
*********************************************************
-->
        <typeId root="2.16.840.1.113883.1.3" extension="POCD_HD000040"/>
        <templateId root="2.16.840.1.113883.10.20.1"/> <!-- CCD v1.0 Templates Root -->
        <id root="db734647-fc99-424c-a864-7e3cda82e703"/>
        <code code="34133-9" codeSystem="2.16.840.1.113883.6.1" displayName="Summarization
of episode note"/>
        <title>Good Health Clinic Continuity of Care Document</title>
        <effectiveTime value="20000407130000+0500"/>
        <confidentialityCode code="N" codeSystem="2.16.840.1.113883.5.25"/>
        <languageCode code="en-US"/>
        <recordTarget>
                <patientRole>
                        <id extension="996-756-495" root="2.16.840.1.113883.19.5"/>
                        <patient>
                                <name>
                                        <given>Henry</given>
```

Another example schema definition for the Encounter canonical (or relevant portion thereof) relates to a result of a procedure encounter, for example a visit with a specialist who takes the patients vital signs:

```xml
<?xml version="1.0"?>
<?xml-stylesheet type="text/xsl" href="CDA.xsl"?>
<!-- The following sample document depicts a fictional character's health summary. Any
resemblance to a real person is coincidental. -->
<!--
Henry Levin the 7th goes to see his primary care doctor, Dr. Doctor, complaining of
headache.
Dr. Doctor diagnoses Henry Levin the 7th as having probable migraine, but orders a CT
scan of the head to rule out a brain tumor.
Henry Levin the 7th leaves the office, and Dr. Doctor writes a visit note.
Several days later, the CT scan is performed and a report comes back to Dr. Doctor,
showing that there is no brain tumor.
HIN SysID = 76b242b9-1246-4691-bb1d-91bb7336e76f
Local SysID = 81821f47-8139-4766-aff0-81be0674de8f
-->
<ClinicalDocument xmlns="urn:hl7-org:v3" xmlns:voc="urn:hl7-org:v3/voc"
xmlns:xsi="http://www.w3.org/2001/XMLSchema-instance" xsi:schemaLocation="urn:hl7-org:v3
CDA.xsd">
    <!--
***********************************************************
CDA Header
***********************************************************
-->
    <typeId root="2.16.840.1.113883.1.3" extension="POCD_HD000040"/>
    <!-- typeId is required in all CDA instances, and fixed as shown here. This is how
you know the instance is a CDA R2 document. -->
    <id root="822beb9c-2560-4c4a-a42b-ce58950fb399" extension="eb7b661b-d302-4c71-a672-d5b7b5833e3f"/>
    <!-- ClinicalDocument.id has cardinality 1..1, and carries the Local ID. -->
    <code code="28570-0" codeSystem="2.16.840.1.113883.6.1" displayName="Procedure Report"/>
    <!-- This code may vary depending on the result report type. -->
    <title>Good Health Clinic Procedure Report</title>
    <effectiveTime value="200004100800"/>
    <!-- The date/time of the procedure report reflects when the specialist dictates
or creates the report, so is typically later then the date/time the procedure was
actually performed. -->
    <confidentialityCode code="N" codeSystem="2.16.840.1.113883.5.25"/>
    <recordTarget>
        <patientRole>
            <id extension="12345" root="76b242b9-1246-4691-bb1d-91bb7336e76f"/>
<!-- HIN patient ID -->
            <id extension="97531" root="81821f47-8139-4766-aff0-81be0674de8f"/>
<!-- Local patient ID -->
            <patient>
                <name>
                    <given>Henry</given>
                    <family>Levin</family>
                    <suffix>the 7th</suffix>
                </name>
                <administrativeGenderCode code="M" codeSystem="2.16.840.1.113883.5.1"/>
                <birthTime value="19320924"/>
            </patient>
        </patientRole>
    </recordTarget>
    <author>
        <time value="200004071300"/>
        <assignedAuthor>
            <id extension="124060a7-02e9-4c60-a917-4d8729fe0234" root="76b242b9-1246-4691-bb1d-91bb7336e76f"/> <!-- HIN ID -->
            <id extension="433433433" root="81821f47-8139-4766-aff0-81be0674de8f"/> <!-- Local provider ID -->
            <assignedPerson>
                <name>
                    <given>Peter</given>
                    <family>Pulmonologist</family>
                    <suffix>MD</suffix>
                </name>
            </assignedPerson>
        </assignedAuthor>
    </author>
    <custodian>
        <assignedCustodian>
            <representedCustodianOrganization>
                <id extension="81821f47-8139-4766-aff0-81be0674de8f"
root="76b242b9-1246-4691-bb1d-91bb7336e76f"/> <!-- HIN ID -->
                <id root="81821f47-8139-4766-aff0-81be0674de8f"/> <!-- Local
```

-continued

```
ID -->
                <name>Good Health Clinic</name>
            </representedCustodianOrganization>
        </assignedCustodian>
    </custodian>
    <!-- HIN's id.extension equals Local's id.root. -->
    <legalAuthenticator>
        <time value="200004071300"/>
        <signatureCode code="S"/>
        <assignedEntity>
            <id extension="124060a7-02e9-4c60-a917-4d8729fe0234" root="76b242b9-
1246-4691-bb1d-91bb7336e76f"/> <!-- HIN ID -->
            <id extension="433433433" root="81821f47-8139-4766-aff0-
81be0674de8f"/> <!-- Local provider ID -->
            <assignedPerson>
                <name>
                    <given>Peter</given>
                    <family>Pulmonologist</family>
                    <suffix>MD</suffix>
                </name>
            </assignedPerson>
        </assignedEntity>
    </legalAuthenticator>
    <inFulfillmentOf>
        <order>
            <id extension="f5470d54-7a99-4a74-af44-a91bfc2cdb46" root="76b242b9-
1246-4691-bb1d-91bb7336e76f"/> <!-- HIN order ID -->
            <id extension="c1cb1553-55fe-452b-a31f-4394a9b25530" root="81821f47-
8139-4766-aff0-81be0674de8f"/> <!-- Local order ID -->
            <code code="23426006" codeSystem="2.16.840.1.113883.6.96"
displayName="Pulmonary function study"/>
        </order>
    </inFulfillmentOf>
    <!-- This is a reference back to the order ID (as opposed to the order document).
-->
    <documentationOf>
        <serviceEvent>
            <id extension="46e11bcd-b24b-43a4-a6ae-2752a3aa7409" root="81821f47-
8139-4766-aff0-81be0674de8f"/> <!-- Local procedure ID -->
            <code code="23426006" codeSystem="2.16.840.1.113883.6.96"
displayName="Pulmonary function study"/>
            <effectiveTime value="200004091030"/>
        </serviceEvent>
    </documentationOf>
    <!-- This shows the procedure that was actually performed, and the date/time of
the procedure. Note that there are several identifiers (e.g. Order, Procedure, Report). -
->
    <!--
****************************************************
CDA Body
****************************************************
-->
    <component>
        <structuredBody>
            <!--
************************************************************************
Findings Section
************************************************************************
-->
<component>
<section>
    <code code="18782-3" codeSystem="2.16.840.1.113883.6.1"/>
    <title>Procedure findings</title>
    <text>
        <list>
            <item>Vital Capacity: 5.65 L</item>
            <item>Total Lung Capacity: 7.76 L</item>
            <item>Residual Volume: 2.17 L</item>
            <item>FEV1: 4.47 L</item>
            <item>FEV1/FEV: 79%</item>
            <item>MVV: 170 L/min</item>
            <item>DLCO: 31.6 mL/min/mm Hg</item>
        </list>
    </text>
    <entry>
        <observation classCode="OBS" moodCode="EVN">
            <code code="268379003" codeSystem="2.16.840.1.113883.6.96"
displayName="Vital capacity"/>
            <statusCode code="completed"/>
```

```
                <effectiveTime value="200004071300"/>
                <value xsi:type="PQ" value="5.65" unit="L"/>
            </observation>
        </entry>
        <entry>
            <observation classCode="OBS" moodCode="EVN">
                <code code="57566009" codeSystem="2.16.840.1.113883.6.96"
displayName="Total lung capacity"/>
                <statusCode code="completed"/>
                <effectiveTime value="200004071300"/>
                <value xsi:type="PQ" value="7.76" unit="L"/>
            </observation>
        </entry>
        <!-- etc, etc, for the other procedure findings ... -->
    </section>
</component>
            <!--
**************************************************************************
Assessment Section
**************************************************************************
-->
<component>
<section>
    <code code="11496-7" codeSystem="2.16.840.1.113883.6.1"/>
    <title>Assessment</title>
    <text>Normal pulmonary function study, with no evidence of obstructive or
restrictive airway disease.</text>
    <entry>
        <observation classCode="COND" moodCode="EVN">
            <code code="ASSERTION" codeSystem="2.16.840.1.113883.5.4"/>
            <statusCode code="completed"/>
            <effectiveTime value="200004071300"/>
            <value xsi:type="CD" code="165018007"
codeSystem="2.16.840.1.113883.6.96" displayName="Lung function testing normal"/>
        </observation>
    </entry>
</section>
</component>
</structuredBody>
</component>
</ClinicalDocument>
```

Exemplary incremental WSDL operations for Encounter include:

TraceEpisodeOfCare (input: startingEncounterCanonical, input: dateRange, output: listofEncountersForEpisode)

This operation traces the relationships of encounters and orders which create related encounters.

The Headwater platform for healthcare can provide a software service definition for Document, e.g. DICOM (Digital Imaging and Communications in Medicine) or scanned paper, including the data and common functions that deliver the service functionality. The Service definition can include an HL7 version 3.0 RIM compliant data structure with the functions to create, read, update and delete the data structure the service represents.

In an exemplary embodiment the schema definition of the canonical Document (e.g. Healthcare Specific Requirements/Services/Healthcare Core Enterprise Data Service/Document) is the continuity of care document (CCD) using the procedures section only to return the links to the associated unstructured documents.

The schema definition(s) of the canonical follows.

A first example schema definition for the Document canonical (or relevant portion thereof) relates to a Document of a CT scan and X-Rays and the radiologist's notes regarding findings:

```
<?xml version="1.0"?>
<?xml-stylesheet type="text/xsl" href="CCD.xsl"?>
<!-- The following sample document depicts a fictional character's health summary. Any
resemblance to a real person is coincidental. -->
<!--
This instance represents a summary of radiology procedures for Henry Levin the 7th, with
references to each order id, procedure (image) id, and report id.
It is a valid CCD (and CDA R2) instance.
HIN SysID = 76b242b9-1246-4691-bb1d-91bb7336e76f
Good Health Clinic SysID = 81821f47-8139-4766-aff0-81be0674de8f
Good Health Imaging Center SysID = 9b693621-6620-458f-aa01-307a61a9a5a9
-->
<ClinicalDocument xmlns="urn:hl7-org:v3" xmlns:voc="urn:hl7-org:v3/voc"
xmlns:xsi="http://www.w3.org/2001/XMLSchema-instance" xmlns:sdtc="urn:hl7-org:sdtc"
xsi:schemaLocation="urn:hl7-org:v3 CCD.xsd">
            <!--
**************************************************************
CDA Header
```

```
***********************************************************
-->
       <typeId root="2.16.840.1.113883.1.3" extension="POCD_HD000040"/>
       <!-- typeId is required in all CDA instances, and fixed as shown here. This is how
you know the instance is a CDA R2 document. -->
       <templateId root="2.16.840.1.113883.10.20.1"/>
       <!-- CCD v1.0 template identifier -->
       <id root="685de007-9353-4c72-8d0a-580d09797423" extension="eb7b661b-d302-4c71-
a672-d5b7b5833e3f"/>
       <!-- ClinicalDocument.id has cardinality 1..1, and carries the Local ID. -->
       <code code="34133-9" codeSystem="2.16.840.1.113883.6.1" displayName="Summarization
of episode note"/>
       <!-- This code is required by CCD. Note that depending on who generates the CCD
(e.g. pharmacy system, radiology system), there will be different types of information. -
->
       <title>Good Health Imaging Center Summary Report</title>
       <effectiveTime value="20000415080000+0500"/>
       <!-- The date/time that the summary report is created. -->
       <confidentialityCode code="N" codeSystem="2.16.840.1.113883.5.25"/>
       <languageCode code="en-US"/>
       <!-- languageCode is required by CCD. -->
       <recordTarget>
              <patientRole>
                     <id extension="12345" root="76b242b9-1246-4691-bb1d-91bb7336e76f"/>
<!-- HIN patient ID -->
                     <id extension="97531" root="81821f47-8139-4766-aff0-81be0674de8f"/>
<!-- Local patient ID -->
                     <patient>
                            <name>
                                   <given>Henry</given>
                                   <family>Levin</family>
                                   <suffix>the 7th</suffix>
                            </name>
                            <administrativeGenderCode code="M"
codeSystem="2.16.840.1.113883.5.1"/>
                            <birthTime value="19320924"/>
                     </patient>
              </patientRole>
       </recordTarget>
       <author>
              <time value="20000415080000+0500"/>
              <assignedAuthor>
                     <id nullFlavor="NI"/>
                     <representedOrganization>
                            <id extension="81821f47-8139-4766-aff0-81be0674de8f"
root="76b242b9-1246-4691-bb1d-91bb7336e76f"/> <!-- HIN ID -->
                            <id root="81821f47-8139-4766-aff0-81be0674de8f"/> <!-- Local
ID -->
                            <name>Good Health Clinic</name>
                     </representedOrganization>
              </assignedAuthor>
       </author>
       <!-- Good Health Imaging Center is the author. Author.time =
ClinicalDocument.effectiveTime for CCD documents.-->
       <informant>
              <assignedEntity>
                     <id nullFlavor="NI"/>
                     <representedOrganization>
                            <id extension="81821f47-8139-4766-aff0-81be0674de8f"
root="76b242b9-1246-4691-bb1d-91bb7336e76f"/> <!-- HIN ID -->
                            <id root="81821f47-8139-4766-aff0-81be0674de8f"/> <!-- Local
ID -->
                            <name>Good Health Clinic</name>
                     </representedOrganization>
              </assignedEntity>
       </informant>
       <!-- Informant reflects the source of information, which in this case is Good
Health Imaging Center. -->
       <custodian>
              <assignedCustodian>
                     <representedCustodianOrganization>
                            <id extension="81821f47-8139-4766-aff0-81be0674de8f"
root="76b242b9-1246-4691-bb1d-91bb7336e76f"/> <!-- HIN ID -->
                            <id root="81821f47-8139-4766-aff0-81be0674de8f"/> <!-- Local
ID -->
                            <name>Good Health Clinic</name>
                     </representedCustodianOrganization>
              </assignedCustodian>
       </custodian>
```

-continued

```
        <!-- HIN's id.extension equals Local's id.root. -->
        <legalAuthenticator>
                <time value="20000415080000+0500"/>
                <signatureCode code="S"/>
                <assignedEntity>
                        <id nullFlavor="NI"/>
                        <representedOrganization>
                                <id extension="81821f47-8139-4766-aff0-81be0674de8f"
root="76b242b9-1246-4691-bb1d-91bb7336e76f"/> <!-- HIN ID -->
                                <id root="81821f47-8139-4766-aff0-81be0674de8f"/> <!-- Local
ID -->
                                <name>Good Health Clinic</name>
                        </representedOrganization>
                </assignedEntity>
        </legalAuthenticator>
        <!-- Document is legally authenticated by the Good Health Clinic. -->
        <documentationOf>
                <serviceEvent classCode="PCPR">
                        <effectiveTime><low value="20000301"/><high
value="20000415"/></effectiveTime>
                </serviceEvent>
        </documentationOf>
        <!-- Reflects the time period being summarized. -->
        <!--
************************************************************
CDA Body
************************************************************
-->
        <component>
                <structuredBody>
                        <!--
************************************************************
Procedure section
************************************************************
-->
<!-- I've used the CCD Procedure section rather than the CCD Results section, since I'm
just enumerating the procedures, without including any results in this summary document.
-->
<component>
<section>
        <templateId root="2.16.840.1.113883.10.20.1.12"/> <!-- Procedures section template
-->
        <code code="47519-4" codeSystem="2.16.840.1.113883.6.1"/>
        <title>Procedures</title>
        <text>
                        <table border="1" width="100%">
                        <thead>
                                <tr><th>Procedure</th><th>Date</th></tr>
                        </thead>
                        <tbody>
                                <tr><td>Chest xray</td><td>27 March 2000</td></tr>
                                <tr><td>CT of brain with and without contrast</td><td>09 April
2000</td></tr>
                        </tbody>
                        </table>
        </text>
        <!--
************************************************************
Chest xray
************************************************************
-->
        <entry>
                <act classCode="ACT" moodCode="EVN">
                        <templateId root="2.16.840.1.113883.10.20.1.29"/> <!-- Procedure
activity template -->
                        <id extension="d96dedf9-0c84-4704-9a06-cbbfe09deae7" root="81821f47-
8139-4766-aff0-81be0674de8f"/> <!-- Local procedure (study) ID -->
                        <code code="399208008" codeSystem="2.16.840.1.113883.6.96"
displayName="Chest xray"/>
                        <statusCode code="completed"/>
                        <effectiveTime value="20000327"/>
                        <entryRelationship typeCode="COMP">
                                <!-- "Component" relationship used to relate the procedure to the
series. -->
                                <act classCode="ACT" moodCode="EVN">
                                        <id extension="07f0c5ab-f14d-4545-81c3-b78ad1eb6b60"
root="81821f47-8139-4766-aff0-81be0674de8f"/> <!-- Local series ID -->
                                        <code code="113015" codeSystem="1.2.840.10008.2.16.4"
codeSystemName="DICOM" displayName="DICOM Series"/>
```

```
                        <entryRelationship typeCode="COMP">
                        <!-- "Component" relationship used to relate the series
to the instance (image). -->
                            <observation classCode="DGIMG" moodCode="EVN">
                                <id extension="cd7e4757-7f60-40c2-b786-
665a7d127b51" root="81821f47-8139-4766-aff0-81be0674de8f"/> <!-- Local instance (image)
ID -->
                                <code code="399208008"
codeSystem="2.16.840.1.113883.6.96" displayName="Chest xray"/>
                                <text
mediaType="application/DICOM"><reference value="http://www.hospital-
stmarco/radiology/wado.php?requestType=WADO &studyUID=d96dedf9-0c84-4704-9a06-
cbbfe09deae7 &seriesUID=07f0c5ab-f14d-4545-81c3-b78ad1eb6b60 &objectUID=cd7e4757-
7f60-40c2-b786-665a7d127b51"/></text>
                                <!-- The Web Access to DICOM Persistent
Objects (WADO) [ftp://medical.nema.org/medical/dicom/2007/07_18pu.pdf] specification
provides a syntax for constructing a URL reference to an image. -->
                            </observation>
                        </entryRelationship>
                    </act>
                </entryRelationship>
                <entryRelationship typeCode="REFR">
                <!-- "Refers to" relationship used to relate the procedure to the
order. -->
                    <observation classCode="OBS" moodCode="RQO">
                        <id extension="36cfc0a1-4238-4096-9ec3-60982917dafb"
root="81821f47-8139-4766-aff0-81be0674de8f"/> <!-- Local order ID -->
                        <code code="399208008"
codeSystem="2.16.840.1.113883.6.96" displayName="Chest xray"/>
                    </observation>
                </entryRelationship>
                <reference typeCode="REFR">
                <!-- "Refers to" relationship used to relate the procedure to the
report. -->
                    <externalDocument>
                        <id root="4d517989-c94a-4900-9615-3d38db728acb"
extension="eb7b661b-d302-4c71-a672-d5b7b5833e3f"/> <!-- Local report ID -->
                        <code code="18748-4" codeSystem="2.16.840.1.113883.6.1"
displayName="Diagnostic Imaging Report"/>
                    </externalDocument>
                </reference>
            </act>
        </entry>
        <!--
******************************************************
CT Scan of brain with and without contrast
******************************************************
-->
        <entry>
            <act classCode="ACT" moodCode="EVN">
                <templateId root="2.16.840.1.113883.10.20.1.29"/> <!-- Procedure
activity template -->
                <id extension="ce1e732e-0d2f-481d-b883-e9daa8342305" root="81821f47-
8139-4766-aff0-81be0674de8f"/> <!-- Local procedure (image) ID -->
                <code code="396209004" codeSystem="2.16.840.1.113883.6.96"
displayName="CT of brain with and without contrast"/>
                <statusCode code="completed"/>
                <effectiveTime value="200004090930"/>
                <entryRelationship typeCode="COMP">
                <!-- "Component" relationship used to relate the procedure to the
series. -->
                    <act classCode="ACT" moodCode="EVN">
                        <id extension="171642c0-d5e9-4867-b254-138639a997dd"
root="81821f47-8139-4766-aff0-81be0674de8f"/> <!-- Local series ID -->
                        <code code="113015" codeSystem="1.2.840.10008.2.16.4"
codeSystemName="DICOM" displayName="DICOM Series"/>
                        <entryRelationship typeCode="COMP">
                            <observation classCode="DGIMG" moodCode="EVN">
                                <id extension="faa53845-e8de-4450-804a-
30594b825e29" root="81821f47-8139-4766-aff0-81be0674de8f"/> <!-- Local instance (image)
ID -->
                                <code code="396209004"
codeSystem="2.16.840.1.113883.6.96" displayName="CT of brain with and without contrast"/>
                            </observation>
                        </entryRelationship>
                        <entryRelationship typeCode="COMP">
                            <observation classCode="DGIMG" moodCode="EVN">
                                <id extension="c63c57be-066e-493b-9bca-
12b1571bddd1" root="81821f47-8139-4766-aff0-81be0674de8f"/> <!-- Local instance (image)
```

```
ID -->
                                    <code code="396209004"
codeSystem="2.16.840.1.113883.6.96" displayName="CT of brain with and without contrast"/>
                                </observation>
                            </entryRelationship>
                            <entryRelationship typeCode="COMP">
                                <observation classCode="DGIMG" moodCode="EVN">
                                    <id extension="0a467a47-4aa1-43cd-bdf1-
1dc3fdbe9a36" root="81821f47-8139-4766-aff0-81be0674de8f"/> <!-- Local instance (image)
ID -->
                                    <code code="396209004"
codeSystem="2.16.840.1.113883.6.96" displayName="CT of brain with and without contrast"/>
                                </observation>
                            </entryRelationship>
                            <!-- etc, etc - a CT Scan contains many images. -->
                        </act>
                    </entryRelationship>
                    <entryRelationship typeCode="REFR">
                    <!-- "Refers to" relationship used to relate the procedure to the
order. -->
                        <observation classCode="OBS" moodCode="RQO">
                            <id extension="f377aa56-145f-4d6a-95d8-69ebdc51f0b4"
root="76b242b9-1246-4691-bb1d-91bb7336e76f"/> <!-- HIN order ID -->
                            <id extension="cb9ad034-52a7-453d-8bd3-1ea0af3a542a"
root="81821f47-8139-4766-aff0-81be0674de8f"/> <!-- Local order ID -->
                            <code code="34227000"
codeSystem="2.16.840.1.113883.6.96" displayName="CT of brain"/>
                        </observation>
                    </entryRelationship>
                    <reference typeCode="REFR">
                    <!-- "Refers to" relationship used to relate the procedure to the
report. -->
                        <externalDocument>
                            <id root="5cc58dd0-f4bc-44ba-9a6b-613535ebac7e"
extension="eb7b661b-d302-4c71-a672-d5b7b5833e3f"/> <!-- Local report ID -->
                            <code code="18748-4" codeSystem="2.16.840.1.113883.6.1"
displayName="Diagnostic Imaging Report"/>
                        </externalDocument>
                    </reference>
                </act>
            </entry>
        </section>
    </component>
</structuredBody>
</component>
</ClinicalDocument>
```

Exemplary incremental WSDL operations for Document include:

ExtractDocumentPaths (input: documentCanonicalXML, output: key-value pair array<documentDesc, documentURL>)

This operation effectively extracts the image URLs and their directly corresponding descriptive text from the canonical XML. It basically extracts segments which follow this pattern:

```
<code code="399208008"
 codeSystem="2.16.840.1.113883.6.96"
 displayName="Chest xray"
/>
<text mediaType="application/DICOM">
<reference value="http://www.hospital-
                    stmarco/radiology/wado.-
                    php?requestType=WADO
                    &studyUID=d96dedf9-0c84-4704-9a06-
                    cbbfe09deae7
                    &seriesUID=07f0c5ab-f14d-4545-81c3-
                    b78ad1eb6b60
                    &objectUID=cd7e4757-7f60-40c2-
                    b786-665a7d127b51"
/>
</text>
```

An exemplary embodiment of the Headwater platform for healthcare provides a software service definition for a Health Record (summary and full history) including the data and common functions that deliver the service functionality. The Service definition includes an H7 version 3.0 RIM compliant data structure with the functions to create, read, update and delete the data structure the service represents.

An exemplary schema definition of the Health Record (e.g. Healthcare Specific Requirements/Services/Healthcare Core Enterprise Data Service/Personal Health Record) canonical involves the continuity of care document (CCD) using all sections with associated time scales.

An example schema definition for the HealthRecord canonical (or relevant portion thereof) is found below, for example in relation to an exemplary CCD document that represents a personal health record:

```xml
                        <family>Levin</family>
                        <suffix>the 7th</suffix>
                    </name>
                    <administrativeGenderCode code="M"
codeSystem="2.16.840.1.113883.5.1"/>
                    <birthTime value="19320924"/>
                </patient>
                <providerOrganization>
                    <id root="2.16.840.1.113883.19.5"/>
                    <name>Good Health Clinic</name>
                </providerOrganization>
            </patientRole>
    </recordTarget>
    <author>
        <time value="20000407130000+0500"/>
        <assignedAuthor>
            <id root="20cf14fb-b65c-4c8c-a54d-b0cca834c18c"/>
            <assignedPerson>

<name><prefix>Dr.</prefix><given>Robert</given><family>Dolin</family></name>
            </assignedPerson>
            <representedOrganization>
                    <id root="2.16.840.1.113883.19.5"/>
                    <name>Good Health Clinic</name>
            </representedOrganization>
        </assignedAuthor>
    </author>
    <informant>
        <assignedEntity>
            <id nullFlavor="NI"/>
            <representedOrganization>
                    <id root="2.16.840.1.113883.19.5"/>
                    <name>Good Health Clinic</name>
            </representedOrganization>
        </assignedEntity>
    </informant>
    <custodian>
        <assignedCustodian>
            <representedCustodianOrganization>
```

```xml
                <id root="2.16.840.1.113883.19.5"/>
                <name>Good Health Clinic</name>
            </representedCustodianOrganization>
        </assignedCustodian>
    </custodian>
    <legalAuthenticator>
        <time value="20000407130000+0500"/>
        <signatureCode code="S"/>
        <assignedEntity>
            <id nullFlavor="NI"/>
            <representedOrganization>
                <id root="2.16.840.1.113883.19.5"/>
                <name>Good Health Clinic</name>
            </representedOrganization>
        </assignedEntity>
    </legalAuthenticator>
    <participant typeCode="IND">
        <associatedEntity classCode="GUAR">
            <id root="4ff51570-83a9-47b7-91f2-93ba30373141"/>
            <addr>
                <streetAddressLine>17 Daws Rd.</streetAddressLine>
                <city>Blue Bell</city>
                <state>MA</state>
                <postalCode>02368</postalCode>
            </addr>
            <telecom value="tel:(888)555-1212"/>
            <associatedPerson>
                <name>
                    <given>Kenneth</given>
                    <family>Ross</family>
                </name>
            </associatedPerson>
        </associatedEntity>
    </participant>
    <participant typeCode="IND">
        <associatedEntity classCode="NOK">
            <id root="4ac71514-6a10-4164-9715-f8d96af48e6d"/>
            <code code="65656005" codeSystem="2.16.840.1.113883.6.96" displayName="Biiological mother"/>
```

```xml
                    <telecom value="tel:(999)555-1212"/>
                    <associatedPerson>
                            <name>
                                    <given>Henrietta</given>
                                    <family>Levin</family>
                            </name>
                    </associatedPerson>
            </associatedEntity>
    </participant>
    <documentationOf>
            <serviceEvent classCode="PCPR">
                    <effectiveTime><low value="19320924"/><high
value="20000407"/></effectiveTime>
                    <performer typeCode="PRF">
                            <functionCode code="PCP" codeSystem="2.16.840.1.113883.5.88"/>
                            <time><low value="1990"/><high value='20000407'/></time>
                            <assignedEntity>
                                    <id root="20cf14fb-b65c-4c8c-a54d-b0cca834c18c"/>
                                    <assignedPerson>

<name><prefix>Dr.</prefix><given>Robert</given><family>Dolin</family></name>
                                    </assignedPerson>
                                    <representedOrganization>
                                            <id root="2.16.840.1.113883.19.5"/>
                                            <name>Good Health Clinic</name>
                                    </representedOrganization>
                            </assignedEntity>
                    </performer>
            </serviceEvent>
    </documentationOf>
    <!--
**********************************************************
CDA Body
**********************************************************
-->
    <component>
            <structuredBody>
                            <!--
**********************************************************
```

```
Purpose section
********************************************************
-->
<component>
<section>
      <templateId root='2.16.840.1.113883.10.20.1.13'/> <!-- Purpose section template --
>
      <code code="48764-5" codeSystem="2.16.840.1.113883.6.1"/>
      <title>Summary Purpose</title>
      <text>Transfer of care</text>
      <entry typeCode="DRIV">
            <act classCode="ACT" moodCode="EVN">
                  <templateId root='2.16.840.1.113883.10.20.1.30'/> <!-- Purpose
activity template -->
                  <code code="23745001" codeSystem="2.16.840.1.113883.6.96"
displayName="Documentation procedure"/>
                  <statusCode code="completed"/>
                  <entryRelationship typeCode="RSON">
                        <act classCode="ACT" moodCode="EVN">
                              <code code="308292007"
codeSystem="2.16.840.1.113883.6.96" displayName="Transfer of care"/>
                              <statusCode code="completed"/>
                        </act>
                  </entryRelationship>
            </act>
      </entry>
</section>
</component>
                              <!--
********************************************************
Payers section
********************************************************
-->
<component>
<section>
      <templateId root='2.16.840.1.113883.10.20.1.9'/> <!-- Payers section template -->
      <code code="48768-6" codeSystem="2.16.840.1.113883.6.1"/>
      <title>Payers</title>
      <text>
```

```
            <table border="1" width="100%">
                    <thead>
                    <tr><th>Payer name</th><th>Policy type / Coverage
type</th><th>Covered party ID</th> <th>Authorization(s)</th></tr>
                    </thead>
                    <tbody>
                        <tr>
                            <td>Good Health Insurance</td>
                            <td>Extended healthcare / Self</td>
                            <td>14d4a520-7aae-11db-9fe1-0800200c9a66</td>
                            <td>Colonoscopy</td>
                        </tr>
                    </tbody>
            </table>
    </text>
    <entry typeCode="DRIV">
        <act classCode="ACT" moodCode="DEF">
            <templateId root='2.16.840.1.113883.10.20.1.20'/> <!-- Coverage
activity template -->
            <id root="1fe2cdd0-7aad-11db-9fe1-0800200c9a66"/>
            <code code="48768-6" codeSystem="2.16.840.1.113883.6.1"
displayName="Payment sources"/>
            <statusCode code="completed"/>
            <entryRelationship typeCode="COMP">
                <act classCode="ACT" moodCode="EVN">
                    <templateId root='2.16.840.1.113883.10.20.1.26'/> <!--
Policy activity template -->
                    <id root="3e676a50-7aac-11db-9fe1-0800200c9a66"/>
                    <code code="EHCPOL" codeSystem="2.16.840.1.113883.5.4"
displayName="Extended healthcare"/>
                    <statusCode code="completed"/>
                    <performer typeCode="PRF">
                        <assignedEntity>
                            <id root="329fcdf0-7ab3-11db-9fe1-
0800200c9a66"/>
                            <representedOrganization>
                                <name>Good Health Insurance</name>
                            </representedOrganization>
                        </assignedEntity>
```

```xml
                </performer>
                <participant typeCode="COV">
                    <participantRole>
                        <id root="14d4a520-7aae-11db-9fe1-0800200c9a66"/>
                        <code code="SELF" codeSystem="2.16.840.1.113883.5.111" displayName="Self"/>
                    </participantRole>
                </participant>
                <entryRelationship typeCode="REFR">
                    <act classCode="ACT" moodCode="EVN">
                        <templateId root='2.16.840.1.113883.10.20.1.19'/> <!-- Authorization activity template -->
                        <id root="f4dce790-8328-11db-9fe1-0800200c9a66"/>
                        <code nullFlavor="NA"/>
                        <entryRelationship typeCode="SUBJ">
                            <procedure classCode="PROC" moodCode="PRMS">
                                <code code="73761001" codeSystem="2.16.840.1.113883.6.96" displayName="Colonoscopy"/>
                            </procedure>
                        </entryRelationship>
                    </act>
                </entryRelationship>
            </act>
        </entry>
</section>
</component>
                            <!--
*******************************************************
Advance Directives section
*******************************************************
-->
<component>
<section>
```

```
        <templateId root='2.16.840.1.113883.10.20.1.1'/> <!-- Advance directives section
template -->
        <code code="42348-3" codeSystem="2.16.840.1.113883.6.1"/>
        <title>Advance Directives</title>
        <text>
            <table border="1" width="100%">
                <thead>

<tr><th>Directive</th><th>Description</th><th>Verification</th><th>Supporting
Document(s)</th></tr>
                </thead>
                <tbody>
                    <tr>
                        <td>Resuscitation status</td>
                        <td><content ID="AD1">Do not resuscitate</content></td>
                        <td>Dr. Robert Dolin, Nov 07, 1999</td>
                        <td><linkHtml href="AdvanceDirective.b50b7910-7ffb-4f4c-
bbe4-177ed68cbbf3.pdf">Advance directive</linkHtml></td>
                    </tr>
                </tbody>
            </table>
        </text>
        <entry typeCode="DRIV">
            <observation classCode="OBS" moodCode="EVN">
                <templateId root='2.16.840.1.113883.10.20.1.17'/> <!-- Advance
directive observation template -->
                <id root="9b54c3c9-1673-49c7-aef9-b037ed72ed27"/>
                <code code="304251008" codeSystem="2.16.840.1.113883.6.96"
displayName="Resuscitation"/>
                <statusCode code="completed"/>
                <value xsi:type="CD" code="304253006"
codeSystem="2.16.840.1.113883.6.96" displayName="Do not resuscitate">
                    <originalText><reference value="#AD1"/></originalText>
                </value>
                <participant typeCode="VRF">
                    <templateId root='2.16.840.1.113883.10.20.1.58'/> <!--
Verification of an advance directive observation template -->
                    <time value="19991107"/>
                    <participantRole>
```

```xml
                                <id root="20cf14fb-b65c-4c8c-a54d-b0cca834c18c"/>
                        </participantRole>
                    </participant>
                    <entryRelationship typeCode="REFR">
                        <observation classCode="OBS" moodCode="EVN">
                            <templateId root='2.16.840.1.113883.10.20.1.37'/> <!-- Advance directive status observation template -->
                            <code code="33999-4" codeSystem="2.16.840.1.113883.6.1" displayName="Status"/>
                            <statusCode code="completed"/>
                            <value xsi:type="CE" code="15240007" codeSystem="2.16.840.1.113883.6.96" displayName="Current and verified"/>
                        </observation>
                    </entryRelationship>
                    <reference typeCode="REFR">
                        <externalDocument>
                            <templateId root='2.16.840.1.113883.10.20.1.36'/> <!-- Advance directive reference template -->
                            <id root="b50b7910-7ffb-4f4c-bbe4-177ed68cbbf3"/>
                            <code code="371538006" codeSystem="2.16.840.1.113883.6.96" displayName="Advance directive"/>
                            <text mediaType="application/pdf"><reference value="AdvanceDirective.b50b7910-7ffb-4f4c-bbe4-177ed68cbbf3.pdf"/></text>
                        </externalDocument>
                    </reference>
                </observation>
            </entry>
</section>
</component>
                            <!--
*********************************************************
Functional Status section
*********************************************************
-->
<component>
<section>
    <templateId root='2.16.840.1.113883.10.20.1.5'/> <!-- Functional status section template -->
    <code code="47420-5" codeSystem="2.16.840.1.113883.6.1"/>
```

```xml
<title>Functional Status</title>
<text>
    <table border="1" width="100%">
        <thead>
        <tr><th>Functional Condition</th> <th>Effective Dates</th> <th>Condition Status</th></tr>
        </thead>
        <tbody>
        <tr><td>Dependence on cane</td><td>1998</td><td>Active</td></tr>
        <tr><td>Memory impairment</td><td>1999</td><td>Active</td></tr>
        </tbody>
    </table>
</text>
<entry typeCode="DRIV">
    <act classCode="ACT" moodCode="EVN">
        <templateId root='2.16.840.1.113883.10.20.1.27'/> <!-- Problem act template -->
        <id root="6z2fa88d-4174-4909-aece-db44b60a3abb"/>
        <code nullFlavor="NA"/>
        <entryRelationship typeCode="SUBJ">
            <observation classCode="OBS" moodCode="EVN">
                <templateId root='2.16.840.1.113883.10.20.1.28'/> <!-- Problem observation template -->
                <id root="fd07111a-b15b-4dce-8518-1274d07f142a"/>
                <code code="ASSERTION" codeSystem="2.16.840.1.113883.5.4"/>
                <statusCode code="completed"/>
                <effectiveTime><low value="1998"/></effectiveTime>
                <value xsi:type="CD" code="105504002" codeSystem="2.16.840.1.113883.6.96" displayName="Dependence on cane"/>
                <entryRelationship typeCode="REFR">
                    <observation classCode="OBS" moodCode="EVN">
                        <templateId root='2.16.840.1.113883.10.20.1.44'/> <!-- Status of functional status observation template -->
                        <code code="33999-4" codeSystem="2.16.840.1.113883.6.1" displayName="Status"/>
                        <statusCode code="completed"/>
```

```xml
                                        <value xsi:type="CE" code="55561003"
codeSystem="2.16.840.1.113883.6.96" displayName="Active"/>
                                </observation>
                        </entryRelationship>
                </observation>
            </entryRelationship>
        </act>
    </entry>
    <entry typeCode="DRIV">
        <act classCode="ACT" moodCode="EVN">
            <templateId root='2.16.840.1.113883.10.20.1.27'/> <!-- Problem act template -->
            <id root="64606e86-c080-11db-8314-0800200c9a66"/>
            <code nullFlavor="NA"/>
            <entryRelationship typeCode="SUBJ">
                <observation classCode="OBS" moodCode="EVN">
                    <templateId root='2.16.840.1.113883.10.20.1.28'/> <!-- Problem observation template -->
                    <id root="6be2930a-c080-11db-8314-0800200c9a66"/>
                    <code code="ASSERTION" codeSystem="2.16.840.1.113883.5.4"/>
                    <statusCode code="completed"/>
                    <effectiveTime><low value="1999"/></effectiveTime>
                    <value xsi:type="CD" code="386807006"
codeSystem="2.16.840.1.113883.6.96" displayName="Memory impairment"/>
                    <entryRelationship typeCode="REFR">
                        <observation classCode="OBS" moodCode="EVN">
                            <templateId root='2.16.840.1.113883.10.20.1.44'/> <!-- Status of functional status observation template -->
                            <code code="33999-4" codeSystem="2.16.840.1.113883.6.1" displayName="Status"/>
                            <statusCode code="completed"/>
                            <value xsi:type="CE" code="55561003"
codeSystem="2.16.840.1.113883.6.96" displayName="Active"/>
                        </observation>
                    </entryRelationship>
                </observation>
            </entryRelationship>
```

```
            </act>
        </entry>
</section>
</component>
                <!--
********************************************************
Problems section
********************************************************
-->
<component>
<section>
        <templateId root='2.16.840.1.113883.10.20.1.11'/> <!-- Problem section template --
>
        <code code="11450-4" codeSystem="2.16.840.1.113883.6.1"/>
        <title>Problems</title>
        <text>
                <table border="1" width="100%">
                        <thead>
                                <tr><th>Condition</th><th>Effective Dates</th><th>Condition
Status</th></tr>
                        </thead>
                        <tbody>
                                <tr><td>Asthma</td><td>1950</td><td>Active</td></tr>
                                <tr><td>Pneumonia</td><td>Jan 1997</td><td>Resolved</td></tr>
                                <tr><td>"</td><td>Mar 1999</td><td>Resolved</td></tr>
                                <tr><td>Myocardial Infarction</td><td>Jan
1997</td><td>Resolved</td></tr>
                        </tbody>
                </table>
        </text>
        <entry typeCode="DRIV">
                <act classCode="ACT" moodCode="EVN">
                        <templateId root='2.16.840.1.113883.10.20.1.27'/> <!-- Problem act
template -->
                        <id root="6a2fa88d-4174-4909-aece-db44b60a3abb"/>
                        <code nullFlavor="NA"/>
                        <entryRelationship typeCode="SUBJ">
                                <observation classCode="OBS" moodCode="EVN">
```

```xml
                                    <templateId root='2.16.840.1.113883.10.20.1.28'/> <!--
Problem observation template -->
                                    <id root="d11275e7-67ae-11db-bd13-0800200c9a66"/>
                                    <code code="ASSERTION"
codeSystem="2.16.840.1.113883.5.4"/>
                                    <statusCode code="completed"/>
                                    <effectiveTime><low value="1950"/></effectiveTime>
                                    <value xsi:type="CD" code="195967001"
codeSystem="2.16.840.1.113883.6.96" displayName="Asthma"/>
                                    <entryRelationship typeCode="REFR">
                                        <observation classCode="OBS" moodCode="EVN">
                                            <templateId
root='2.16.840.1.113883.10.20.1.50'/> <!-- Problem status observation template -->
                                            <code code="33999-4"
codeSystem="2.16.840.1.113883.6.1" displayName="Status"/>
                                            <statusCode code="completed"/>
                                            <value xsi:type="CE" code="55561003"
codeSystem="2.16.840.1.113883.6.96" displayName="Active"/>
                                        </observation>
                                    </entryRelationship>
                                </observation>
                            </entryRelationship>
                        </act>
                    </entry>
                    <entry typeCode="DRIV">
                        <act classCode="ACT" moodCode="EVN">
                            <templateId root='2.16.840.1.113883.10.20.1.27'/> <!-- Problem act
template -->
                            <id root="ec8a6ff8-ed4b-4f7e-82c3-e98e58b45de7"/>
                            <code nullFlavor="NA"/>
                            <entryRelationship typeCode="SUBJ">
                                <observation classCode="OBS" moodCode="EVN">
                                    <templateId root='2.16.840.1.113883.10.20.1.28'/> <!--
Problem observation template -->
                                    <id root="ab1791b0-5c71-11db-b0de-0800200c9a66"/>
                                    <code code="ASSERTION"
codeSystem="2.16.840.1.113883.5.4"/>
                                    <statusCode code="completed"/>
                                    <effectiveTime><low value="199701"/></effectiveTime>
```

```xml
                                        <value xsi:type="CD" code="233604007"
codeSystem="2.16.840.1.113883.6.96" displayName="Pneumonia"/>
                                        <entryRelationship typeCode="REFR">
                                                <observation classCode="OBS" moodCode="EVN">
                                                        <templateId
root='2.16.840.1.113883.10.20.1.50'/> <!-- Problem status observation template -->
                                                        <code code="33999-4"
codeSystem="2.16.840.1.113883.6.1" displayName="Status"/>
                                                        <statusCode code="completed"/>
                                                        <value xsi:type="CE" code="413322009"
codeSystem="2.16.840.1.113883.6.96" displayName="Resolved"/>
                                                </observation>
                                        </entryRelationship>
                                </observation>
                        </entryRelationship>
                </act>
        </entry>
        <entry typeCode="DRIV">
                <act classCode="ACT" moodCode="EVN">
                        <templateId root='2.16.840.1.113883.10.20.1.27'/> <!-- Problem act
template -->
                        <id root="d11275e9-67ae-11db-bd13-0800200c9a66"/>
                        <code nullFlavor="NA"/>
                        <entryRelationship typeCode="SUBJ">
                                <observation classCode="OBS" moodCode="EVN">
                                        <templateId root='2.16.840.1.113883.10.20.1.28'/> <!--
Problem observation template -->
                                        <id root="9d3d416d-45ab-4da1-912f-4583e0632000"/>
                                        <code code="ASSERTION"
codeSystem="2.16.840.1.113883.5.4"/>
                                        <statusCode code="completed"/>
                                        <effectiveTime><low value="199903"/></effectiveTime>
                                        <value xsi:type="CD" code="233604007"
codeSystem="2.16.840.1.113883.6.96" displayName="Pneumonia"/>
                                        <entryRelationship typeCode="REFR">
                                                <observation classCode="OBS" moodCode="EVN">
                                                        <templateId
root='2.16.840.1.113883.10.20.1.50'/> <!-- Problem status observation template -->
```

```xml
                                        <code code="33999-4" codeSystem="2.16.840.1.113883.6.1" displayName="Status"/>
                                        <statusCode code="completed"/>
                                        <value xsi:type="CE" code="413322009" codeSystem="2.16.840.1.113883.6.96" displayName="Resolved"/>
                                    </observation>
                                </entryRelationship>
                            </observation>
                        </entryRelationship>
                        <entryRelationship typeCode="SUBJ" inversionInd="true">
                            <observation classCode="OBS" moodCode="EVN">
                                <templateId root="2.16.840.1.113883.10.20.1.41"/> <!-- Episode observation template -->
                                <code code="ASSERTION" codeSystem="2.16.840.1.113883.5.4"/>
                                <statusCode code="completed"/>
                                <value xsi:type="CD" code="404684003" codeSystem="2.16.840.1.113883.6.96" displayName="Clinical finding">
                                    <qualifier>
                                        <name code="246456000" displayName="Episodicity"/>
                                        <value code="288527008" displayName="New episode"/>
                                    </qualifier>
                                </value>
                                <entryRelationship typeCode="SAS">
                                    <act classCode="ACT" moodCode="EVN">
                                        <id root="ec8a6ff8-ed4b-4f7e-82c3-e98e58b45de7"/>
                                        <code nullFlavor="NA"/>
                                    </act>
                                </entryRelationship>
                            </observation>
                        </entryRelationship>
                    </act>
                </entry>
                <entry typeCode="DRIV">
                    <act classCode="ACT" moodCode="EVN">
```

```xml
                    <templateId root='2.16.840.1.113883.10.20.1.27'/> <!-- Problem act template -->
                    <id root="5a2c903c-bd77-4bd1-ad9d-452383fbfefa"/>
                    <code nullFlavor="NA"/>
                    <entryRelationship typeCode="SUBJ">
                        <observation classCode="OBS" moodCode="EVN">
                            <templateId root='2.16.840.1.113883.10.20.1.28'/> <!-- Problem observation template -->
                            <code code="ASSERTION" codeSystem="2.16.840.1.113883.5.4"/>
                            <statusCode code="completed"/>
                            <effectiveTime><low value="199701"/></effectiveTime>
                            <value xsi:type="CD" code="22298006" codeSystem="2.16.840.1.113883.6.96" displayName="Myocardial infarction"/>
                            <entryRelationship typeCode="REFR">
                                <observation classCode="OBS" moodCode="EVN">
                                    <templateId root='2.16.840.1.113883.10.20.1.50'/> <!-- Problem status observation template -->
                                    <code code="33999-4" codeSystem="2.16.840.1.113883.6.1" displayName="Status"/>
                                    <statusCode code="completed"/>
                                    <value xsi:type="CE" code="413322009" codeSystem="2.16.840.1.113883.6.96" displayName="Resolved"/>
                                </observation>
                            </entryRelationship>
                        </observation>
                    </entryRelationship>
            </act>
        </entry>
</section>
</component>
            <!--
********************************************************
Family History section
********************************************************
-->
<component>
<section>
```

```
        <templateId root="2.16.840.1.113883.10.20.1.4"/> <!-- Family history section
template -->
        <code code="10157-6" codeSystem="2.16.840.1.113883.6.1"/>
        <title>Family history</title>
        <text>
            <paragraph>Father (deceased)</paragraph>
            <table border="1" width="100%">
                <thead>
                    <tr><th>Diagnosis</th><th>Age At Onset</th></tr>
                </thead>
                <tbody>
                    <tr><td>Myocardial Infarction (cause of
death)</td><td>57</td></tr>
                    <tr><td>Hypertension</td><td>40</td></tr>
                </tbody>
            </table>
            <paragraph>Mother (alive)</paragraph>
            <table border="1" width="100%">
                <thead>
                    <tr><th>Diagnosis</th><th>Age At Onset</th></tr>
                </thead>
                <tbody>
                    <tr><td>Asthma</td><td>30</td></tr>
                </tbody>
            </table>
        </text>
        <entry typeCode="DRIV">
            <organizer moodCode="EVN" classCode="CLUSTER">
                <templateId root="2.16.840.1.113883.10.20.1.23"/> <!-- Family history
organizer template -->
                <statusCode code="completed"/>
                <subject>
                    <relatedSubject classCode="PRS">
                        <code code="9947008" codeSystem="2.16.840.1.113883.6.96"
displayName="Biological father"/>
                        <subject>
                            <administrativeGenderCode code="M"
codeSystem="2.16.840.1.113883.5.1" displayName="Male"/>
                            <birthTime value="1912"/>
```

```
                </subject>
            </relatedSubject>
        </subject>
        <component>
            <observation classCode="OBS" moodCode="EVN">
                <templateId root="2.16.840.1.113883.10.20.1.42"/> <!-- Family history cause of death observation template -->
                <id root="d42ebf70-5c89-11db-b0de-0800200c9a66"/>
                <code code="ASSERTION" codeSystem="2.16.840.1.113883.5.4"/>
                <statusCode code="completed"/>

<value xsi:type="CD" code="22298006" codeSystem="2.16.840.1.113883.6.96" displayName="MI"/>
                <entryRelationship typeCode="CAUS">
                    <observation classCode="OBS" moodCode="EVN">
                        <id root="6898fae0-5c8a-11db-b0de-0800200c9a66"/>
                        <code code="ASSERTION" codeSystem="2.16.840.1.113883.5.4"/>
                        <statusCode code="completed"/>
                        <value xsi:type="CD" code="419099009" codeSystem="2.16.840.1.113883.6.96" displayName="Dead"/>
                    </observation>
                </entryRelationship>
                <entryRelationship typeCode="SUBJ" inversionInd="true">
                    <observation classCode="OBS" moodCode="EVN">
                        <templateId root="2.16.840.1.113883.10.20.1.38"/> <!-- Age observation template -->
                        <code code="397659008" codeSystem="2.16.840.1.113883.6.96" displayName="Age"/>
                        <statusCode code="completed"/>
                        <value xsi:type="INT" value="57"/>
                    </observation>
                </entryRelationship>
            </observation>
        </component>
        <component>
            <observation classCode="OBS" moodCode="EVN">
```

```xml
                                        <templateId root="2.16.840.1.113883.10.20.1.22"/> <!-- Family history observation template -->
                                        <id root="5bfe3ec0-5c8b-11db-b0de-0800200c9a66"/>
                                        <code code="ASSERTION" codeSystem="2.16.840.1.113883.5.4"/>
                                        <statusCode code="completed"/>
                                        <value xsi:type="CD" code="59621000" codeSystem="2.16.840.1.113883.6.96" displayName="HTN"/>
                                        <entryRelationship typeCode="SUBJ" inversionInd="true">
                                                <observation classCode="OBS" moodCode="EVN">
                                                        <templateId root="2.16.840.1.113883.10.20.1.38"/> <!-- Age observation template -->
                                                        <code code="397659008" codeSystem="2.16.840.1.113883.6.96" displayName="Age"/>
                                                        <statusCode code="completed"/>
                                                        <value xsi:type="INT" value="40"/>
                                                </observation>
                                        </entryRelationship>
                                </observation>
                        </component>
                </organizer>
        </entry>
        <entry typeCode="DRIV">
                <organizer moodCode="EVN" classCode="CLUSTER">
                        <templateId root="2.16.840.1.113883.10.20.1.23"/> <!-- Family history organizer template -->
                        <statusCode code="completed"/>
                        <subject>
                                <relatedSubject classCode="PRS">
                                        <code code="65656005" codeSystem="2.16.840.1.113883.6.96" displayName="Biological mother"/>
                                        <subject>
                                                <administrativeGenderCode code="F" codeSystem="2.16.840.1.113883.5.1" displayName="Female"/>
                                                <birthTime value="1912"/>
                                        </subject>
                                </relatedSubject>
                        </subject>
                        <component>
```

```xml
                        <observation classCode="OBS" moodCode="EVN">
                                <templateId root="2.16.840.1.113883.10.20.1.22"/> <!--
Family history observation template -->
                                <id root="a13c6160-5c8b-11db-b0de-0800200c9a66"/>
                                <code code="ASSERTION"
codeSystem="2.16.840.1.113883.5.4"/>
                                <statusCode code="completed"/>
                                <effectiveTime>
                                        <low value="1942"/>
                                </effectiveTime>
                                <value xsi:type="CD" code="195967001"
codeSystem="2.16.840.1.113883.6.96" displayName="Asthma"/>
                        </observation>
                </component>
        </organizer>
    </entry>
</section>
</component>
                <!--
********************************************************
Social History section
********************************************************
-->
<component>
<section>
    <templateId root="2.16.840.1.113883.10.20.1.15"/> <!-- Social history section
template -->
    <code code="29762-2" codeSystem="2.16.840.1.113883.6.1"/>
    <title>Social History</title>
    <text>
        <table border="1" width="100%">
            <thead>
                <tr><th>Social History
Element</th><th>Description</th><th>Effective Dates</th></tr>
            </thead>
            <tbody>
                <tr><td>Cigarette smoking</td><td>1 pack per day</td><td>1947
- 1972</td></tr>
                <tr><td>"</td><td>None</td><td>1973 - </td></tr>
```

```
                    <tr><td>Alcohol consumption</td><td>None</td><td>1973 -
</td></tr>
                </tbody>
            </table>
        </text>
        <entry typeCode="DRIV">
            <observation classCode="OBS" moodCode="EVN">
                <templateId root="2.16.840.1.113883.10.20.1.33"/> <!-- Social history
observation template -->
                <id root="9b56c25d-9104-45ee-9fa4-e0f3afaa01c1"/>
                <code code="230056004" codeSystem="2.16.840.1.113883.6.96"
displayName="Cigarette smoking"/>
                <statusCode code="completed"/>
                <effectiveTime><low value="1947"/><high
value="1972"/></effectiveTime>
                <value xsi:type="ST">1 pack per day</value>
            </observation>
        </entry>
        <entry typeCode="DRIV">
            <observation classCode="OBS" moodCode="EVN">
                <templateId root="2.16.840.1.113883.10.20.1.33"/> <!-- Social history
observation template -->
                <id root="45efb604-7049-4a2e-ad33-d38556c9636c"/>
                <code code="230056004" codeSystem="2.16.840.1.113883.6.96"
displayName="Cigarette smoking"/>
                <statusCode code="completed"/>
                <effectiveTime><low value="1973"/></effectiveTime>
                <value xsi:type="ST">None</value>
                <entryRelationship typeCode="SUBJ" inversionInd="true">
                    <observation classCode="OBS" moodCode="EVN">
                        <templateId root="2.16.840.1.113883.10.20.1.41"/> <!--
Episode observation template -->
                        <code code="ASSERTION"
codeSystem="2.16.840.1.113883.5.4"/>
                        <statusCode code="completed"/>
                        <value xsi:type="CD" code="404684003"
codeSystem="2.16.840.1.113883.6.96" displayName="Clinical finding">
                            <qualifier>
```

```xml
                                        <name code="246456000"
displayName="Episodicity"/>
                                        <value code="288527008" displayName="New
episode"/>
                                    </qualifier>
                                </value>
                                <entryRelationship typeCode="SAS">
                                    <observation classCode="OBS" moodCode="EVN">
                                        <id root="9b56c25d-9104-45ee-9fa4-
e0f3afaa01c1"/>
                                        <code code="230056004"
codeSystem="2.16.840.1.113883.6.96" displayName="Cigarette smoking"/>
                                    </observation>
                                </entryRelationship>
                            </observation>
                        </entryRelationship>
                    </observation>
            </entry>
            <entry typeCode="DRIV">
                <observation classCode="OBS" moodCode="EVN">
                    <templateId root="2.16.840.1.113883.10.20.1.33"/> <!-- Social history
observation template -->
                    <id root="37f76c51-6411-4e1d-8a37-957fd49d2cef"/>
                    <code code="160573003" codeSystem="2.16.840.1.113883.6.96"
displayName="Alcohol consumption"/>
                    <statusCode code="completed"/>
                    <effectiveTime><low value="1973"/></effectiveTime>
                    <value xsi:type="ST">None</value>
                </observation>
            </entry>
</section>
</component>
                <!--
********************************************************
Alerts section
********************************************************
-->
<component>
<section>
```

```xml
<templateId root="2.16.840.1.113883.10.20.1.2"/> <!-- Alerts section template -->
<code code="48765-2" codeSystem="2.16.840.1.113883.6.1"/>
<title>Allergies, Adverse Reactions, Alerts</title>
<text>
        <table border="1" width="100%">
            <thead>
                <tr><th>Substance</th><th>Reaction</th><th>Status</th></tr>
            </thead>
            <tbody>
                <tr><td>Penicillin</td><td>Hives</td><td>Active</td></tr>
                <tr><td>Aspirin</td><td>Wheezing</td><td>Active</td></tr>
                <tr><td>Codeine</td><td>Nausea</td><td>Active</td></tr>
            </tbody>
        </table>
</text>
<entry typeCode="DRIV">
        <act classCode="ACT" moodCode="EVN">
            <templateId root='2.16.840.1.113883.10.20.1.27'/> <!-- Problem act template -->
            <id root="36e3e930-7b14-11db-9fe1-0800200c9a66"/>
            <code nullFlavor="NA"/>
            <entryRelationship typeCode="SUBJ">
                <observation classCode="OBS" moodCode="EVN">
                    <templateId root='2.16.840.1.113883.10.20.1.18'/> <!-- Alert observation template -->
                    <id root="4adc1020-7b14-11db-9fe1-0800200c9a66"/>
                    <code code="ASSERTION" codeSystem="2.16.840.1.113883.5.4"/>
                    <statusCode code="completed"/>
                    <value xsi:type="CD" code="282100009" codeSystem="2.16.840.1.113883.6.96" displayName="Adverse reaction to substance"/>
                    <participant typeCode="CSM">
                        <participantRole classCode="MANU">
                            <playingEntity classCode="MMAT">
                                <code code="70618" codeSystem="2.16.840.1.113883.6.88" displayName="Penicillin"/>
                            </playingEntity>
                        </participantRole>
                    </participant>
```

```xml
                                <entryRelationship typeCode="MFST" inversionInd="true">
                                    <observation classCode="OBS" moodCode="EVN">
                                        <templateId root='2.16.840.1.113883.10.20.1.54'/> <!-- Reaction observation template -->
                                        <code code="ASSERTION" codeSystem="2.16.840.1.113883.5.4"/>
                                        <statusCode code="completed"/>
                                        <value xsi:type="CD" code="247472004" codeSystem="2.16.840.1.113883.6.96" displayName="Hives"/>
                                    </observation>
                                </entryRelationship>
                                <entryRelationship typeCode="REFR">
                                    <observation classCode="OBS" moodCode="EVN">
                                        <templateId root='2.16.840.1.113883.10.20.1.39'/> <!-- Alert status observation template -->
                                        <code code="33999-4" codeSystem="2.16.840.1.113883.6.1" displayName="Status"/>
                                        <statusCode code="completed"/>
                                        <value xsi:type="CE" code="55561003" codeSystem="2.16.840.1.113883.6.96" displayName="Active"/>
                                    </observation>
                                </entryRelationship>
                            </observation>
                        </entryRelationship>
                    </act>
                </entry>
                <entry typeCode="DRIV">
                    <act classCode="ACT" moodCode="EVN">
                        <templateId root='2.16.840.1.113883.10.20.1.27'/> <!-- Problem act template -->
                        <id root="eb936010-7b17-11db-9fe1-0800200c9a66"/>
                        <code nullFlavor="NA"/>
                        <entryRelationship typeCode="SUBJ">
                            <observation classCode="OBS" moodCode="EVN">
                                <templateId root='2.16.840.1.113883.10.20.1.18'/> <!-- Alert observation template -->
                                <id root="eb936011-7b17-11db-9fe1-0800200c9a66"/>
                                <code code="ASSERTION" codeSystem="2.16.840.1.113883.5.4"/>
```

```xml
                                        <statusCode code="completed"/>
                                        <value xsi:type="CD" code="282100009"
codeSystem="2.16.840.1.113883.6.96" displayName="Adverse reaction to substance"/>
                                        <participant typeCode="CSM">
                                                <participantRole classCode="MANU">
                                                        <playingEntity classCode="MMAT">
                                                                <code code="1191"
codeSystem="2.16.840.1.113883.6.88" displayName="Aspirin"/>
                                                        </playingEntity>
                                                </participantRole>
                                        </participant>
                                        <entryRelationship typeCode="MFST" inversionInd="true">
                                                <observation classCode="OBS" moodCode="EVN">
                                                        <templateId
root='2.16.840.1.113883.10.20.1.54'/> <!-- Reaction observation template -->
                                                        <code code="ASSERTION"
codeSystem="2.16.840.1.113883.5.4"/>
                                                        <statusCode code="completed"/>
                                                        <value xsi:type="CD" code="56018004"
codeSystem="2.16.840.1.113883.6.96" displayName="Wheezing"/>
                                                </observation>
                                        </entryRelationship>
                                        <entryRelationship typeCode="REFR">
                                                <observation classCode="OBS" moodCode="EVN">
                                                        <templateId
root='2.16.840.1.113883.10.20.1.39'/> <!-- Alert status observation template -->
                                                        <code code="33999-4"
codeSystem="2.16.840.1.113883.6.1" displayName="Status"/>
                                                        <statusCode code="completed"/>
                                                        <value xsi:type="CE" code="55561003"
codeSystem="2.16.840.1.113883.6.96" displayName="Active"/>
                                                </observation>
                                        </entryRelationship>
                                </observation>
                        </entryRelationship>
                </act>
        </entry>
        <entry typeCode="DRIV">
                <act classCode="ACT" moodCode="EVN">
```

```xml
                    <templateId root='2.16.840.1.113883.10.20.1.27'/> <!-- Problem act template -->
                    <id root="c3df3b61-7b18-11db-9fe1-0800200c9a66"/>
                    <code nullFlavor="NA"/>
                    <entryRelationship typeCode="SUBJ">
                        <observation classCode="OBS" moodCode="EVN">
                            <templateId root='2.16.840.1.113883.10.20.1.18'/> <!-- Alert observation template -->
                            <id root="c3df3b60-7b18-11db-9fe1-0800200c9a66"/>
                            <code code="ASSERTION" codeSystem="2.16.840.1.113883.5.4"/>
                            <statusCode code="completed"/>
                            <value xsi:type="CD" code="282100009" codeSystem="2.16.840.1.113883.6.96" displayName="Adverse reaction to substance"/>
                            <participant typeCode="CSM">
                                <participantRole classCode="MANU">
                                    <playingEntity classCode="MMAT">
                                        <code code="2670" codeSystem="2.16.840.1.113883.6.88" displayName="Codeine"/>
                                    </playingEntity>
                                </participantRole>
                            </participant>
                            <entryRelationship typeCode="MFST" inversionInd="true">
                                <observation classCode="OBS" moodCode="EVN">
                                    <templateId root='2.16.840.1.113883.10.20.1.54'/> <!-- Reaction observation template -->
                                    <code code="ASSERTION" codeSystem="2.16.840.1.113883.5.4"/>
                                    <statusCode code="completed"/>
                                    <value xsi:type="CD" code="73879007" codeSystem="2.16.840.1.113883.6.96" displayName="Nausea"/>
                                </observation>
                            </entryRelationship>
                            <entryRelationship typeCode="REFR">
                                <observation classCode="OBS" moodCode="EVN">
                                    <templateId root='2.16.840.1.113883.10.20.1.39'/> <!-- Alert status observation template -->
                                    <code code="33999-4" codeSystem="2.16.840.1.113883.6.1" displayName="Status"/>
```

```xml
                                        <statusCode code="completed"/>
                                        <value xsi:type="CE" code="55561003"
codeSystem="2.16.840.1.113883.6.96" displayName="Active"/>
                                    </observation>
                                </entryRelationship>
                            </observation>
                        </entryRelationship>
                    </act>
                </entry>
            </section>
        </component>
                        <!--
********************************************************
Medications section
********************************************************
-->
<component>
<section>
    <templateId root="2.16.840.1.113883.10.20.1.8"/> <!-- Medications section template
-->
    <code code="10160-0" codeSystem="2.16.840.1.113883.6.1"/>
    <title>Medications</title>
    <text>
        <table border="1" width="100%">
            <thead>
                <tr><th>Medication</th><th>Instructions</th><th>Start Date</th><th>Status</th></tr>
            </thead>
            <tbody>
                <tr><td>Albuterol inhalant</td><td>2 puffs QID PRN wheezing</td><td> </td><td>Active</td></tr>
                <tr><td>Clopidogrel (Plavix)</td><td>75mg PO daily</td><td> </td><td>Active</td></tr>
                <tr><td>Metoprolol</td><td>25mg PO BID</td><td> </td><td>Active</td></tr>
                <tr><td>Prednisone</td><td>20mg PO daily</td><td>Mar 28, 2000</td><td>Active</td></tr>
                <tr><td>Cephalexin (Keflex)</td><td>500mg PO QID x 7 days (for bronchitis)</td><td>Mar 28, 2000</td><td>No longer active</td></tr>
```

```xml
            </tbody>
        </table>
    </text>
        <informant>
        <assignedEntity>
            <id extension="996-756-495" root="2.16.840.1.113883.19.5"/>
            <representedOrganization>
                <id root="2.16.840.1.113883.19.5"/>
                <name>Good Health Clinic</name>
            </representedOrganization>
        </assignedEntity>
    </informant>
    <entry typeCode="DRIV">
        <substanceAdministration classCode="SBADM" moodCode="EVN">
            <templateId root="2.16.840.1.113883.10.20.1.24"/> <!-- Medication activity template -->
            <id root="cdbd33f0-6cde-11db-9fe1-0800200c9a66"/>
            <statusCode code="active"/>
            <effectiveTime xsi:type="PIVL_TS">
                <period value="6" unit="h"/>
            </effectiveTime>
            <routeCode code="IPINHL" codeSystem="2.16.840.1.113883.5.112" codeSystemName="RouteOfAdministration" displayName="Inhalation, oral"/>
            <doseQuantity value="2"/>
            <administrationUnitCode code="415215001" codeSystem="2.16.840.1.113883.6.96" displayName="Puff"/>
            <consumable>
                <manufacturedProduct>
                    <templateId root="2.16.840.1.113883.10.20.1.53"/> <!-- Product template -->
                    <manufacturedMaterial>
                        <code code="307782" codeSystem="2.16.840.1.113883.6.88" displayName="Albuterol 0.09 MG/ACTUAT inhalant solution">
                            <originalText>Albuterol inhalant</originalText>
                        </code>
                    </manufacturedMaterial>
                </manufacturedProduct>
```

```xml
                        </consumable>
                        <precondition typeCode="PRCN">
                                <criterion>
                                        <code code="ASSERTION" codeSystem="2.16.840.1.113883.5.4"/>
                                        <value xsi:type="CE" code="56018004" codeSystem="2.16.840.1.113883.6.96" displayName="Wheezing"/>
                                </criterion>
                        </precondition>
                </substanceAdministration>
        </entry>
        <entry typeCode="DRIV">
                <substanceAdministration classCode="SBADM" moodCode="EVN">
                        <templateId root="2.16.840.1.113883.10.20.1.24"/> <!-- Medication activity template -->
                        <id root="cdbd5b05-6cde-11db-9fe1-0800200c9a66"/>
                        <statusCode code="active"/>
                        <effectiveTime xsi:type="PIVL_TS">
                                <period value="24" unit="h"/>
                        </effectiveTime>
                        <routeCode code="PO" codeSystem="2.16.840.1.113883.5.112" codeSystemName="RouteOfAdministration"/>
                        <doseQuantity value="1"/>
                        <consumable>
                                <manufacturedProduct>
                                        <templateId root="2.16.840.1.113883.10.20.1.53"/> <!-- Product template -->
                                        <manufacturedMaterial>
                                                <code code="309362" codeSystem="2.16.840.1.113883.6.88" displayName="Clopidogrel 75 MG oral tablet">
                                                        <originalText>Clopidogrel</originalText>
                                                </code>
                                                <name>Plavix</name>
                                        </manufacturedMaterial>
                                </manufacturedProduct>
                        </consumable>
                </substanceAdministration>
        </entry>
        <entry typeCode="DRIV">
```

```xml
<substanceAdministration classCode="SBADM" moodCode="EVN">
    <templateId root="2.16.840.1.113883.10.20.1.24"/> <!-- Medication activity template -->
    <id root="cdbd5b01-6cde-11db-9fe1-0800200c9a66"/>
    <statusCode code="active"/>
    <effectiveTime xsi:type="PIVL_TS">
        <period value="12" unit="h"/>
    </effectiveTime>
    <routeCode code="PO" codeSystem="2.16.840.1.113883.5.112" codeSystemName="RouteOfAdministration"/>
    <doseQuantity value="1"/>
    <consumable>
        <manufacturedProduct>
            <templateId root="2.16.840.1.113883.10.20.1.53"/> <!-- Product template -->
            <manufacturedMaterial>
                <code code="430618" codeSystem="2.16.840.1.113883.6.88" displayName="Metoprolol 25 MG oral tablet">
                    <originalText>Metoprolol</originalText>
                </code>
            </manufacturedMaterial>
        </manufacturedProduct>
    </consumable>
</substanceAdministration>
</entry>
<entry typeCode="DRIV">
    <substanceAdministration classCode="SBADM" moodCode="EVN">
        <templateId root="2.16.840.1.113883.10.20.1.24"/> <!-- Medication activity template -->
        <id root="cdbd5b03-6cde-11db-9fe1-0800200c9a66"/>
        <statusCode code="active"/>
        <effectiveTime xsi:type="IVL_TS">
            <low value="20000328"/>
        </effectiveTime>
        <effectiveTime xsi:type="PIVL_TS" operator="A">
            <period value="24" unit="h"/>
        </effectiveTime>
        <routeCode code="PO" codeSystem="2.16.840.1.113883.5.112" codeSystemName="RouteOfAdministration"/>
```

```xml
                    <doseQuantity value="1"/>
                    <consumable>
                        <manufacturedProduct>
                            <templateId root="2.16.840.1.113883.10.20.1.53"/> <!-- Product template -->
                            <manufacturedMaterial>
                                <code code="312615" codeSystem="2.16.840.1.113883.6.88" displayName="Prednisone 20 MG oral tablet">
                                    <originalText>Prednisone</originalText>
                                </code>
                            </manufacturedMaterial>
                        </manufacturedProduct>
                    </consumable>
                </substanceAdministration>
            </entry>
            <entry typeCode="DRIV">
                <substanceAdministration classCode="SBADM" moodCode="EVN">
                    <templateId root="2.16.840.1.113883.10.20.1.24"/> <!-- Medication activity template -->
                    <id root="cdbd5b07-6cde-11db-9fe1-0800200c9a66"/>
                    <statusCode code="completed"/>
                    <effectiveTime xsi:type="IVL_TS">
                        <low value="20000328"/>
                        <high value="20000404"/>
                    </effectiveTime>
                    <effectiveTime xsi:type="PIVL_TS" operator="A">
                        <period value="6" unit="h"/>
                    </effectiveTime>
                    <routeCode code="PO" codeSystem="2.16.840.1.113883.5.112" codeSystemName="RouteOfAdministration"/>
                    <doseQuantity value="1"/>
                    <consumable>
                        <manufacturedProduct>
                            <templateId root="2.16.840.1.113883.10.20.1.53"/> <!-- Product template -->
                            <manufacturedMaterial>
                                <code code="197454" codeSystem="2.16.840.1.113883.6.88" displayName="Cephalexin 500 MG oral tablet">
                                    <originalText>Cephalexin</originalText>
```

```
                                </code>
                                <name>Keflex</name>
                            </manufacturedMaterial>
                        </manufacturedProduct>
                    </consumable>
                    <entryRelationship typeCode="RSON">
                        <observation classCode="COND" moodCode="EVN">
                            <templateId root="2.16.840.1.113883.10.20.1.28"/> <!--
Problem observation template -->
                            <id root="cdbd5b08-6cde-11db-9fe1-0800200c9a66"/>
                            <code code="ASSERTION"
codeSystem="2.16.840.1.113883.5.4"/>
                            <statusCode code="completed"/>
                            <effectiveTime xsi:type="IVL_TS">
                                <low value="20000328"/>
                            </effectiveTime>
                            <value xsi:type="CE" code="32398004"
codeSystem="2.16.840.1.113883.6.96" displayName="Bronchitis"/>
                        </observation>
                    </entryRelationship>
                </substanceAdministration>
            </entry>
        </section>
    </component>
                <!--
**********************************************************
Medical Equipment section
**********************************************************
-->
<component>
<section>
    <templateId root="2.16.840.1.113883.10.20.1.7"/> <!-- Medical equipment section
template -->
    <code code="46264-8" codeSystem="2.16.840.1.113883.6.1"/>
    <title>Medical Equipment</title>
    <text>
        <table border="1" width="100%">
            <thead>
                <tr><th>Supply/Device</th><th>Date Supplied</th></tr>
```

```
                </thead>
                <tbody>
                        <tr><td>Automatic implantable
cardioverter/defibrillator</td><td>Nov 1999</td></tr>
                        <tr><td>Total hip replacement
prosthesis</td><td>1998</td></tr>
                        <tr><td>Wheelchair</td><td>1999</td></tr>
                </tbody>
        </table>
    </text>
    <entry typeCode="DRIV">
        <supply classCode="SPLY" moodCode="EVN">
                <templateId root="2.16.840.1.113883.10.20.1.34"/> <!-- Supply
activity template -->
                <id root="2413773c-2372-4299-bbe6-5b0f60664446"/>
                <statusCode code="completed"/>
                <effectiveTime xsi:type="IVL_TS"><center
value="199911"/></effectiveTime>
                <participant typeCode="DEV">
                        <participantRole classCode="MANU">
                                <templateId root="2.16.840.1.113883.10.20.1.52"/> <!--
Product instance template -->
                                <playingDevice>
                                        <code code="72506001"
codeSystem="2.16.840.1.113883.6.96" displayName="Automatic implantable
cardioverter/defibrillator"/>
                                </playingDevice>
                        </participantRole>
                </participant>
        </supply>
    </entry>
    <entry typeCode="DRIV">
        <supply classCode="SPLY" moodCode="EVN">
                <templateId root="2.16.840.1.113883.10.20.1.34"/> <!-- Supply
activity template -->
                <id root="230b0ab7-206d-42d8-a947-ab4f63aad795"/>
                <statusCode code="completed"/>
                <effectiveTime xsi:type="IVL_TS"><center
value="1998"/></effectiveTime>
```

```xml
<participant typeCode="DEV">
    <participantRole classCode="MANU">
        <templateId root="2.16.840.1.113883.10.20.1.52"/> <!-- Product instance template -->
        <id root="03ca01b0-7be1-11db-9fe1-0800200c9a66"/>
        <playingDevice>
            <code code="304120007" codeSystem="2.16.840.1.113883.6.96" displayName="Total hip replacement prosthesis"/>
        </playingDevice>
        <scopingEntity>
            <id root="0abea950-5b40-4b7e-b8d9-2a5ea3ac5500"/>
            <desc>Good Health Prostheses Company</desc>
        </scopingEntity>
    </participantRole>
</participant>
            </supply>
        </entry>
        <entry typeCode="DRIV">
            <supply classCode="SPLY" moodCode="EVN">
                <templateId root="2.16.840.1.113883.10.20.1.34"/> <!-- Supply activity template -->
                <id root="c4ffe98e-3cd3-4c54-b5bd-08ecb80379e0"/>
                <statusCode code="completed"/>
                <effectiveTime xsi:type="IVL_TS"><center value="1999"/></effectiveTime>
                <participant typeCode="DEV">
                    <participantRole classCode="MANU">
                        <templateId root="2.16.840.1.113883.10.20.1.52"/> <!-- Product instance template -->
                        <playingDevice>
                            <code code="58938008" codeSystem="2.16.840.1.113883.6.96" displayName="Wheelchair"/>
                        </playingDevice>
                    </participantRole>
                </participant>
            </supply>
        </entry>
</section>
</component>
```

```
                <!--
********************************************************
Immunizations section
********************************************************
-->
<component>
<section>
        <templateId root="2.16.840.1.113883.10.20.1.6"/> <!-- Immunizations section
template -->
        <code code="11369-6" codeSystem="2.16.840.1.113883.6.1"/>
        <title>Immunizations</title>
        <text>
                <table border="1" width="100%">
                        <thead>
                                <tr><th>Vaccine</th><th>Date</th><th>Status</th></tr>
                        </thead>
                        <tbody>
                                <tr><td>Influenza virus vaccine, IM</td><td>Nov
1999</td><td>Completed</td></tr>
                                <tr><td>Influenza virus vaccine, IM</td><td>Dec
1998</td><td>Completed</td></tr>
                                <tr><td>Pneumococcal polysaccharide vaccine, IM</td><td>Dec
1998</td><td>Completed</td></tr>
                                <tr><td>Tetanus and diphtheria toxoids,
IM</td><td>1997</td><td>Completed</td></tr>
                        </tbody>
                </table>
        </text>
        <entry typeCode="DRIV">
                <substanceAdministration classCode="SBADM" moodCode="EVN">
                        <templateId root="2.16.840.1.113883.10.20.1.24"/> <!-- Medication
activity template -->
                        <id root="e6f1ba43-c0ed-4b9b-9f12-f435d8ad8f92"/>
                        <statusCode code="completed"/>
                        <effectiveTime xsi:type="IVL_TS"><center
value="199911"/></effectiveTime>
                        <routeCode code="IM" codeSystem="2.16.840.1.113883.5.112"
codeSystemName="RouteOfAdministration" displayName="Intramuscular injection"/>
                        <consumable>
```

```xml
                    <manufacturedProduct>
                            <templateId root="2.16.840.1.113883.10.20.1.53"/> <!-- Product template -->
                            <manufacturedMaterial>
                                    <code code="88" codeSystem="2.16.840.1.113883.6.59" displayName="Influenza virus vaccine">
                                            <originalText>Influenza virus vaccine</originalText>
                                    </code>
                            </manufacturedMaterial>
                    </manufacturedProduct>
            </consumable>
        </substanceAdministration>
    </entry>
    <entry typeCode="DRIV">
        <substanceAdministration classCode="SBADM" moodCode="EVN">
            <templateId root="2.16.840.1.113883.10.20.1.24"/> <!-- Medication activity template -->
            <id root="115f0f70-1343-4938-b62f-631de9749a0a"/>
            <statusCode code="completed"/>
            <effectiveTime xsi:type="IVL_TS"><center value="199812"/></effectiveTime>
            <routeCode code="IM" codeSystem="2.16.840.1.113883.5.112" codeSystemName="RouteOfAdministration" displayName="Intramuscular injection"/>

<consumable>
                    <manufacturedProduct>
                            <templateId root="2.16.840.1.113883.10.20.1.53"/> <!-- Product template -->
                            <manufacturedMaterial>
                                    <code code="88" codeSystem="2.16.840.1.113883.6.59" displayName="Influenza virus vaccine">
                                            <originalText>Influenza virus vaccine</originalText>
                                    </code>
                            </manufacturedMaterial>
                    </manufacturedProduct>
            </consumable>
        </substanceAdministration>
```

```xml
        </entry>
        <entry typeCode="DRIV">
            <substanceAdministration classCode="SBADM" moodCode="EVN">
                <templateId root="2.16.840.1.113883.10.20.1.24"/> <!-- Medication activity template -->
                <id root="78598407-9f16-42d5-8ffd-09281a60fe33"/>
                <statusCode code="completed"/>
                <effectiveTime xsi:type="IVL_TS"><center value="199812"/></effectiveTime>
                <routeCode code="IM" codeSystem="2.16.840.1.113883.5.112" codeSystemName="RouteOfAdministration" displayName="Intramuscular injection"/>
                <consumable>
                    <manufacturedProduct>
                        <templateId root="2.16.840.1.113883.10.20.1.53"/> <!-- Product template -->
                        <manufacturedMaterial>
                            <code code="33" codeSystem="2.16.840.1.113883.6.59" displayName="Pneumococcal polysaccharide vaccine">
                                <originalText>Pneumococcal polysaccharide vaccine</originalText>
                            </code>
                        </manufacturedMaterial>
                    </manufacturedProduct>
                </consumable>
            </substanceAdministration>
        </entry>
        <entry typeCode="DRIV">
            <substanceAdministration classCode="SBADM" moodCode="EVN">
                <templateId root="2.16.840.1.113883.10.20.1.24"/> <!-- Medication activity template -->
                <id root="261e94a0-95fb-4975-b5a5-c8e12c01c1bc"/>
                <statusCode code="completed"/>
                <effectiveTime xsi:type="IVL_TS"><center value="1997"/></effectiveTime>
                <routeCode code="IM" codeSystem="2.16.840.1.113883.5.112" codeSystemName="RouteOfAdministration" displayName="Intramuscular injection"/>
                <consumable>
                    <manufacturedProduct>
```

```
                                        <templateId root="2.16.840.1.113883.10.20.1.53"/> <!--
Product template -->
                                        <manufacturedMaterial>
                                            <code code="09"
codeSystem="2.16.840.1.113883.6.59" displayName="Tetanus and diphtheria toxoids">
                                                <originalText>Tetanus and diphtheria
toxoids</originalText>
                                            </code>
                                        </manufacturedMaterial>
                                    </manufacturedProduct>
                                </consumable>
                            </substanceAdministration>
                        </entry>
                </section>
            </component>
                            <!--
**********************************************************
Vital Signs section
**********************************************************
-->
<component>
<section>
        <templateId root="2.16.840.1.113883.10.20.1.16"/> <!-- Vital signs section
template -->
        <code code="8716-3" codeSystem="2.16.840.1.113883.6.1"/>
        <title>Vital Signs</title>
        <text>
                <table border="1" width="100%">
                        <thead>
                                <tr><th align="right">Date / Time: </th><th>Nov 14,
1999</th><th>April 7, 2000</th></tr>
                        </thead>
                        <tbody>
                                <tr><th align="left">Height</th><td>177 cm</td><td>177
cm</td></tr>
                                <tr><th align="left">Weight</th><td>86 kg</td><td>88
kg</td></tr>
                                <tr><th align="left">Blood Pressure</th><td>132/86
mmHg</td><td>145/88 mmHg</td></tr>
```

```xml
                        </tbody>
                </table>
        </text>
        <entry typeCode="DRIV">
                <organizer classCode="CLUSTER" moodCode="EVN">
                        <templateId root="2.16.840.1.113883.10.20.1.35"/> <!-- Vital signs organizer template -->
                        <id root="c6f88320-67ad-11db-bd13-0800200c9a66"/>
                        <code code="46680005" codeSystem="2.16.840.1.113883.6.96" displayName="Vital signs"/>
                        <statusCode code="completed"/>
                        <effectiveTime value="19991114"/>
                        <component>
                                <observation classCode="OBS" moodCode="EVN">
                                        <templateId root="2.16.840.1.113883.10.20.1.31"/> <!-- Result observation template -->
                                        <id root="c6f88321-67ad-11db-bd13-0800200c9a66"/>
                                        <code code="50373000" codeSystem="2.16.840.1.113883.6.96" displayName="Body height"/>
                                        <statusCode code="completed"/>
                                        <effectiveTime value="19991114"/>
                                        <value xsi:type="PQ" value="177" unit="cm"/>
                                </observation>
                        </component>
                        <component>
                                <observation classCode="OBS" moodCode="EVN">
                                        <templateId root="2.16.840.1.113883.10.20.1.31"/> <!-- Result observation template -->
                                        <id root="c6f88322-67ad-11db-bd13-0800200c9a66"/>
                                        <code code="27113001" codeSystem="2.16.840.1.113883.6.96" displayName="Body weight"/>
                                        <statusCode code="completed"/>
                                        <effectiveTime value="19991114"/>
                                        <value xsi:type="PQ" value="86" unit="kg"/>
                                </observation>
                        </component>
                        <component>
                                <observation classCode="OBS" moodCode="EVN">
```

```xml
                                <templateId root="2.16.840.1.113883.10.20.1.31"/> <!-- Result observation template -->
                                <id root="c6f88323-67ad-11db-bd13-0800200c9a66"/>
                                <code code="271649006" codeSystem="2.16.840.1.113883.6.96" displayName="Systolic BP"/>
                                <statusCode code="completed"/>
                                <effectiveTime value="19991114"/>
                                <value xsi:type="PQ" value="132" unit="mm[Hg]"/>
                            </observation>
                        </component>
                        <component>
                            <observation classCode="OBS" moodCode="EVN">
                                <templateId root="2.16.840.1.113883.10.20.1.31"/> <!-- Result observation template -->
                                <id root="c6f88324-67ad-11db-bd13-0800200c9a66"/>
                                <code code="271650006" codeSystem="2.16.840.1.113883.6.96" displayName="Diastolic BP"/>
                                <statusCode code="completed"/>
                                <effectiveTime value="19991114"/>
                                <value xsi:type="PQ" value="86" unit="mm[Hg]"/>
                            </observation>
                        </component>
                    </organizer>
                </entry>
                <entry typeCode="DRIV">
                    <organizer classCode="CLUSTER" moodCode="EVN">
                        <templateId root="2.16.840.1.113883.10.20.1.35"/> <!-- Vital signs organizer template -->
                        <id root="d11275e0-67ae-11db-bd13-0800200c9a66"/>
                        <code code="46680005" codeSystem="2.16.840.1.113883.6.96" displayName="Vital signs"/>
                        <statusCode code="completed"/>
                        <effectiveTime value="20000407"/>
                        <component>
                            <observation classCode="OBS" moodCode="EVN">
                                <templateId root="2.16.840.1.113883.10.20.1.31"/> <!-- Result observation template -->
                                <id root="d11275e1-67ae-11db-bd13-0800200c9a66"/>
```

```xml
                    <code code="50373000" codeSystem="2.16.840.1.113883.6.96" displayName="Body height"/>
                    <statusCode code="completed"/>
                    <effectiveTime value="20000407"/>
                    <value xsi:type="PQ" value="177" unit="cm"/>
                </observation>
            </component>
            <component>
                <observation classCode="OBS" moodCode="EVN">
                    <templateId root="2.16.840.1.113883.10.20.1.31"/> <!-- Result observation template -->
                    <id root="d11275e2-67ae-11db-bd13-0800200c9a66"/>
                    <code code="27113001" codeSystem="2.16.840.1.113883.6.96" displayName="Body weight"/>
                    <statusCode code="completed"/>
                    <effectiveTime value="20000407"/>
                    <value xsi:type="PQ" value="88" unit="kg"/>
                </observation>
            </component>
            <component>
                <observation classCode="OBS" moodCode="EVN">
                    <templateId root="2.16.840.1.113883.10.20.1.31"/> <!-- Result observation template -->
                    <id root="d11275e3-67ae-11db-bd13-0800200c9a66"/>
                    <code code="271649006" codeSystem="2.16.840.1.113883.6.96" displayName="Systolic BP"/>
                    <statusCode code="completed"/>
                    <effectiveTime value="20000407"/>
                    <value xsi:type="PQ" value="145" unit="mm[Hg]"/>
                </observation>
            </component>
            <component>
                <observation classCode="OBS" moodCode="EVN">
                    <templateId root="2.16.840.1.113883.10.20.1.31"/> <!-- Result observation template -->
                    <id root="d11275e4-67ae-11db-bd13-0800200c9a66"/>
                    <code code="271650006" codeSystem="2.16.840.1.113883.6.96" displayName="Diastolic BP"/>
                    <statusCode code="completed"/>
```

```xml
                    <effectiveTime value="20000407"/>
                    <value xsi:type="PQ" value="88" unit="mm[Hg]"/>
                </observation>
            </component>
        </organizer>
    </entry>
</section>
</component>
            <!--
*********************************************************
Results section
*********************************************************
-->
<component>
<section>
    <templateId root="2.16.840.1.113883.10.20.1.14"/> <!-- Results section template -->
    <code code="30954-2" codeSystem="2.16.840.1.113883.6.1"/>
    <title>Results</title>
    <text>
        <table border="1" width="100%">
            <thead>
                <tr><th> </th><th>March 23, 2000</th><th>April 06, 2000</th></tr>
            </thead>
            <tbody>
                <tr><td colspan="3"><content styleCode="BoldItalics">Hematology</content></td></tr>
                <tr><td>HGB (M 13-18 g/dl; F 12-16 g/dl)</td><td>13.2</td><td> </td></tr>
                <tr><td>WBC (4.3-10.8 10+3/ul)</td><td>6.7</td><td> </td></tr>
                <tr><td>PLT (135-145 meq/l)</td><td>123*</td><td> </td></tr>
                <tr><td colspan="3"><content styleCode="BoldItalics">Chemistry</content></td></tr>
                <tr><td>NA (135-145meq/l)</td><td> </td><td>140</td></tr>
                <tr><td>K (3.5-5.0 meq/l)</td><td> </td><td>4.0</td></tr>
                <tr><td>CL (98-106 meq/l)</td><td> </td><td>102</td></tr>
```

```
                    <tr><td>HCO3 (18-23
meq/1)</td><td> </td><td>35*</td></tr>
                </tbody>
            </table>
        </text>
        <entry typeCode="DRIV">
            <organizer classCode="BATTERY" moodCode="EVN">
                <templateId root="2.16.840.1.113883.10.20.1.32"/> <!-- Result
organizer template -->
                <id root="7d5a02b0-67a4-11db-bd13-0800200c9a66"/>
                <code code="43789009" codeSystem="2.16.840.1.113883.6.96"
displayName="CBC WO DIFFERENTIAL"/>
                <statusCode code="completed"/>
                <effectiveTime value="200003231430"/>
                <component>
                    <observation classCode="OBS" moodCode="EVN">
                        <templateId root="2.16.840.1.113883.10.20.1.31"/> <!--
Result observation template -->
                        <id root="107c2dc0-67a5-11db-bd13-0800200c9a66"/>
                        <code code="30313-1" codeSystem="2.16.840.1.113883.6.1"
displayName="HGB"/>
                        <statusCode code="completed"/>
                        <effectiveTime value="200003231430"/>
                        <value xsi:type="PQ" value="13.2" unit="g/dl"/>
                        <interpretationCode code="N"
codeSystem="2.16.840.1.113883.5.83"/>
                        <referenceRange>
                            <observationRange>
                                <text>M 13-18 g/dl; F 12-16 g/dl</text>
                            </observationRange>
                        </referenceRange>
                    </observation>
                </component>
                <component>
                    <observation classCode="OBS" moodCode="EVN">
                        <templateId root="2.16.840.1.113883.10.20.1.31"/> <!--
Result observation template -->
                        <id root="8b3fa370-67a5-11db-bd13-0800200c9a66"/>
```

```xml
                                        <code code="33765-9" codeSystem="2.16.840.1.113883.6.1"
displayName="WBC"/>
                                        <statusCode code="completed"/>
                                        <effectiveTime value="200003231430"/>
                                        <value xsi:type="PQ" value="6.7" unit="10+3/ul"/>
                                        <interpretationCode code="N"
codeSystem="2.16.840.1.113883.5.83"/>
                                        <referenceRange>
                                            <observationRange>
                                                <value xsi:type="IVL_PQ">
                                                    <low value="4.3" unit="10+3/ul"/>
                                                    <high value="10.8" unit="10+3/ul"/>
                                                </value>
                                            </observationRange>
                                        </referenceRange>
                                    </observation>
                                </component>
                                <component>
                                    <observation classCode="OBS" moodCode="EVN">
                                        <templateId root="2.16.840.1.113883.10.20.1.31"/> <!--
Result observation template -->
                                        <id root="80a6c740-67a5-11db-bd13-0800200c9a66"/>
                                        <code code="26515-7" codeSystem="2.16.840.1.113883.6.1"
displayName="PLT"/>
                                        <statusCode code="completed"/>
                                        <effectiveTime value="200003231430"/>
                                        <value xsi:type="PQ" value="123" unit="10+3/ul"/>
                                        <interpretationCode code="L"
codeSystem="2.16.840.1.113883.5.83"/>
                                        <referenceRange>
                                            <observationRange>
                                                <value xsi:type="IVL_PQ">
                                                    <low value="150" unit="10+3/ul"/>
                                                    <high value="350" unit="10+3/ul"/>
                                                </value>
                                            </observationRange>
                                        </referenceRange>
                                    </observation>
                                </component>
```

```xml
                </organizer>
        </entry>
        <entry typeCode="DRIV">
                <organizer classCode="BATTERY" moodCode="EVN">
                        <templateId root="2.16.840.1.113883.10.20.1.32"/> <!-- Result organizer template -->
                        <id root="a40027e0-67a5-11db-bd13-0800200c9a66"/>
                        <code code="20109005" codeSystem="2.16.840.1.113883.6.96" displayName="LYTES"/>
                        <statusCode code="completed"/>
                        <effectiveTime value="200004061300"/>
                        <component>
                                <observation classCode="OBS" moodCode="EVN">
                                        <templateId root="2.16.840.1.113883.10.20.1.31"/> <!-- Result observation template -->
                                        <id root="a40027e1-67a5-11db-bd13-0800200c9a66"/>
                                        <code code="2951-2" codeSystem="2.16.840.1.113883.6.1" displayName="NA"/>
                                        <statusCode code="completed"/>
                                        <effectiveTime value="200004061300"/>
                                        <value xsi:type="PQ" value="140" unit="meq/l"/>
                                        <interpretationCode code="N" codeSystem="2.16.840.1.113883.5.83"/>
                                        <referenceRange>
                                                <observationRange>
                                                        <value xsi:type="IVL_PQ">
                                                                <low value="135" unit="meq/l"/>
                                                                <high value="145" unit="meq/l"/>
                                                        </value>
                                                </observationRange>
                                        </referenceRange>
                                </observation>
                        </component>
                        <component>
                                <observation classCode="OBS" moodCode="EVN">
                                        <templateId root="2.16.840.1.113883.10.20.1.31"/> <!-- Result observation template -->
                                        <id root="a40027e2-67a5-11db-bd13-0800200c9a66"/>
```

```xml
                              <code code="2823-3" codeSystem="2.16.840.1.113883.6.1" displayName="K"/>
                              <statusCode code="completed"/>
                              <effectiveTime value="200004061300"/>
                              <value xsi:type="PQ" value="4.0" unit="meq/l"/>
                              <interpretationCode code="N" codeSystem="2.16.840.1.113883.5.83"/>
                              <referenceRange>
                                  <observationRange>
                                      <value xsi:type="IVL_PQ">
                                          <low value="3.5" unit="meq/l"/>
                                          <high value="5.0" unit="meq/l"/>
                                      </value>
                                  </observationRange>
                              </referenceRange>
                          </observation>
                      </component>
                      <component>
                          <observation classCode="OBS" moodCode="EVN">
                              <templateId root="2.16.840.1.113883.10.20.1.31"/> <!-- Result observation template -->
                              <id root="a40027e3-67a5-11db-bd13-0800200c9a66"/>
                              <code code="2075-0" codeSystem="2.16.840.1.113883.6.1" displayName="CL"/>
                              <statusCode code="completed"/>
                              <effectiveTime value="200004061300"/>
                              <value xsi:type="PQ" value="102" unit="meq/l"/>
                              <interpretationCode code="N" codeSystem="2.16.840.1.113883.5.83"/>
                              <referenceRange>
                                  <observationRange>
                                      <value xsi:type="IVL_PQ">
                                          <low value="98" unit="meq/l"/>
                                          <high value="106" unit="meq/l"/>
                                      </value>
                                  </observationRange>
                              </referenceRange>
                          </observation>
                      </component>
```

```xml
            <component>
                    <observation classCode="OBS" moodCode="EVN">
                            <templateId root="2.16.840.1.113883.10.20.1.31"/> <!-- Result observation template -->
                            <id root="a40027e4-67a5-11db-bd13-0800200c9a66"/>
                            <code code="1963-8" codeSystem="2.16.840.1.113883.6.1" displayName="HCO3"/>
                            <statusCode code="completed"/>
                            <effectiveTime value="200004061300"/>
                            <value xsi:type="PQ" value="35" unit="meq/l"/>
                            <interpretationCode code="H" codeSystem="2.16.840.1.113883.5.83"/>
                            <referenceRange>
                                    <observationRange>
                                            <value xsi:type="IVL_PQ">
                                                    <low value="18" unit="meq/l"/>
                                                    <high value="23" unit="meq/l"/>
                                            </value>
                                    </observationRange>
                            </referenceRange>
                    </observation>
            </component>
        </organizer>
    </entry>
</section>
</component>
            <!--
********************************************************
Procedures section
********************************************************
-->
<component>
<section>
    <templateId root="2.16.840.1.113883.10.20.1.12"/> <!-- Procedures section template -->
    <code code="47519-4" codeSystem="2.16.840.1.113883.6.1"/>
    <title>Procedures</title>
    <text>
            <table border="1" width="100%">
```

```
                        <thead>
                                <tr><th>Procedure</th><th>Date</th></tr>
                        </thead>
                        <tbody>
                                <tr><td><content ID="Proc1">Total hip replacement,
left</content></td><td>1998</td></tr>
                        </tbody>
                </table>
        </text>
        <entry typeCode="DRIV">
                <procedure classCode="PROC" moodCode="EVN">
                        <templateId root="2.16.840.1.113883.10.20.1.29"/> <!-- Procedure
activity template -->
                        <id root="e401f340-7be2-11db-9fe1-0800200c9a66"/>
                        <code code="52734007" codeSystem="2.16.840.1.113883.6.96"
displayName="Total hip replacement">
                                <originalText><reference value="#Proc1"/></originalText>
                                <qualifier>
                                        <name code="272741003" displayName="Laterality"/>
                                        <value code="7771000" displayName="Left"/>
                                </qualifier>
                        </code>
                        <statusCode code="completed"/>
                        <effectiveTime value="1998"/>
                        <participant typeCode="DEV">
                                <participantRole classCode="MANU">
                                        <templateId root="2.16.840.1.113883.10.20.1.52"/> <!--
Product instance template -->
                                        <id root="03ca01b0-7be1-11db-9fe1-0800200c9a66"/>
                                </participantRole>
                        </participant>
                </procedure>
        </entry>
</section>
</component>

<!--
**********************************************************
Encounters section
```

```
*********************************************************
-->
<component>
<section>
        <templateId root="2.16.840.1.113883.10.20.1.3"/> <!-- Encounters section template
-->
        <code code="46240-8" codeSystem="2.16.840.1.113883.6.1"/>
        <title>Encounters</title>
        <text>
                <table border="1" width="100%">
                        <thead>
                                <tr><th>Encounter</th><th>Location</th><th>Date</th></tr>
                        </thead>
                        <tbody>
                                <tr><td>Checkup Examination</td><td>Good Health
Clinic</td><td>Apr 07, 2000</td></tr>
                        </tbody>
                </table>
        </text>
        <entry typeCode="DRIV">
                <encounter classCode="ENC" moodCode="EVN">
                        <templateId root="2.16.840.1.113883.10.20.1.21"/> <!-- Encounter
activity template -->
                        <id root="2a620155-9d11-439e-92b3-5d9815ff4de8"/>
                        <code code="GENRL" codeSystem="2.16.840.1.113883.5.4"
displayName="General">
                                <originalText>Checkup Examination</originalText>
                        </code>
                        <effectiveTime value="20000407"/>
                        <participant typeCode="LOC">
                                <templateId root="2.16.840.1.113883.10.20.1.45"/> <!--
Location participation template -->
                                <participantRole classCode="SDLOC">
                                        <id root="2.16.840.1.113883.19.5"/>
                                        <playingEntity classCode="PLC">
                                                <name>Good Health Clinic</name>
                                        </playingEntity>
                                </participantRole>
                        </participant>
```

```
                </encounter>
        </entry>
</section>
</component>
                        <!--
********************************************************
Plan of Care section
********************************************************
-->
<component>
<section>
        <templateId root="2.16.840.1.113883.10.20.1.10"/> <!-- Plan of Care section
template -->
        <code code="18776-5" codeSystem="2.16.840.1.113883.6.1"/>
        <title>Plan</title>
            <text>
            <table border="1" width="100%">
                <thead>
                <tr><th>Planned Activity</th><th>Planned Date</th></tr>
                </thead>
                <tbody>
                <tr><td>Pulmonary function test</td><td>April 21, 2000</td></tr>
                </tbody>
            </table>
        </text>
        <entry typeCode="DRIV">
                <observation classCode="OBS" moodCode="RQO">
                        <templateId root="2.16.840.1.113883.10.20.1.25"/> <!-- Plan of
Activity activity template -->
                        <id root="9a6d1bac-17d3-4195-89a4-1121bc809b4a"/>
                        <code code="23426006" codeSystem="2.16.840.1.113883.6.96"
displayName="Pulmonary function test"/>
                        <statusCode code="new"/>
                        <effectiveTime><center value="20000421"/></effectiveTime>
                </observation>
        </entry>
</section>
</component>
</structuredBody>
```

```
</component>
</ClinicalDocument>
```

Exemplary incremental WSDL operations for the Personal Health Record canonical can include: RenderAsCCR-WithID (input: patientRecordID, output: personalHealthRecordAsCCR); and RenderAsCCRWithCCD (input: personalHealthRecordCanonicalAsCCD, output: personalHealthRecordAsCCR).

In an exemplary embodiment, these additional operations can effectively render the Personal Health Record canonical in another XML format either by loading a different CRUD and re-extracting data from the source ( . . . WithID) or by doing an XSLT transformation inside the operation ( . . . WithCCD).

Exemplary embodiments of the Headwater platform for healthcare can provide a software service definition or canonical for Insurance (claims and referrals) including the data and common functions that deliver the service functionality. The Service definition can include an H7 version 3.0 RIM compliant data structure with the functions to create, read, update and delete the data structure the service represents.

Exemplary embodiments of the Headwater platform for healthcare can also provide a software service definition for Scheduling and Appointments including the data and common functions that deliver the service functionality. An exemplary Service definition can include an H7 version 3.0 RIM compliant data structure with the functions to create, read, update and delete the data structure the service represents.

In exemplary embodiments of the present invention, a schedule is used as an intermediary response to an order. When an order is placed, a schedule is generated to describe when and where the order can be filled. Once the order is filled, the encounter/result is generated.

A schedule is also a unique canonical in that its core and incremental WSDL operations can be implemented as two separate implementations: 1) Scheduling (which is the implementation of the core canonical operations and the XML payload listed below) and 2) ScheduleDefinitionAndFulfillment (which is the implementation of the extended WSDL operations below).

An exemplary schema definition of the Scheduling canonical follows.

In an exemplary embodiment, an exemplary schema definition (or relevant portion thereof) follows that relates to scheduling a response for a encounter:

```
<?xml version="1.0"?>
<!-- The following sample document depicts a fictional character's health summary. Any
resemblance to a real person is coincidental. -->
<ClinicalDocument xmlns="urn:hl7-org:v3" xmlns:voc="urn:hl7-org:v3/voc"
xmlns:xsi="http://www.w3.org/2001/XMLSchema-instance" xsi:schemaLocation="urn:hl7-org:v3
CDA.xsd">
    <!--
**********************************************************
CDA Header
**********************************************************
-->
    <typeId root="2.16.840.1.113883.1.3" extension="POCD_HD000040"/>
    <!-- typeId is required in all CDA instances, and fixed as shown here. This is how
you know the instance is a CDA R2 document. -->
    <id root="7218c766-f23a-40eb-bb6e-8e2cef61d3cc" extension="eb7b661b-d302-4c71-
a672-d5b7b5833e3f"/>
    <!-- ClinicalDocument.id has cardinality 1..1, and carries the Local ID. -->
    <code code="410538000" codeSystem="2.16.840.1.113883.6.96" displayName="Scheduling
procedure"/>
    <!-- This can be a fixed code, since the scheduling details are included below. -->
    <title>Good Health Clinic Scheduling Report</title>
    <!-- This can be a fixed value, used for rendering, or could be left out. -->
    <effectiveTime value="200004080732"/>
    <!-- Required by CDA, and is the time of document creation. -->
    <confidentialityCode code="N" codeSystem="2.16.840.1.113883.5.25"/>
    <recordTarget>
        <patientRole>
            <id extension="12345" root="76b242b9-1246-4691-bb1d-91bb7336e76f"/>
<!-- HIN patient ID -->
            <id extension="97531" root="81821f47-8139-4766-aff0-81be0674de8f"/>
<!-- Local patient ID -->
            <patient>
                <name>
                    <given>Henry</given>
                    <family>Levin</family>
                    <suffix>the 7th</suffix>
                </name>
                <administrativeGenderCode code="M"
codeSystem="2.16.840.1.113883.5.1"/>
                <birthTime value="19320924"/>
            </patient>
        </patientRole>
    </recordTarget>
    <author>
        <time value="200004080732"/>
        <assignedAuthor>
            <id extension="ee540aa1-41d2-42cb-9fb4-bdc067e2208c" root="76b242b9-
1246-4691-bb1d-91bb7336e76f"/> <!-- HIN provider ID -->
            <id extension="9e8c06a4-f23e-4aba-9113-74dd6747f1b0" root="81821f47-
8139-4766-aff0-81be0674de8f"/> <!-- Local provider ID -->
        </assignedAuthor>
    </author>
```

```
        <!-- Different workflows may ascribe authorship to a device and/or to a clinician.
In this example, the author is a device. -->
        <custodian>
            <assignedCustodian>
                <representedCustodianOrganization>
                    <id extension="81821f47-8139-4766-aff0-81be0674de8f"
root="76b242b9-1246-4691-bb1d-91bb7336e76f"/> <!-- HIN ID -->
                    <id root="81821f47-8139-4766-aff0-81be0674de8f"/> <!-- Local
ID -->
                    <name>Good Health Clinic</name>
                </representedCustodianOrganization>
            </assignedCustodian>
        </custodian>
        <!-- HIN's id.extension equals Local's id.root. -->
        <legalAuthenticator>
            <time value="200004080732"/>
            <signatureCode code="S"/>
            <assignedEntity>
                <id nullFlavor="NI"/>
                <representedOrganization>
                    <id extension="81821f47-8139-4766-aff0-81be0674de8f"
root="76b242b9-1246-4691-bb1d-91bb7336e76f"/> <!-- HIN ID -->
                    <id root="81822.f47-8139-4766-aff0-81be0674de8f"/> <!-- Local
ID -->
                    <name>Good Health Clinic</name>
                </representedOrganization>
            </assignedEntity>
        </legalAuthenticator>
        <!-- In this example, the scheduling event document is auto-generated, and is
legally authenticated by the organization. -->
        <inFulfillmentOf>
            <order>
                <id extension="1b98e875-1765-4ee9-9978-a337fd0e7e89" root="76b242b9-
1246-4691-bb1d-91bb7336e76f"/> <!-- HIN order ID -->
                <id extension="90fdaa33-f769-4ad9-b380-724f53534ed1" root="81821f47-
8139-4766-aff0-81be0674de8f"/> <!-- Local order ID -->
                <code code="185389009" codeSystem="2.16.840.1.113883.6.96"
displayName="Follow-up visit"/>
            </order>
        </inFulfillmentOf>
        <!-- This is a reference back to the order ID (as opposed to the order document).
-->
        <!--
***********************************************************
CDA Body
***********************************************************
-->
        <component>
            <structuredBody>
                <!--
***********************************************************
Plan section
***********************************************************
-->
<component>
<section>
    <code code="18776-5" codeSystem="2.16.840.1.113883.6.1"/>
    <title>Plan</title>
    <text>Return visit with Dr. Dolin</text>
    <entry>
        <act classCode="ACT" moodCode="APT">
            <!-- A scheduling event is an Act in APT (appointment) mood. (Note that
CDA's scope didn't include scheduling, so the representation here is not completely
analagous with the HL7 V3 Scheduling domain model). -->
            <id extension="6f17f6fb-e8e3-4ec0-9855-c53120fbb15c" root="76b242b9-
1246-4691-bb1d-91bb7336e76f"/> <!-- HIN schedule ID -->
            <id extension="392e9a72-bacb-4511-ae08-37692babd258" root="81821f47-
8139-4766-aff0-81be0674de8f"/> <!-- Local schedule ID -->
            <code code="185389009" codeSystem="2.16.840.1.113883.6.96"
displayName="Follow-up visit"/>
            <statusCode code="completed"/>
            <effectiveTime value="200004280930"/>
            <!-- Time when the service is scheduled for. -->
            <participant typeCode="LOC">
                <participantRole classCode="SDLOC">
                    <code code="GIM" codeSystem="2.16.840.1.113883.5.10588"
displayName="General internal medicine clinic"/>
                    <addr/>
                    <telecom/>
```

```xml
                </participantRole>
            </participant>
            <!-- Location where the service is scheduled for. -->
            <entryRelationship typeCode="COMP">
                <encounter classCode="ENC" moodCode="APT">
                    <code code="185389009" codeSystem="2.16.840.1.113883.6.96" displayName="Follow-up visit"/>
                    <participant typeCode="ATND">
                    <!-- The ATND (Attending) participant shows who the encounter is scheduled with. -->
                        <participantRole>
                            <id extension="2223222" root="76b242b9-1246-4691-bb1d-91bb7336e76f"/> <!-- HIN provider ID -->
                            <id extension="34455655443" root="81821f47-8139-4766-aff0-81be0674de8f"/> <!-- Local provider ID -->
                            <playingEntity>
                                <name>
                                    <given>Robert</given>
                                    <family>Doctor</family>
                                    <suffix>MD</suffix>
                                </name>
                            </playingEntity>
                        </participantRole>
                    </participant>
                </encounter>
            </entryRelationship>
        </act>
    </entry>
</section>
</component>
</structuredBody>
</component>
</ClinicalDocument>
```

Another exemplary schema definition (or relevant portion thereof) relates to scheduling a response for a procedure, for example:

```xml
<?xml version="1.0"?>
<!-- The following sample document depicts a fictional character's health summary. Any resemblance to a real person is coincidental. -->
<ClinicalDocument xmlns="urn:hl7-org:v3" xmlns:voc="urn:hl7-org:v3/voc" xmlns:xsi="http://www.w3.org/2001/XMLSchema-instance" xsi:schemaLocation="urn:hl7-org:v3 CDA.xsd">
    <!--
    *********************************************************
    CDA Header
    *********************************************************
    -->
    <typeId root="2.16.840.1.113883.1.3" extension="POCD_HD000040"/>
    <!-- typeId is required in all CDA instances, and fixed as shown here. This is how you know the instance is a CDA R2 document. -->
    <id root="320eb621-bf5e-41d4-97b5-62c2ac359891" extension="eb7b661b-d302-4c71-a672-d5b7b5833e3f"/>
    <!-- ClinicalDocument.id has cardinality 1..1, and carries the Local ID. -->
    <code code="410538000" codeSystem="2.16.840.1.113883.6.96" displayName="Scheduling procedure"/>
    <!-- This can be a fixed code, since the scheduling details are included below. -->
    <title>Good Health Clinic Scheduling Report</title>
    <!-- This can be a fixed value, used for rendering, or could be left out. -->
    <effectiveTime value="200004080730"/>
    <!-- Required by CDA, and is the time of document creation. -->
    <confidentialityCode code="N" codeSystem="2.16.840.1.113883.5.25"/>
    <recordTarget>
        <patientRole>
            <id extension="12345" root="76b242b9-1246-4691-bb1d-91bb7336e76f"/> <!-- HIN patient ID -->
            <id extension="97531" root="81821f47-8139-4766-aff0-81be0674de8f"/> <!-- Local patient ID -->
            <patient>
                <name>
                    <given>Henry</given>
                    <family>Levin</family>
                    <suffix>the 7th</suffix>
                </name>
                <administrativeGenderCode code="M"
```

```
codeSystem="2.16.840.1.113883.5.1"/>
                        <birthTime value="19320924"/>
                </patient>
        </patientRole>
</recordTarget>
<author>
        <time value="200004080730"/>
        <assignedAuthor>
                <id extension="ee540aa1-41d2-42cb-9fb4-bdc067e2208c" root="76b242b9-1246-4691-bb1d-91bb7336e76f"/> <!-- HIN provider ID -->
                <id extension="9e8c06a4-f23e-4aba-9113-74dd6747f1b0" root="81821f47-8139-4766-aff0-81be0674de8f"/> <!-- Local provider ID -->
        </assignedAuthor>
</author>
<!-- Different workflows may ascribe authorship to a device and/or to a clinician.
In this example, the author is a device. -->
<custodian>
        <assignedCustodian>
                <representedCustodianOrganization>
                        <id extension="81821f47-8139-4766-aff0-81be0674de8f" root="76b242b9-1246-4691-bb1d-91bb7336e76f"/> <!-- HIN ID -->
                        <id root="81821f47-8139-4766-aff0-81be0674de8f"/> <!-- Local ID -->
                        <name>Good Health Clinic</name>
                </representedCustodianOrganization>
        </assignedCustodian>
</custodian>
<!-- HIN's id.extension equals Local's id.root. -->
<legalAuthenticator>
        <time value="200004080730"/>
        <signatureCode code="S"/>
        <assignedEntity>
                <id nullFlavor="NI"/>
                <representedOrganization>
                        <id extension="81821f47-8139-4766-aff0-81be0674de8f" root="76b242b9-1246-4691-bb1d-91bb7336e76f"/> <!-- HIN ID -->
                        <id root="81821f47-8139-4766-aff0-81be0674de8f"/> <!-- Local ID -->
                        <name>Good Health Clinic</name>
                </representedOrganization>
        </assignedEntity>
</legalAuthenticator>
<!-- In this example, the scheduling event document is auto-generated, and is
legally authenticated by the organization. -->
<inFulfillmentOf>
        <order>
                <id extension="f5470d54-7a99-4a74-af44-a91bfc2cdb46" root="76b242b9-1246-4691-bb1d-91bb7336e76f"/> <!-- HIN order ID -->
                <id extension="c1cb1553-55fe-452b-a31f-4394a9b25530" root="81821f47-8139-4766-aff0-81be0674de8f"/> <!-- Local order ID -->
                <code code="23426006" codeSystem="2.16.840.1.113883.6.96" displayName="Pulmonary function study"/>
        </order>
</inFulfillmentOf>
<!-- This is a reference back to the order ID (as opposed to the order document). -->
<!--
********************************************************
CDA Body
********************************************************
-->
        <component>
                <structuredBody>
                        <!--
********************************************************
Plan section
********************************************************
-->
<component>
<section>
        <code code="18776-5" codeSystem="2.16.840.1.113883.6.1"/>
        <title>Plan</title>
        <text>Pulmonary function study</text>
        <entry>
                <act classCode="ACT" moodCode="APT">
                        <!-- A scheduling event is an Act in APT (appointment) mood. (Note that
CDA's scope didn't include scheduling, so the representation here is not completely
analogous with the HL7 V3 Scheduling domain model). -->
                        <id extension="794e3f08-a7f9-4124-866a-7b341cb2537c" root="76b242b9-
```

```
1246-4691-bb1d-91bb7336e76f"/> <!-- HIN schedule ID -->
            <id extension="9c4d9972-a981-4f26-8089-0e6c240d38c9" root="81821f47-
8139-4766-aff0-81be0674de8f"/> <!-- Local schedule ID -->
            <code code="23426006" codeSystem="2.16.840.1.113883.6.96"
displayName="Pulmonary function study"/>
            <statusCode code="completed"/>
            <effectiveTime value="200004091030"/>
            <!-- Time when the service is scheduled for. -->
            <participant typeCode="LOC">
                <participantRole classCode="SDLOC">
                    <code code="GIM" codeSystem="2.16.840.1.113883.5.10588"
displayName="General internal medicine clinic"/>
                    <addr/>
                    <telecom/>
                </participantRole>
            </participant>
            <!-- Location where the service is scheduled for. -->
        </act>
    </entry>
</section>
</component>
</structuredBody>
</component>
</ClinicalDocument>
```

Another exemplary schema definition (or relevant portion thereof) for the Scheduling canonical relates to scheduling a response for a lab imaging, etc.:

```
<?xml version="1.0"?>
<!-- The following sample document depicts a fictional character's health summary. Any
resemblance to a real person is coincidental. -->
<ClinicalDocument xmlns="urn:hl7-org:v3" xmlns:voc="urn:hl7-org:v3/voc"
xmlns:xsi="http://www.w3.org/2001/XMLSchema-instance" xsi:schemaLocation="urn:hl7-org:v3
CDA.xsd">
    <!--
**********************************************************
CDA Header
**********************************************************
-->
    <typeId root="2.16.840.1.113883.1.3" extension="POCD_HD000040"/>
    <!-- typeId is required in all CDA instances, and fixed as shown here. This is how
you know the instance is a CDA R2 document. -->
    <id root="b20f844c-ed0a-46fe-8de9-fe559230931e" extension="eb7b661b-d302-4c71-
a672-d5b7b5833e3f"/>
    <!-- ClinicalDocument.id has cardinality 1..1, and carries the Local ID. -->
    <code code="410538000" codeSystem="2.16.840.1.113883.6.96" displayName="Scheduling
procedure"/>
    <!-- This can be a fixed code, since the scheduling details are included below. -->
    <title>Good Health Clinic Scheduling Report</title>
    <!-- This can be a fixed value, used for rendering, or could be left out. -->
    <effectiveTime value="200004080731"/>
    <!-- Required by CDA, and is the time of document creation. -->
    <confidentialityCode code="N" codeSystem="2.16.840.1.113883.5.25"/>
    <recordTarget>
        <patientRole>
            <id extension="12345" root="76b242b9-1246-4691-bb1d-91bb7336e76f"/>
<!-- HIN patient ID -->
            <id extension="97531" root="81821f47-8139-4766-aff0-81be0674de8f"/>
<!-- Local patient ID -->
            <patient>
                <name>
                    <given>Henry</given>
                    <family>Levin</family>
                    <suffix>the 7th</suffix>
                </name>
                <administrativeGenderCode code="M"
codeSystem="2.16.840.1.113883.5.1"/>
                <birthTime value="19320924"/>
            </patient>
        </patientRole>
    </recordTarget>
    <author>
        <time value="200004080731"/>
        <assignedAuthor>
            <id extension="ee540aa1-41d2-42cb-9fb4-bdc067e2208c" root="76b242b9-
```

```
1246-4691-bb1d-91bb7336e76f"/> <!-- HIN provider ID -->
                <id extension="9e8c06a4-f23e-4aba-9113-74dd6747f1b0" root="81821f47-
8139-4766-aff0-81be0674de8f"/> <!-- Local provider ID -->
            </assignedAuthor>
        </author>
        <!-- Different workflows may ascribe authorship to a device and/or to a clinician.
In this example, the author is a device. -->
        <custodian>
            <assignedCustodian>
                <representedCustodianOrganization>
                    <id extension="81821f47-8139-4766-aff0-81be0674de8f"
root="76b242b9-1246-4691-bb1d-91bb7336e76f"/> <!-- HIN ID -->
                    <id root="81821f47-8139-4766-aff0-81be0674de8f"/> <!-- Local
ID -->
                    <name>Good Health Clinic</name>
                </representedCustodianOrganization>
            </assignedCustodian>
        </custodian>
        <!-- HIN's id.extension equals Local's id.root. -->
        <legalAuthenticator>
            <time value="200004080731"/>
            <signatureCode code="S"/>
            <assignedEntity>
                <id nullFlavor="NI"/>
                <representedOrganization>
                    <id extension="81821f47-8139-4766-aff0-81be0674de8f"
root="76b242b9-1246-4691-bb1d-91bb7336e76f"/> <!-- HIN ID -->
                    <id root="81821f47-8139-4766-aff0-81be0674de8f"/> <!-- Local
ID -->
                    <name>Good Health Clinic</name>
                </representedOrganization>
            </assignedEntity>
        </legalAuthenticator>
        <!-- In this example, the scheduling event document is auto-generated, and is
legally authenticated by the organization. -->
        <inFulfillmentOf>
            <order>
                <id extension="f377aa56-145f-4d6a-95d8-69ebdc51f0b4" root="76b242b9-
1246-4691-bb1d-91bb7336e76f"/> <!-- HIN order ID -->
                <id extension="cb9ad034-52a7-453d-8bd3-1ea0af3a542a" root="81821f47-
8139-4766-aff0-81be0674de8f"/> <!-- Local order ID -->
                <code code="34227000" codeSystem="2.16.840.1.113883.6.96"
displayName="CT of brain"/>
            </order>
        </inFulfillmentOf>
        <!-- This is a reference back to the order ID (as opposed to the order document).
-->
        <!--
***********************************************************
CDA Body
***********************************************************
-->
        <component>
            <structuredBody>
                <!--
***********************************************************
Plan section
***********************************************************
-->
<component>
<section>
    <code code="18776-5" codeSystem="2.16.840.1.113883.6.1"/>
    <title>Plan</title>
    <text>CT of brain with and without contrast</text>
    <entry>
        <act classCode="ACT" moodCode="APT">
            <!-- A scheduling event is an Act in APT (appointment) mood. (Note that
CDA's scope didn't include scheduling, so the representation here is not completely
analagous with the HL7 V3 Scheduling domain model). -->
            <id extension="f7ecae42-cf2c-41c7-b0fb-26bd03e6ba2b" root="76b242b9-
1246-4691-bb1d-91bb7336e76f"/> <!-- HIN schedule ID -->
            <id extension="20b4e790-3a2f-4e44-9ece-32a57d3eef49" root="81821f47-
8139-4766-aff0-81be0674de8f"/> <!-- Local schedule ID -->
            <code code="396209004" codeSystem="2.16.840.1.113883.6.96"
displayName="CT of brain with and without contrast"/>
            <statusCode code="completed"/>
            <effectiveTime value="200004090930"/>
            <!-- Time when the service is scheduled for. -->
            <participant typeCode="LOC">
```

```
                <participantRole classCode="SDLOC">
                        <code code="GIM" codeSystem="2.16.840.1.113883.5.10588"
displayName="General internal medicine clinic"/>
                        <addr/>
                        <telecom/>
                </participantRole>
            </participant>
            <!-- Location where the service is scheduled for. -->
        </act>
    </entry>
</section>
</component>
</structuredBody>
</component>
</ClinicalDocument>
```

Exemplary incremental operations for the Scheduling canonical include: BookAppointment (input: patientRecordID, input: serviceProviderID, input: appointmentDateTime, input: schedulingNotes, output: errorCode, output: schedulingID); ConfirmAppointment (input: patientRecordID, input: serviceProviderID, input: appointmentDateTime, input: schedulingNotes, output: errorCode, output: schedulingID); RescheduleAppointment (input: patientRecordID, input: serviceProviderID, input: oldAppointmentDateTime, input: newAppointmentDateTime, input: schedulingNotes, output: errorCode, output: schedulingID); CancelAppointment (input: patientRecordID, input: serviceProviderID, input: appointmentDateTime, input: schedulingNotes, output: errorCode, output: schedulingID); and ListAvailableSlots (input: serviceProviderID, output: arrayOf <availableDateTimes>, output: errorCode).

One or more of these operations can effectively represent optional implementations that can be used to wrap a temporary data store or the API of a scheduling application which can then in turn generate the scheduling canonical. In an exemplary embodiment, these APIs provide a common API from which applications can do scheduling across a HIN network.

Exemplary use models of canonicals, for example with respect Longitudinal Health Records, Multi-Provider Care, and Automated Claims Processing were described further above with respect for example to FIGS. 10-18. In exemplary embodiments, these three usage models and three deployment models are implemented. Each usage model can be implemented using one of the three deployment models, which makes for a matrix of nine possible implementations of how the canonicals could be use.

Other canonicals can additionally or optionally be provided, including for example Location, Accounting, Material, Event, and ACL. In an exemplary embodiment, these optional canonicals are not required to support the targeted uses cases of EMR data integration, longitudinal health record, multi-provider care, or automated claims processing. Location capabilities can be effectively modeled in the Service Provider canonical and the RLS service, and in this case an additional web service is not required. In an exemplary embodiment, Accounting is not required to meet targeted use cases. Insurance can be modeled to support all the claims processing requirements. Material and Event can be modeled within the Order, Encounter and Result canonicals, so that separate web services and XML payloads are not required. Finally, in an exemplary embodiment ACL (e.g. Access Control List) as a security capability can be implemented not as a canonical, but instead as a combination of core CBR functionality and external services (such as LDAP, Portal authentication, and so forth).

As mentioned earlier, exemplary embodiments of the present invention enable Canonicals to be semantically interoperable, and enable supporting services. In particular, WSDL operations and high-level architecture for exemplary supporting services for the canonicals will now be discussed, and Controlled Medical Vocabulary (CMT), Enterprise Master Person Index (EMPI), and the Record Locator Service (RLS) will be covered in greater detail.

With respect to CMT, exemplary embodiments of the Headwater platform for healthcare can provide mechanisms to define, use, interpret, and translate between controlled medical vocabularies that define diagnosis, disease states, treatment actions and medication. In an exemplary embodiment, these controlled medical vocabularies are defined as structured codes which are mapped into fields in the canonical form. This requirement can be satisfied through an ecosystem-enabling initiative with one or many healthcare ISVs (Independent Software Vendor), for example Apelon.

In an exemplary embodiment, the CMVT WSDL definition has at least the following capabilities. Ability to identify and associate the attributes to a canonical data type which requirement medical code translation (both in terms of local-system-to-canonical and canonical-to-local-system). Ability to identify a validated code set and associated mapping for each attribute and each data flow (aka local-system-to-canonical and canonical-to-local-system). Ability to associate a default code for an attribute if an explicit mapping cannot be found. Ability to provide the means to search "intelligently" for code mappings if an explicit map can't be found and before the default is used; such as semantic string searching. Ability to provide the API, tools and UI to create code sets, the mappings and their association to canonical data types and attributes.

This can be implemented, for example, using the HSSP (Healthcare Services Specification Project) Controlled Terminology Service (CTS) WSDL definition as it represents an approved standard.

In an exemplary embodiment, the API is a SOAP web services implementation (not Java™); has a fully formed implementation of the Vocabulary and Mapping API per the specifications; contains the TranslateCode( ) implementation of the Messaging API; adds a TranslatedCodeInBatch( ) extension of the Messaging API (which can be modeled specifically or generally on the CTS standard API semantics).

Figure 29:
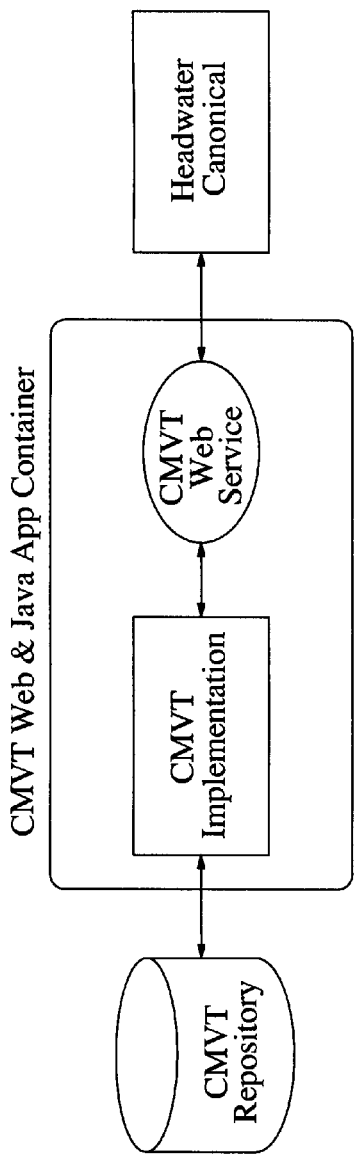
FIG. 29 illustrates an exemplary architecture for implementing CMVT (Controlled Medical Vocabulary Translation) as an external service.

In an exemplary embodiment, the CMVT is implemented as an external service, for example with an architecture as shown in FIG. 29.

Alternatively, a local service implementation can be implemented which calls the Apelon DTS Java™ API.

With respect to Master Patient Index, exemplary embodiments of the Headwater platform for healthcare enable or provide mechanisms to define, use, interpret, and normalize the relational database identifier across systems. Thus, in this scenarios the patient named "Mary Jones" and the doctor named "Bob Smith" are consistently referenced across databases, transactions and services. This requirement can, for example, be satisfied through an ecosystem-enabling initiative with one or many healthcare ISVs, for example the company Initiate.

In an exemplary embodiment, an implementation of an EMPI WSDL definition includes at least the following capabilities: an ability to manage cross-system record ID associations for at least the patient and provider canonicals with the WSDL operations described below. These operations include the following. First, an ability to support at least the entity IndentifyingTraits structure described below. A customizable attribute structure with the tools and APIs to build, query and populate that structure is preferred. Second, CreateEntity (input: canonicalTypeName, input: localRecordID, input: SYSTEMID, input: entityIndentifyingTraits, output: errorCode). This function inserts a canonical record id, key attributes, and the source system into the EMPI repository for implicit linking with other matching records (based on the configured matching algorithm). Also, UpdateEntityTraitValues (input: canonicalTypeName, input: localRecordID, input: SYSTEMID, input: entityIndentifyingTraits, output: errorCode). This function updates the identified EMPI record in the repository. RemoveEntity (input: canonicalTypeName, input: localRecordID, input: SYSTEMID, input: entityIndentifyingTraits, output: errorCode) is a function to delete a canonical record from the EMPI repository. GetAllEntityTraits (input: canonicalTypeName, input: localRecordID, input: SYSTEMID, output: entityIndentifyingTraits, output: errorCode) retrieves the identifying attributes of an EMPI record given a local record ID and CBR ID.

FindEntitiesByTraits (input: canonicalTypeName, input: entityIndentifyingTraits, output: arrayOf<localRecordID, SYSTEMID>, output: errorCode). This operation provides the means to provide a broad search of all records in the EMPI which match some criteria in the identifying attributes (such as find all records who match the name "Jones, Bob". ListLinkedEntities (input: canonicalTypeName, input: localRecordID, input: SYSTEMID, input: entityIndentifyingTraits, output: arrayOf<localRecordID, SYSTEMID>, output: errorCode). This operation provides the means to implement a specific search for the directly linked records to the one specified by the inputs. ListUnlikedEntities (input: canonicalTypeName, input: localRecordID, input: SYSTEMID, input: entityIndentifyingTraits, output: arrayOf<localRecordID, SYSTEMID, entityIndentifyingTraits>, output: errorCode). This operation provides the means to find duplicatly specified, yet unlinked records in the EMPI repository. It filters the record set to only return matching, but unlinked records (where ListLinkedEntities( ) returns all matches linked or not). LinkEntities (input: canonicalTypeName, input: sourceLocalRecordID, input: sourceSYSTEMID, input: targetLocalRecordID, input: targetSYSTEMID, output: errorCode). This operation provides the means to create an explicit linking between the source and target record IDs in the EMPI repository. UnlinkEntities (input: canonicalTypeName, input: sourceLocalRecordID, input: sourceSYSTEMID, input: targetLocalRecordID, input: targetSYSTEMID, input: reasonCode, output: errorCode). This operation provides the means for explicitly breaking the link between the source and target record IDs in the EMPI repository. MergeEntities (input: canonicalTypeName, input: sourceLocalRecordID, input: sourceSYSTEMID, input: targetLocalRecordID, input: targetSYSTEMID, output: errorCode). This operation provides the means to explicitly consolidate EMPI member records in the EMPI repository. The source record is effectively merged into the target, leaving only the resulting target record in the EMPI repository. Identifying attributes in the target which are empty are filled from the source, and existing attributes in the target remain AS-IS. The source record is inactivated in the EMPI repository at the successful end of this operation. UnMergeEntities (input: canonicalTypeName, input: sourceLocalRecordID, input: sourceSYSTEMID, input: targetLocalRecordID, input: targetSYSTEMID, input: reason Code, output: errorCode). This operation provides the means to explicitly un-consolidate EMPI member records in the EMPI repository. The source record is effectively copied to the target, leaving both the source and resulting target record in the EMPI repository as inactivated records until manually resolved. InactivateEntity (input: canonicalTypeName, input: localRecordID, input: SYSTEMID, input: entityIndentifyingTraits, output: errorCode). This operation marks the record as "inactive" in the EMPI repository, effectively marking it available for Get( ) or List( ) operations at the canonical level but not from the EMPI repository. ReactivateEntity (input: canonicalTypeName, input: localRecordID, input: SYSTEMID, input: entityIndentifyingTraits, output: errorCode). This operation marks the record as "active" in the EMPI repository, effectively marking it as logically un-deleted. DescribeEntityTraits (input: canonicalTypeName, output: entityTraitExtractXSL, output: entityTraitXSD, output: errorCode). This operations calls the HWCanonicalManager to find the XSL and XSD which represents the identifying traits of the specified canonical.

With respect to parameters for these functions, canonicalTypeName is the name of the canonical data type to process in the EMPI service, such as "PATIENTPROFILE", "SERVICEPROVIDER". "canonicalTypeName" is an input parameter. "localRecordID" is a GUID or alphanumeric ID which uniquely identifies the data representing the canonical record in the underlying local system. "localRecordID" is an input parameter. "SYSTEMID" is a GUID or alphanumeric ID which uniquely identifies the local system and its associated CBR. Note: A HIN is considered a local system by the EMPI service. "SYSTEMID" is an input parameter. "entityIndentifyingTraits" is an input parameter representing an XML structure which represents the attributes which will describe the key demographics of an EMPI record. Key example includes:

```
<xs:complexType name="indentifyingAttributes">
<xs:sequence>
<xs:element name="addressLine1" nillable="true" type="xs:string" />
<xs:element name="addressLine2" nillable="true" type="xs:string" />
<xs:element name="city" nillable="true" type="xs:string" />
<xs:element name="firstName" nillable="true" type="xs:string" />
<xs:element name="lastName" nillable="true" type="xs:string" />
<xs:element name="memIdNum" nillable="true" type="xs:string" />
<xs:element name="phoneNumber" nillable="true" type="xs:string" />
<xs:element name="sex" nillable="true" type="xs:string" />
<xs:element name="sourceId" nillable="true" type="xs:string" />
<xs:element name="ssn" nillable="true".
```

"entityIndentifyingTraits" is an input parameter representing an XML structure which represents the attributes which will describe the key demographics of an EMPI record. Key example includes:

```
<xs:complexType name="indentifyingAttributes">
<xs:sequence>
<xs:element name="addressLine1" nillable="true" type="xs:string" />
<xs:element name="addressLine2" nillable="true" type="xs:string".
```

"entityIndentifyingTraits" is an input parameter representing an XML structure which represents the attributes which will describe the key demographics of an EMPI record. Key example includes:

```
<xs:complexType name="indentifyingAttributes">
<xs:sequence>
<xs:element name="addressLine1" nillable="true" type="xs:string" />
<xs:element name="addressLine2" nillable="true" type="xs:string" />
<xs:element name="city" nillable="true" type="xs:string" />
<xs:element name="firstName" nillable="true" type="xs:string" />
<xs:element name="lastName" nillable="true" type="xs:string" />
<xs:element name="memIdNum" nillable="true" type="xs:string" />
<xs:element name="phoneNumber" nillable="true" type="xs:string" />
<xs:element name="sex" nillable="true" type="xs:string" />
<xs:element name="sourceId" nillable="true" type="xs:string" />
<xs:element name="ssn" nillable="true" type="xs:string" />
<xs:element name="state" nillable="true" type="xs:string" />
<xs:element name="zip" nillable="true" type="xs:string" />
</xs:sequence>
</xs:complexType>.
```

"sourceLocalRecordID" is an input parameter representing a GUID or alphanumeric ID which identifies the local record used as a source in the Link/Unlink/Merge/Unmerge (aka Link . . . ) operations.

"sourceSYSTEMID" is an input parameter representing a GUID or alphanumeric ID which identifies the CBR/local system used as a source in the Link . . . operations.

"targetLocalRecordID" is an input parameter representing a GUID or alphanumeric ID which identifies the local record used as a target in the Link . . . operations.

"targetSYSTEMID" is an input parameter representing a GUID or alphanumeric ID which identifies the CBR/local system used as a target in the Link . . . operations.

"reason Code" is an input parameter and an alphanumeric code to describe why a EMPI record was unlinked or unmerged. Specific meanings of specific codes is implementation dependent.

"arrayOf<localRecordID, SYSTEMID, entityIndentifyingTraits>" is an output parameter that is a result set for the various EMPI search operations. It is an array/sequence which for each element in the array there is a relationship between the EMPI record ID, CBR ID, and an instance of identifying attributes.

"errorCode" is an output parameter that indicates an exception/result code from the EMPI operations.

"entityIndentifyingTraits" is an output parameter. It has a same XML structure as before, except in this case it is used as an output and is populated by the EMPI as a result rather than as the client for an input. This is a configurable structure and is defined in the canonical meta-data.

"entityTraitExtractXSL" is an output parameter representing an XML style sheet which extracts the XML canonical attributes into a valid instance of the specific canonical's entityIdentifyingTraits.

"entityTraitXSD" is an output parameter that indicates the schema which can be used to validate an instance of entityIdentifyingTraits when passed as parameters across EMPI WSDL operations calls.

Figure 30:
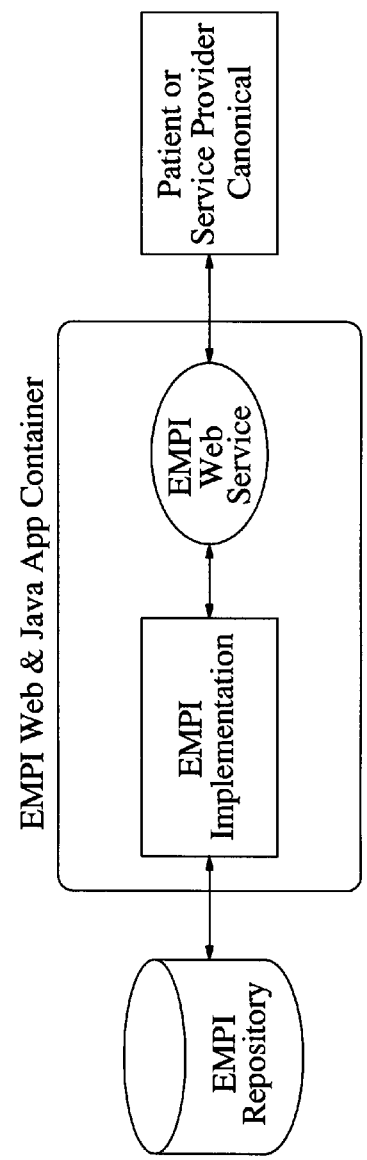
FIG. 30 illustrates an exemplary architecture view for implementing EMPI (Enterprise Master Patient Index) as an external service.

In an exemplary embodiment, the EMPI can be implemented as an external service. An exemplary architecture view is shown in FIG. 30. In an exemplary embodiment, the EMPI external service is integrated into the canonical workflows and the implementation of the WSDL and the integration between the EMPI services and the canonicals is validated. Alternatively, a local service implementation can be provided which calls the Initiate™ Identity Hub Java™ API.

With respect to Record Locator Services (RLS), an exemplary embodiment of the Headwater platform for healthcare enables or provides a mechanism to issue a request for discovery across multiple instances of the platform to aggregate a view of a patients medical, insurance, or drug history in order to support distributed HIN architectures (e.g., ones in which a centralized repository is not used).

The RLS operations can for example be implemented either as a Java™ local service or as CBR workflows, or an appropriate combination of the two. In an exemplary embodiment, a mechanism is provided to customize the RLS so that it can extract more than just record ID's from the canonical into the underlying SQL data store and data model as required for the site deployment needs for record location searching.

In exemplary embodiments, the RLS API has the following capabilities or attributes. The RLS record ID can, and advantageously is, put in the canonical data payload as an ID with the "RLS:" flag listed in front of the id statement. The RLS can support place holder relationships to detect and manage outstanding transactions. In an exemplary embodiment, "*hw_null*" in the targetRecordID field in a CreateRLSRelationship( ) call is used to establish that placeholder. UpdateRLSRelationsip( ) can provide a way to overwrite that placeholder with real data once (or after) it is established. In an exemplary embodiment, the HIN record ID and system IDs are optional parameters on all RLS operations. In an exemplary embodiment, a full canonical XML record is stored in the underlying RLS tables. In this scenario, the RLS service implementation provides code hooks for customization whereby a deployment could perform incremental processing on the canonical XML prior to final storage in the RLS.

In an exemplary embodiment, WSDL operations for the RLS include:

AddRLSEntry (input: canonicalTypeName, input: localRecordID, input: localCBR_ID, input: hinRecordID, input: hinCBR_ID, input: canonicalXMLRecord, output: rlsEntryID, output: errorCode). This operation adds an entry to the RLS log for a single canonical instance. Records the date and time stamp of the creation, the record ids (local and global/HIN), the type of canonical, the canonical XML record instance, and the CBR GUID where the record came from.

UpdateRLSEntry (input: canonicalTypeName, input: localRecordID, input: localCBR_ID, input: hinRecordID, input: hinCBR_ID, output: rlsEntryID, output: errorCode). This operation updates the HIN record data for an established localRecordID (since hinRecordIDs can be NULL on insert).

DeleteRLSEntry (input: canonicalTypeName, input: localRecordID, input: localCBR_ID, input: hinRecordID, input: hinCBR_ID, output: rlsEntryID, output: errorCode). This operation deletes an established RLS entry.

CreateRLSEntryRelationship (input: source CanonicalTypeName, input: sourceLocalRecordID, input: sourceLocalCBR_ID, input: sourceHinRecordID, input: sourceHinCBR_ID, input: source CanonicalXMLRecord, input: targetCanonicalTypeName, input: targetLocalRecordID, input: targetLocalCBR_ID, input: targetHinRecordID, input: targetHinCBR_ID, input: targetCanonicalXMLRecord, output: rlsEntryRelationshipID, output: errorCode). This operation establishes relationships across canonical data types (such as order->schedule->result->document).

UpdateRLSEntryRelationship (input: source CanonicalTypeName, input: sourceLocalRecordID, input: sourceLocalCBR_ID, input: sourceHinRecordID, input: sourceHinCBR_ID, input: source CanonicalXMLRecord, input: targetCanonicalTypeName, input: targetLocalRecordID, input: targetLocalCBR_ID, input: targetHinRecordID, input: targetHinCBR_ID, input: targetCanonicalXMLRecord, output: rlsEntryRelationshipID, output: errorCode). This operation updates the target relationship data based on the source search criteria (such as order->schedule->result->document).

DeleteRLSEntryReleationship (input: source CanonicalTypeName, input: sourceLocalRecordID, input: sourceLocalCBR_ID, input: sourceHinRecordID, input: sourceHinCBR_ID, input: targetCanonicalTypeName, input: targetLocalRecordID, input: targetLocalCBR_ID, input: targetHinRecordID, input: targetHinCBR_ID, output: rlsEntryRelationshipID, output: errorCode). This operation deletes relationships across canonical data types.

LocateSourceByFilter (input: XMLSearchStruct, input: includeRelatedRecords input: maxResultStreams, input: previousResultID, output: arrayOf<canonicalTypeName, localRecordID, localCBR_ID, hinRecordID, hinCBR_ID>, output: errorCode, output: finishedFlag, output: resultID). This operation searches the RLS record cache by canonical type attributes to find the record ID and CBR ID of records which match the search criteria. Will also returned related records in the output array if the includeRelatedRecords parameter is set to TRUE (default is false).

The descriptions for the RLS WSDL operation parameters include the following:

"canonicalTypeName" is an input parameter denoting the string identifier of the canonical such as "ENCOUNTER", "ORDER", etc.

"localRecordID" is an input parameter denoting the GUID or alphanumeric id of the local record representation of the canonical.

"localCBR_ID" is an input parameter denoting the GUID or alphanumeric id of the CBR for the canonical.

"hinRecordID" is an input parameter denoting the GUID or alphanumeric id of the HIN record representation of the canonical.

"hinCBR_ID" is an input parameter denoting the GUID or alphanumeric id of the HIN CBR for the canonical.

"canonicalXMLRecord" is an input parameter denoting the XML instance payload which contains the canonical data.

"includeRelatedRecords" is a boolean input parameter—that if TRUE, results in or returns RLS relationships.

"source CanonicalTypeName" is an input parameter that is a string identifier of the canonical such as "ENCOUNTER", "ORDER", etc. representing the source (parent) of a relationship.

"sourceLocalRecordID" is an input parameter that denotes the GUID or alphanumeric id of the local record representation of the canonical representing the source (parent) of a relationship.

"sourceLocalCBR_ID" is an input parameter that denotes the GUID or alphanumeric id of the CBR for the canonical representing the source (parent) of a relationship.

"sourceHinRecordID" is an input parameter that denotes the GUID or alphanumeric id of the HIN record representation of the canonical representing the source (parent) of a relationship.

"sourceHinCBR_ID" is an input parameter that denotes the GUID or alphanumeric id of the HIN CBR for the canonical representing the source (parent) of a relationship.

"sourceCanonicalXMLRecord" is an input parameter that denotes the XML instance payload which contains the canonical data representing the source (parent) of a relationship.

"targetCanonicalTypeName" is an input parameter that denotes the string identifier of the canonical such as "ENCOUNTER", "ORDER", etc. representing the target (child) of a relationship.

"targetLocalRecordID" is an input parameter that denotes the GUID or alphanumeric id of the local record representation of the canonical representing the target (child) of a relationship.

"targetLocalCBR_ID" is an input parameter that denotes the GUID or alphanumeric id of the CBR for the canonical representing the target (child) of a relationship.

"targetHinRecordID" is an input parameter that denotes the GUID or alphanumeric id of the HIN record representation of the canonical representing the target (child) of a relationship.

"targetHinCBR_ID" is an input parameter that denotes the GUID or alphanumeric id of the HIN CBR for the canonical representing the target (child) of a relationship.

"targetCanonicalXMLRecord" is an input parameter that denotes the XML instance payload which contains the canonical data representing the target (child) of a relationship.

"XMLSearchStruct" is an input parameter that denotes filter criteria for an RLS search of the same type used by the canonical Get( ) and List( ) operations.

"maxResultStreams" is an input parameter that sets the maximum number of return calls to the LocateCBRSourceByFilter( ) method (i.e. max number of result sets).

"previousResultID" is an input parameter that denotes a GUID id result token which describes a cookie that the underlying implementation can use to match the caller to the underlying result set.

"resultID" is an output parameter that denotes the GUID id result token which describes a cookie the underlying implementation can use to match the caller to a following call to LocateCBRSourceByFilter( ) if the finishedFlag is FALSE.

"finishedFlag" is an output parameter that is a boolean flag that returns TRUE if all records in the underlying result set were packaged into a single return of the output: arrayOf<canonicalTypeName, localRecordID, localCBR_ID, hinRecordID, hinCBR_ID>. If the value is FALSE, then the LocateCBRSourceByFilter( ) operation needs to be repeatedly called to extract the rest of the result set until the flag returns TRUE.

"arrayOf<canonicalTypeName, localRecordID, localCBR_ID, hinRecordID, hinCBR_ID>" is an output parameter that is a result set which associates the canonical to its associated record.

"rlsEntryRelationshipID" is an output parameter that denotes an RLS record id for the relationship.

"rlsEntryID" is an output parameter that denotes an RLS record id for the RLS entry.

"errorCode" is an output parameter that denotes an exception/result code from the RLS operations.

With respect to Business Rule processing extension(s), exemplary embodiments of Headwater can support customizable business rule processing extensions for inclusion into healthcare transaction workflows to provide end-user/site configuration of input parameters and conditional processing actions during each step of the workflow. Headwater can enable or provide a mechanism to extend an established workflow in the beginning, end or any point in the middle for conditional processing (if-then-else) by writing Java™ code extensions. In an exemplary embodiment, Business Rules for canonicals are available in several forms, including the following:

Incremental checks or algorithms on workflows in the RLS, CRUD, or canonical services. Those incremental checks or algorithms can be implemented through either incremental steps in the workflow process or as Java™ local services.

Constraints on the validation process for canonical records. This involves specifying the name of either a schematron or the address of a WSDL (local or external service) to implement a canonical validation function. At the start of every canonical operation, a check of the canonicalSignifier XML (which is defined further below definition) can be performed to execute the following actions. First, confirm that the XML document conforms to the XSD definition stored in the canonicalSignifier structure. Second, check the canonicalSignifier for the existence of a <SchemaConstraintDef/>segment. If the <SchemaConstraintDef/>segment is undefined, then the only action taken will be the XSD schema validation. However, if the <SchemaConstraintDef/>segment is defined, then in an exemplary embodiment the canonical workflow either: a) invokes a local service which implements ExecuteSchematron(input: schemaTronLocation, input: canonicalXMLPayload, output: errorCode); invokes a local service which implements ValidateCanonicalSchema(input: canonicalXMLPayload, output: errorCode); or invokes an external service which implements ValidateCanonicalSchema(input: canonicalXMLPayload, output: errorCode). Next, the <SchemaConstraintDef/>/<SchemaConstraintType/>will indicate whether a schematron, local service, or external service should be used to execute the constraint check. Each canonical can be implemented with a baseline constraint definition, as described further above.

Exemplary embodiments of the present invention can also provide or ensure non-functional capabilities for canonicals in the Headwater system. Exemplary Headwater appliances or CBRs can include a high-performance XML and workflow processing engine. In addition or in the alternative, in an exemplary embodiment the performance, scalability and resource utilization of the canonical implementations and related supporting services are optimized or enhanced.

In particular, in exemplary embodiments of the invention, the following performance benchmarks are met and can be exceeded. The patient data (profile, medical record, prescriptions, claims, referrals) can be processed (routed, transformed, and stored) within a 24-hour period after it is received. This can scale, for example from a small HIN of 500,000 patients to a large HIN of over 50 million patients. In an exemplary embodiment, the Headwater appliances and resulting Headwater system or network and associated architecture are capable of processing in the 24-hour period in which it is received for an average of 10 patient data transactions per patient per year in an HIN instance.

In an exemplary embodiment of the invention, for reasons of scalability within the "four walls" of a lab, hospital, payer, and so forth, etc., Headwater appliances or CBRs and the related canonicals can support extended integration to other integration products as described, for example, below.

Figure 31:
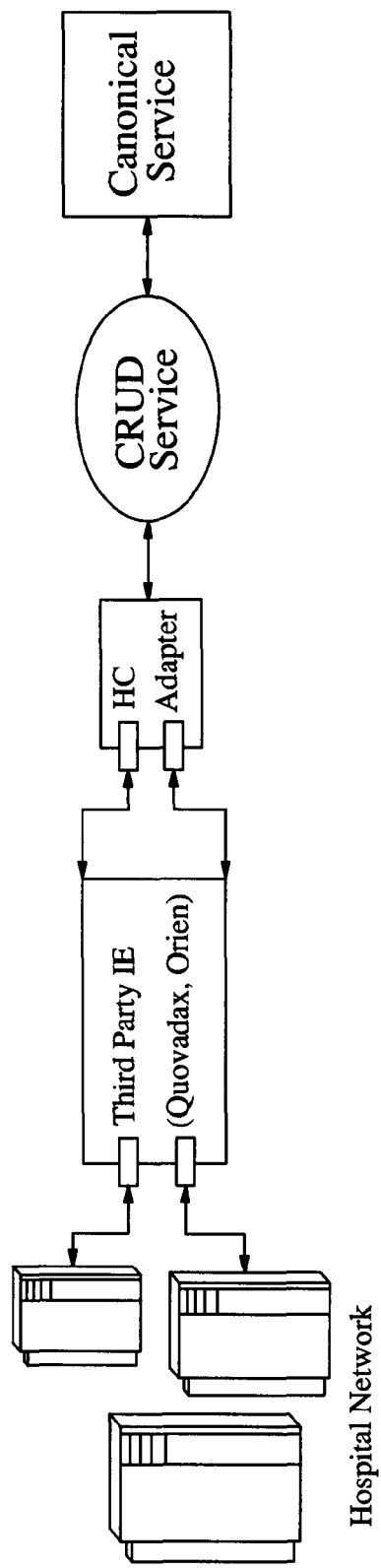
FIG. 31 illustrates a visual representation of an exemplary architecture for providing a loose coupling to a healthcare-specific integration engine (HCIE) with web services based interfaces.

In an exemplary embodiment, the Headwater appliance or network solution can provide a loose coupling to a healthcare-specific integration engine (HCIE) with web services based interfaces. This means that there is, advantageously, no specific requirement for a healthcare integration engine as part of the core runtime. Integration engine examples are Itemfield™ and Quovadx™; in this scenario, an IE provides translation adaptors. FIG. 31 provides a visual representation of such an architecture.

In an exemplary embodiment, as part of the validation process of a Headwater-based system the integration of an HC (Health Care) Adaptor enabled CRUD service can be validated using either FTP or MLLP protocol with a third party integration engine (minimally either MS BizTalk with the HL7 accelerator or Quovadax).

The following glossary of terms provides definitions for use throughout this document.

"Canonical": a Headwater term which refers to a standardized representation of data and functions. Examples include Patient, Order, Encounter, etc.

"CBR": Content Based Router or Headwater appliance, which can form a key software component in the Headwater architecture and which can provide the ESB and XML acceleration and firewall capabilities of the Headwater platform.

"CBR Local Service": a WSDL service implementation which is implemented in the CBR Java™ stack.

CBR External Service: A WSDL service implementation which is implemented external to the CBR runtime and is called through one of the supported CBR transport bindings (such as SOAP, JMS, etc.).

CBR Workflow: A BPEL-based workflow which is defined and executed within the CBR run time. CBR maps WSDL operations to workflows for execution.

ItemField: $3^{rd}$ party technology that can embedded in CBR to provide transform functionality to map HL7, X12, CCR, and NCPDP data formats to a canonical XML representation.

HIN: Health Information Network which is a collaboration among government agencies, hospitals, labs, doctor offices, pharmacies and insurance companies to share patient, clinical and financial information across a community of care.

HL7: Health-Level Seven which is a Healthcare industry standards body which defines information technology standards for healthcare with a specific focus on data interopability across clinical systems and healthcare business processes.

CDA: Clinical Document Architecture which is an approved HL7 standard which implements the HL7 version 3.0 reference information model (RIM) in XML.

CCR: Continuity of Care Record which is an ATSM (ANSI) standard for representing a personal health record for an individual. It is an XML structure which provides a standardize definition of patient demographics, medical history, and relationships to clinical professionals (like primary/family doctor).

CCD: Continuity of Care Document which is an approved joint HL7 and ANSI standard for representing the content of a CCR under the CDA specification.

NCPDP: Standard for representing electronic drug prescriptions.

X12: Standard for representing claims, referrals and claim payments.

RLS: Record Locator Service.

CRUD: Create, Read, Update, and Delete Service.

EMPI: Enterprise Master Patient Index Service.

CMVT: Controlled Medical Vocabulary Translation Service.

XFRM: Transform.

In exemplary embodiments, the canonicalSignifier is a meta-data schema that can be used to describe the structural and semantic definition of the canonical. The canonicalSignifier describes the core XSD of the canonical type, along with other necessary descriptions to fully define the semantic behavior of the canonical. In an exemplary embodiment, the canonicalSignifier has the following basic structure:

```
<HWCanonicalSignifier>
    <CanonicalID>
        <CanonicalTypeName>
            <name="Patient" />
        </CanonicalTypeName>
        <CanonicalTypeID>
            <id="some GUID or alphanumeric id"/>
        </CanonicalTypeID>
        <CanonicalTypeVersion>
            <version="1.0" />
        </CanonicalTypeVersion>
    </CanonicalID>
    <CanonicalSchema>
        <!-This is a sequence of hierarchical schemas and constraint actions--/>
        <CanonicalSchemaSegment>
            <SchemaName="CDA R2" />
            <SchemaDefinition="contains XSD or url to the XSD" />
                <SchemaRendering="contains XSL or URL to the XSL" />
            <SchemaConstraintsDef>
                <SchemaConstraintType=SCHEMATRON or LOCAL_SERVICE or REMOTE_SERVICE />
                <SchemaConstraints="constains either the location of schematron or service with WSDL def to execute constraint checking " />
            </SchemaConstraintsDef>
                <!-Additional nested schema segments -->
                <!-Such as: POCD_MO040, etc. -->
        </CanonicalSchemaSegment>
    </CanonicalSchema>
</HWCanonicalSignifier>
```

In exemplary embodiments, the XMLSearchStruct is an XML schema designed to send search/filter and sort criteria to the Get( ) and List( ) canonical operations. It is an XML structure that can effectively represent the basic semantics of an SQL-like query using either query-by-example semantics or query-by-filter with attributes to be selected (as named by the canonical XSD), filter/search expressions (with AND+OR combinations), and then order by expressions.

In an exemplary embodiment, the basic structure of the XMLSearchStruct is:

```
<HWXMLSearch>
    <HWCanonicalSignifierName>
        <!-canonical signifier name for the search in being executed--/>
    </HWCanonicalSignifierName>
<!-XML SEARCH WILL EITHER BE SEARCH_BY_EXAMPLE OR SEARCH_BY_FILTER--/>
<!-SEARCH BY EXAMPLE FIRST--/>
    <SearchByExample>
        <!-XML document which is compliant to the canonical signifier which tells the Get( ) or List( ) operations to find other canonicals "like" the one here--/>
    </SearchByExample>
<!-OR SEARCH BY FILTER--/>
    <SearchByFilter>
        <SearchAttributes> <!-sequence of attributes--/>
            <Attribute>
                <name="field#1" />
            </Attribute>
            <Attribute>
                <name="field#2" />
            </Attribute>
            <Attribute>
                <name="field#3" />
            </Attribute>
        </SearchAttributes>
        <FilterCriteria> <!-sequence of expressions--/>
            <Expression> <!-like an open brackets--/>
                <value="field#1" = 'xyz' />
                <operator=AND />
                <value="field#2" != 10 />
                <operator=OR />
                <value="field#3" > 30 />
            </Expression> <!-like a closed brackets--/>
        </FilterCriteria>
        <OrderCriteria> <!-sequence of attributes--/>
            <Attribute>
                <name="field#1" />
                    <direction=ASCENDING />
            </Attribute>
        </OrderCriteria>
    </SearchByFilter>
</HWXMLSearch>
```

"putRequestSrcStruct" is an XML payload that can be used for the WSDL Put( ) operation to provide the necessary header data for the RLS and audit entry that will become associated to the canonical when the data is written to the Headwater platform. "putRequestSrcStruct" identifies the source so that appropriate rules regarding routing, patient consent, and so forth can be processed by the Put( ) operation prior to the actual write to the underlying destination. In an exemplary embodiment, "putRequestSrcStruct" has the following basic structure:

```
<HWPutRequestSrcStruct>
    <HWCanonicalSignifierName>
        <!-canonical signifier name for the put in being executed--/>
    </HWCanonicalSignifierName>
    <SecurityContext>
        <SourceIdentity
                identityName="username or system_name"
        </SourceIdentity>
    </SecurityContext>
    <CBRContext>
        <CBRName>
            Name = "blah GUID"
        </CBRName>
        <NetworkName>
            Name = "blah.myhitorg.com"
        </NetworkName>
        <NetworkAddress>
            Address = "168.12.15.165"
        </NetworkAddress>
    </CBRContext>
</HWPutRequestSrcStruct>
```

In exemplary embodiments, "initializeRequestSrcStruct" is an XML payload for the WSDL Initialize( ) operation, and can provide the necessary header data for the RLS and audit entry that will become associated to the canonical when the data is written to the Headwater platform. It identifies the source so that the appropriate rules regarding routing, patient consent, etc can be processed by the Initialize( ) operation prior to the actual write to the targeted destinations. In an exemplary embodiment, "initializeRequestSrcStruct" has the following basic structure:

```
<HWInitialzieRequestSrcStruct>
    <HWCanonicalSignifierName>
        <!-canonical signifier name for the initialize in being executed--/>
    </HWCanonicalSignifierName>
    <InitializeContext>
        initializeWorkflowName =
            "PATIENT_INITIALIZE_FROM_ECLIPSYS"
```

```
        </InitializeContext >
        <SecurityContext>
            <SourceIdentity
                    identityName="username or system_name"
            </SourceIdentity>
        </SecurityContext>
        <CBRContext>
                <CBRName>
                    Name = "blah GUID"
                </CBRName>
                <NetworkName>
                    Name = "blah.myhitorg.com"
                </NetworkName>
                <NetworkAddress>
                    Address = "168.12.15.165"
                </NetworkAddress>
        </CBRContext>
    </HWInitialzieRequestSrcStruct>
```

In exemplary embodiments, "canonicalRecordLocationStruct" is an XML structure that is used by the RLS service and the canonical Locate( ) operation to identify the CBR location of specific canonical record instances. "canonicalRecordLocationStruct" can be used to extract the CBR location(s) of a canonical record so that the Get( ) operation can be called on the appropriate CBR(s) to retrieve the right instances of desired canonical records across a network of CBR deployments. In an exemplary embodiment, "canonicalRecordLocationStruct" has the following basic structure:

```
    <HWCanonicalRecordLocationStruct>
        <HWCanonicalSignifierName>
            <!-canonical signifier name for the search in being
                executed--/>
        </HWCanonicalSignifierName>
        <CanonicalRecordID>
            recordID = "GUID or Alphanumeric record ID for
                instance"
        </CanonicalRecordID>
        <CBRContext>
                <CBRName>
                    Name = "blah GUID"
                </CBRName>
                <NetworkName>
                    Name = "blah.myhitorg.com"
                </NetworkName>
                <NetworkAddress>
                    Address = "168.12.15.165"
                </NetworkAddress>
        </CBRContext>
    </HWCanonicalRecordLocationStruct>
```

As previously mentioned, exemplary embodiments of the Headwater system can support different usage models, and one of those models involves the patient's care being delivered by multiple service providers who are effectively supporting a single health care event across multiple transactions and service providers. Each provider needs some common data, and each downstream transaction builds an association to each upstream one. As also noted elsewhere herein, exemplary embodiments of the Headwater system can support various uses of Longitudinal Health Records. Described below are examples, to illustrate or suggest how various aspects of the invention can come into play given specific scenarios.

A first process example illustrating multi-provider care, starts with a visit to a primary care physician and transitions to a specialist. However, in practice this usage model could start at a family doctor, primary care, local clinic, etc and involve downstream interactions with other doctors (could be initial visit at clinic/ER and follow up at primary care) or service providers (like labs or pharmacy).

The baseline case has the following steps or segments:
1. Patient visits primary care physician, eligibility check.
2. Primary care physician refers Patient to Specialist.
3. Primary care EHR sent to specialist.
4. Primary care electronically files claim; correctness check done.
5. Patient schedules appointment with Specialist, eligibility check.
6. Patient visits Specialist.
7. Specialist orders prescription and labs for patient.
8. Specialist EHR sends order to pharmacy and lab.
9. System checks for drug interaction.
10. System checks for duplicate lab tests.
11. Patient schedules appointment with lab.
12. Patient fills prescription.
13. Pharmacy electronically files claim; correctness check done.
14. Pharmacy reports to Specialist prescription is/is not filled.
15. Patient completes lab work.
16. Lab sends results to Specialist HER.
17. Lab electronically files claim; correctness check done.
18. Specialist reviews lab results; makes recommendations.
19. Specialist EMR records are sent back to primary care physician.
20. Specialist electronically files claim; correctness check done.
21. Payer processes electronic claims and pays providers.
22. Patient may view updated health record and claims status electronically.

With respect to a Longitudinal Health Record, consider a fictional patient, Blu Waters, who is a 66 year old part time employee of the commercial fishing company Florida Grouper located in Fort Meyers Beach Fla. Blu Waters was honorably discharged from the U.S. Marine Corps, (II Marine Expeditionary Forces (MEF) at Camp Lejeune, N.C.) with a rank of Lieutenant Colonel after 22 years of service. He had been stationed at several bases both within United States and overseas, including Japan and Iraq. While serving in Operation Iraq Freedom (OIF), While in the Marine Corps, Blu Waters had numerous radiological and laboratory work ups to determine the cause of gastrointestinal problems. A diagnosis of gastroesophageal reflux disease (GERD) and Barrett's esophogitis was noted on his discharge physical. Blu Waters currently receives treatment for his GERD at the Naval Hospital in Pensacola Fla. Mr. Waters carries health insurance under TRICARE for Life and most of his primary care health needs are provided by the Warf Medical Group Clinic located near the fishing docks in Fort Meyers Beach Fla.

[Step 0—Things that happened before the story] Our narrative begins with additional background information relating to recent events. Blu Waters is visiting his son in Tampa Fla. They are driving to a local restaurant when Mr. Waters starts to experience chest pain. He's in eyesight of Precious Heart Medical Center (PHMC), so gets off the freeway and presents to the PHMC emergency room. Upon admission to the PHMC emergency room, the triage nurse, Nancy Nightingale asks Mr. Waters to provide his insurance information, and learns that he has health care coverage through TRICARE.

Eric Emergency, MD begins an evaluation, including a targeted history and physical, of Blu Waters. When Mr. Waters is asked about other significant past medical events, he relates that he had numerous tests for GI problems while in the military. He's been using a prescription H2-blocker, which initially helped his GI symptoms, but less so lately. Vital signs are normal. Sublingual nitroglycerin and oxygen by nasal cannula have been applied, and Blu Waters is currently chest pain free. An electrocardiogram shows no evidence of acute myocardial infarction.

[Step 1—Query for document listing] Dr. Emergency queries the Florida Health Information Network (HIN) to determine what information is available on Mr. Water's medical history. In addition to the medical records from Warf Medical Group Clinic, he also notes that links are available to Mr. Water's medical history in the. With Mr. Water's permission, Dr. Emergency queries for available documents.

[Step 2—Respond with document listing] Dr. Emergency's query finds or reports several pertinent documents: a recent electrocardiogram report at Warf Medical Group and, from two years previous, endoscopy and coronary angiogram reports at the Naval Hospital in Pensacola.

[Step 3—Query for specific documents with content] Dr. Emergency selects documents from the listing, requests and receives access to (or content from) the selected documents. In this example, Dr. Emergency selects and receives all three documents.

[Step 4—Respond with requested documents] Dr. Emergency reviews the clinical documents obtained from Warf Medical Group Clinic, and the Naval Hospital in Pensacola. The previous coronary angiogram report found no evidence of coronary artery disease, and the previous electrocardiogram was also normal. Dr. Emergency reviews the records with Blu, confirming that the patient believes the data to be correct and up to date, including the diagnosis of gastroesophageal reflux disease (GERD). Emergency room lab results on Blu Waters come back normal, as does a chest x-ray. Dr. Emergency diagnoses Blu Waters as experiencing an exacerbation of his GERD, reassures him that his heart is okay. Dr Emergency discharges him from the emergency room with a prescription for a Proton Pump Inhibitor and advises Blu to follow up with his primary care provider. Dr. Emergency then enters an emergency room visit note into the PHMC electronic medical record.

[Step 5—Availability of new documents] Two weeks later Blu Waters is seen in follow-up with his primary care provider Dr. Big Fisher at the Warf Medical Group Clinic. Blu Waters explains that he had an emergency room visit and that his medications were changed. He forgot to bring the prescription in and doesn't remember the name of the new medication. Dr. Fisher explains that it is a new and stronger medication for his GERD called a proton pump inhibitor and that the information from his visit to the Precious Heart Medical Center emergency room was provided to him by his staff from the HIN when he checked in to the clinic. Although Mr. Waters is now symptom free, Dr. Fisher recommends a repeat surveillance endoscopy to exclude dysplastic changes of his esophogitis. He explains that his recent medical information will be available to the physicians at the Naval Hospital in Pensacola when he sees them for the endoscopy.

In accordance with exemplary embodiments of the invention, the Steps 0-5 described above were incorporated into the story, or enabled, in the following ways. When Mr. Waters was registered with Warf Medical Group Clinic previously, his identity was matched to other providers in the HIN through communication over the HIN MPI. The identity of his Medical Record is linked to the HIN through the Gateway and MPI.

With respect to [Step 1—Query for document listing], Dr. Emergency logs in to the secure HIN system, and submits a query for a listing of all clinical documents for Blu Waters over the past 2 years.

With respect to [Step 2—Respond with document listing], as a component of Dr Emergency's request for available documents (for example, web portal access to the HIN), finds an identity match at the Warf Medical Group Clinic and the. A query for documents within 2 years is sent to both. The Warf Medical Group Clinic sends a response back, showing viewable but non-persistent data that Blu Waters recently had an electrocardiogram, and also shows lab results, medication profile, and several progress notes are available. The gateway sends a response back viewable but non-persistent data that his Discharge Medical Summary, medication history, laboratory results, endoscopic report and coronary angiogram are available from EMR, the 's electronic medical record.

With respect to [Step 3—Query for specific documents with content], Dr. Emergency selects the documents of interest from the HIN web page. Based upon Dr. Emergency's selection, the HIN queries Warf Medical Group Clinic and the gateway for the Warf Medical Group Clinic electrocardiogram results and the endoscopy and coronary angiogram reports from the EMR.

With respect to [Step 4—Respond with requested documents], The Warf Medical Group Clinic retrieves the electrocardiogram result from their EMR and sends the documents to the HIN (viewable/non-persistent). The gateway retrieves the endoscopy and coronary angiogram reports from EMR and sends the documents to the HIN (viewable/non-persistent).The HIN makes these documents available for viewing by Dr. Emergency through the HIN secure web page. During the HIN web page log-out process, the viewable health data on Blu Waters ceases to exist at PHMC.

With respect to [Step 5—Availability of new documents], PHMC registers the newly entered emergency visit note, along with other associated items (e.g., lab results), within Mr. Waters's PHMC electronic medical record, and also registers these documents in the HIN gateway, for possibly retrieval by other providers, as appropriate (i.e. Warf Medical Group Clinic and Naval Hospital Pensacola).

It will be understood that each block of any flowchart illustration(s), and combinations of blocks in the flowchart illustration(s), as well as procedures, operations and code described herein, can be implemented in different orders or sequences and can be implemented by computer program instructions executing in one or more computers or processors, in various local, remote, central or distributed forms of processing. These instructions can be stored in one or more volatile and/or non-volatile memory devices or other storage devices. These program instructions may be provided to one or more processor to produce a machine, such that the instructions, which execute on the processor(s), create mechanisms for implementing the actions specified in the flowchart block or blocks. Those skilled in the art will recognize that the machine can be hardware that executes software, hardware combined with software and/or firmware, read-only-memory, or any other data storage, and can also be implemented as a hardware device that is configured to perform one or more of the functions or actions described herein. For example, the computer program instructions may be executed by a processor to cause a series of operational steps to be performed by the processor to produce a computer implemented process such that the instructions, which execute on the processor to provide steps for implementing the actions specified in the flowchart block or blocks. The computer program instructions may also cause at least some of the operational steps shown in the blocks of the flowchart and/or processes described herein to be performed in parallel. Moreover, some of the steps may also be performed across more than one processor, such as might arise in a multi-processor computer system. In addition, one or more blocks or combinations of blocks in the flowchart illustrations or code descriptions may also be performed concurrently with other blocks or combinations of blocks, or even in a different sequence than illustrated without departing from the scope or spirit of the invention. Accordingly, blocks of the flowchart illustration(s) and/or of processes or code described herein support combinations of mechanisms for performing the specified actions, combinations of steps for performing the specified actions and program instruction means for performing the specified actions. It will also be understood that each block of the flowchart illustration(s) and/or processes and code described herein, and combinations of blocks in the flowchart illustration(s) and/or processes and code described herein, may be implemented by special purpose hardware-based systems which perform the specified actions or steps, or combinations of special purpose hardware and computer instructions. Some or all of the various aspects of the invention can be implemented in hardware, in software running on hardware, or any combination of hardware and software.

The examples provided should not be construed as narrowing the embodiments of the invention, and are intended merely to provide a better understanding. Thus, other mechanisms may therefore be employed, without departing from the scope of the invention.

The above specification, examples, and data provide a complete description of the manufacture and use of the composition of the invention. Since many embodiments of the invention may be made without departing from the spirit and scope of the invention, the invention resides in the claims hereinafter appended.

What is claimed as new and desired to be protected by Letters Patent is:

1. A device comprising:
   a processor configured to validate data for compliance with a canonical standard in accordance with a metric;
   a communication port configured to provide a connection between the device and an entity associated with the device; and
   a memory configured to store a translation key configured to map information between a first form compliant with the canonical standard and a second form compliant with an information standard of the entity associated with the device,
   wherein the processor is further configured to:
   transform information that is in the second form into the first form or vice-versa based on the translation key,
   validate the transformed information in accordance with the metric, and generate diagnostic information associated with the validate of the transformed information,
   indicate, responsive to a failure of a validation of the transformed information in accordance with the metric, that the translation key is inaccurate, and convey the diagnostic information provided by the validate for a determination as to whether the translation key needs to be corrected,
   assign or obtain, for each communication transferred through the device between a network device connected with the device and the entity associated with the device, a local identification label that identifies the device and the entity, the local identification label including a device identifier, an entity identifier, and a network identifier, and
   transmit, via the communication port, the local identification label to the network device.

2. The device of claim 1, wherein the communication port is further configured to receive a new communication from any of the entities associated with the device, and wherein the processor is further configured to assign or obtain a unique network identification label for the new communication.

3. The device of claim 1, wherein the communication port is further configured to connect with other devices to form a network.

4. The device of claim 3, wherein the processor is further configured to:
   associate the local identification label with the communication;
   store, in the memory, a copy of the communication and a copy of the local identification label.

5. The device of claim 4, wherein the processor is further configured to receive and store, in the memory, local identification labels associated with the communication by the other devices.

6. The device of claim 3, wherein the canonical standard enables structural and semantic standardization or normalization of data within the network.

7. The device of claim 3, wherein all communications between the device and the other device in the network comply with the canonical standard.

8. A computer-readable non-transitory medium having information stored thereon, the information comprising:
   a metric for validating data electronically communicated in a network between content-based routers for compliance with a canonical standard;
   a translation key configured to map information between a first form compliant with the canonical standard and a second form compliant with an information standard of an entity associated with a content-based router device; and
   instructions when executed on a processor cause a processor to:
   enable electronic communication between the content-based router device and the entity associated with the content-based router device;
   transform information that is in the second form into the first form and vice versa based on the translation key;
   validate the transformed information in accordance with the metric and generate associated diagnostic information;
   indicate, responsive to a failure of a validation of the transformed information in accordance with the metric, that the translation key is inaccurate, and convey the diagnostic information for a determination as to whether the translation key needs to be corrected,
   assign or obtain, for each communication transferred through the content-based router device between a network device connected with the content-based router device and the entity associated with the content-based router device, a local identification label that identifies the content-based router device and the entity, the local identification label including a content-based router device identifier, an entity identifier, and a network identifier, and transmit, via the communication port, the local identification label to the network device.

9. The computer-readable medium of claim 8, wherein the instructions further cause the processor to:
enable receiving a new communication from the entity associated with the content-based router device; and
obtain or assign a unique network identification label for the new communication.

10. The computer-readable medium of claim 8, wherein the instructions further cause the processor to enable connection between the content-based router device and other content-based router devices forming the network.

11. The computer-readable medium of claim 10, wherein the instructions further cause the processor to:
associate the local identification label with the communication;
store, in a memory, a copy of the communication and a copy of the local identification label.

\* \* \* \* \*